US012575319B2

(12) United States Patent
Shiomi et al.

(10) Patent No.: US 12,575,319 B2
(45) Date of Patent: Mar. 10, 2026

(54) ORGANIC ELECTROLUMINESCENCE DEVICE AND ELECTRONIC DEVICE

(71) Applicant: IDEMITSU KOSAN CO., LTD., Tokyo (JP)

(72) Inventors: Takushi Shiomi, Sodegaura (JP); Hisato Matsumoto, Sodegaura (JP); Hiromi Nakano, Sodegaura (JP); Toshinari Ogiwara, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 901 days.

(21) Appl. No.: 17/345,427

(22) Filed: Jun. 11, 2021

(65) Prior Publication Data

US 2023/0033529 A1 Feb. 2, 2023

(30) Foreign Application Priority Data

Jun. 12, 2020 (JP) ................................ 2020-102554

(51) Int. Cl.
*H10K 85/60* (2023.01)
*C07D 498/04* (2006.01)
(Continued)

(52) U.S. Cl.
CPC ......... *H10K 85/657* (2023.02); *C07D 498/04* (2013.01); *C09K 11/06* (2013.01);
(Continued)

(58) Field of Classification Search
CPC .................. C07D 498/04; C09K 11/06; C09K 2211/1018; H10K 50/11; H10K 50/12;
(Continued)

(56) References Cited

U.S. PATENT DOCUMENTS

2012/0080670 A1* 4/2012 Park ................................ 257/40
2018/0366677 A1 12/2018 Tsang et al.
(Continued)

FOREIGN PATENT DOCUMENTS

CN 110492006 A 11/2019
WO WO 2017/115833 A1 7/2017

OTHER PUBLICATIONS

English translation of CN 109378392, and the original CN 109378392, Wei Jinbei, Feb. 22, 2019 (Year: 2019).*
(Continued)

*Primary Examiner* — Seokmin Jeon
(74) *Attorney, Agent, or Firm* — Oblon, McClelland, Maier & Neustadt, L.L.P.

(57) ABSTRACT

An organic EL device includes: an anode, a cathode, and an emitting layer, in which the emitting layer contains a first compound of a formula (1), a second compound of a formula (2), and a third compound that exhibits delayed fluorescence, and singlet energies $S_1$ of the first compound, the second compound, and the third compound satisfy Numerical Formula 1 and Numerical Formula 2.

$$S_1(M1) > S_1(M3) \quad \text{(Numerical Formula 1)}$$

$$S_1(M2) > S_1(M3) \quad \text{(Numerical Formula 2)}$$

$$A—L—B \quad (1)$$

(Continued)

-continued (a1)

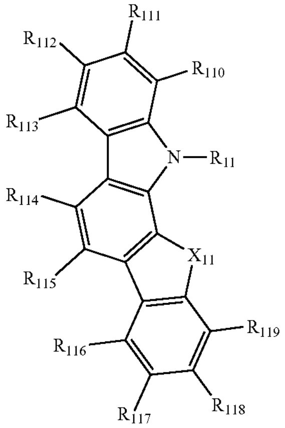

(2)

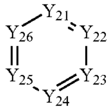

(2A)

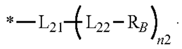

In the formula (1), A represents a group of a formula (a1) or the like, L represents a linking group or the like, and B represents an aryl group or the like. The first compound of the formula (1) has no carbonyl group. In the formula (2), $Y_{21}$ to $Y_{26}$ each independently represent an N atom, $CR_A$, or the like. $R_A$ represents a substituent, a group of a formula (2A), or the like.

15 Claims, 5 Drawing Sheets

(51) Int. Cl.

| | |
|---|---|
| ***C09K 11/06*** | (2006.01) |
| ***H10K 50/11*** | (2023.01) |
| ***H10K 50/12*** | (2023.01) |
| ***H10K 101/00*** | (2023.01) |
| ***H10K 101/20*** | (2023.01) |

(52) U.S. Cl.

CPC ....... *H10K 85/654* (2023.02); *H10K 85/6572* (2023.02); *C09K 2211/1018* (2013.01); *H10K 50/11* (2023.02); *H10K 50/12* (2023.02); *H10K 2101/20* (2023.02); *H10K 2101/90* (2023.02)

(58) Field of Classification Search

CPC .. H10K 50/121; H10K 85/654; H10K 85/657; H10K 85/6572; H10K 2101/20; H10K 2101/90; H01L 51/5012; H01L 51/5024; H01L 51/5028; H01L 51/0067; H01L 51/0071; H01L 51/0072; H01L 2251/5384

See application file for complete search history.

(56) References Cited

U.S. PATENT DOCUMENTS

| | | | | |
|---|---|---|---|---|
| 2021/0050546 | A1 | 2/2021 | Li et al. | |
| 2021/0126203 | A1* | 4/2021 | Jung | H01L 51/0072 |
| 2021/0151683 | A1* | 5/2021 | Sakaino | H01L 51/008 |
| 2023/0113918 | A1* | 4/2023 | Ozawa | C09K 11/02 |

OTHER PUBLICATIONS

Myoung-Seon Gong et al. “Synthesis and device properties of mCP analogues based on fused-ring carbazole moiety”, Org. Electronics 2017, vol. 42, p. 66-74 (Year: 2017).*

Adachi, “Yuki Hando-tai no Debaisu Bussei (Device Physics of Organic Semiconductors)”, Kodansha, Apr. 1, 2012, 19 pages (with English Machine Translation).

Uoyama et al., “Highly efficient organic light-emitting diodes from delayed fluorescence”, Nature, vol. 492, 2012, 7 pages.

* cited by examiner

ORGANIC ELECTROLUMINESCENCE DEVICE AND ELECTRONIC DEVICE

The entire disclosure of Japanese Patent Application No. 2020-102554, filed Jun. 12, 2020 is expressly incorporated by reference herein.

TECHNICAL FIELD

The present invention relates to an organic electroluminescence device and an electronic device.

BACKGROUND ART

When a voltage is applied to an organic electroluminescence device (hereinafter, occasionally referred to as an "organic EL device"), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies has been made to improve a performance of the organic EL device.

For instance, it is expected to further efficiently emit the organic EL device using triplet excitons in addition to singlet excitons. In view of the above, a highly efficient fluorescent organic EL device using thermally activated delayed fluorescence (hereinafter, sometimes simply referred to as "delayed fluorescence") has been proposed and studied.

A TADF (Thermally Activated Delayed Fluorescence) mechanism uses such a phenomenon that inverse intersystem crossing from triplet excitons to singlet excitons thermally occurs when a material having a small energy difference (ΔST) between singlet energy level and triplet energy level is used. Thermally activated delayed fluorescence is explained in "Yuki Hando-tai no Debaisu Bussei (Device Physics of Organic Semiconductors)" (edited by ADACHI, Chihaya, published by Kodansha, issued on Apr. 1, 2012, on pages 261-268).

As a compound exhibiting TADF properties (hereinafter also referred to as a TADF compound), for example, a compound in which a donor moiety and an acceptor moiety are bonded in a molecule is known.

Examples of Literatures relating to an organic EL device include Literature 1 (International Publication No. 2017/115833) and Literature 2 (Chinese Patent Application Publication No. 110492006).

Literature 1 discloses that a "first host material" and a "second host material" are used in an emitting layer using a TADF compound. In Examples of Literature 1, 3,3'-di(9H-carbazole-9-yl)-1,1-biphenyl (mCBP) and a compound having an azine ring (e.g., compound T2T) are used as two types of "host materials".

Literature 2 discloses, in Examples, a device in which a TADF compound (e.g., a compound DB-1), an indenocarbazole compound (e.g., a compound H6 or H7), and a compound having an azine ring (e.g., a compound H4) are used in an emitting layer.

In order to improve a performance of an electronic device such as a display, an organic EL device has been required to be highly improved in performance.

SUMMARY OF THE INVENTION

An object of the invention is to provide an organic electroluminescence device having higher performance, in particular, capable of improving a luminous efficiency and to provide an electronic device including the organic electroluminescence device.

An organic electroluminescence device according to an aspect of the invention includes: an anode; a cathode; and an emitting layer between the anode and the cathode, in which the emitting layer contains a first compound represented by the formula (1), a second compound represented by the formula (2), and a third compound that exhibits delayed fluorescence, a singlet energy $S_1(M1)$ of the first compound and a singlet energy $S_1(M3)$ of the third compound satisfy a relationship of a numerical formula (Numerical Formula 1), and a singlet energy $S_1(M2)$ of the second compound and the singlet energy $S_1(M3)$ of the third compound satisfy a relationship of a numerical formula (Numerical Formula 2).

(Numerical Formula 1)

$$S_1(M1) > S_1(M3)$$

(Numerical Formula 2)

$$2S_1(M2) > S_1(M3)$$

(1)

A—L—B (a1)

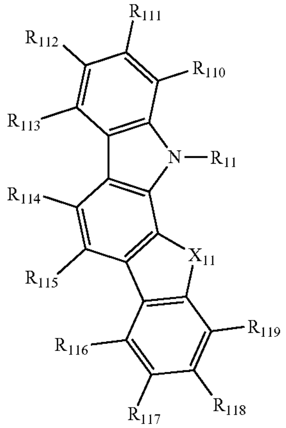

(a2)

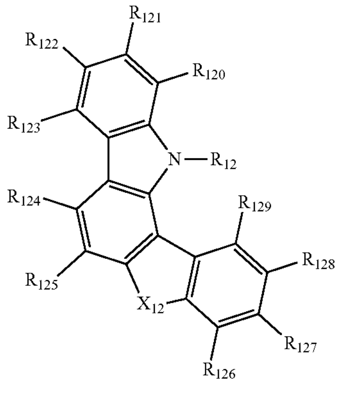

-continued (a3)

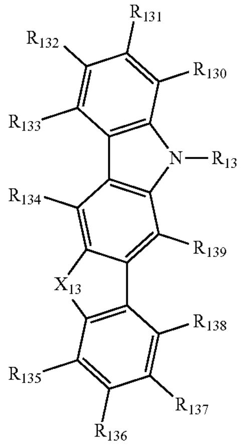

(a4)

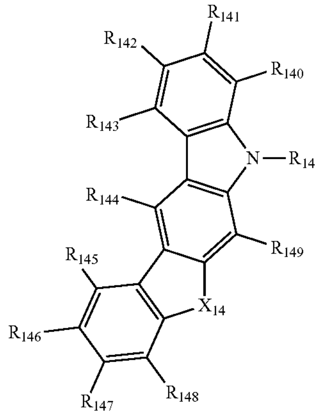

(a5)

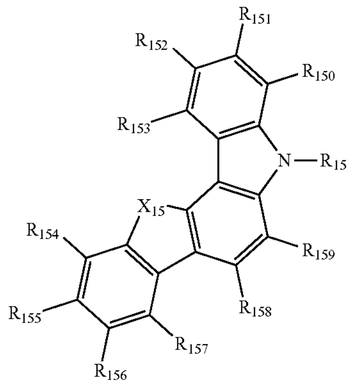

(a6)

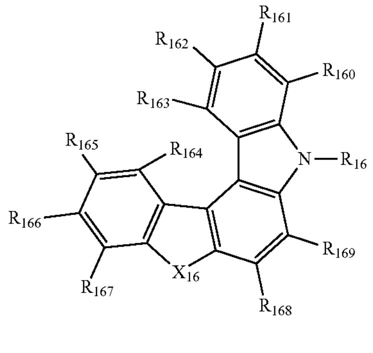

In the formula (1): A is a group represented by a formula (a1), (a2), (a3) (a4), (a5), or (a6);

L is a single bond, a substituted or unsubstituted arylene group having 6 to 25 ring carbon atoms, a substituted or unsubstituted divalent heterocyclic group having 5 to 22 ring atoms, a divalent group formed by bonding two groups selected from the group consisting of a substituted or unsubstituted arylene group having 6 to 25 ring carbon atoms and a substituted or unsubstituted divalent heterocyclic group having 5 to 22 ring atoms, or a divalent group formed by bonding three groups selected from the group consisting of a substituted or unsubstituted arylene group having 6 to 25 ring carbon atoms and a substituted or unsubstituted divalent heterocyclic group having 5 to 22 ring atoms; and B is a substituted or unsubstituted aryl group having 6 to 50 ring carbon atoms, or a substituted or unsubstituted heterocyclic group having 5 to 50 ring atoms.

It should be noted that the first compound represented by the formula (1) does not have a carbonyl group in a molecule.

In the formulae (a1) to (a6):

$R_{11}$, $R_{12}$, $R_{13}$, $R_{14}$, $R_{15}$, and $R_{16}$ are each independently a substituent or a single bond bonded to or L;

$X_{11}$, $X_{12}$, $X_{13}$, $X_{14}$, $X_{15}$, and $X_{16}$ are each independently an oxygen atom or a sulfur atom;

$R_{110}$ to $R_{119}$ are each independently a hydrogen atom, a substituent, or a single bond bonded to L, or at least one pair of a pair of $R_{110}$ and $R_{111}$, a pair of $R_{111}$ and $R_{112}$, a pair of $R_{112}$ and $R_{113}$, a pair of $R_{114}$ and $R_{115}$, a pair of $R_{116}$ and $R_{117}$, a pair of $R_{117}$ and $R_{118}$, or a pair of $R_{118}$ and $R_{119}$ are bonded to each other to form a ring;

one of $R_{110}$ to $R_{119}$ and $R_{11}$ is a single bond bonded to L;

$R_{120}$ to $R_{129}$ are each independently a hydrogen atom, a substituent, or a single bond bonded to L, or at least one pair of a pair of $R_{120}$ and $R_{121}$, a pair of $R_{121}$ and $R_{122}$, a pair of $R_{122}$ and $R_{123}$, a pair of $R_{124}$ and $R_{125}$, a pair of $R_{126}$ and $R_{127}$, a pair of $R_{127}$ and $R_{128}$, or a pair of $R_{128}$ and $R_{129}$ are bonded to each other to form a ring;

one of $R_{120}$ to $R_{129}$ and $R_{12}$ is a single bond bonded to L;

$R_{130}$ to $R_{139}$ are each independently a hydrogen atom, a substituent, or a single bond bonded to L, or at least one pair of a pair of $R_{130}$ and $R_{131}$, a pair of $R_{131}$ and $R_{132}$, a pair of $R_{132}$ and $R_{133}$, a pair of $R_{135}$ and $R_{136}$, a pair of $R_{136}$ and $R_{137}$, or a pair of $R_{137}$ and $R_{138}$ are bonded to each other to form a ring;

one of $R_{130}$ to $R_{139}$ and $R_{13}$ is a single bond bonded to L;

$R_{140}$ to $R_{149}$ are each independently a hydrogen atom, a substituent, or a single bond bonded to L, or at least one pair of a pair of $R_{140}$ and $R_{141}$, a pair of $R_{141}$ and $R_{142}$, a pair of $R_{142}$ and $R_{143}$, a pair of $R_{145}$ and $R_{146}$, a pair of $R_{146}$ and $R_{147}$, or a pair of $R_{147}$ and $R_{148}$ are bonded to each other to form a ring;

one of $R_{140}$ to $R_{149}$ and $R_{14}$ is a single bond bonded to L;

$R_{150}$ to $R_{159}$ are each independently a hydrogen atom, a substituent, or a single bond bonded to L, or at least one pair of a pair of $R_{150}$ and $R_{151}$, a pair of $R_{151}$ and $R_{152}$, a pair of $R_{152}$ and $R_{153}$, a pair of $R_{154}$ and $R_{155}$, a pair of $R_{155}$ and $R_{156}$, a pair of $R_{156}$ and $R_{157}$, or a pair of $R_{158}$ and $R_{159}$ are bonded to each other to form a ring;

one of $R_{150}$ to $R_{159}$ and $R_{15}$ is a single bond bonded to L;

$R_{160}$ to $R_{169}$ are each independently a hydrogen atom, a substituent, or a single bond bonded to L, or at least one pair of a pair of $R_{160}$ and $R_{161}$, a pair of $R_{161}$ and $R_{162}$, a pair of $R_{162}$ and $R_{163}$, a pair of $R_{164}$ and $R_{165}$, a pair of $R_{165}$ and $R_{166}$, a pair of $R_{166}$ and $R_{167}$, or a pair of $R_{168}$ and $R_{169}$ are bonded to each other to form a ring; and one of $R_{160}$ to $R_{169}$ and $R_{16}$ is a single bond bonded to L.

$R_{110}$ to $R_{169}$ and $R_{11}$ to $R_{16}$ as a substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxyl group a substituted or unsubstituted alkoxy group having 1 to 30 carbon atoms, a substituted or unsubstituted aryloxy group having 6 to 30 ring carbon atoms, a group represented by —$N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group a substituted boryl group, or a substituted or unsubstituted arylthio group having 6 to 30 ring carbon atoms;

Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

Two Rz in —$N(Rz)_2$ are mutually the same or different.

(2)

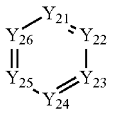

(2A)

$$*-L_{21}\left(L_{22}-R_B\right)_{n2}$$

In the formula (2):

$Y_{21}$ to $Y_{26}$ are each independently a nitrogen atom or $CR_A$, and at least one of $Y_{21}$ to $Y_{26}$ is a nitrogen atom;

$R_A$ is a hydrogen atom, a substituent or a group represented by the formula (2A), or at least one pair of adjacent ones of $R_A$ are bonded to each other to form a ring;

$R_B$ is a substituent;

when a plurality of $R_B$ are present, the plurality of $R_B$ are the same or different;

* represents a bonding position to a carbon atom in a six-membered ring in the formula (2);

$L_{21}$ is a single bond, a substituted or unsubstituted arylene group having 6 to 25 ring carbon atoms, a trivalent, tetravalent, pentavalent, or hexavalent group derived from the arylene group, a substituted or unsubstituted divalent heterocyclic group having 5 to 22 ring atoms, a trivalent, tetravalent, pentavalent, or hexavalent group derived from the heterocyclic group, or a divalent group formed by bonding two groups selected from the group consisting of a substituted or unsubstituted arylene group having 6 to 25 ring carbon atoms and a substituted or unsubstituted divalent heterocyclic group having 5 to 22 ring atoms, or a trivalent, tetravalent, pentavalent or hexavalent group derived from the divalent group;

$L_{22}$ is a single bond, a substituted or unsubstituted arylene group having 6 to 22 ring carbon atoms, or a substituted or unsubstituted divalent heterocyclic group having 5 to 22 ring atoms;

n2 is 1, 2, 3, 4, or 5;

when $L_{21}$ is a single bond, n2 is 1, and $L_{22}$ is bonded to a carbon atom in the six-membered ring in the formula (2);

when a plurality of $L_{22}$ are present, the plurality of $L_{22}$ are the same or different;

$R_A$ and $R_B$ as a substituent are each independently a halogen atom, a cyano group, a substituted or unsubstituted aryl group having 6 to 50 ring carbon atoms, a substituted or unsubstituted heterocyclic group having 5 to 50 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxyl group a substituted or unsubstituted alkoxy group having 1 to 30 carbon atoms, a substituted or unsubstituted aryloxy group having 6 to 30 ring carbon atoms, a group represented by —$N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group a substituted boryl group, or a substituted or unsubstituted arylthio group having 6 to 30 ring carbon atoms; and Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

Two Rz in —$N(Rz)_2$ are mutually the same or different.

A substituent for a "substituted or unsubstituted" group as $R_{110}$ to $R_{169}$, $R_{11}$ to $R_{16}$, L and B in the formula (1) and a substituent for a "substituted or unsubstituted" group as $L_{21}$, $L_{22}$, $R_A$ and $R_B$ in the formula (2) are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxyl group a substituted or unsubstituted alkoxy group having 1 to 30 carbon atoms, a substituted or unsubstituted aryloxy group having 6 to 30 ring carbon atoms, a group represented by —$N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group a substituted boryl group, or a substituted or unsubstituted arylthio group having 6 to 30 ring carbon atoms; and Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

Two Rz in —$N(Rz)_2$ are mutually the same or different.

Another aspect of the invention provides an electronic device including the organic electroluminescence device according to any one of the above aspects of the invention.

According to the aspects of the invention, it is possible to provide the organic electroluminescence device having higher performance, in particular, capable of improving luminous efficiency and the electronic device including the organic electroluminescence device.

BRIEF DESCRIPTION OF DRAWING(S)

FIG. 1 schematically shows an exemplary arrangement of an organic electroluminescence device according to a first exemplary embodiment of the invention.

FIG. 2 schematically shows a device that measures transient PL.

Figure 5:
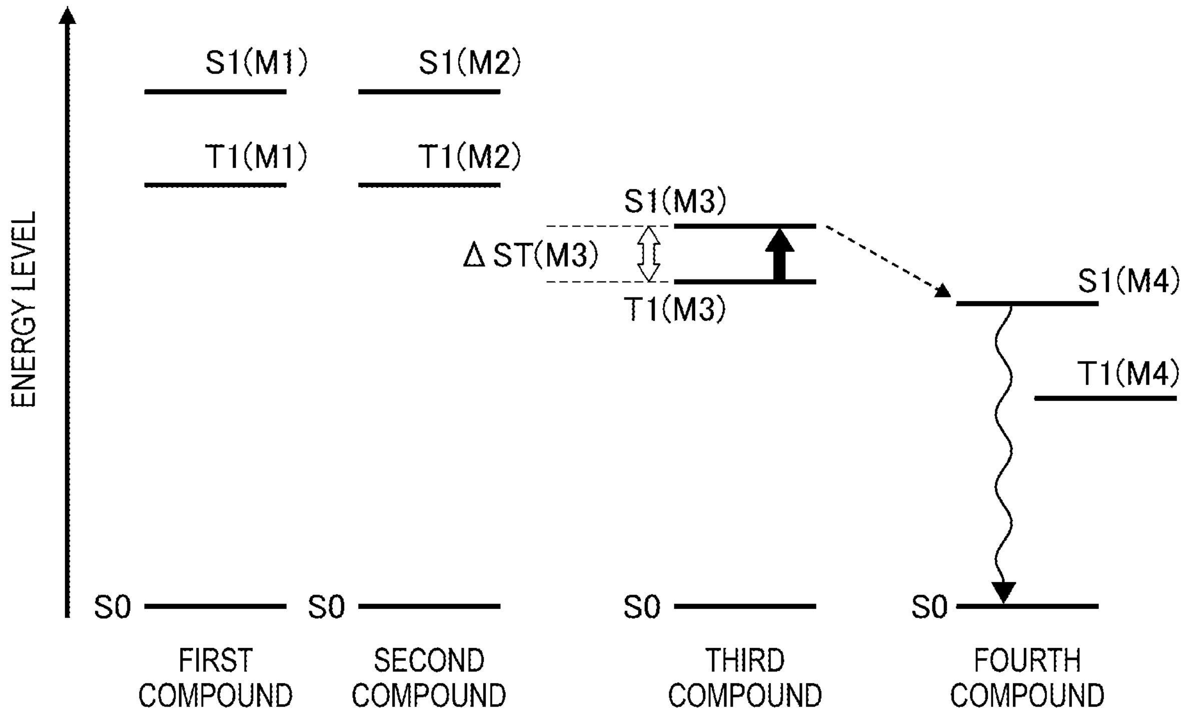

FIG. 5 schematically shows a relationship in energy level and energy transfer between a first compound, a second compound, a third compound, and a fourth compound in an emitting layer of an exemplary organic electroluminescence device according to the first exemplary embodiment of the invention.

DESCRIPTION OF EMBODIMENT(S)

First Exemplary Embodiment

An arrangement of an organic EL device according to a first exemplary embodiment of the invention will be described below.

The organic EL device includes an anode, a cathode, and an organic layer between the anode and the cathode. This organic layer includes at least one layer formed of an organic compound. Alternatively, the organic layer includes a plurality of layers formed of an organic compound(s). The organic layer may further include an inorganic compound. In the organic EL device of the exemplary embodiment, at least one of the organic layer(s) is an emitting layer. Accordingly, the organic layer may consist of a single emitting layer or, alternatively, may further include at least one layer usable in organic EL devices. Examples of the layer usable in the organic EL device, which are not particularly limited, include at least one layer selected from the group consisting of a hole injecting layer, hole transporting layer, electron blocking layer, electron injecting layer, electron transporting layer, and hole blocking layer.

The organic EL device of the exemplary embodiment includes an emitting layer between the anode and the cathode.

Figure 1:
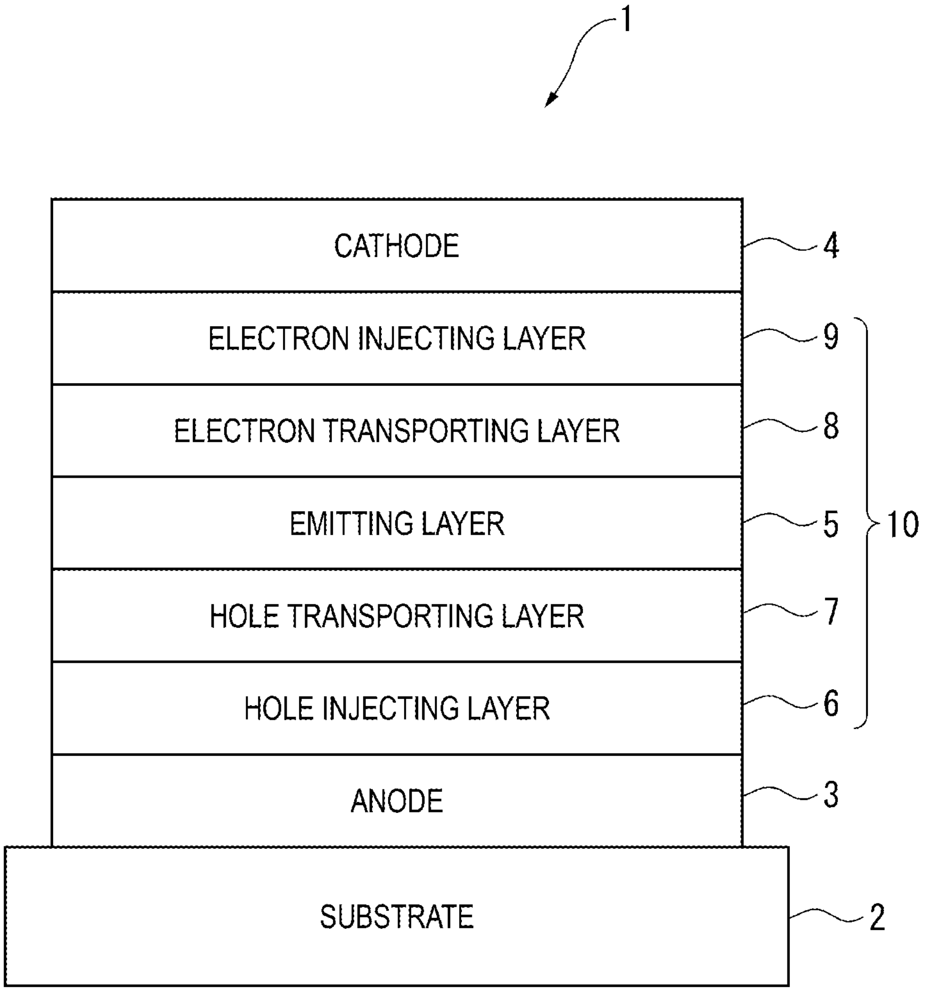

FIG. 1 schematically shows an example of an organic EL device according to the first exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5, an electron transporting layer 8, and an electron injecting layer 9, which are sequentially layered on the anode 3.

In an exemplary arrangement of the first exemplary embodiment, the emitting layer may contain a metal complex.

In an exemplary arrangement of the first exemplary embodiment, it is preferable that the emitting layer does not contain a phosphorescent material (dopant material).

In an exemplary arrangement of the first exemplary embodiment, it is preferable that the emitting layer does not contain a heavy-metal complex and a phosphorescent rare-earth metal complex. Examples of the heavy-metal complex herein include iridium complex, osmium complex, and platinum complex.

In an exemplary arrangement of the first exemplary embodiment, it is also preferable that the emitting layer does not contain a metal complex.

In the organic EL device of the exemplary embodiment, the emitting layer contains a first compound represented by the formula (1), a second compound represented by the formula (2), and a third compound that emits delayed fluorescence.

The first compound and the second compound are mutually different in structure.

The first compound and the second compound each are preferably a host material.

In the exemplary embodiment, it is preferable that the delayed fluorescent third compound is also a host material.

Herein, in order to distinguish between the first, second, and third compounds, the first compound and the second compound in a form of the host material are occasionally referred to as "matrix" for convenience of explanation.

A case where the first compound and the second compound are mixed is occasionally referred to as a "co-matrix".

The third compound in a form of the host material may be simply referred to as a "host material".

A host material having hole injectability may be referred to as a "p-host", and a host material having electron injectability may be referred to as an n-host".

In the following description, the first compound, the second compound, and the third compound in a form of the host material when are not particularly distinguished from each other are collectively referred to as a "host material".

In the exemplary embodiment, the first compound is preferably a matrix with relatively high hole injectability (i.e., p-host). The second compound is preferably a matrix with relatively high electron injectability (i.e., n-host).

The inventors have found that an organic EL device can be highly improved in performance, in particular, in luminous efficiency by using the first compound represented by the formula (1) and the second compound represented by the formula (2) as a "comatrix" together with the third compound that exhibits delayed fluorescence.

Literature 1 describes that a case where a hole-injectable carbazole compound (mCBP: p-host) and an electron-injectable triazine compound (compound T2T: n-host) are contained as the "comatrix" together with the delayed fluorescent compound in the emitting layer more improves the luminous efficiency of the device than a case where only one type of the carbazole compound (mCBP) is contained as the host material in the emitting layer.

As a result of dedicated studies, the inventors have found that the luminous efficiency is further improved by using a higher hole-injectable benzofurocarbazole compound or benzothienocarbazole compound as the p-host.

In general, in a delayed fluorescent compound, a moiety having a large absolute value of an energy level of LUMO (lowest unoccupied molecular orbital) is often introduced into a molecule in order to reduce ΔST, and in conjunction with this introduction, an absolute value of an energy level of HOMO (highest occupied molecular orbital) of the entire molecule is often increased. However, when the absolute value of the HOMO energy level is increased, hole injection from the adjacent hole transporting layer into the emitting layer may be hindered, making it impossible to supply an appropriate amount of holes to the emitting layer.

In the exemplary embodiment, since the benzofurocarbazole compound or benzothienocarbazole compound (the first compound represented by formula (1)), hole injectability of which is more appropriately improved than the carbazole compound, is contained together with the delayed fluorescent compound (the third compound) into the emitting layer, hindrance of hole injection from the hole transporting layer to the emitting layer, which is to be caused by the increase in the absolute value of the HOMO energy level, can be inhibited to supply an appropriate amount of holes into the emitting layer. It is considered that higher efficiency of the device can be achieved as a result. Moreover, in a "comatrix" device containing both the p-host and the n-host in the emitting layer, due to a large supply amount of electrons that are paired charges, a degree of a higher efficiency of the device obtained when the supply amount of holes from the hole transporting layer to the emitting layer is increased is considered more remarkable.

Literature 1 discloses a device containing mCBP and a compound T2T (a compound having a triazine ring) as the "comatrix" together with the delayed fluorescent compound in the emitting layer. This device, which corresponds to an organic EL device in Comparative 1 described below, exhibited a lower luminous efficiency than those in all Examples.

Literature 2 discloses a device containing a compound H6 or H7 (an indenocarbazole compound) and a compound H4 (a compound having a triazine ring) as the "comatrix" together with the delayed fluorescent compound in the emitting layer. This device, which corresponds to organic EL devices in Comparatives 2 and 3 described below, exhibited a lower luminous efficiency than those in all Examples. This is presumed to be because the indenocarbazole compound as disclosed in Literature 2, due to an excessively high donor performance, forms an aggregate with a delayed fluorescent compound having a high acceptor performance (a compound having a large absolute value of an energy level of LUMO (lowest unoccupied molecular orbital)). It may be also presumed that this is because the indenocarbazole compound as disclosed in Literature 2 causes an excessively large amount of holes in the emitting layer due to an excessively high hole injectability.

Literature 2 also discloses a "compound having both benzofurocarbazole and a carbonyl group" such as a compound H8. A device in which an emitting layer contains the compound H8, a compound having a triazine ring (i.e., comatrix), and a delayed fluorescent compound, which corresponds to an organic EL device in Comparative 4 described below, exhibited a lower luminous efficiency than those in all Examples. This is presumed to be because a pair of electrons in an n-orbital of the carbonyl group form an aggregate with other materials.

The organic EL device according to the exemplary embodiment can be improved in luminous efficiency as compared with conventional organic EL devices.

Further, according to the exemplary embodiment, a high-performance organic EL device is achievable.

High performance means an improvement in at least one of luminous efficiency, device lifetime, drive voltage, and luminance.

According to the exemplary embodiment, it can be expected to improve, in addition to the luminous efficiency, at least one of the device lifetime, drive voltage, and luminance.

Explanation is made below about an aspect of the first exemplary embodiment where the emitting layer contains the first compound, the second compound, and the third compound, and further contains a fluorescent fourth compound.

Emitting Layer

First Compound

The emitting layer of the exemplary embodiment contains a first compound represented by a formula (1) below.

The first compound of the exemplary embodiment may be a thermally activated delayed fluorescent compound or a compound exhibiting no thermally activated delayed fluorescence.

The first compound of the exemplary embodiment is preferably a compound exhibiting no thermally activated delayed fluorescence.

A—L—B (1)

(a1)

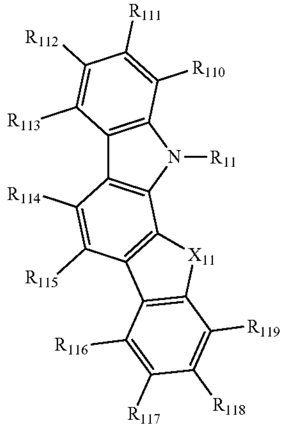

(a2)

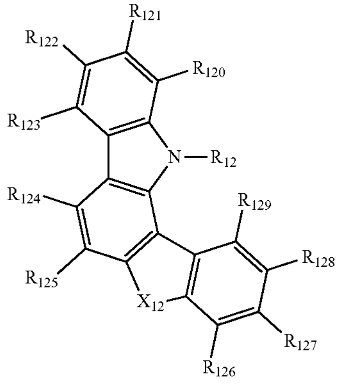

-continued (a3)

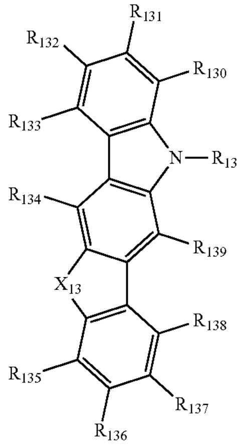

(a4)

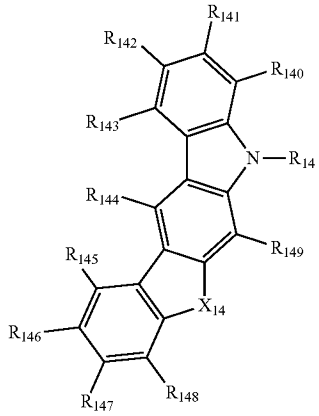

(a5)

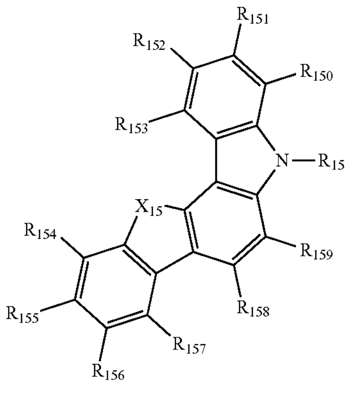

(a6)

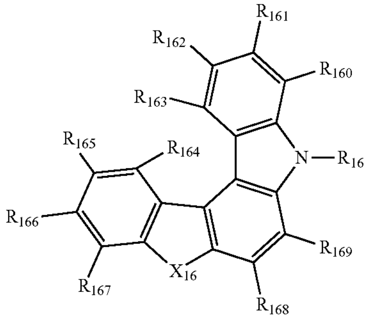

In the formula (1): A is a group represented by a formula (a1), (a2), (a3) (a4), (a5), or (a6);

L is a single bond, a substituted or unsubstituted arylene group having 6 to 25 ring carbon atoms, a substituted or unsubstituted divalent heterocyclic group having 5 to 22 ring atoms, a divalent group formed by bonding two groups selected from the group consisting of a substituted or unsubstituted arylene group having 6 to 25 ring carbon atoms and a substituted or unsubstituted divalent heterocyclic group having 5 to 22 ring atoms, or a divalent group formed by bonding three groups selected from the group consisting of a substituted or unsubstituted arylene group having 6 to 25 ring carbon atoms and a substituted or unsubstituted divalent heterocyclic group having 5 to 22 ring atoms; and B is a substituted or unsubstituted aryl group having 6 to 50 ring carbon atoms, or a substituted or unsubstituted heterocyclic group having 5 to 50 ring atoms.

It should be noted that the first compound represented by the formula (1) does not have a carbonyl group in a molecule.

In the formulae (a1) to (a6):

$R_{11}$, $R_{12}$, $R_{13}$, $R_{14}$, $R_{15}$, and $R_{16}$ are each independently a substituent or a single bond bonded to L;

$X_{11}$, $X_{12}$, $X_{13}$, $X_{14}$, $X_{15}$, and $X_{16}$ are each independently an oxygen atom or a sulfur atom;

$R_{110}$ to $R_{119}$ are each independently a hydrogen atom, a substituent, or a single bond bonded to L, or at least one pair of a pair of $R_{110}$ and $R_{111}$, a pair of $R_{111}$ and $R_{112}$, a pair of $R_{112}$ and $R_{113}$, a pair of $R_{114}$ and $R_{115}$, a pair of $R_{116}$ and $R_{117}$, a pair of $R_{117}$ and $R_{118}$, or a pair of $R_{118}$ and $R_{119}$ are bonded to each other to form a ring;

one of $R_{110}$ to $R_{119}$ and $R_{11}$ is a single bond bonded to L;

$R_{120}$ to $R_{129}$ are each independently a hydrogen atom, a substituent, or a single bond bonded to L, or at least one pair of a pair of $R_{120}$ and $R_{121}$, a pair of $R_{121}$ and $R_{122}$, a pair of $R_{122}$ and $R_{123}$, a pair of $R_{124}$ and $R_{125}$, a pair of $R_{126}$ and $R_{127}$, a pair of $R_{127}$ and $R_{128}$, or a pair of $R_{128}$ and $R_{129}$ are bonded to each other to form a ring;

one of $R_{120}$ to $R_{129}$ and $R_{12}$ is a single bond bonded to L;

$R_{130}$ to $R_{139}$ are each independently a hydrogen atom, a substituent, or a single bond bonded to L, or at least one pair of a pair of $R_{130}$ and $R_{131}$, a pair of $R_{131}$ and $R_{132}$, a pair of $R_{132}$ and $R_{133}$, a pair of $R_{135}$ and $R_{136}$, a pair of $R_{136}$ and $R_{137}$, or a pair of $R_{137}$ and $R_{138}$ are bonded to each other to form a ring;

one of $R_{130}$ to $R_{139}$ and $R_{13}$ is a single bond bonded to L;

$R_{140}$ to $R_{149}$ are each independently a hydrogen atom, a substituent, or a single bond bonded to L, or at least one pair of a pair of $R_{140}$ and $R_{141}$, a pair of $R_{141}$ and $R_{142}$, a pair of $R_{142}$ and $R_{143}$, a pair of $R_{145}$ and $R_{146}$, a pair of $R_{146}$ and $R_{147}$, or a pair of $R_{147}$ and $R_{148}$ are bonded to each other to form a ring;

one of $R_{140}$ to $R_{149}$ and $R_{14}$ is a single bond bonded to L;

$R_{150}$ to $R_{159}$ are each independently a hydrogen atom, a substituent, or a single bond bonded to L, or at least one pair of a pair of $R_{150}$ and $R_{151}$, a pair of $R_{151}$ and $R_{152}$, a pair of $R_{152}$ and $R_{153}$, a pair of $R_{154}$ and $R_{155}$, a pair of $R_{155}$ and $R_{156}$, a pair of $R_{156}$ and $R_{157}$, or a pair of $R_{158}$ and $R_{159}$ are bonded to each other to form a ring;

one of $R_{150}$ to $R_{159}$ and $R_{15}$ is a single bond bonded to L, $R_{160}$ to $R_{169}$ are each independently a hydrogen atom, a substituent, or a single bond bonded to L, or at least one pair of a pair of $R_{160}$ and $R_{161}$, a pair of $R_{161}$ and $R_{162}$, a pair of $R_{162}$ and $R_{163}$, a pair of $R_{164}$ and $R_{165}$, a pair of $R_{165}$ and $R_{166}$, a pair of $R_{166}$ and $R_{167}$, or a pair of $R_{168}$ and $R_{169}$ are bonded to each other to form a ring; and one of $R_{160}$ to $R_{169}$ and $R_{16}$ is a single bond bonded to L.

$R_{110}$ to $R_{169}$ and $R_{11}$ to $R_{16}$ as a substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxyl group a substituted or unsubstituted alkoxy group having 1 to 30 carbon atoms, a substituted or unsubstituted aryloxy group having 6 to 30 ring carbon atoms, a group represented by —$N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group a substituted boryl group, or a substituted or unsubstituted arylthio group having 6 to 30 ring carbon atoms; and Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

Two Rz in —$N(Rz)_2$ are mutually the same or different.

A substituent for a "substituted or unsubstituted" group as $R_{110}$ to $R_{169}$, $R_{11}$ to $R_{16}$, L and B in the formula (1) is each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxyl group a substituted or unsubstituted alkoxy group having 1 to 30 carbon atoms, a substituted or unsubstituted aryloxy group having 6 to 30 ring carbon atoms, a group represented by —$N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group a substituted boryl group, or a substituted or unsubstituted arylthio group having 6 to 30 ring carbon atoms; and Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

Two Rz in —$N(Rz)_2$ are mutually the same or different.

The wording "L is a single bond" in the formula (1) means that A is directly bonded to B. For example, the above wording means that when A is a group represented by the formula (a1), B is directly bonded to one of $R_{110}$ to $R_{119}$ and $R_{11}$. The same applies to a case where A is a group represented by one of the formulae (a2) to (a6).

Substituents of First Compound Represented by Formula (1)

$R_{110}$ to $R_{169}$ and $R_{11}$ to R16 in Formulae (a1) to (a6)

It is preferable that $R_{110}$ to $R_{169}$ and $R_{11}$ to $R_{16}$ as a substituent are each independently selected from the group consisting of a substituent group A below.

When each of $R_{110}$ to $R_{169}$ and $R_{11}$ to $R_{16}$ as a substituent has a further substituent, the further substituent (i.e., a substituent for "a substituted or unsubstituted group as $R_{110}$ to $R_{169}$ and $R_{11}$ to $R_{16}$) is each independently preferably selected from the group consisting of the substituent group A, more preferably selected from the group consisting of a substituent group B below.

Substituents of the substituent group A and the substituent group B are groups having a relatively strong electron-donating property.

Substituent Group A

- a substituted or unsubstituted aryl group having 6 to 30 ring carbon atoms
- a substituted or unsubstituted heterocyclic group having 5 to 30 ring atoms except for one having a partial structure of benzene in which at least one carbon is substituted by nitrogen
- a substituted or unsubstituted alkyl group having 1 to 30 carbon atoms
- a substituted or unsubstituted alkyl halide group having 1 to 30 carbon atoms
- a substituted or unsubstituted alkenyl group having 2 to 30 carbon atoms
- a substituted or unsubstituted alkynyl group having 2 to 30 carbon atoms
- a substituted or unsubstituted alkylsilyl group having 3 to 30 carbon atoms
- a substituted or unsubstituted arylsilyl group having 6 to 60 ring carbon atoms
- a substituted or unsubstituted arylphosphoryl group having 6 to 60 ring carbon atoms
- a hydroxyl group
- a substituted or unsubstituted alkoxy group having 1 to 30 carbon atoms
- a substituted or unsubstituted aryloxy group having 6 to 30 ring carbon atoms a group represented by —$N(Rz)_2$ Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms. Two Rz in —$N(Rz)_2$ are mutually the same or different.

- a thiol group
- a substituted or unsubstituted alkylthio group having 1 to 30 carbon atoms
- a substituted or unsubstituted aralkyl group having 7 to 30 ring carbon atoms
- a substituted germanium group
- a substituted or unsubstituted arylthio group having 6 to 30 ring carbon atoms Substituent Group B

- an unsubstituted aryl group having 6 to 30 ring carbon atoms
- an unsubstituted heterocyclic group having 5 to 30 ring atoms except for one having a partial structure of benzene in which at least one carbon is substituted by nitrogen
- an unsubstituted alkyl group having 1 to 30 carbon atoms
- an unsubstituted alkyl halide group having 1 to 30 carbon atoms
- an unsubstituted alkenyl group having 2 to 30 carbon atoms an unsubstituted alkynyl group having 2 to 30 carbon atoms an unsubstituted alkylsilyl group having 3 to 30 carbon atoms an unsubstituted arylsilyl group having 6 to 60 ring carbon atoms an unsubstituted arylphosphoryl group having 6 to 60 ring carbon atoms a hydroxyl group an unsubstituted alkoxy group having 1 to 30 carbon atoms an unsubstituted aryloxy group having 6 to 30 ring carbon atoms a group represented by —N(Rz) 2

Rz is an unsubstituted aryl group having 6 to 30 ring carbon atoms, an unsubstituted heterocyclic group having 5 to 30 ring atoms, or an unsubstituted alkyl group having 1 to 30 carbon atoms. Two Rz in $—N(Rz)_2$ are mutually the same or different.

a thiol group an unsubstituted alkylthio group having 1 to 30 carbon atoms an unsubstituted aralkyl group having 7 to 30 ring carbon atoms a substituted germanium group an unsubstituted arylthio group having 6 to 30 ring carbon atoms B in Formula (1)

It is preferable that B is each independently selected from the group consisting of a substituent group C below.

When B has a further substituent, the further substituent (i.e., a substituent for "a substituted or unsubstituted group as B) is each independently preferably selected from the group consisting of the substituent group A, more preferably selected from the group consisting of the substituent group B.

Substituents of the substituent group C are groups having a relatively strong electron-donating property.

Substituent Group C a substituted or unsubstituted aryl group having 6 to 50 ring carbon atoms a substituted or unsubstituted heterocyclic group having 5 to 50 ring atoms except for one having a partial structure of benzene in which at least one carbon is substituted by nitrogen L in Formula (1)

When L is a linking group, L is preferably each independently selected from the group consisting of a substituent group E below.

When L has a further substituent, the further substituent (i.e., a substituent for "a substituted or unsubstituted group as L) is each independently preferably selected from the group consisting of the substituent group A, more preferably selected from the group consisting of the substituent group B.

Substituents of the substituent group E are groups having a relatively strong electron-donating property.

Substituent Group E a substituted or unsubstituted arylene group having 6 to 25 ring carbon atoms a substituted or unsubstituted divalent heterocyclic group having 5 to 22 ring atoms except for one having a partial structure of benzene in which at least one carbon is substituted by nitrogen a divalent group formed by bonding two groups selected from the group consisting of a substituted or unsubstituted arylene group having 6 to 25 ring carbon atoms and a divalent heterocyclic group except for one having a partial structure of benzene in which at least one carbon is substituted by nitrogen a divalent group formed by bonding three groups selected from the group consisting of a substituted or unsubstituted arylene group having 6 to 25 ring carbon atoms and a divalent heterocyclic group except for one having a partial structure of benzene in which at least one carbon is substituted by nitrogen In the first compound of the exemplary embodiment, A is preferably a group represented by the formula (a1), (a2), (a3), (a4), or (a6).

In the first compound of the exemplary embodiment, A is more preferably a group represented by the formula (a1), (a2), (a3), or (a4).

In the first compound of the exemplary embodiment, A is further preferably a group represented by the formula (a1) or (a4).

In the first compound of the exemplary embodiment, A is still further preferably a group represented by the formula (a1).

In the first compound of the exemplary embodiment, $X_{11}$, $X_{12}$, $X_{13}$, $X_{14}$, $X_{15}$ and $X_{16}$ are preferably oxygen atoms.

The first compound of the exemplary embodiment is preferably a compound represented by a formula (11), (12), (13), (14), (15), or (16) below.

(11)

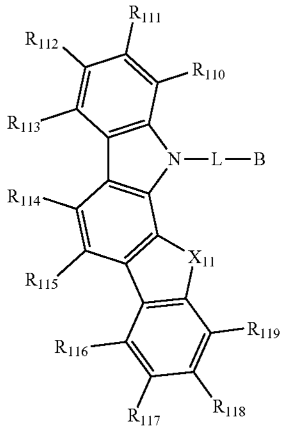

(12)

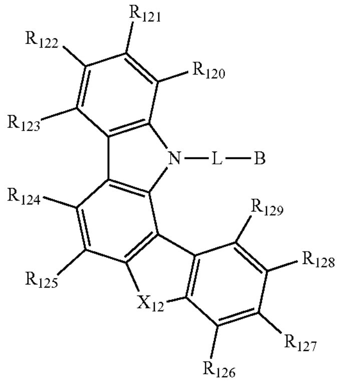

-continued

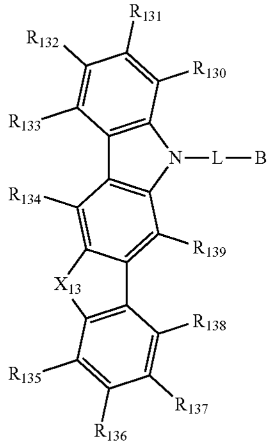

(13)

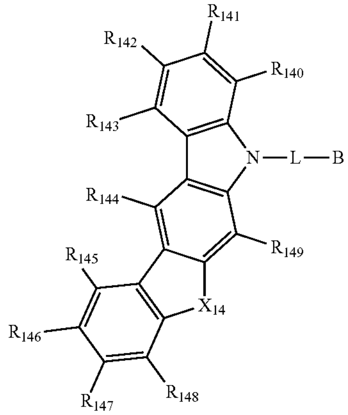

(14)

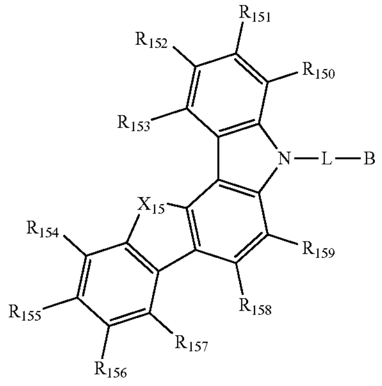

(15)

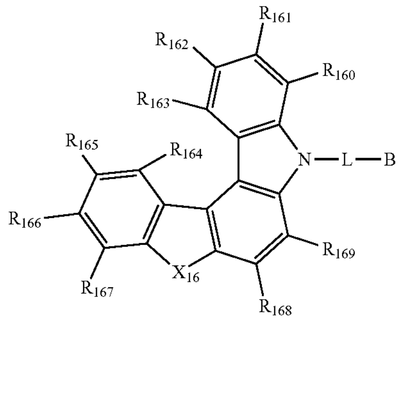

(16)

In the formula (11), L, B, $R_{110}$ to $R_{119}$ and $X_{11}$ each independently represent the same as L, B, $R_{110}$ to $R_{119}$ and $X_{11}$ in the formula (a1).

In the formula (12), L, B, $R_{120}$ to $R_{129}$ and $X_{12}$ each independently represent the same as L, B, $R_{120}$ to $R_{129}$ and $X_{12}$ in the formula (a2).

In the formula (13), L, B, $R_{130}$ to $R_{139}$ and $X_{13}$ each independently represent the same as L, B, $R_{130}$ to $R_{139}$ and $X_{13}$ in the formula (a3).

In the formula (14), L, B, $R_{140}$ to $R_{149}$ and $X_{14}$ each independently represent the same as L, B, $R_{140}$ to $R_{149}$ and $X_{14}$ in the formula (a4).

In the formula (15), L, B, $R_{150}$ to $R_{159}$ and $X_{15}$ each independently represent the same as L, B, $R_{150}$ to $R_{159}$ and $X_{15}$ in the formula (a5).

In the formula (16), L, B, $R_{160}$ to $R_{169}$ and $X_{16}$ each independently represent the same as L, B, $R_{160}$ to $R_{169}$ and $X_{16}$ in the formula (a6).

In the first compound of the exemplary embodiment, it is preferable that $R_{110}$ to $R_{169}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

$R_{11}$ to $R_{16}$ are each independently preferably a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

In the first compound of the exemplary embodiment, it is preferable that $R_{110}$ to $R_{169}$ are each independently a hydrogen atom, a substituted or unsubstituted aryl group having 6 to 30 ring carbon atoms, a substituted or unsubstituted heterocyclic group having 5 to 30 ring atoms except for one having a partial structure of benzene in which at least one carbon is substituted by nitrogen, or a substituted or unsubstituted alkyl group having 1 to 30 carbon atoms.

$R_{11}$ to $R_{16}$ are each independently preferably a substituted or unsubstituted aryl group having 6 to 30 ring carbon atoms, a substituted or unsubstituted heterocyclic group having 5 to 30 ring atoms except for one having a partial structure of benzene in which at least one carbon is substituted by nitrogen, or a substituted or unsubstituted alkyl group having 1 to 30 carbon atoms.

In the first compound of the exemplary embodiment, it is more preferable that $R_{110}$ to $R_{169}$ are each independently a hydrogen atom or a substituted or unsubstituted aryl group having 6 to 30 ring carbon atoms, and $R_{11}$ to $R_{16}$ are each independently a substituted or unsubstituted aryl group having 6 to 30 ring carbon atoms.

In the first compound of the exemplary embodiment, it is further preferable that $R_{110}$ to $R_{169}$ are hydrogen atoms, and $R_{11}$ to $R_{16}$ are each independently a substituted or unsubstituted aryl group having 6 to 30 ring carbon atoms.

In the first compound of the exemplary embodiment, it is preferable that L is a single bond, a substituted or unsubstituted arylene group having 6 to 25 ring carbon atoms, or a substituted or unsubstituted divalent heterocyclic group having 5 to 22 ring atoms.

In the first compound of the exemplary embodiment, it is preferable that L is a single bond, a substituted or unsubstituted arylene group having 6 to 25 ring carbon atoms, or a substituted or unsubstituted divalent heterocyclic group having 5 to 22 ring atoms except for one having a partial structure of benzene in which at least one carbon is substituted by nitrogen.

In the first compound of the exemplary embodiment, it is more preferable that L is a single bond or a substituted or unsubstituted arylene group having 6 to 25 ring carbon atoms.

In the first compound of the exemplary embodiment, it is further preferable that L is a substituted or unsubstituted para-biphenylene group or a substituted or unsubstituted para-terphenylene group.

In the first compound of the exemplary embodiment, it is preferable that B is a substituted or unsubstituted aryl group having 6 to 19 ring carbon atoms or a substituted or unsubstituted heterocyclic group having 5 to 19 ring atoms.

In the first compound of the exemplary embodiment, it is preferable that B is a substituted or unsubstituted aryl group having 6 to 19 ring carbon atoms, or a substituted or unsubstituted heterocyclic group having 5 to 50 ring atoms except for one having a partial structure of benzene in which at least one carbon is substituted by nitrogen.

In the first compound of the exemplary embodiment, B is more preferably any one of groups represented by formulae (b1) to (b17).

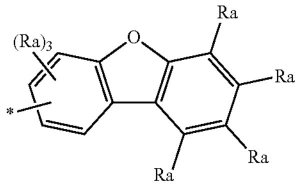

(b1)

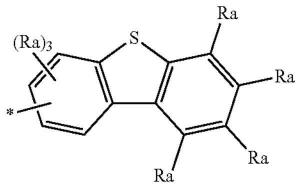

(b2)

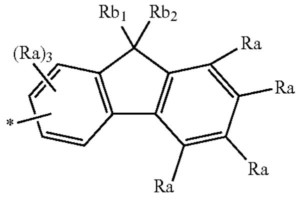

(b3)

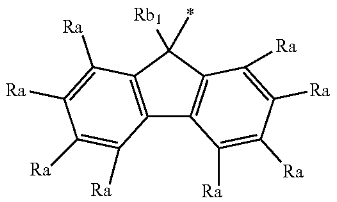

(b4)

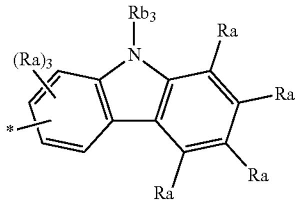

(b5)

-continued

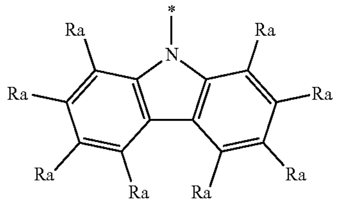

(b6)

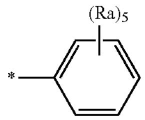

(b7)

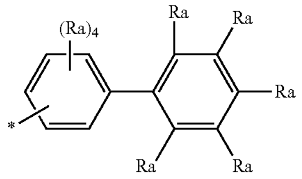

(b8)

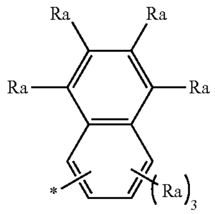

(b9)

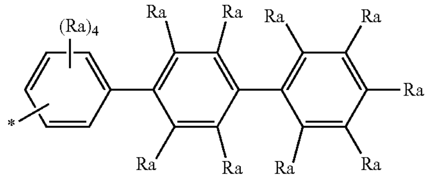

(b10)

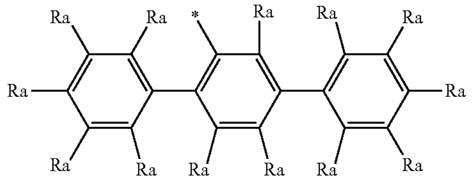

(b11)

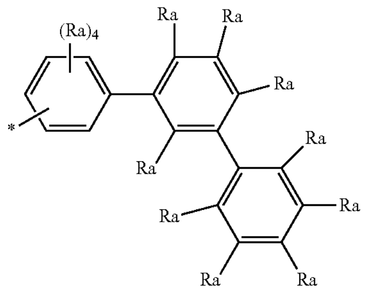

(b12)

-continued (b13)

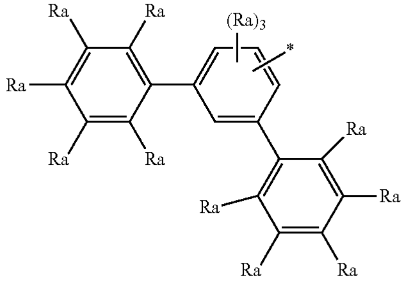

(b14)

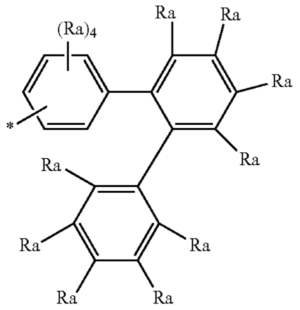

(b15)

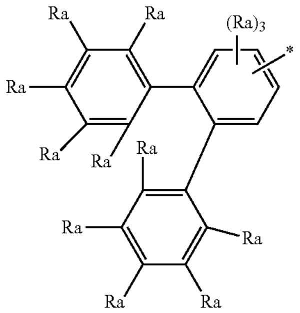

(b16)

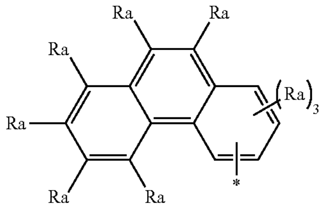

(b17)

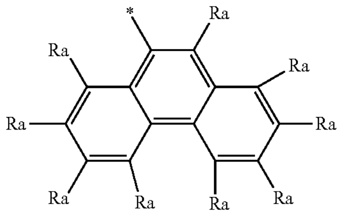

In the formulae (b1) to (b17), Ra is a hydrogen atom or a substituent, or at least one pair of adjacent ones of Ra are bonded to each other to form a ring, a plurality of Ra being mutually the same or different;

$Rb_1$ and $Rb_2$ are each independently a hydrogen atom or a substituent, or a pair of $Rb_1$ and $Rb_2$ are bonded to each other to form a ring;

$Rb_3$ is a hydrogen atom or a substituent; and when Ra, $Rb_1$, $Rb_2$, and $Rb_3$ are each a substituent, the substituent represents the same as the substituent for a "substituted or unsubstituted" group as B in the formula (1).

In the formulae (b1) to (b17), Ra is preferably a hydrogen atom, a substituted or unsubstituted aryl group having 6 to 30 ring carbon atoms, or a substituted or unsubstituted alkyl group having 1 to 30 carbon atoms, more preferably a hydrogen atom.

In the formulae (b3) to (b4), it is preferable that $Rb_1$ and $Rb_2$ are each independently a substituted or unsubstituted aryl group having 6 to 30 ring carbon atoms or a substituted or unsubstituted alkyl group having 1 to 30 carbon atoms, or a pair of $Rb_1$ and $Rb_2$ are bonded to each other to form a ring.

In the formula (b5), it is preferable that $Rb_3$ is a substituted or unsubstituted aryl group having 6 to 30 ring carbon atoms, a substituted or unsubstituted alkyl group having 1 to 30 carbon atoms, or a substituted or unsubstituted heterocyclic group having 5 to 30 ring atoms.

In the first compound of the exemplary embodiment, B is preferably any one of groups represented by the formulae (b1) to (b6).

In the first compound of the exemplary embodiment, when B is a group represented by one of the formulae (b1) to (b17), at least one pair of adjacent ones of Ra are preferably not bonded to each other.

Manufacturing Method of First Compound

The first compound of the exemplary embodiment can be manufactured, for instance, by a method described later in Examples. The first compound of the exemplary embodiment can be manufactured, for instance, by application of known substitution reactions and/or materials depending on a target compound according to reactions described later in Examples.

Specific Examples of First Compound

Specific examples of the first compound of the exemplary embodiment include, for example, the following compounds. However, the invention is not limited to the specific examples of the compounds.

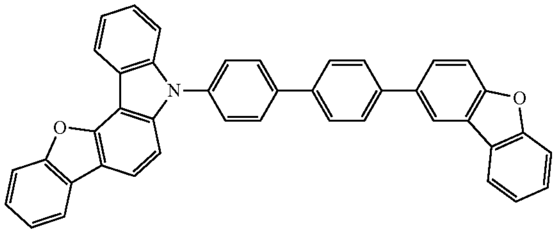

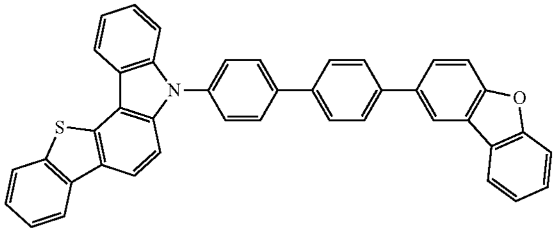

-continued
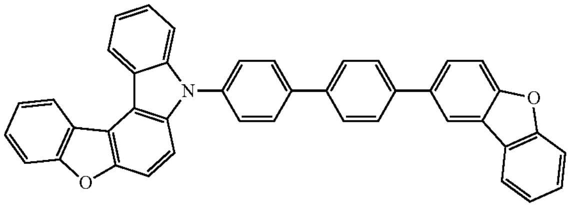
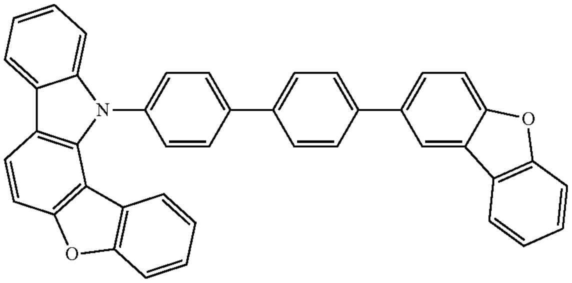
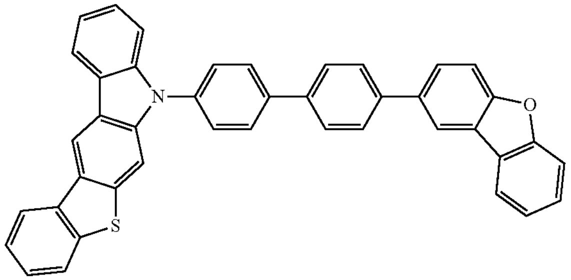
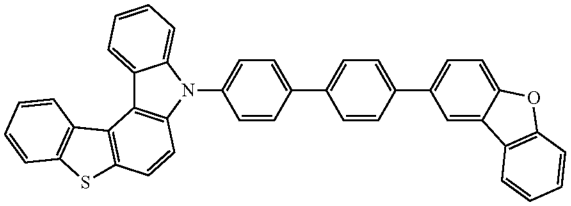
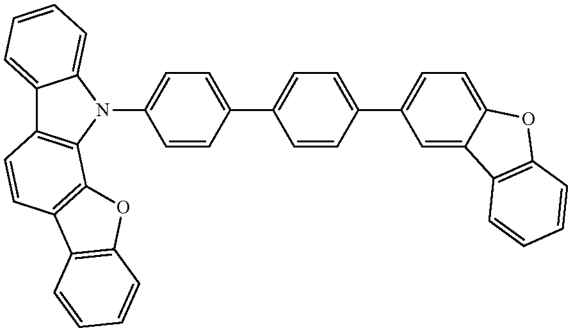
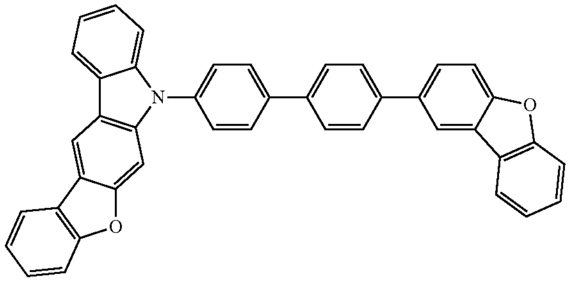
-continued
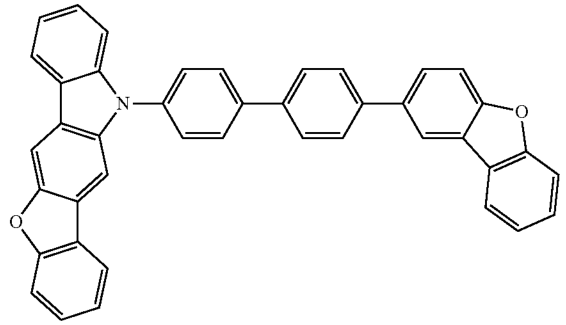
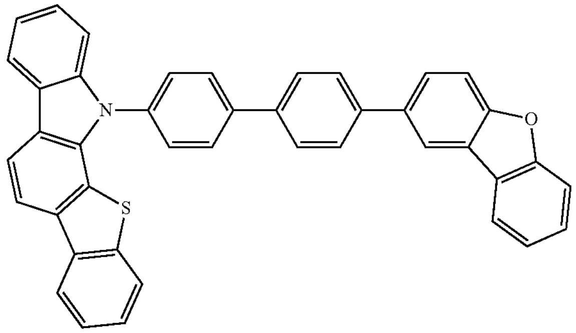
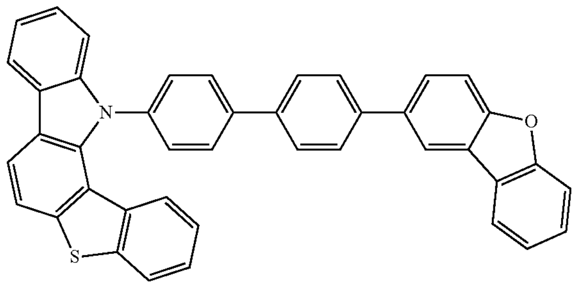
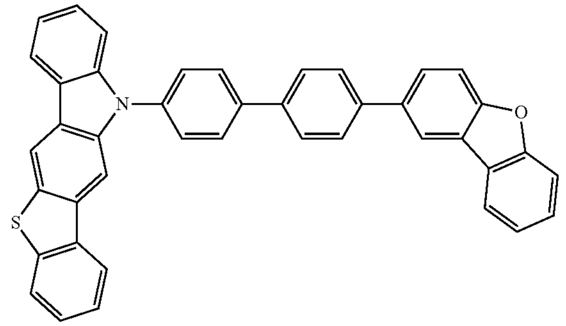
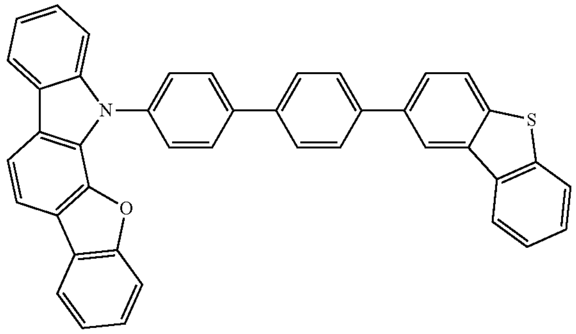

-continued
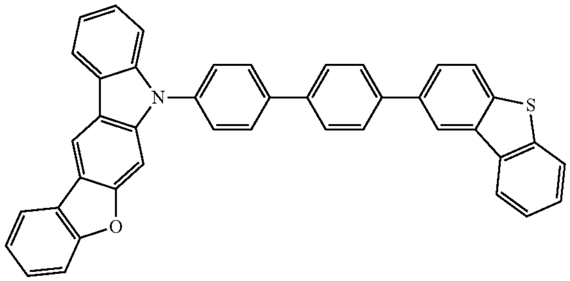
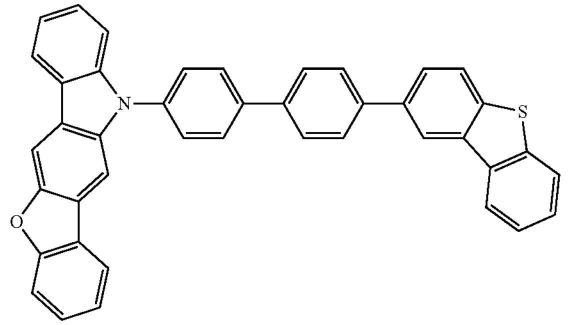
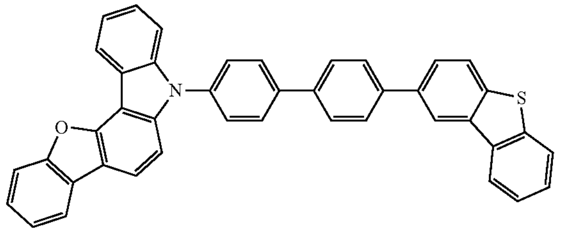
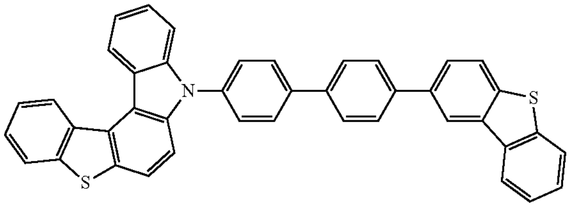
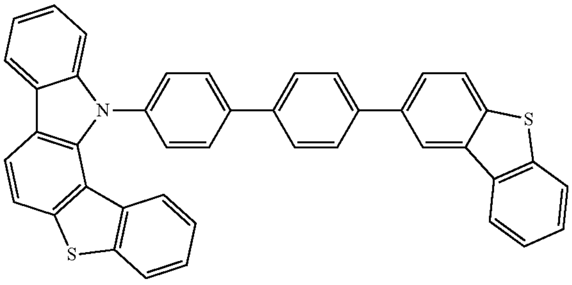
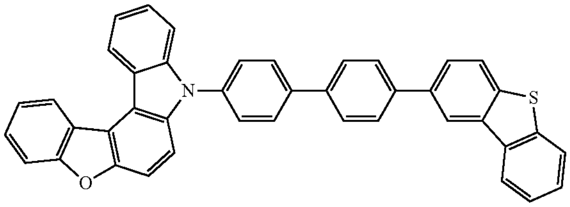
-continued
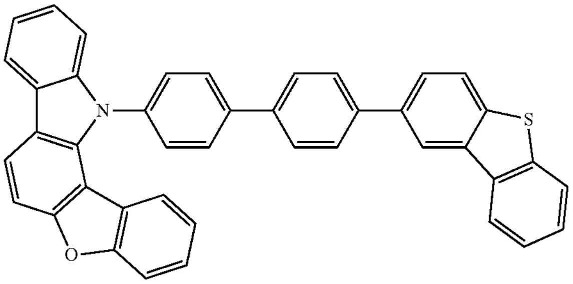
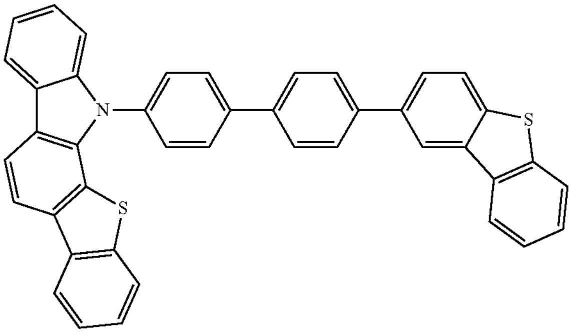
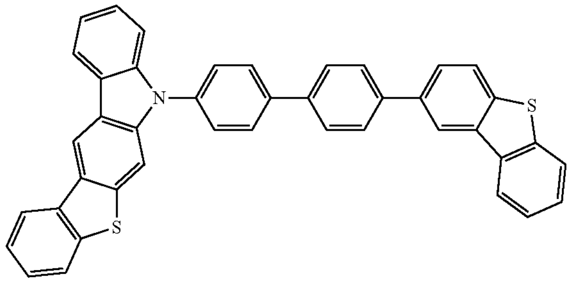
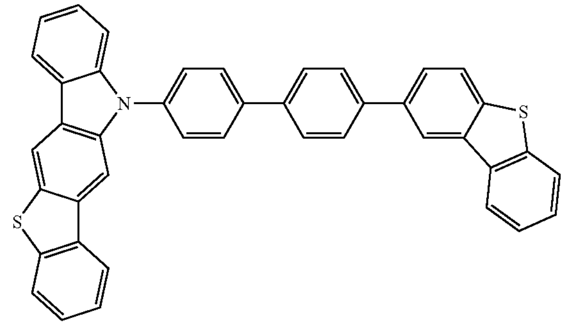
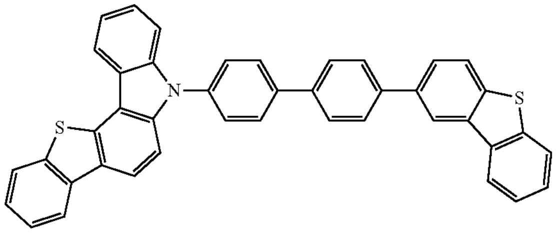

-continued
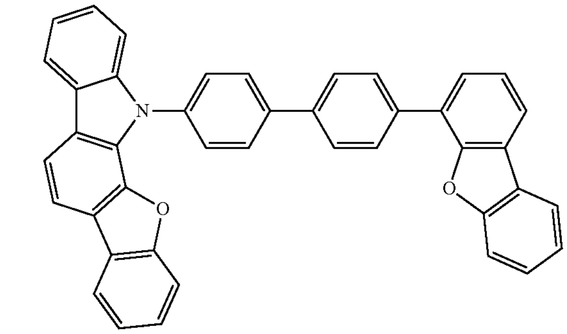
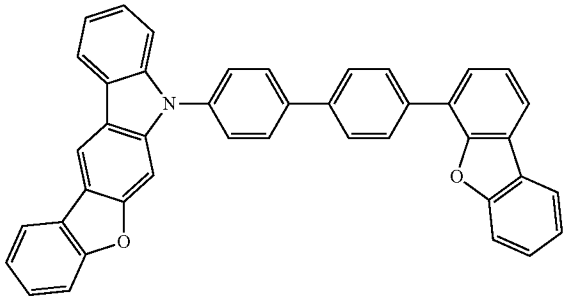
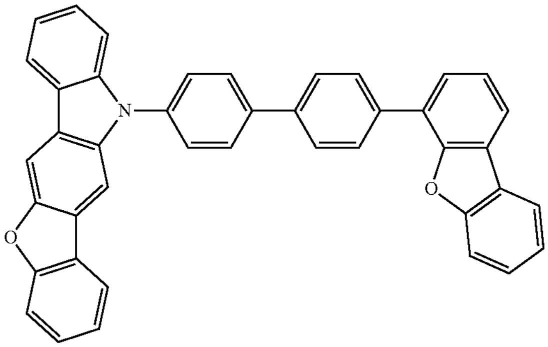
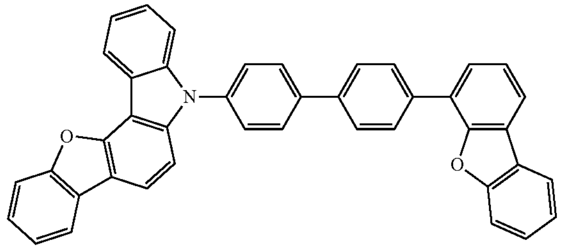
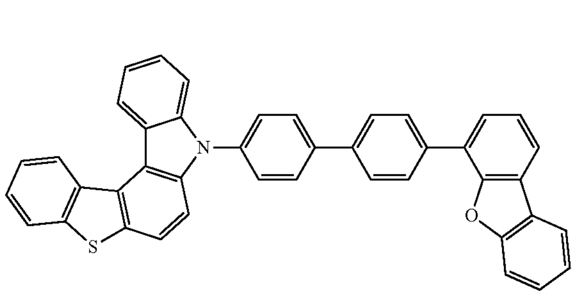
-continued
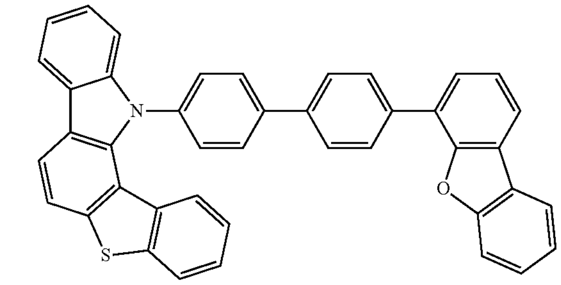
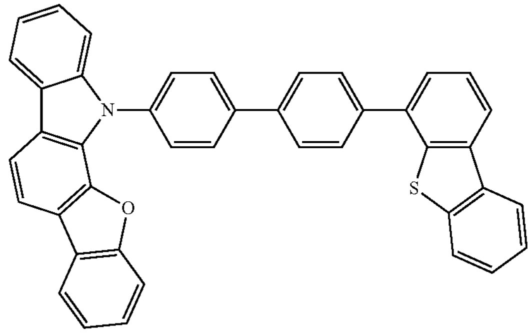
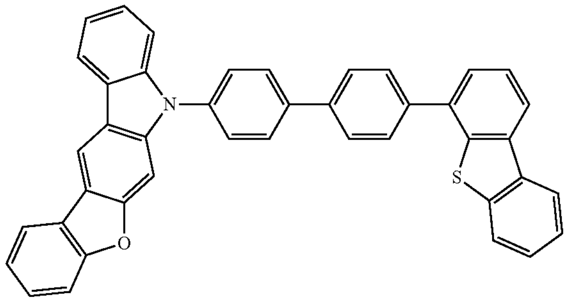
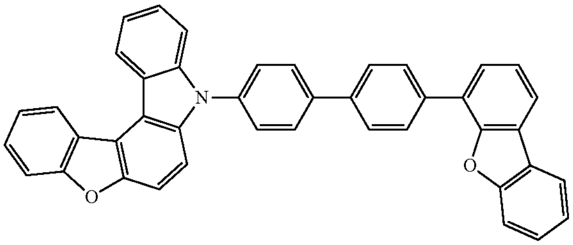
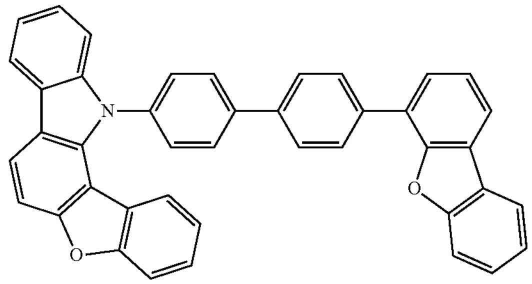

-continued
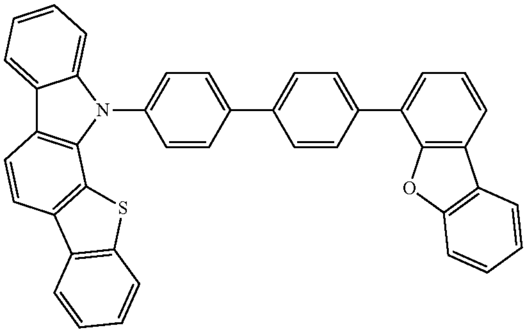
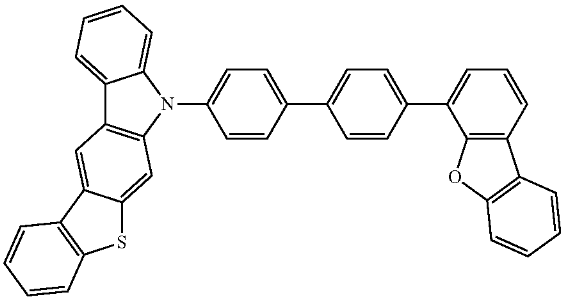
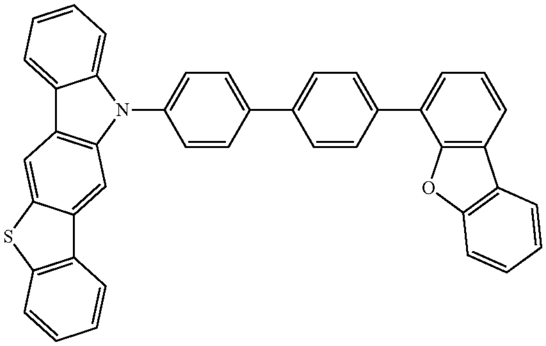
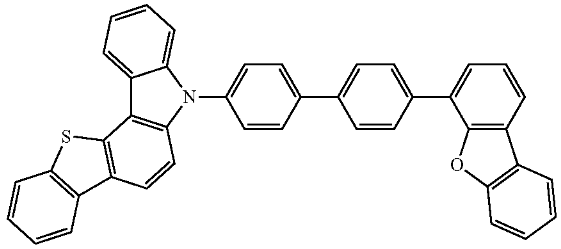
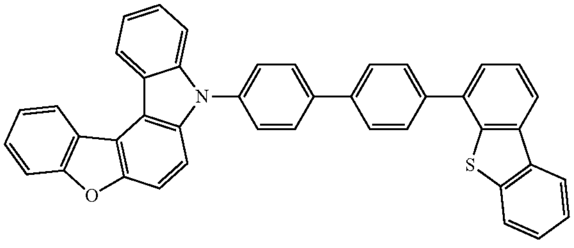
-continued
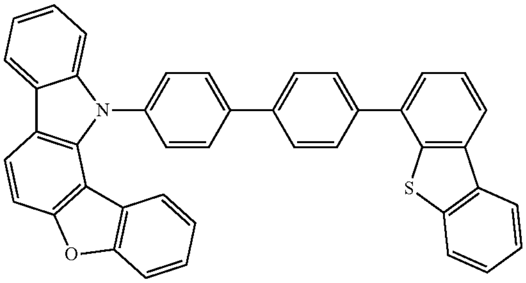
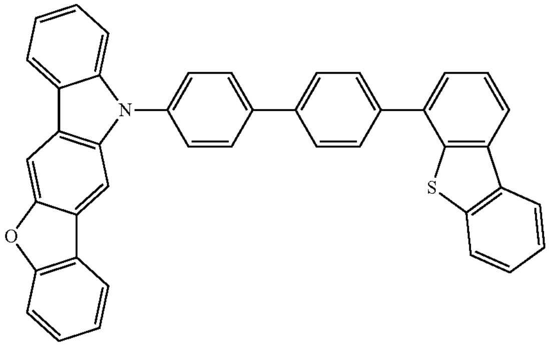
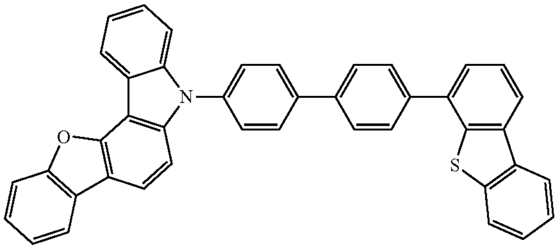
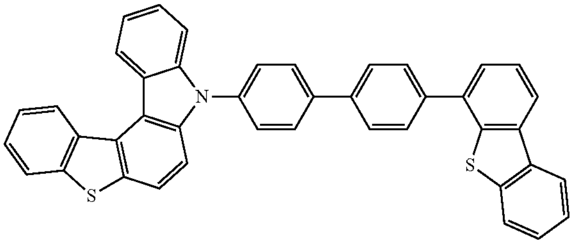
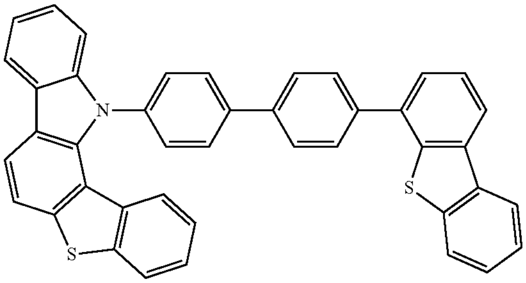
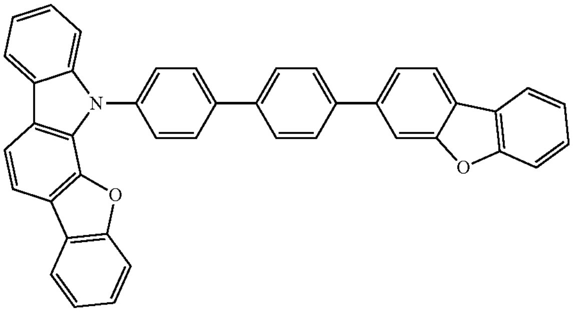

-continued
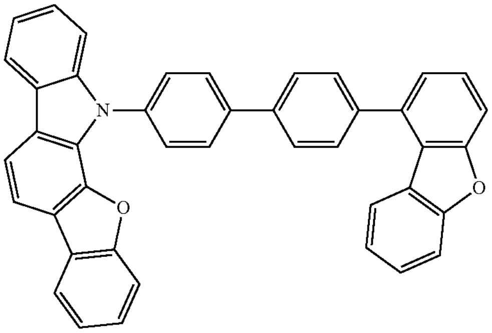
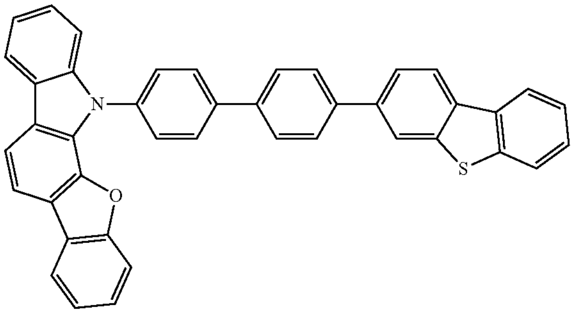
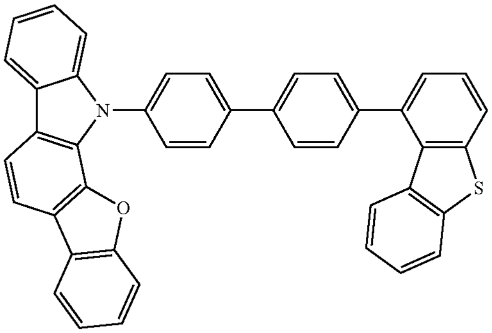
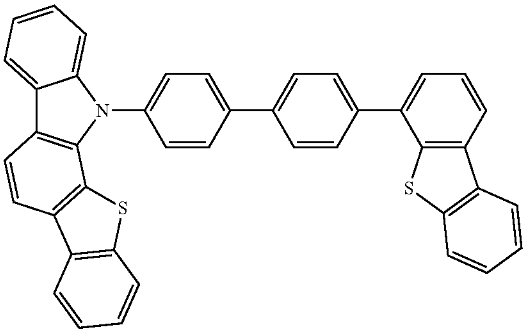
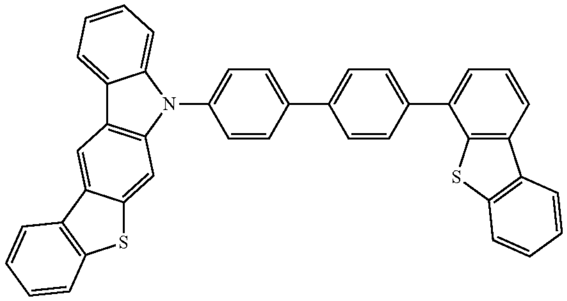
-continued
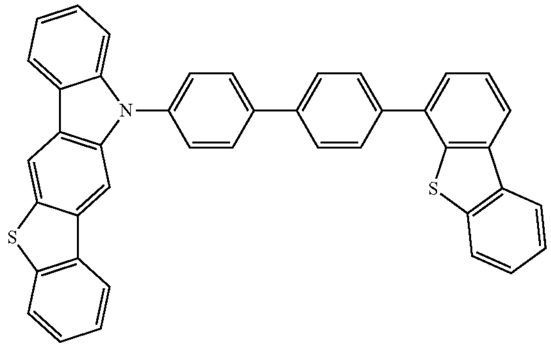
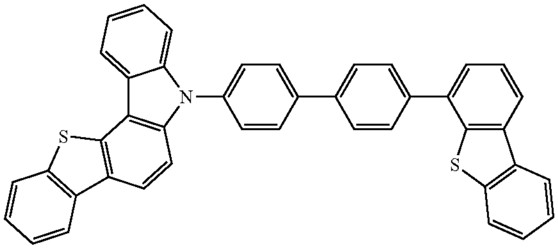
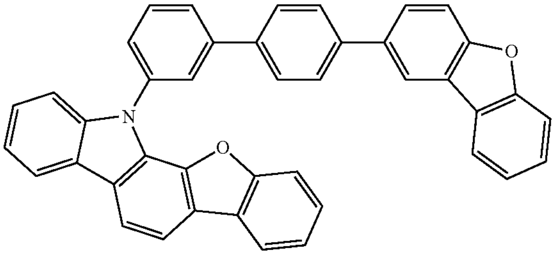
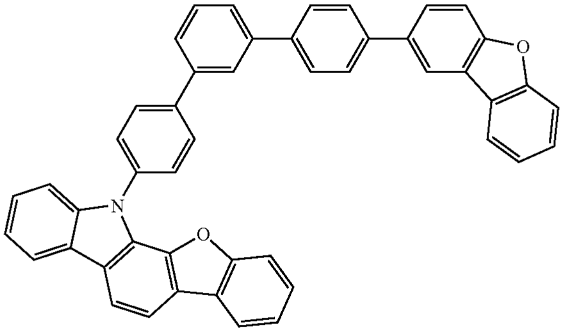
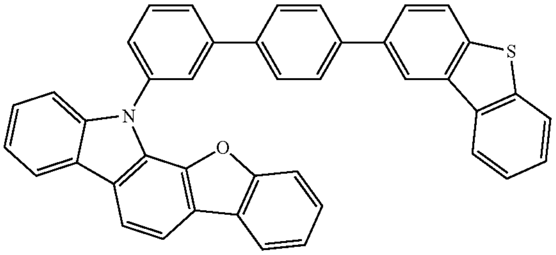

-continued
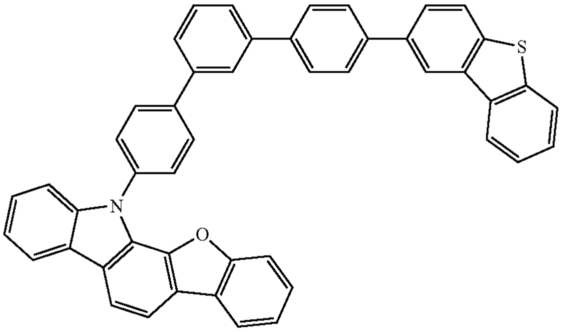
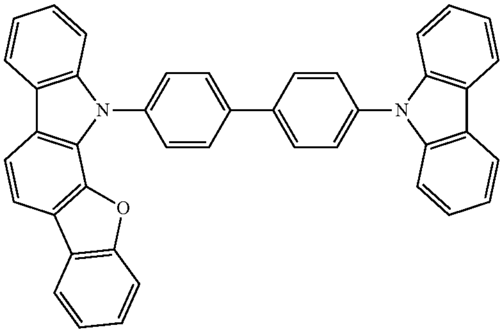
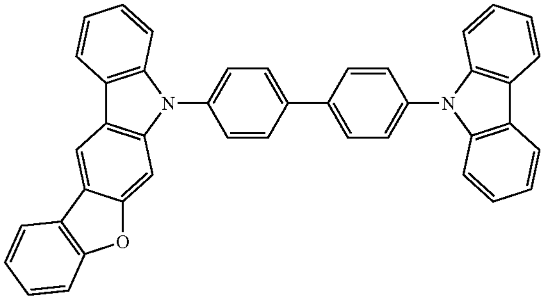
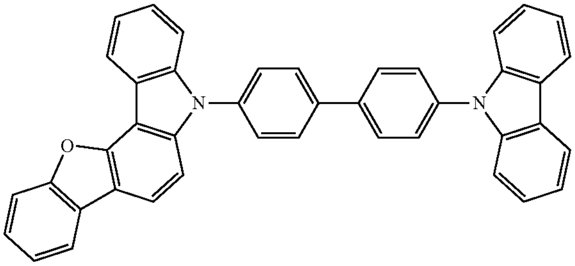
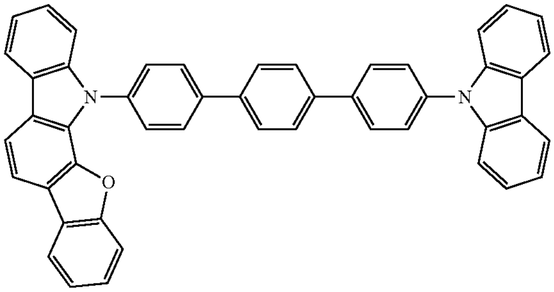
-continued
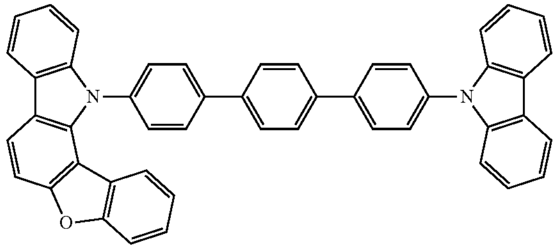
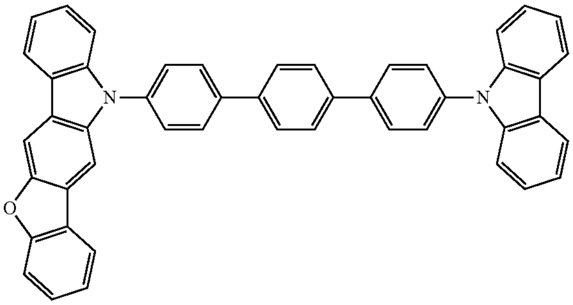
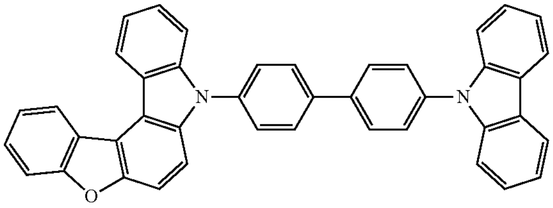
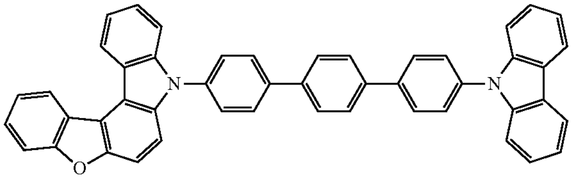
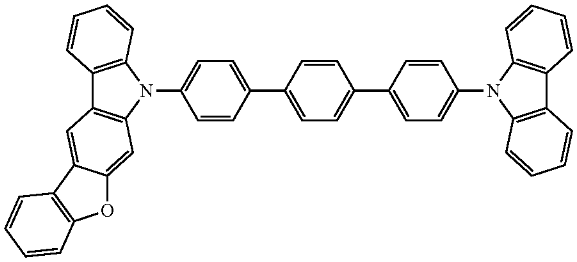
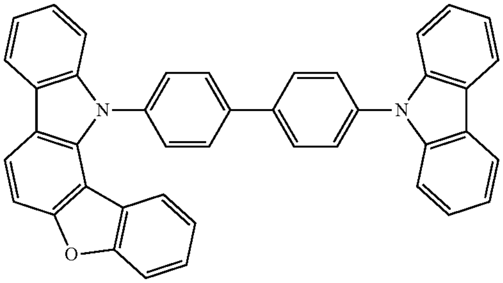
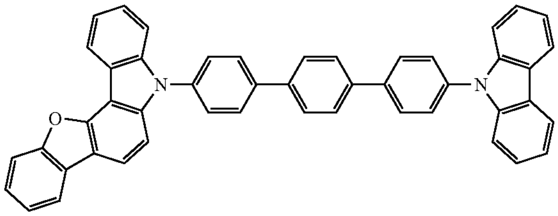

-continued
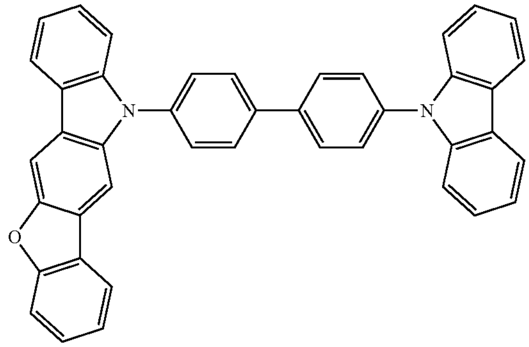
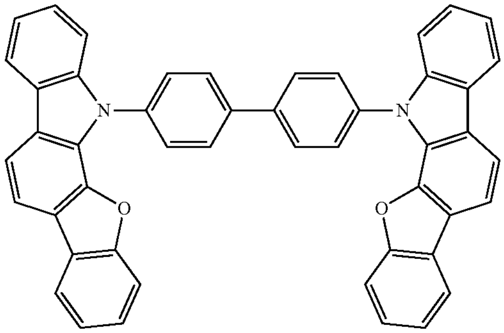
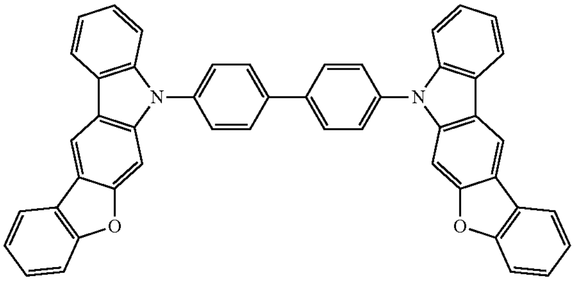
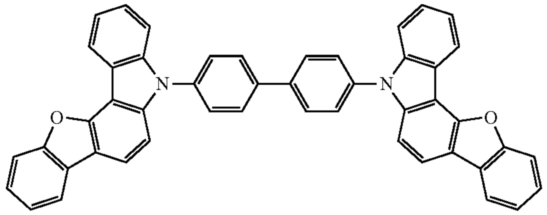
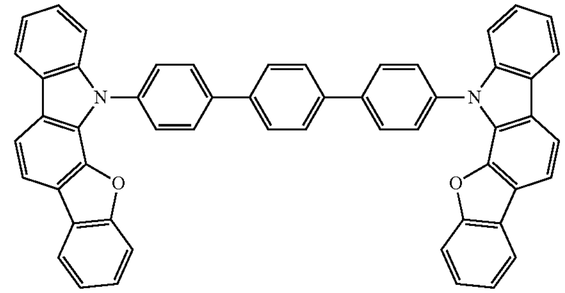
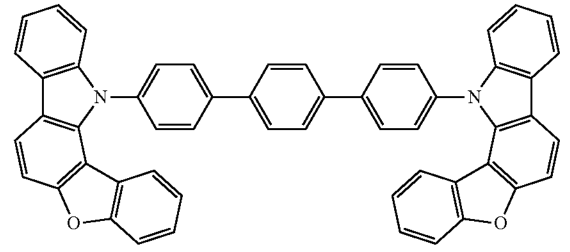
-continued
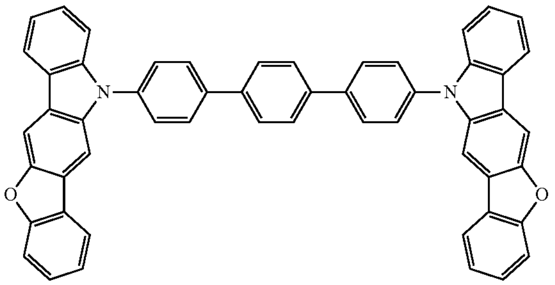
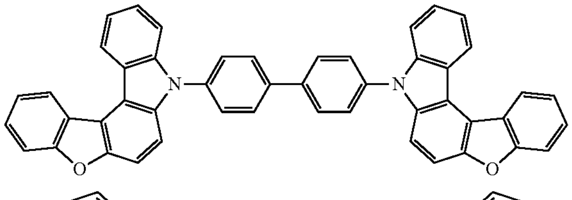
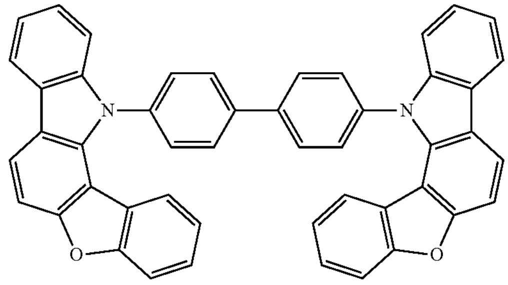
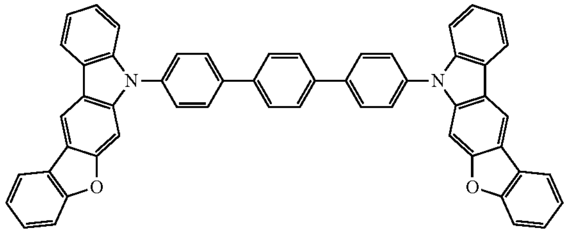
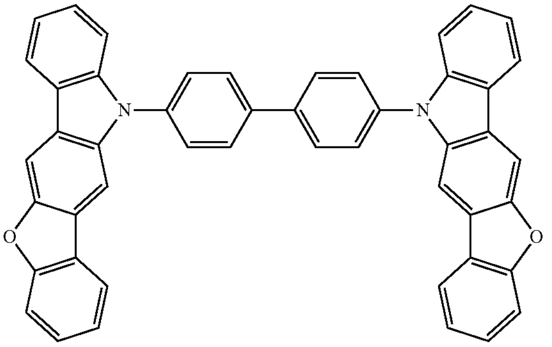
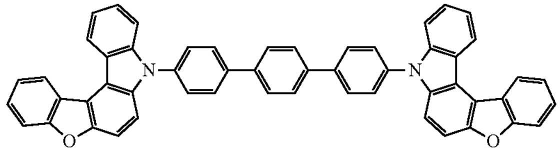
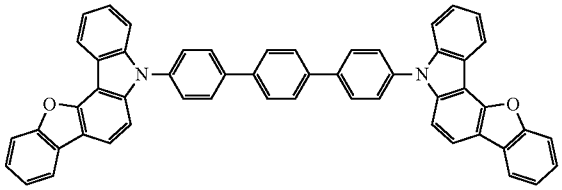

-continued
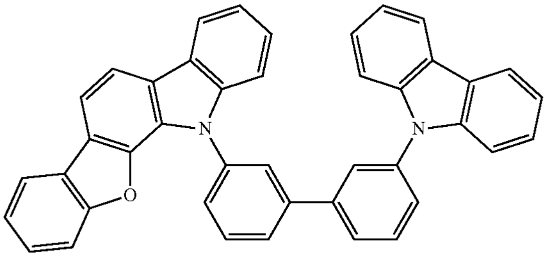
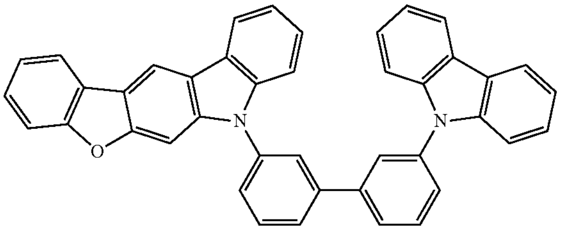
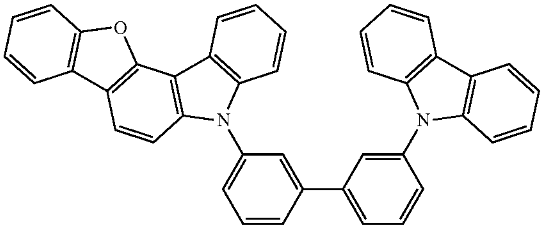
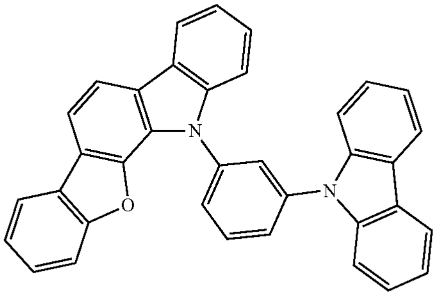
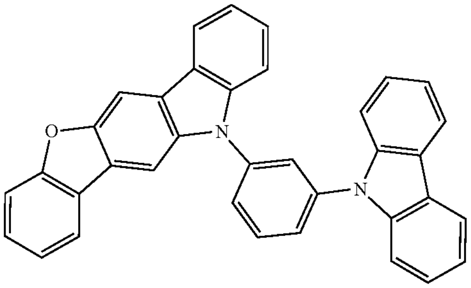
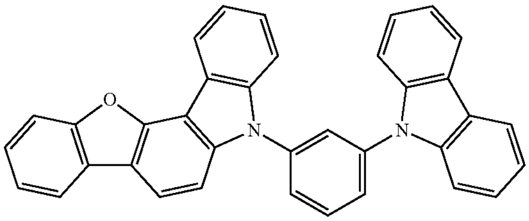
-continued
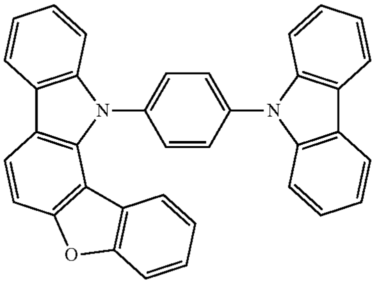
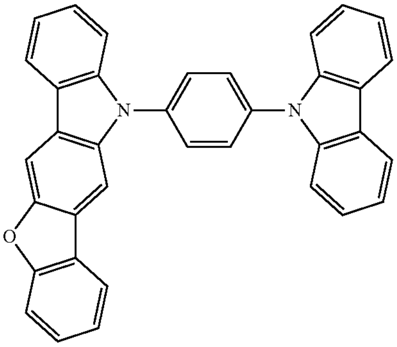
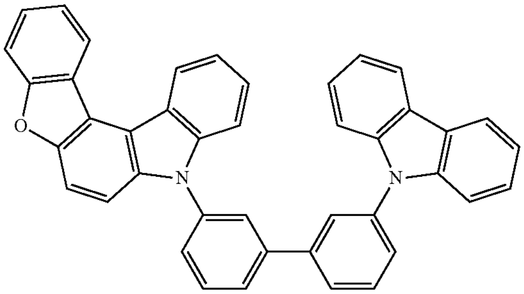
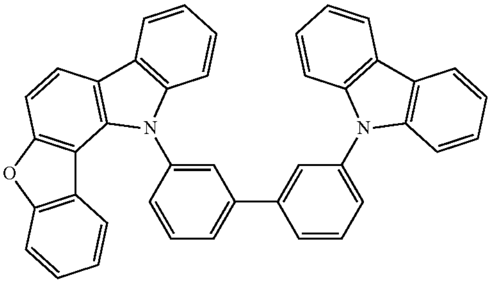
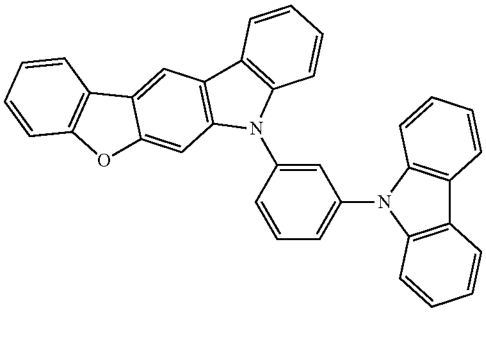

-continued
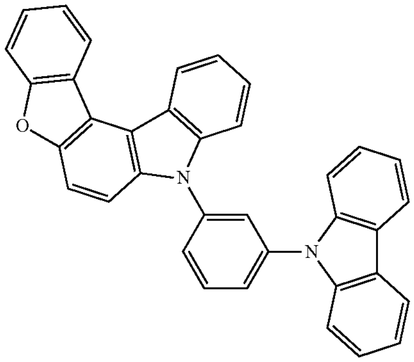
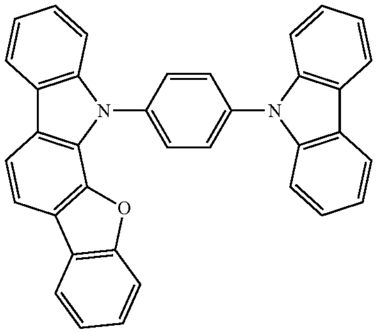
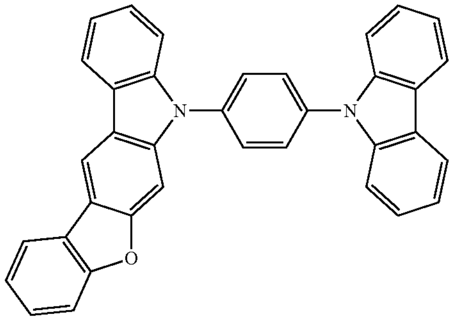
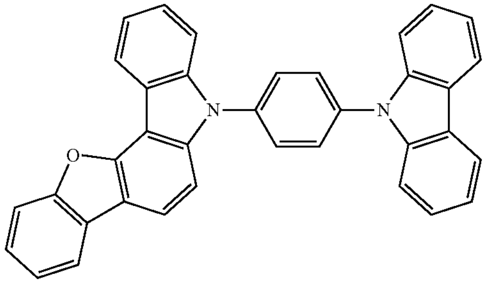
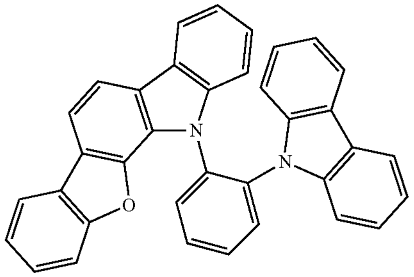
-continued
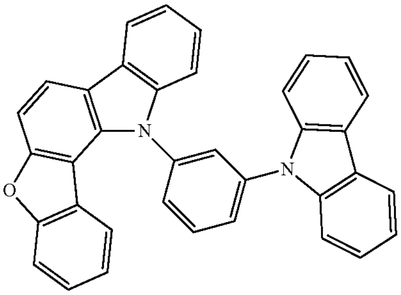
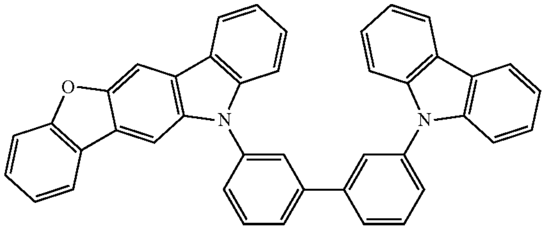
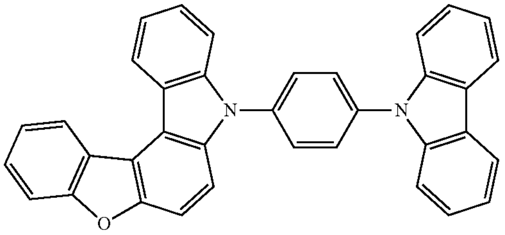
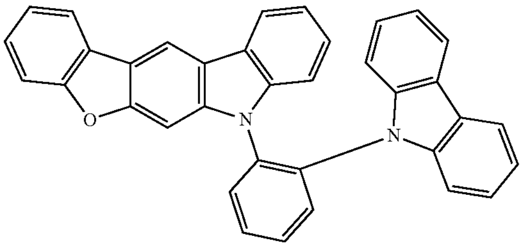
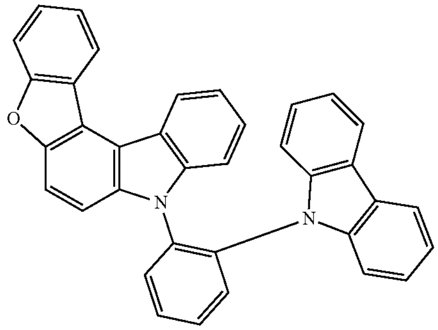
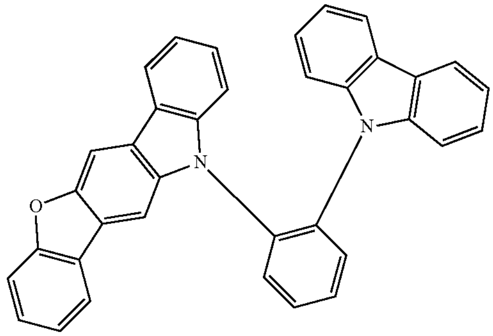

-continued
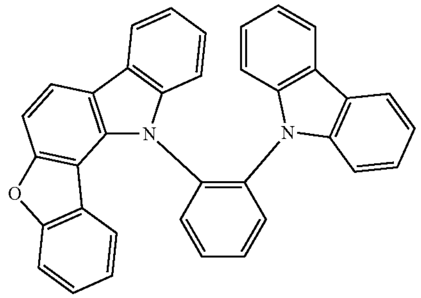
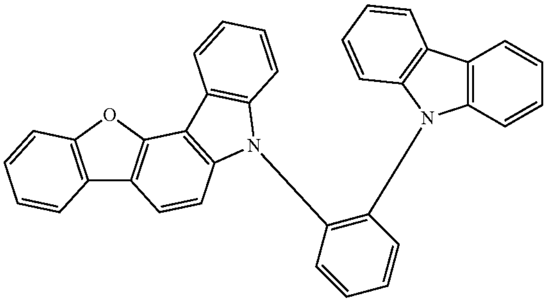
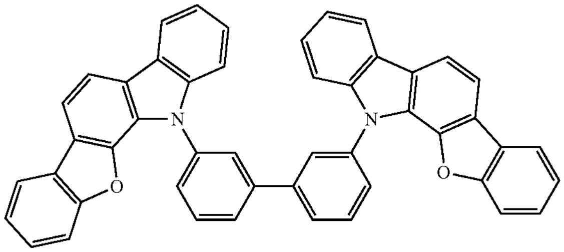
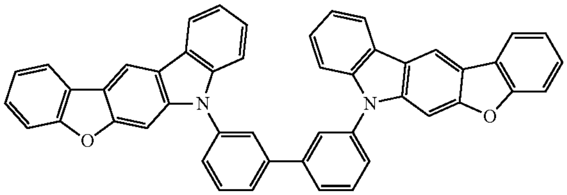
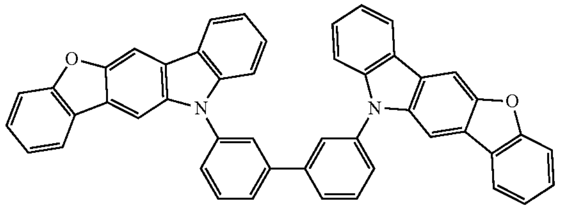
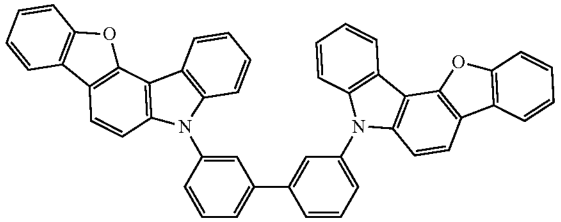
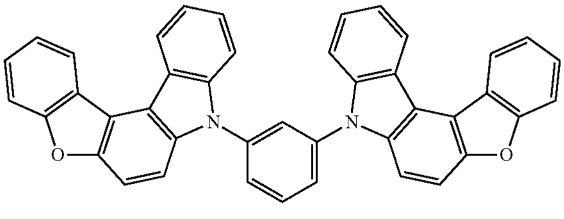
-continued
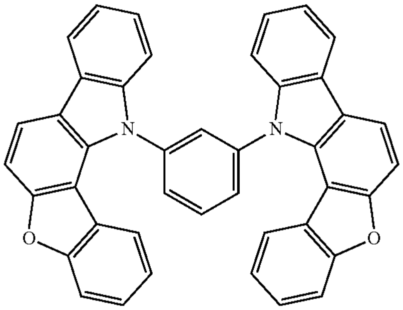
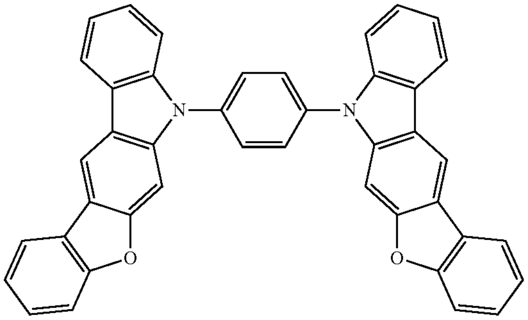
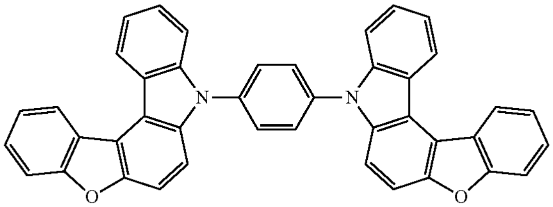
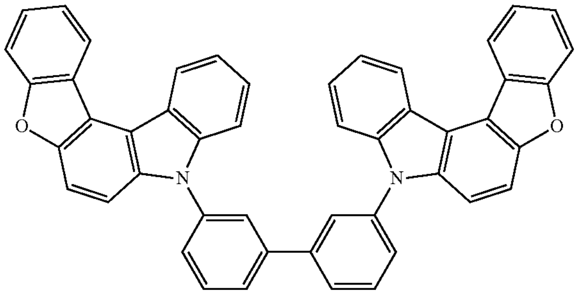
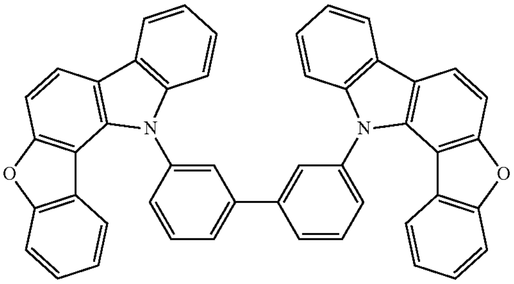

-continued
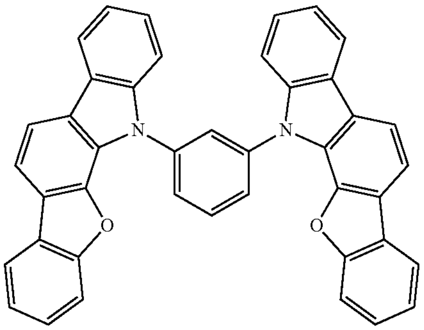
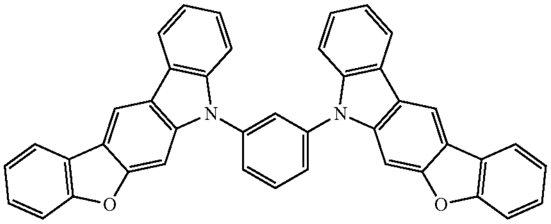
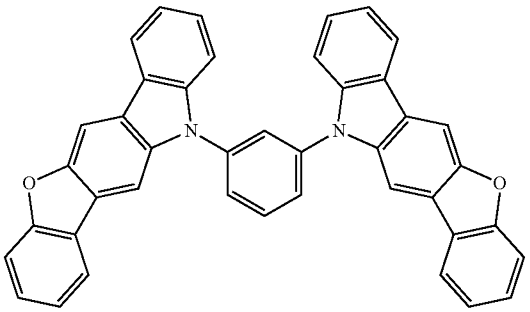
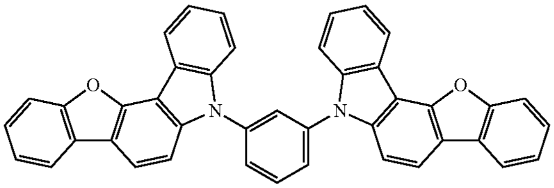
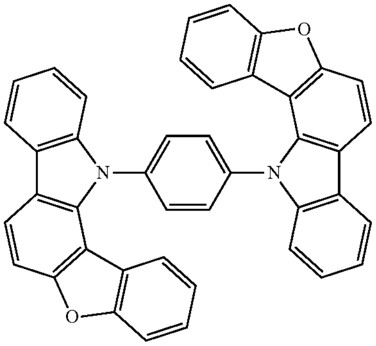
-continued
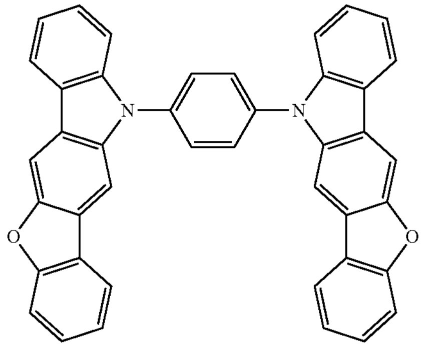
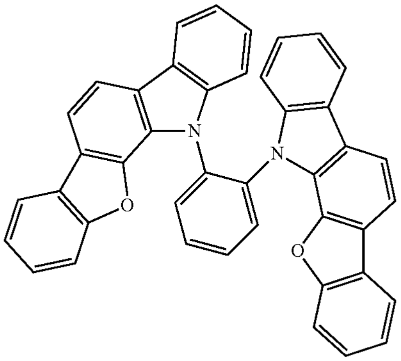
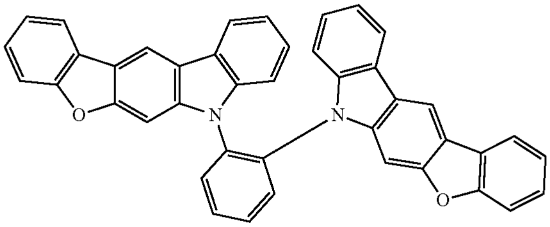
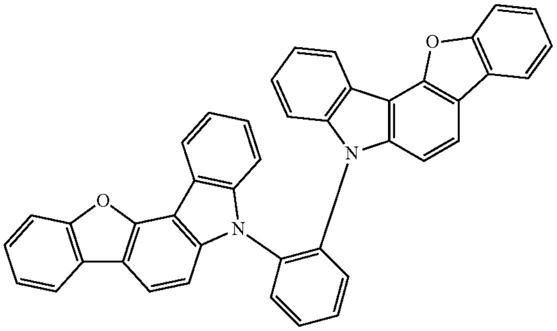
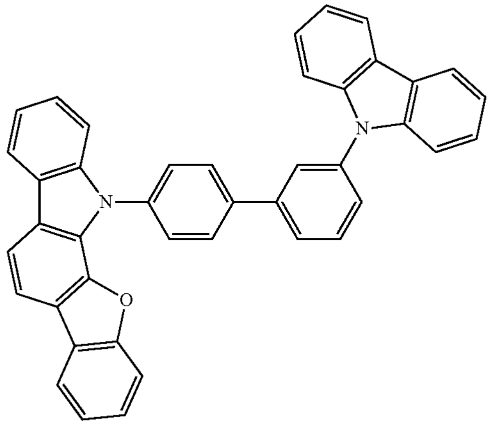

-continued
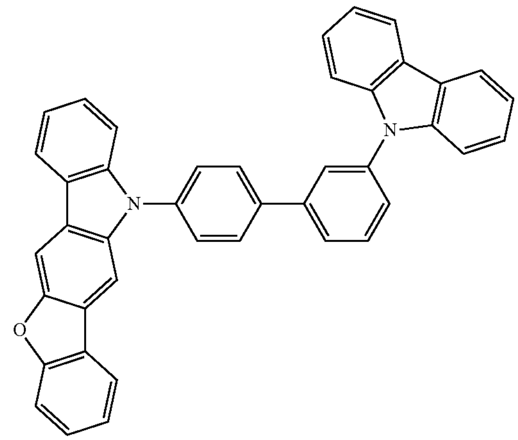
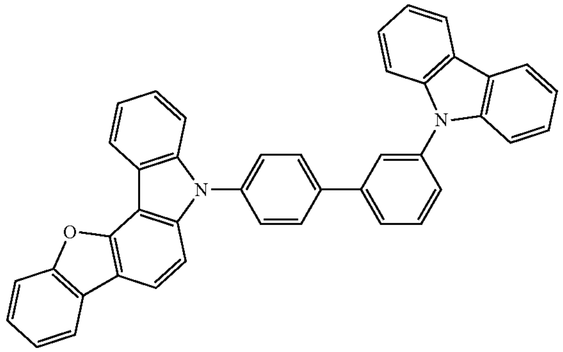
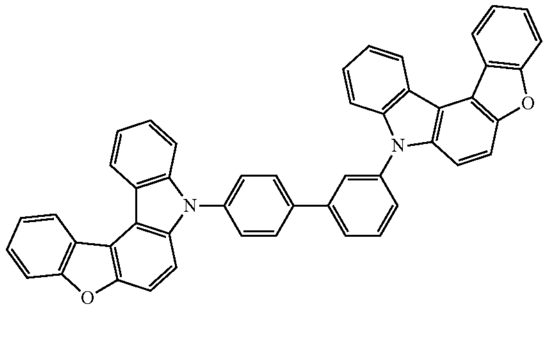
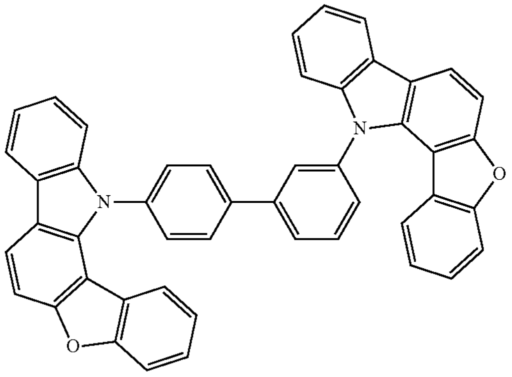
-continued
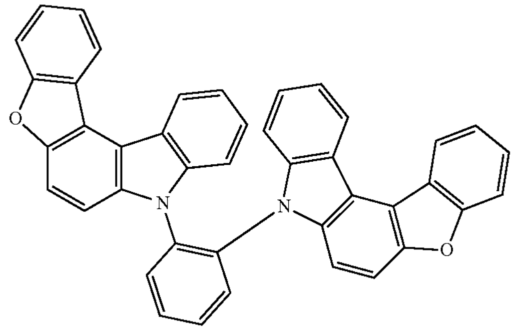
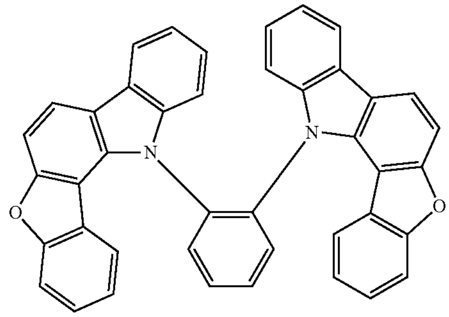
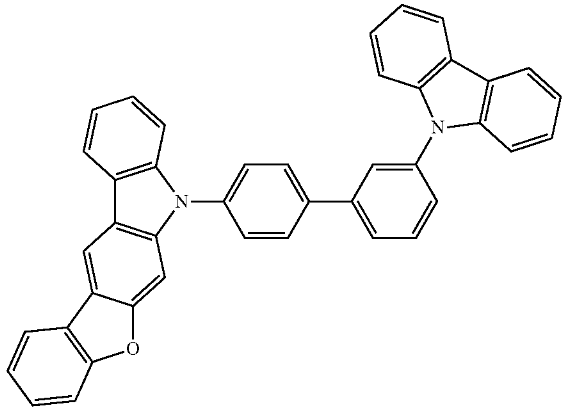
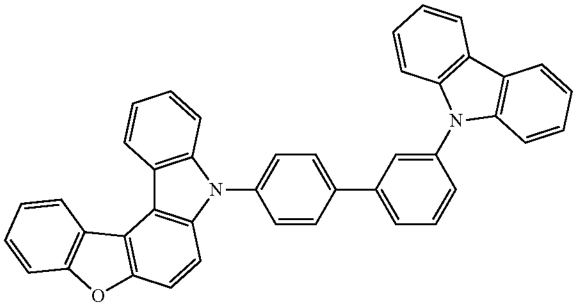

-continued
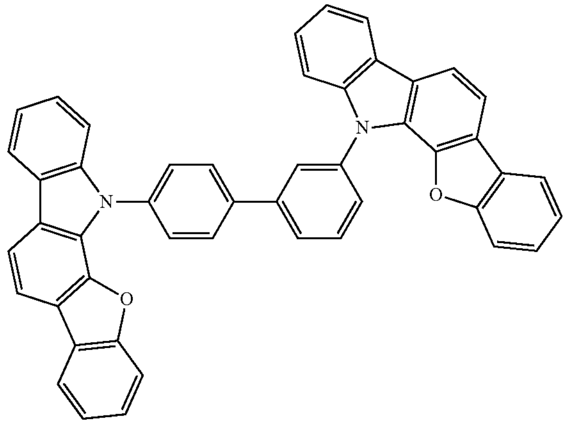
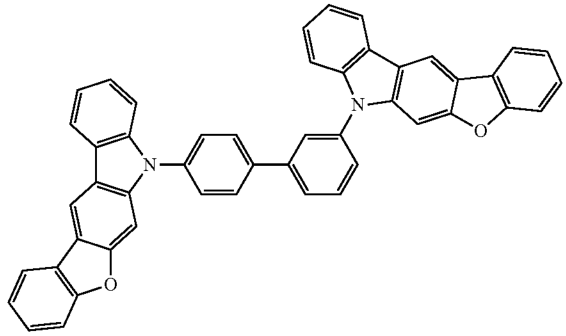
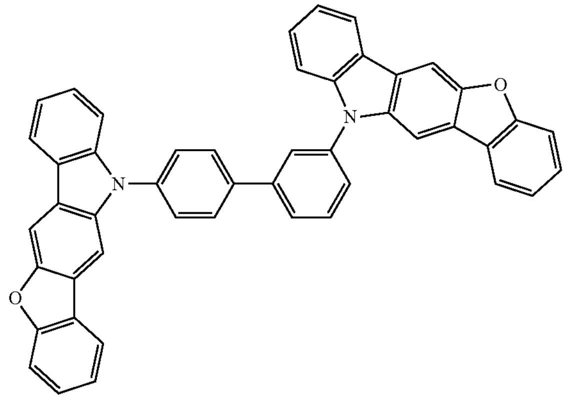
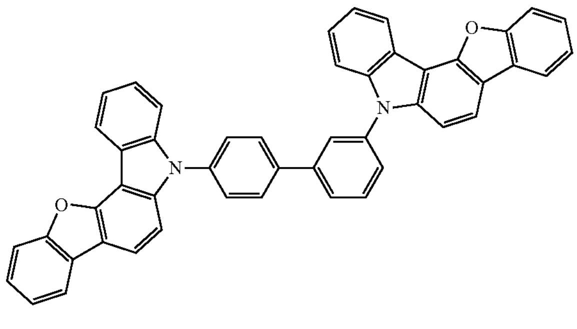
-continued
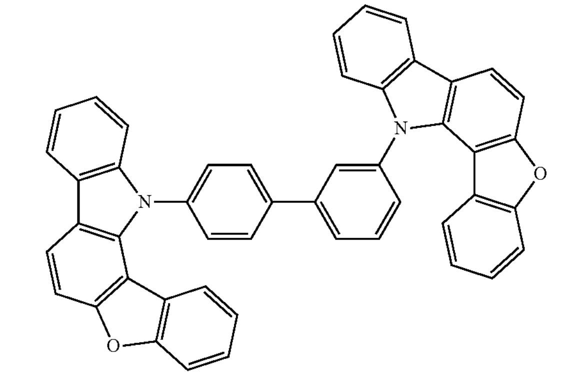
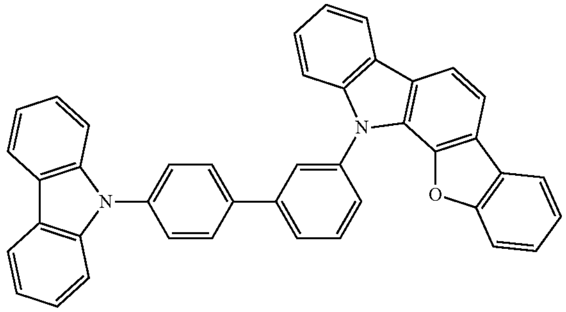
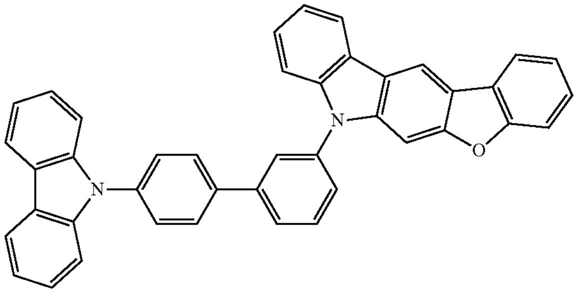
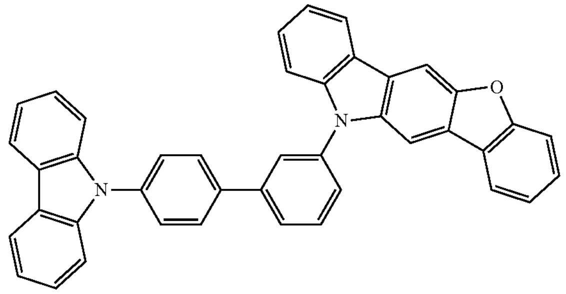
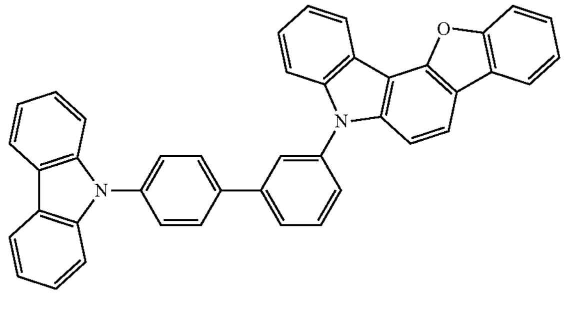

-continued
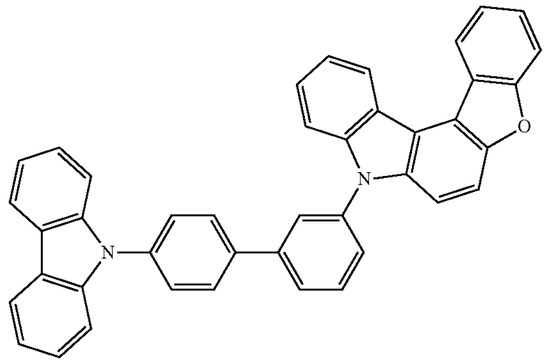
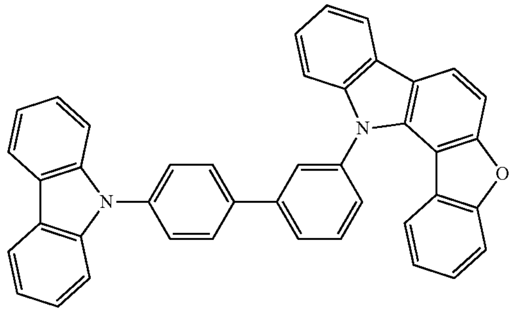
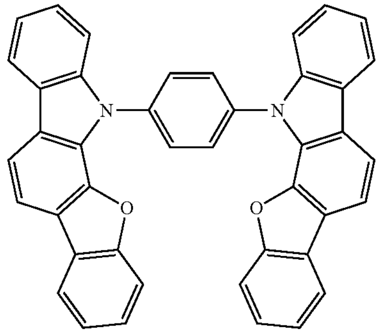
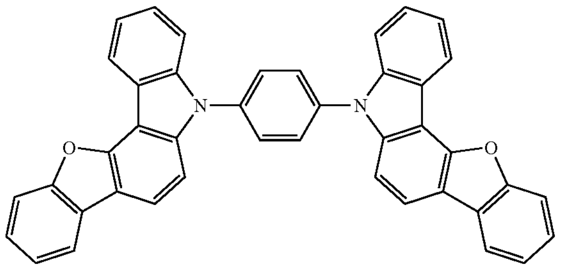
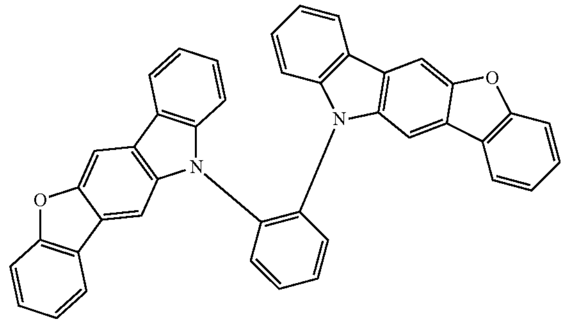
-continued
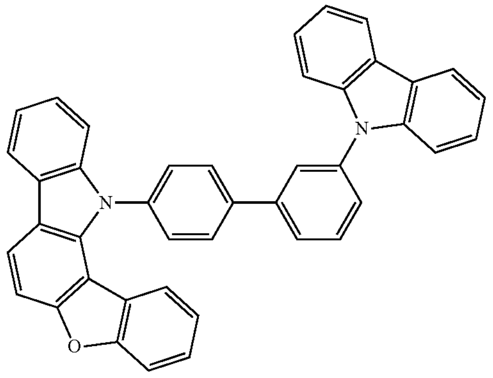
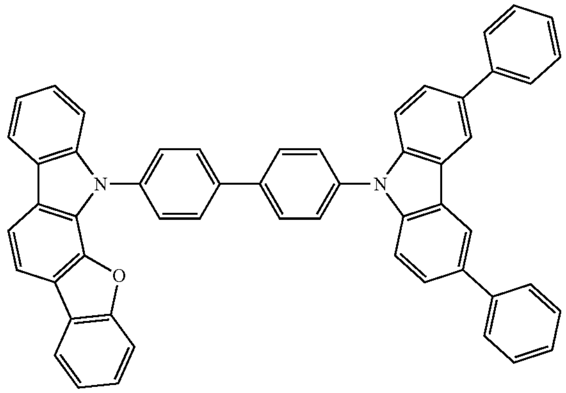
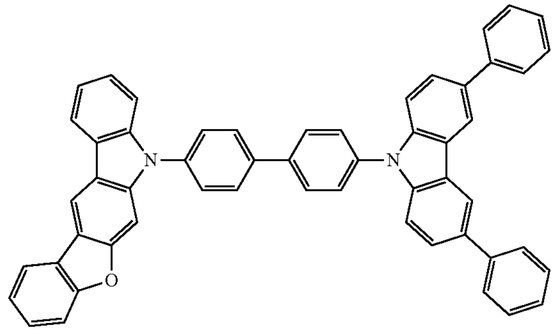
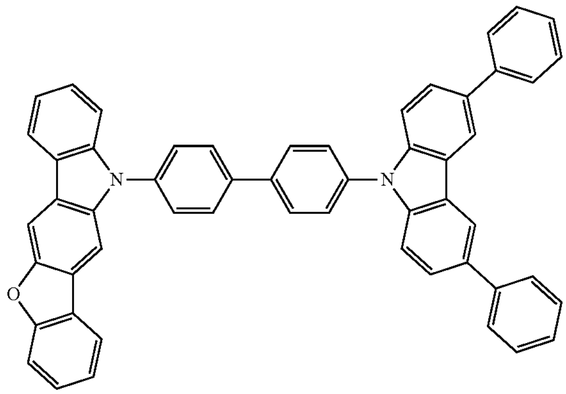

-continued
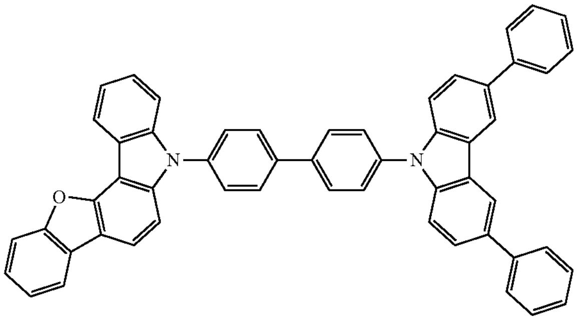
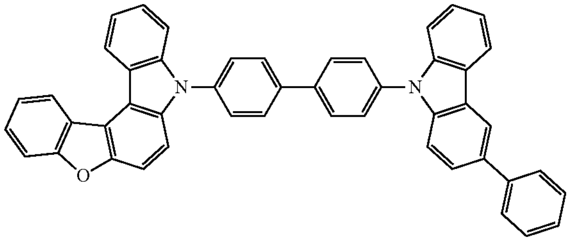
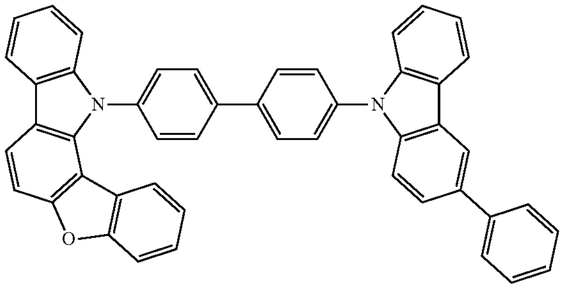
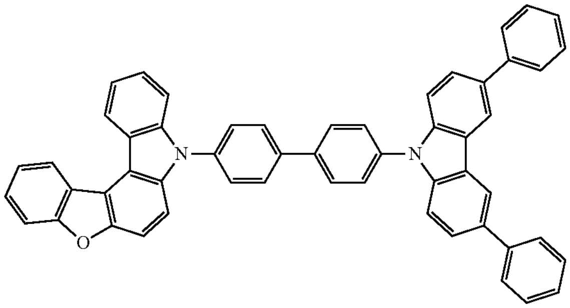
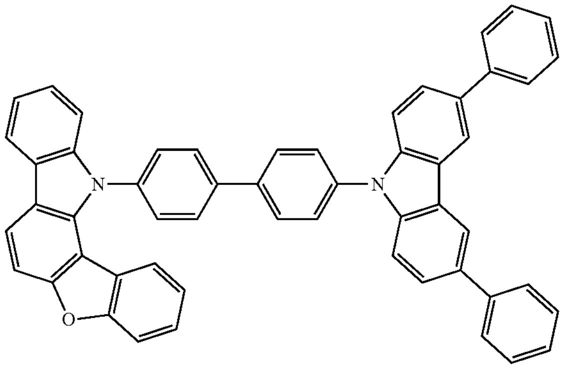
-continued
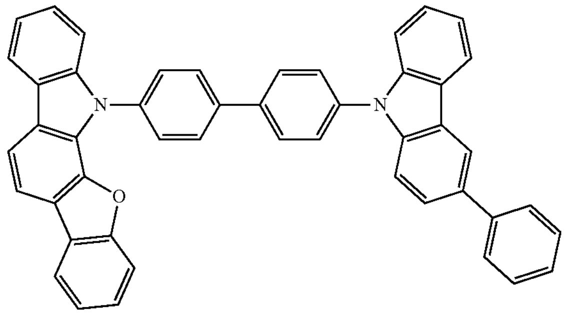
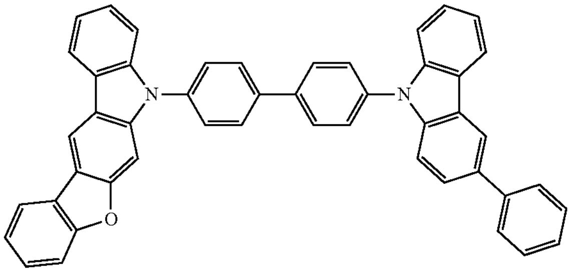
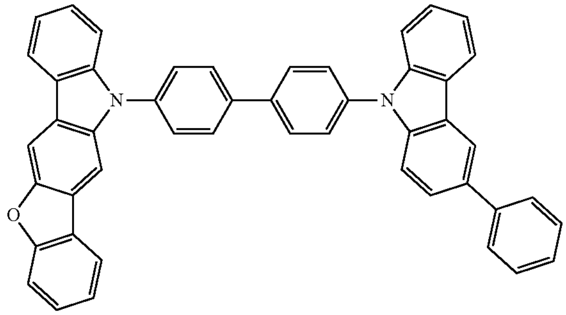
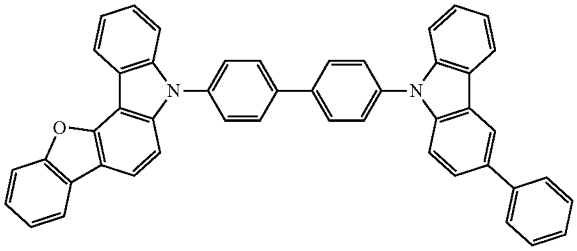
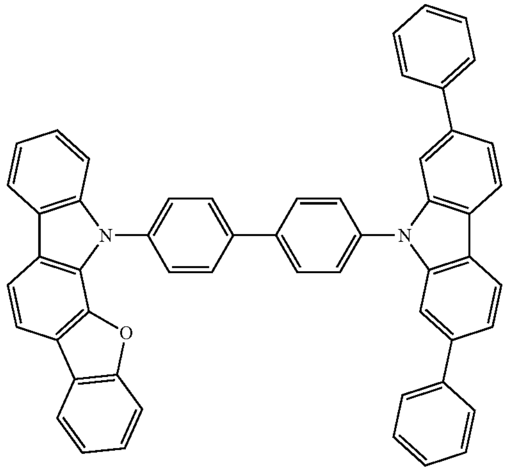

-continued
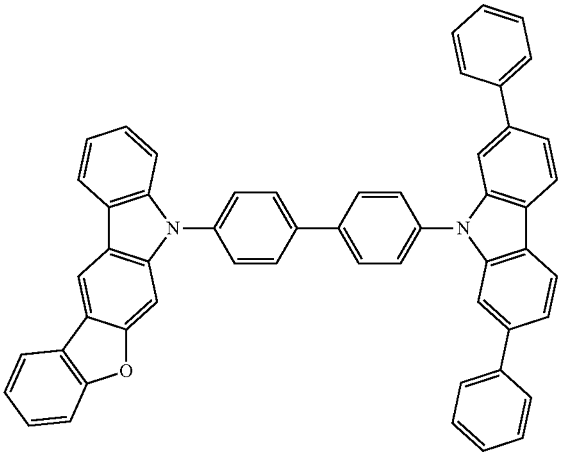
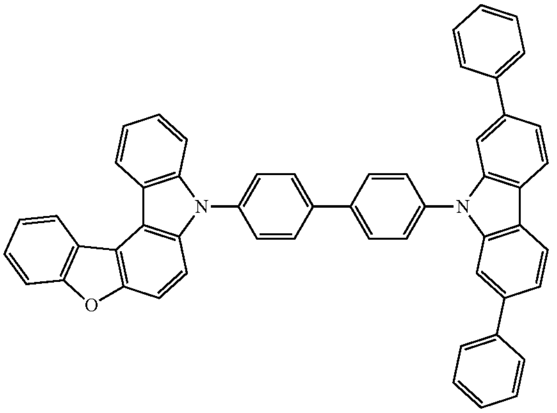
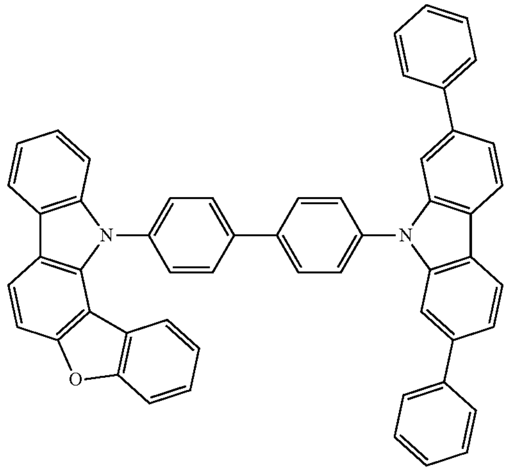
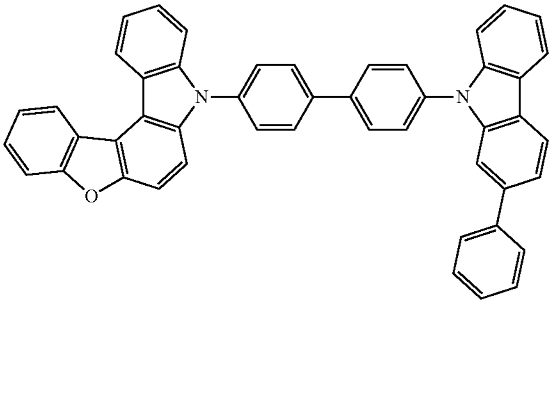
-continued
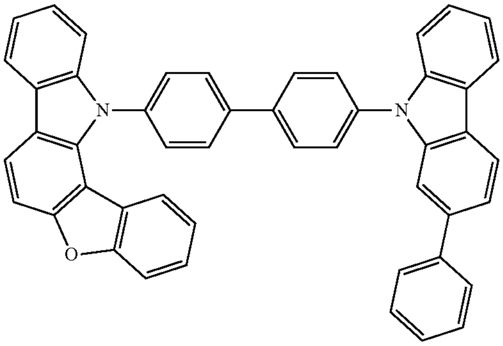
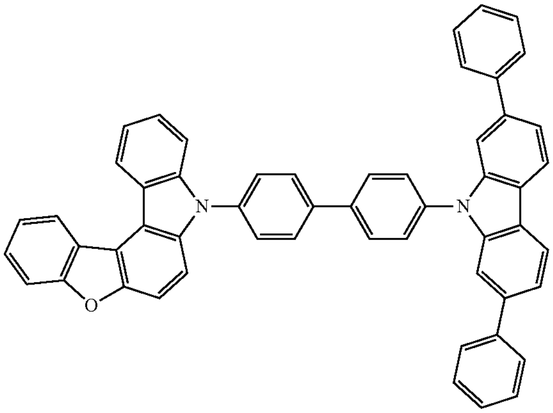
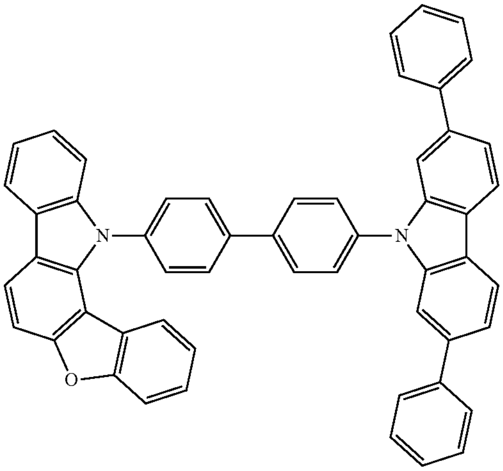
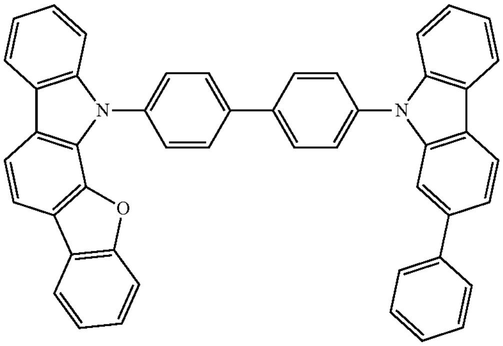

-continued
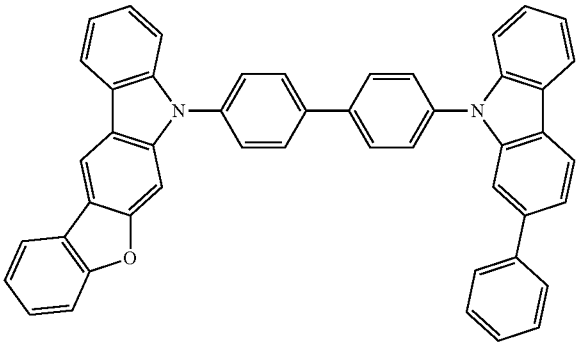
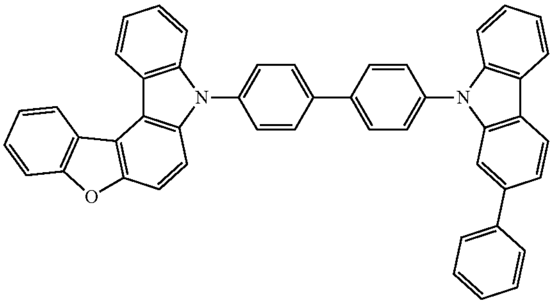
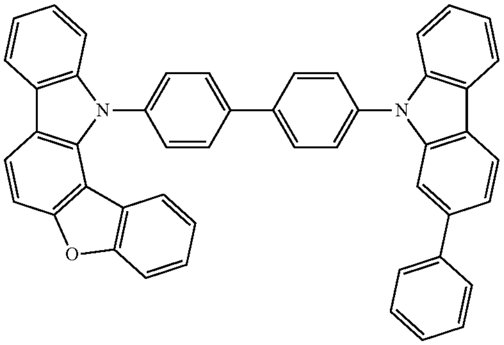
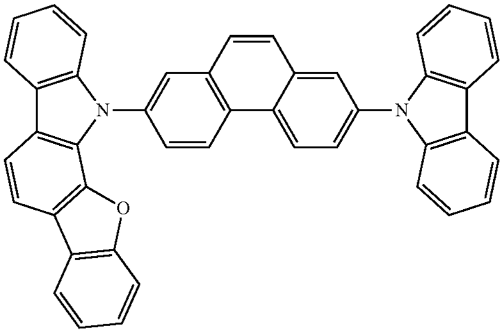
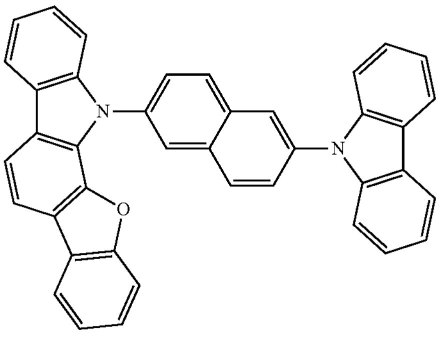
-continued
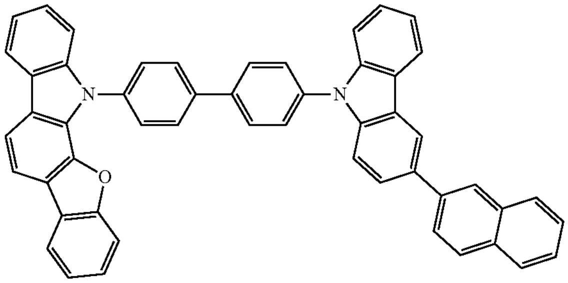
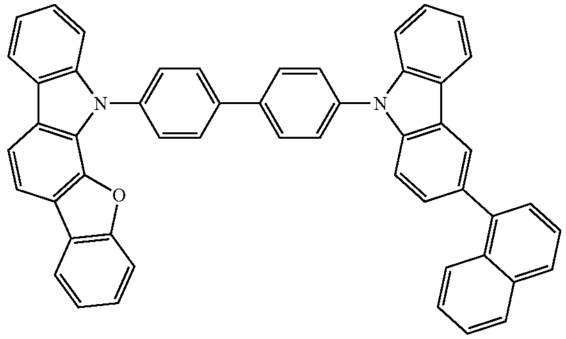
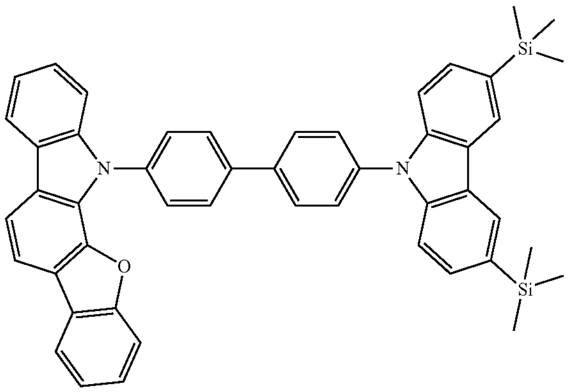
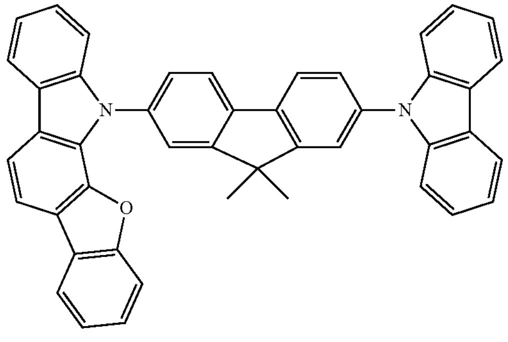
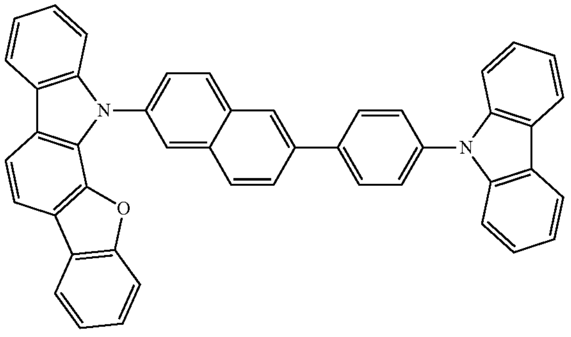

-continued
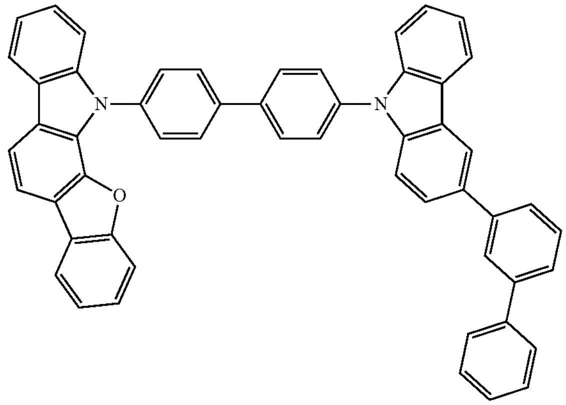
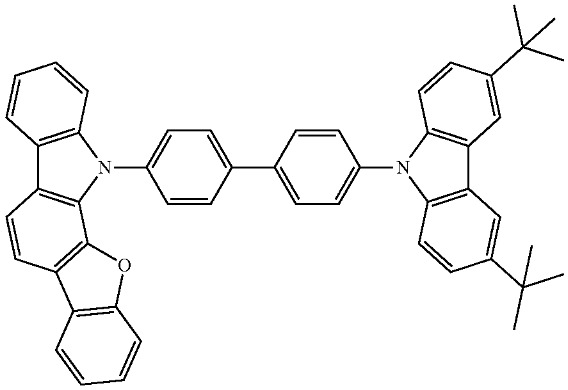
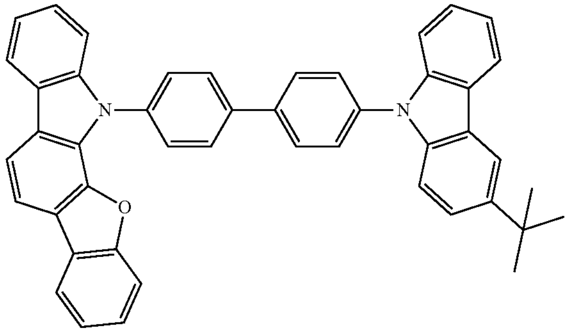
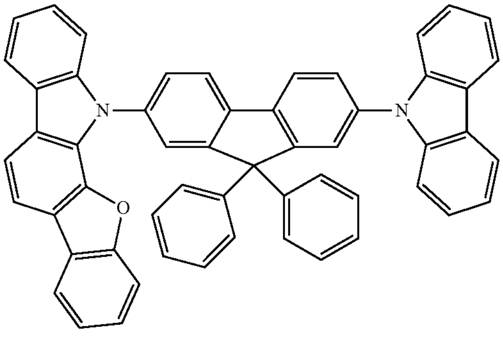
-continued
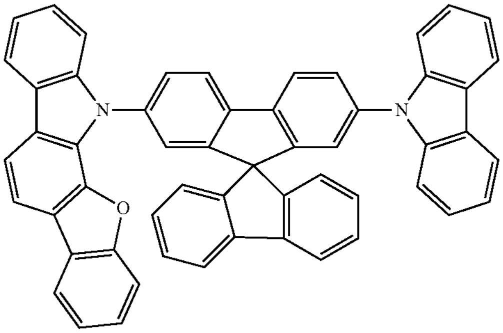
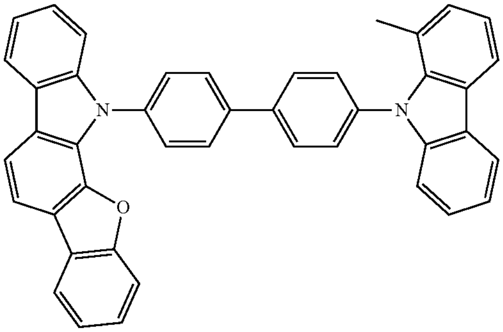
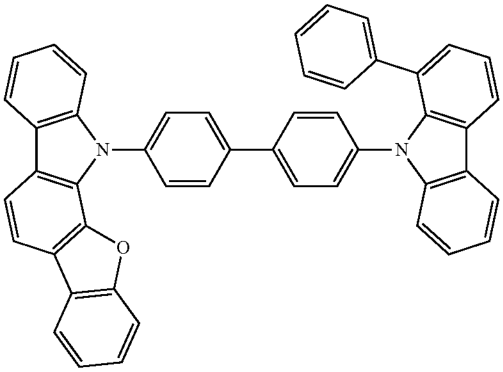
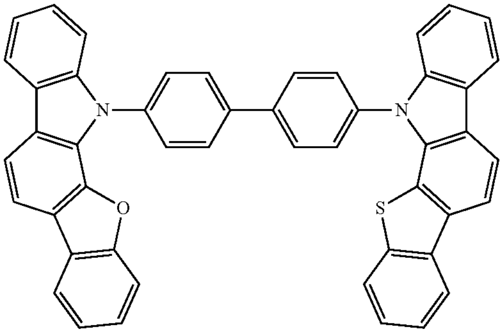
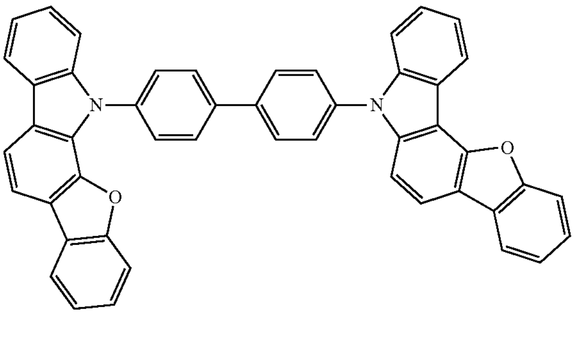

-continued
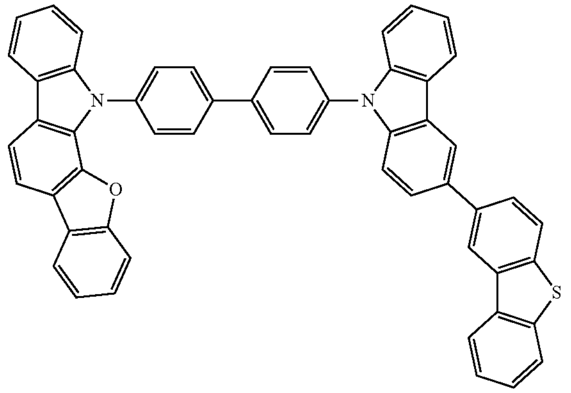
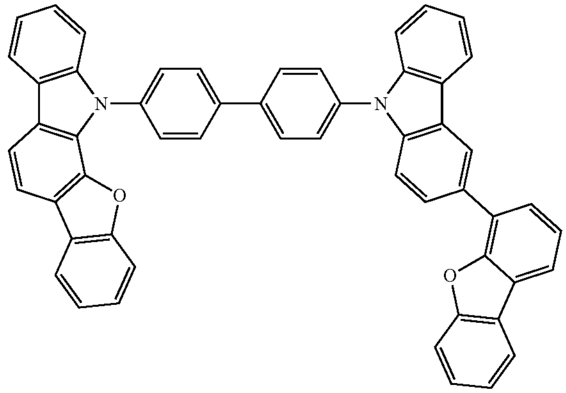
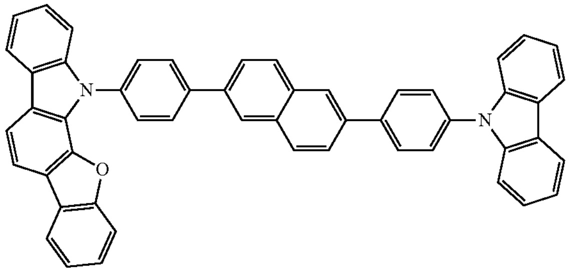
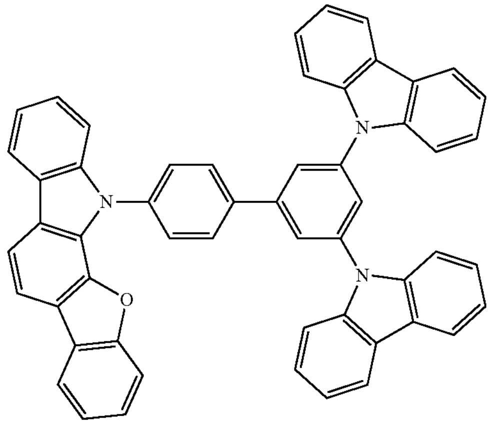
-continued
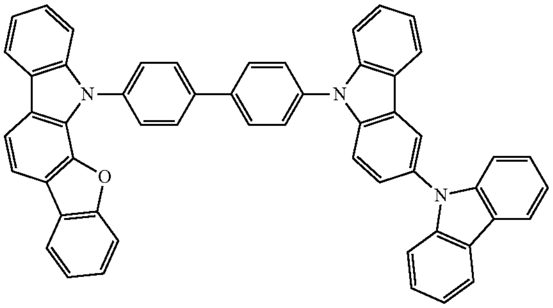
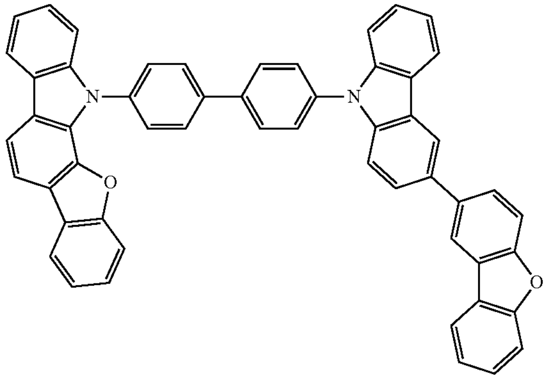
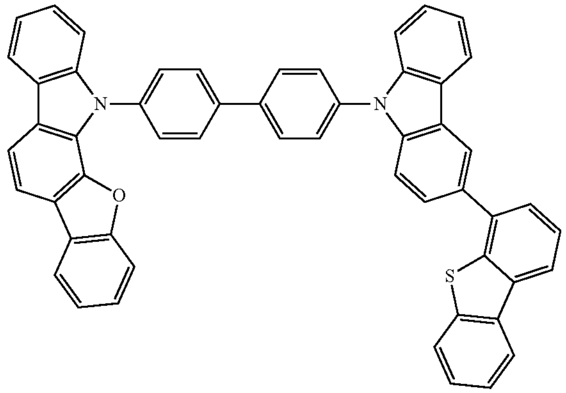
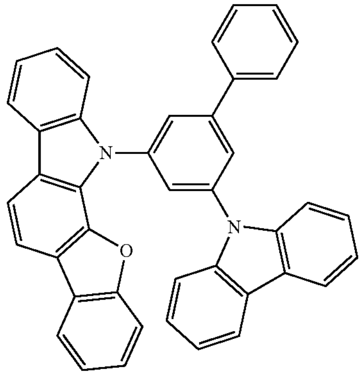

-continued
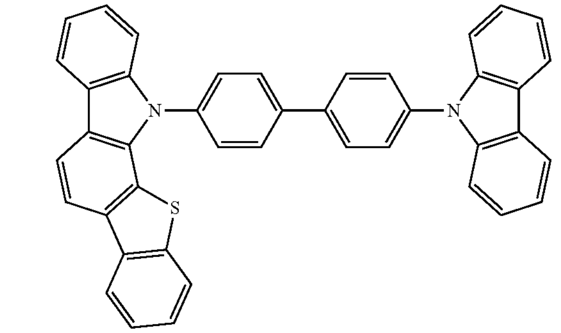
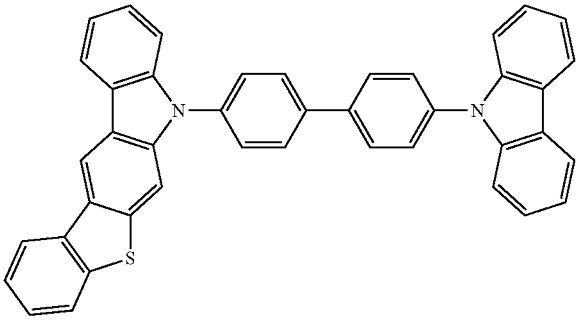
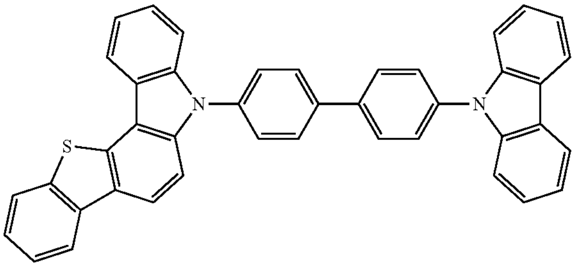
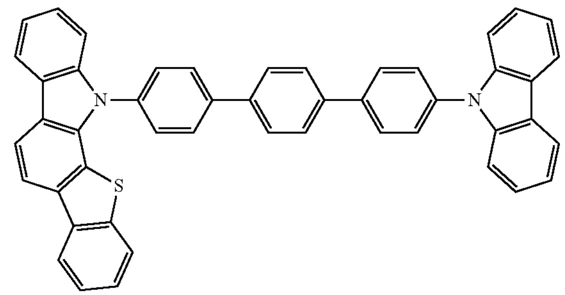
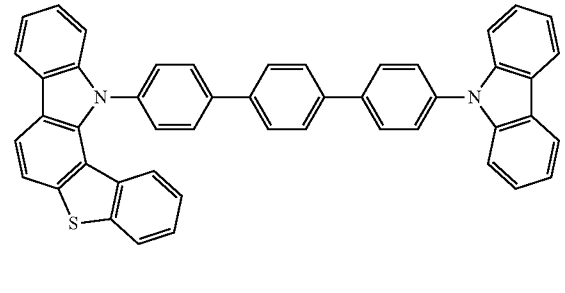
-continued
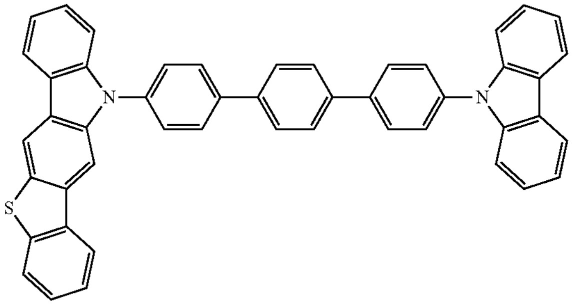
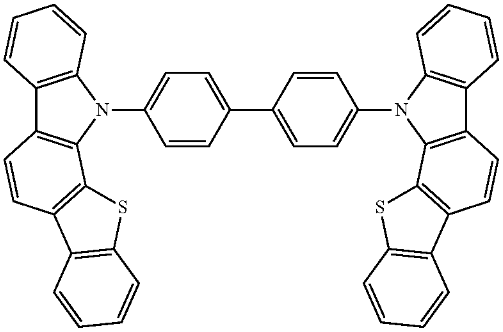
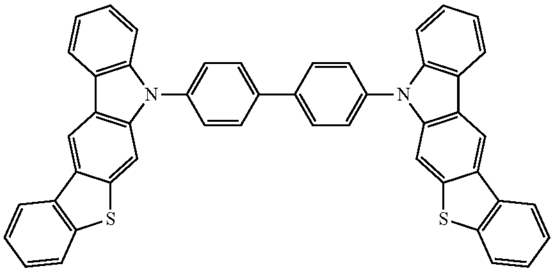
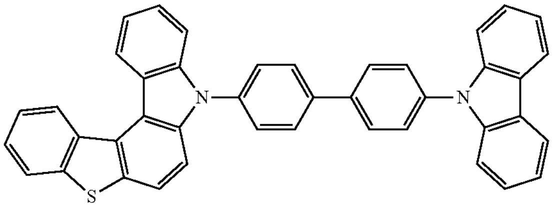
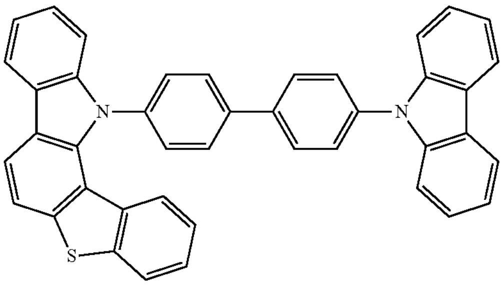
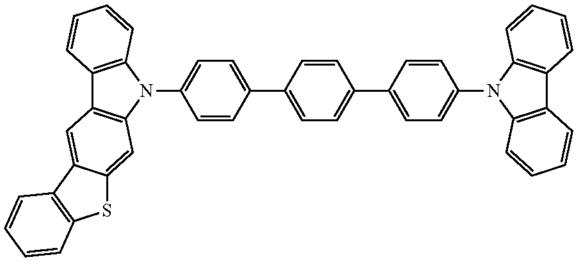

-continued
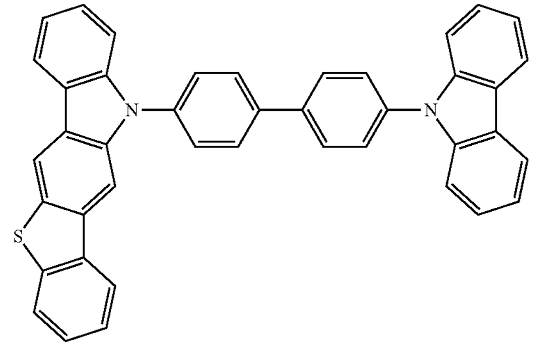
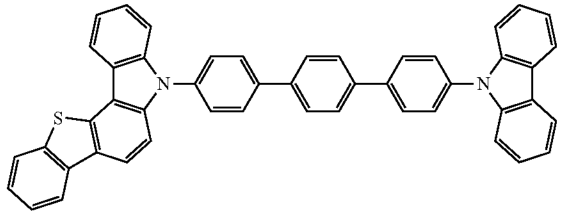
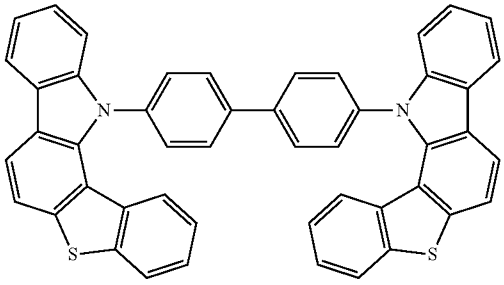
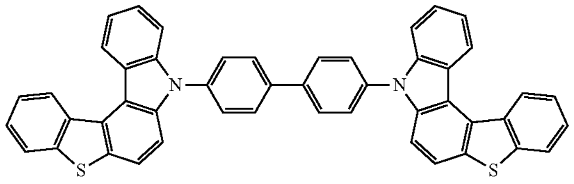
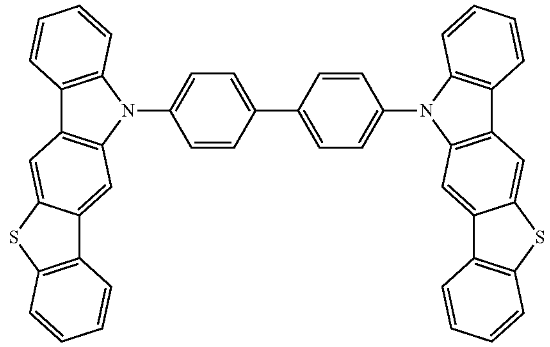
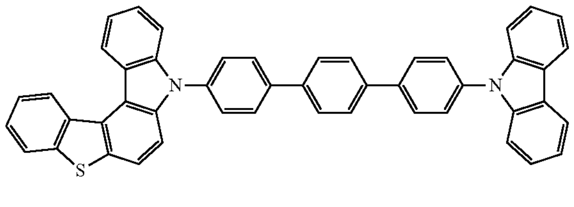
-continued
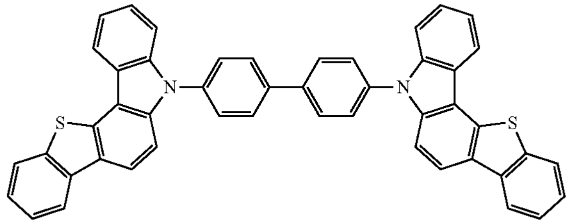
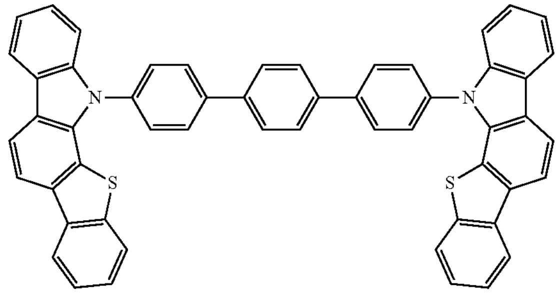
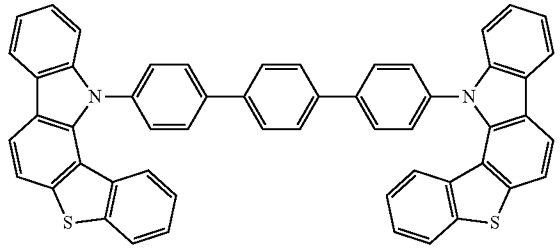
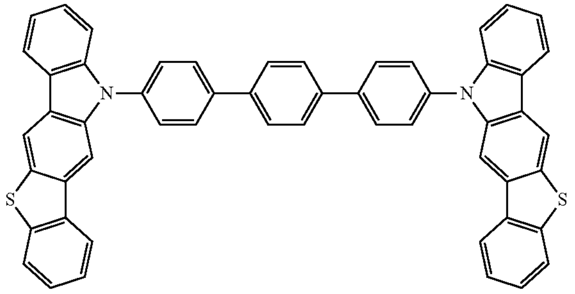
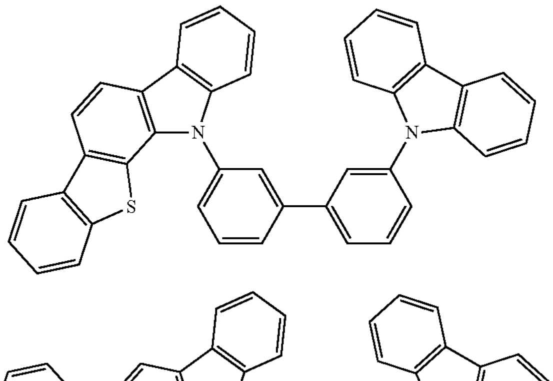
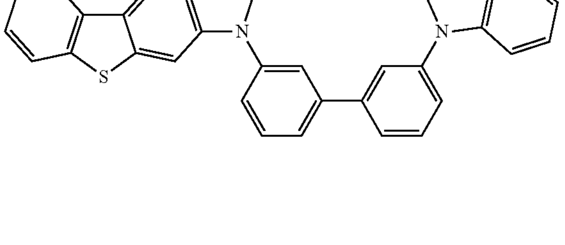

-continued
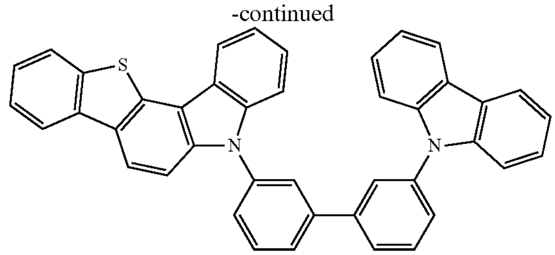
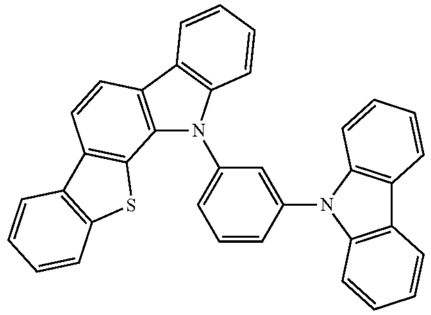
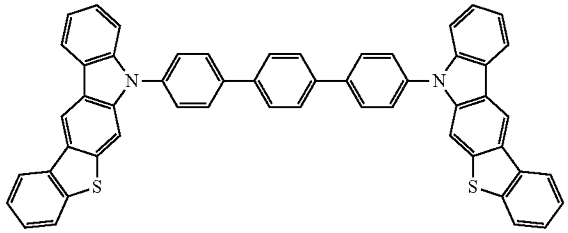
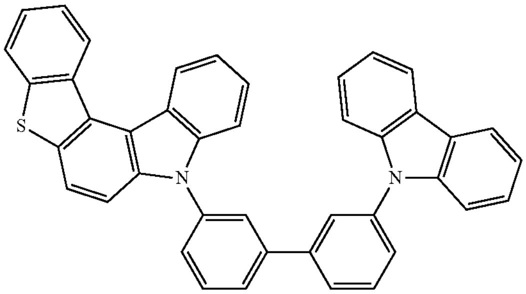
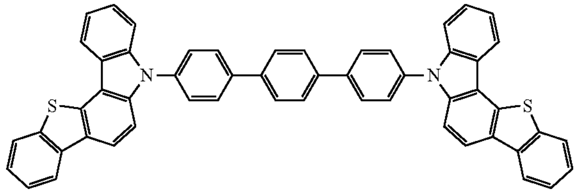
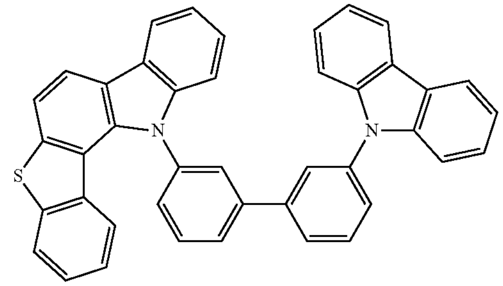
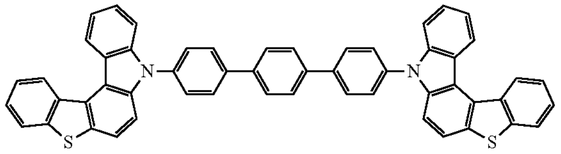
-continued
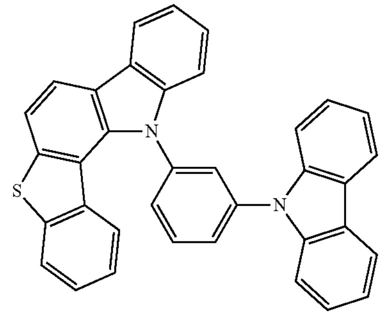
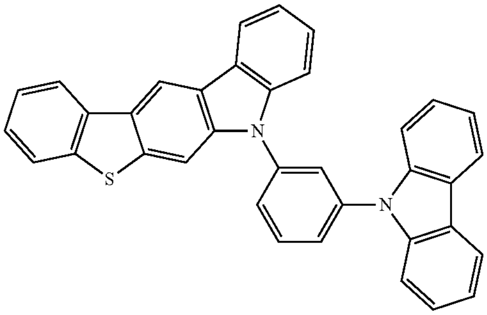
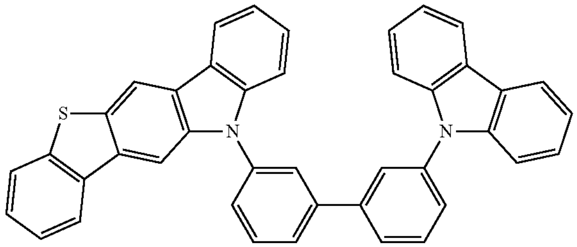
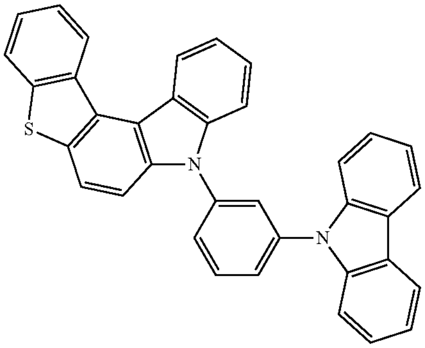
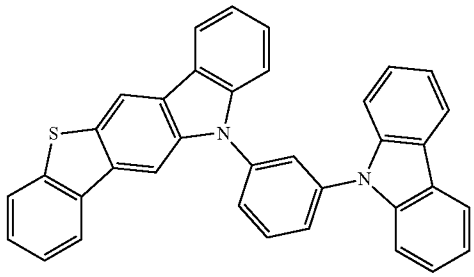
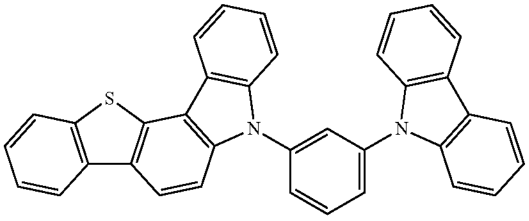

-continued
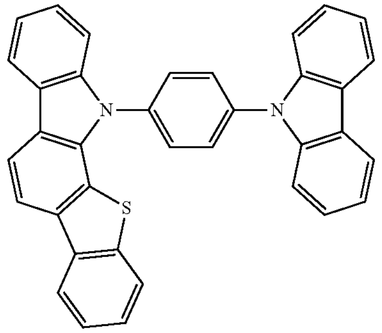
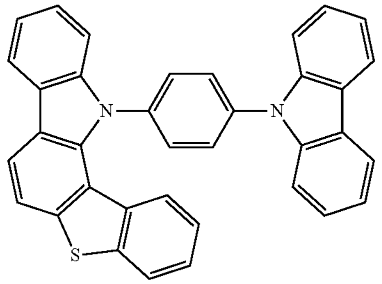
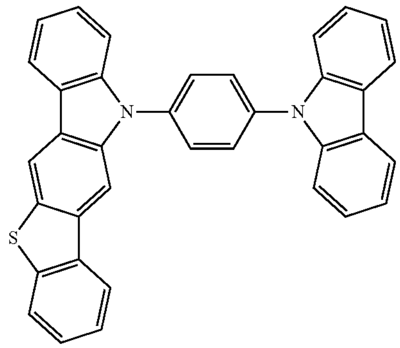
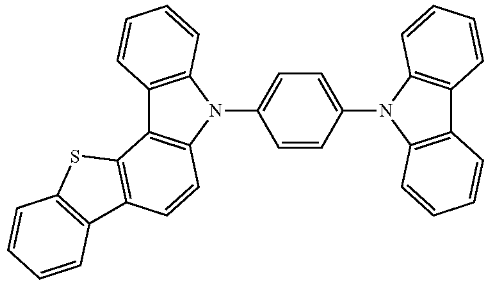
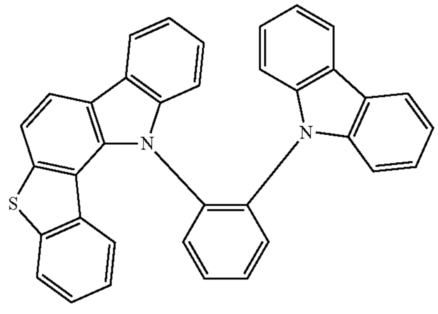
-continued
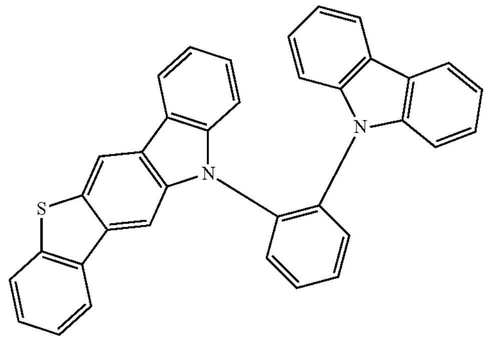
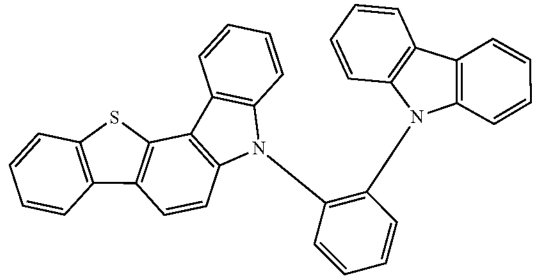
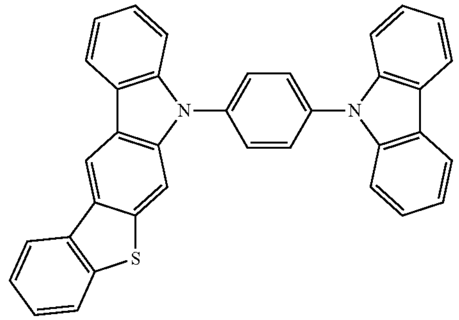
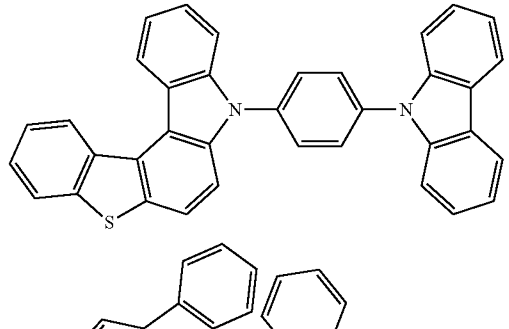
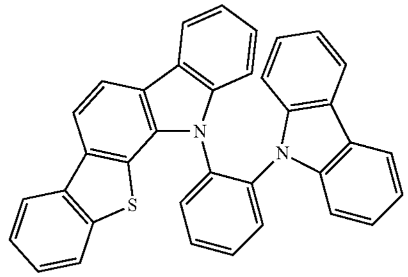
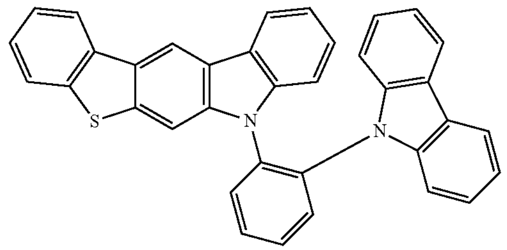

-continued
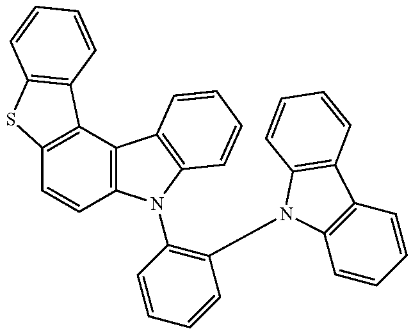
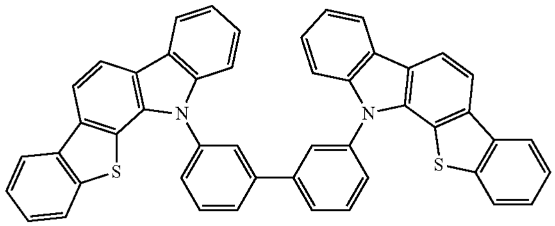
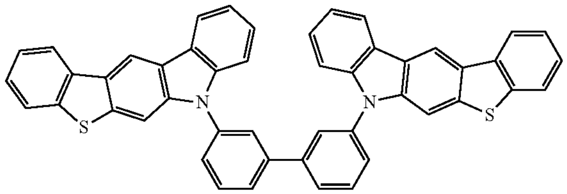
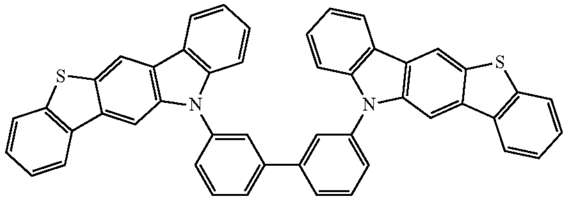
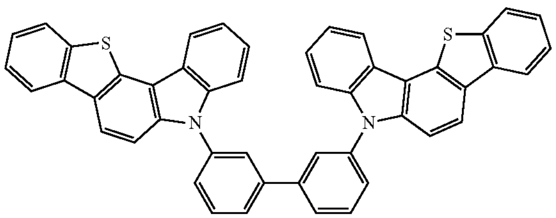
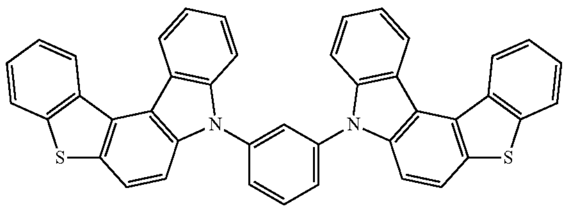
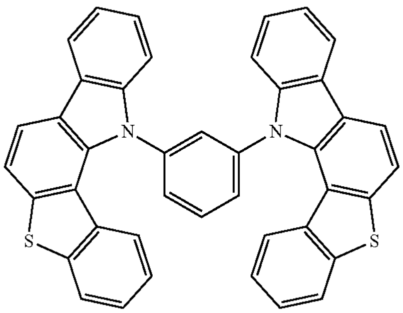
-continued
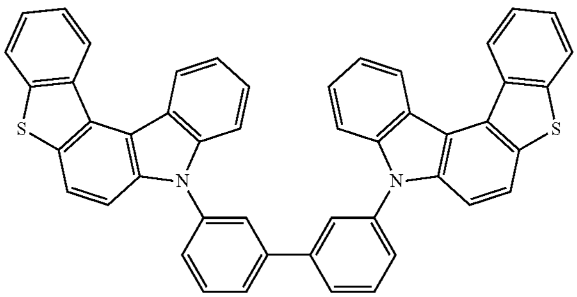
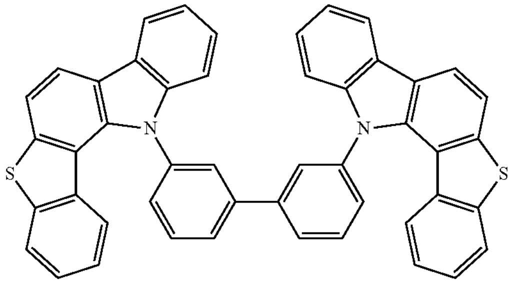
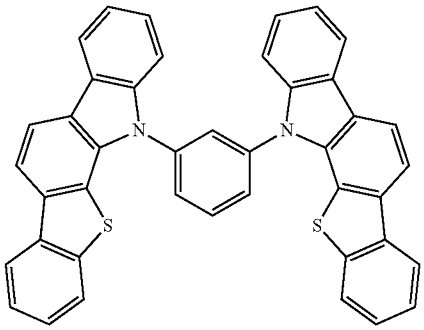
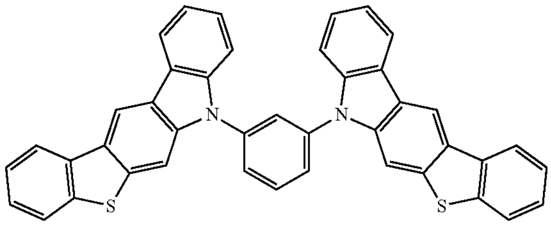
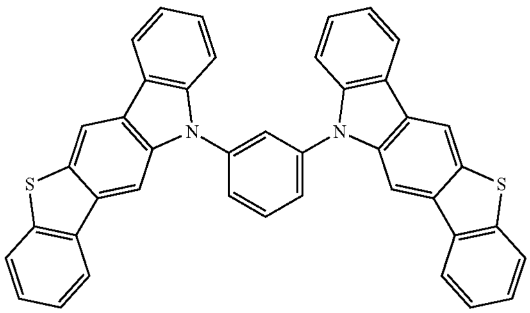
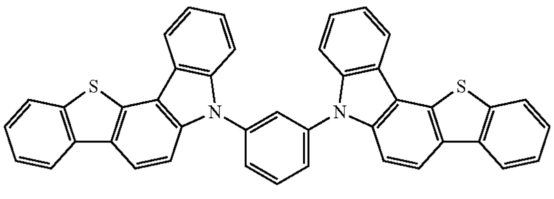

-continued
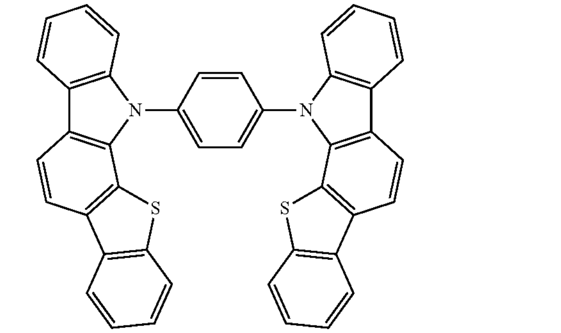
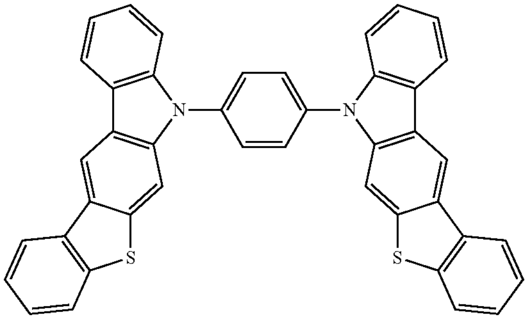
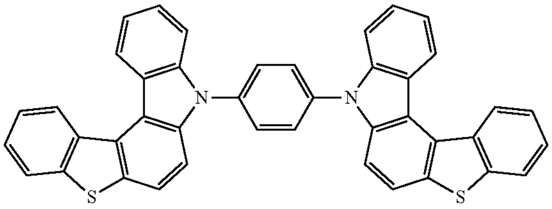
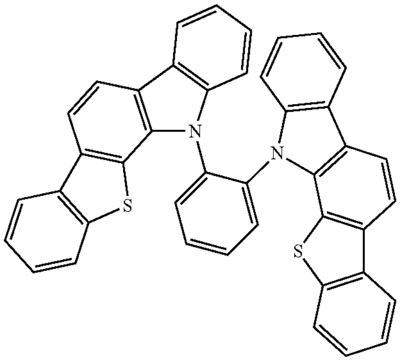
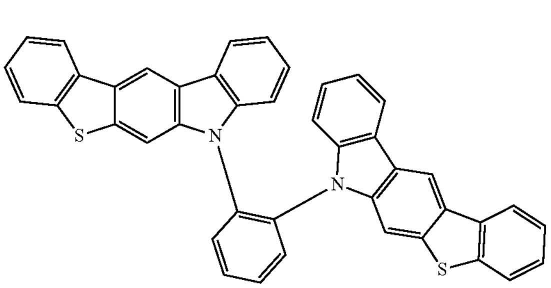
-continued
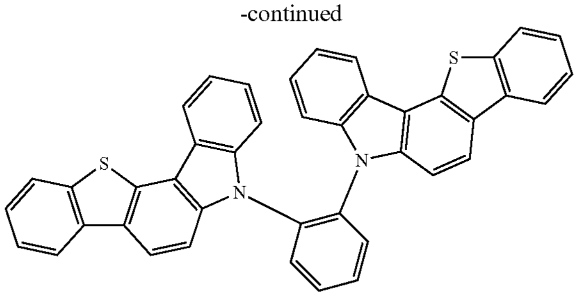
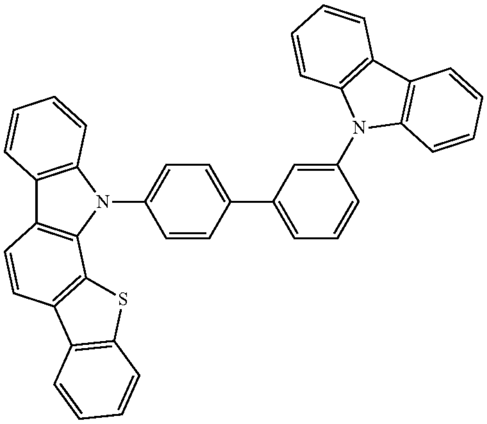
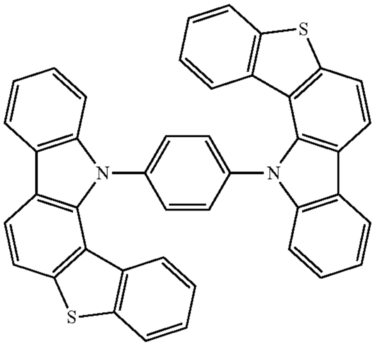
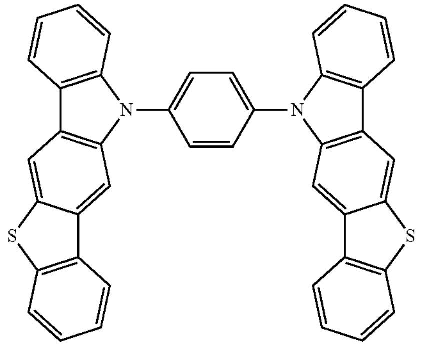
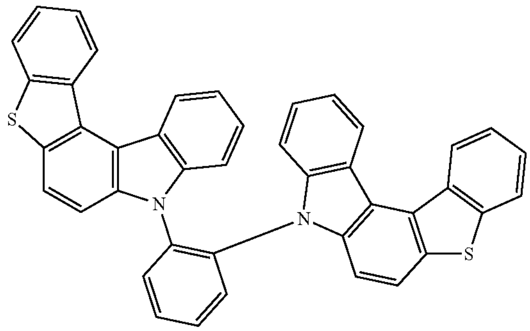

-continued
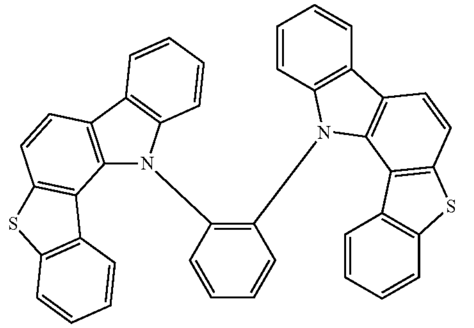
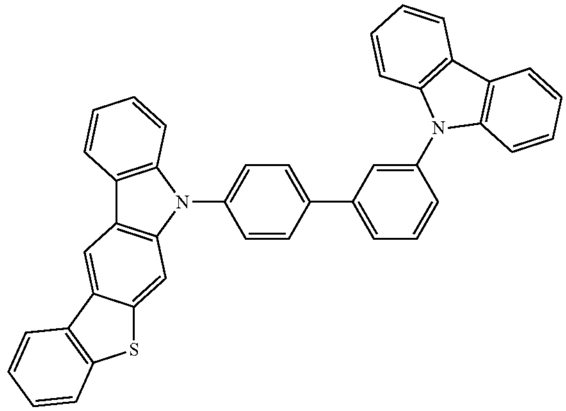
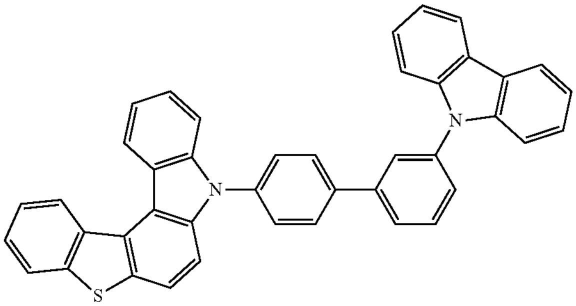
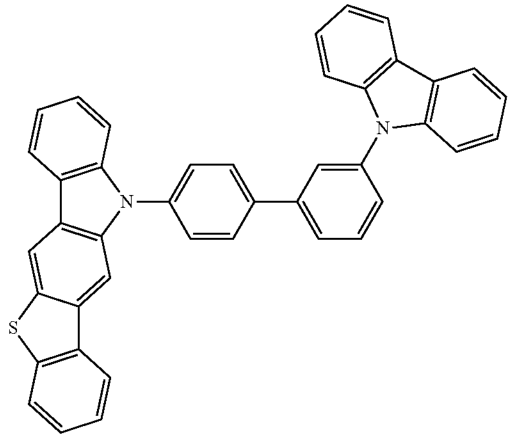
-continued
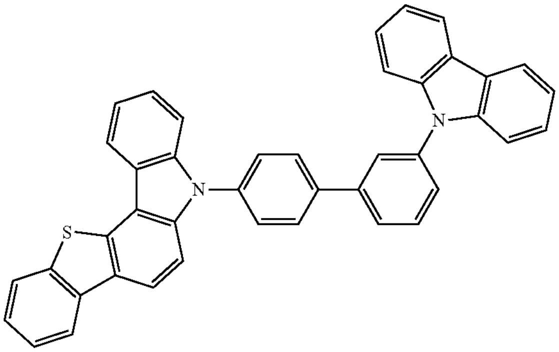
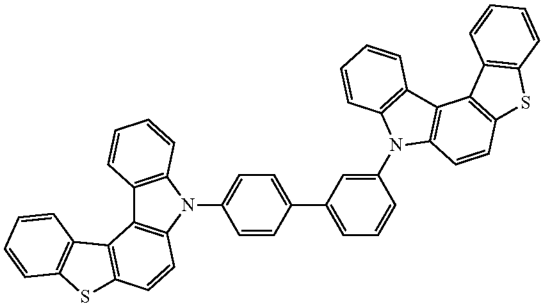
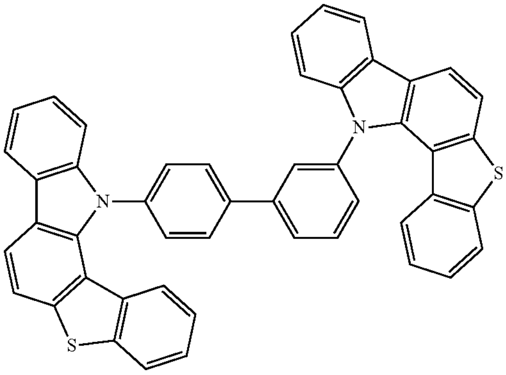
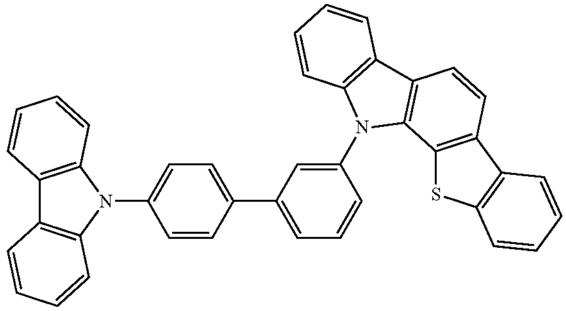
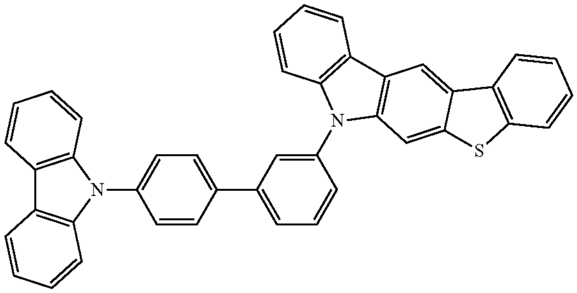

-continued
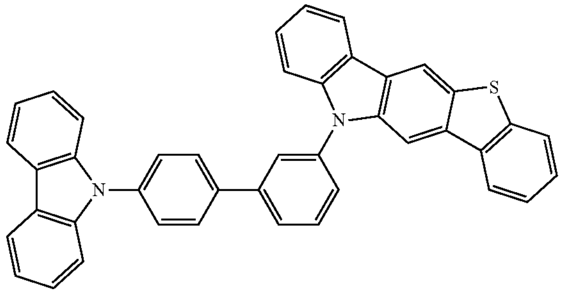
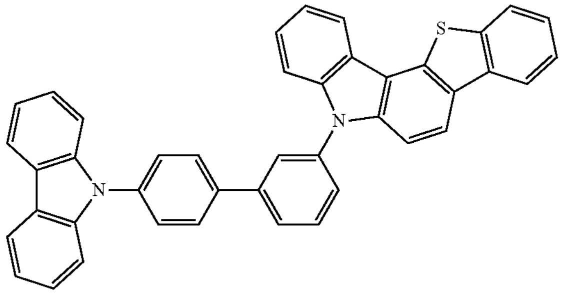
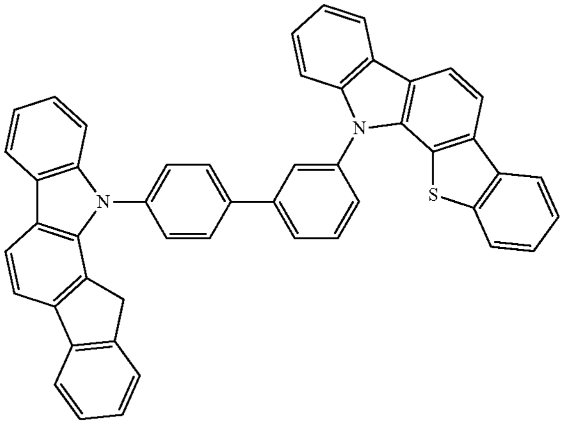
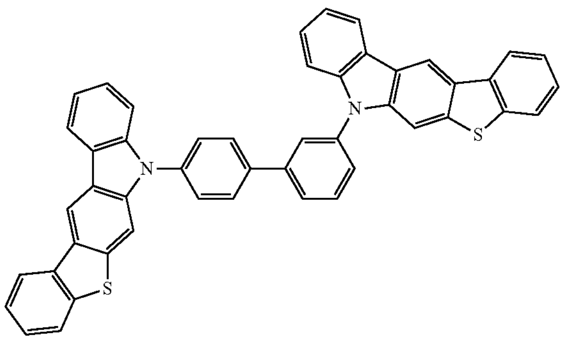
-continued
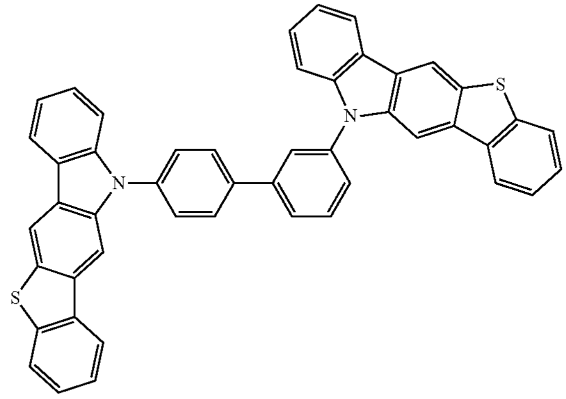
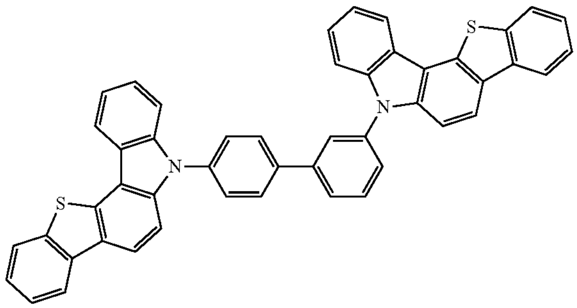
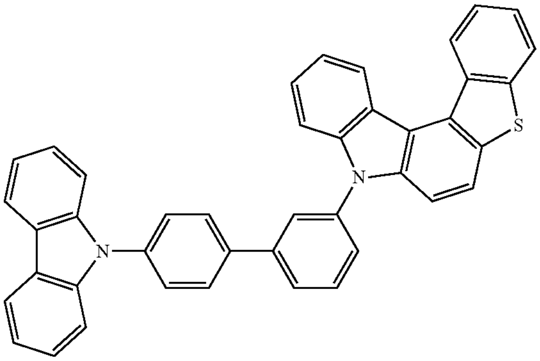
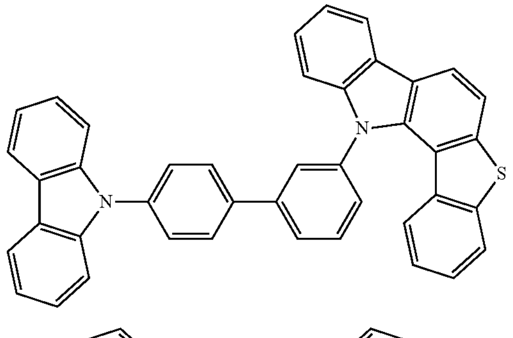
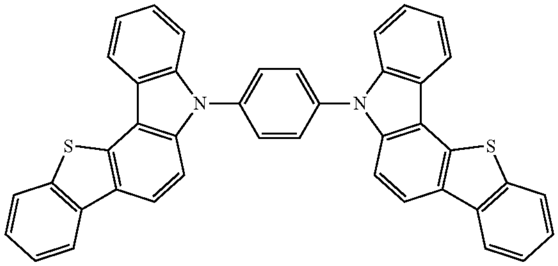

-continued
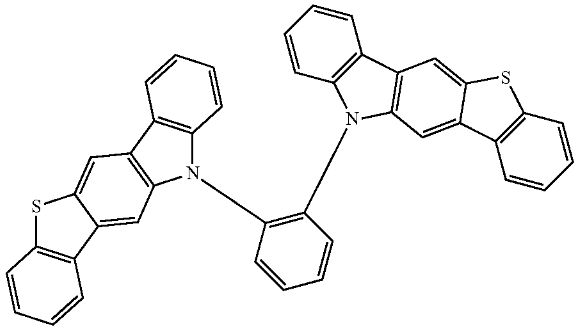
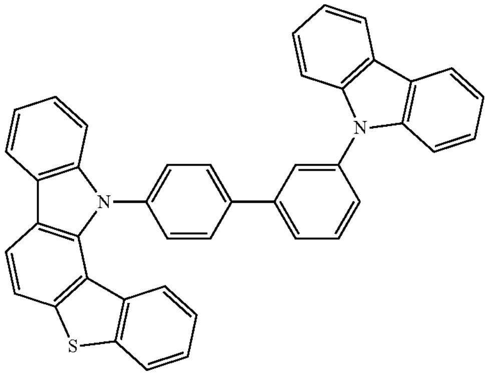
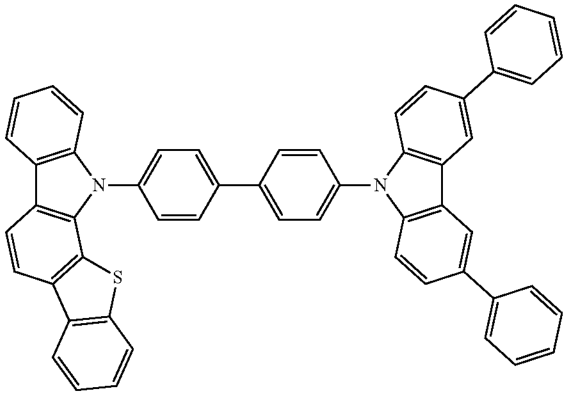
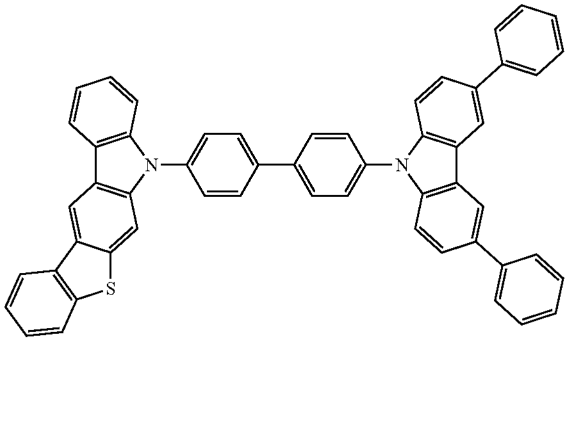
-continued
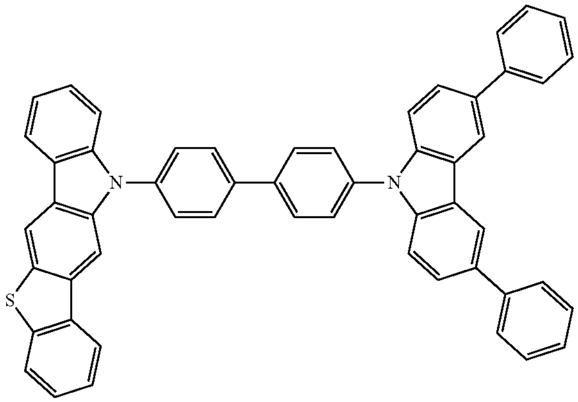
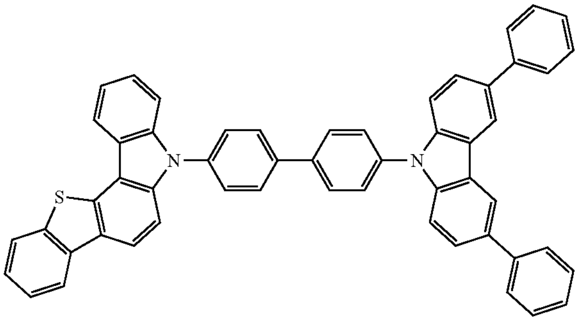
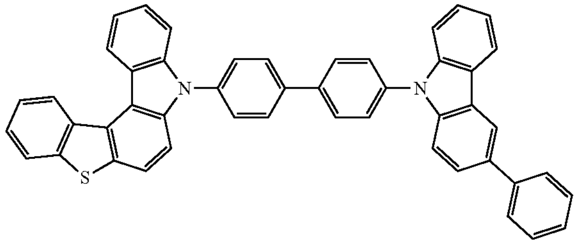
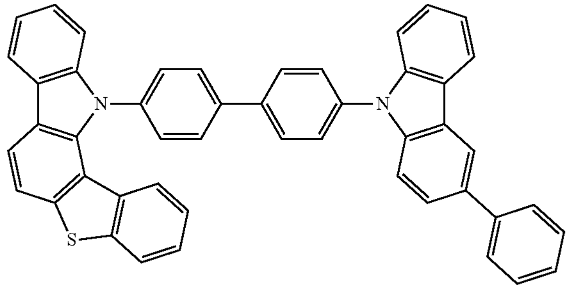
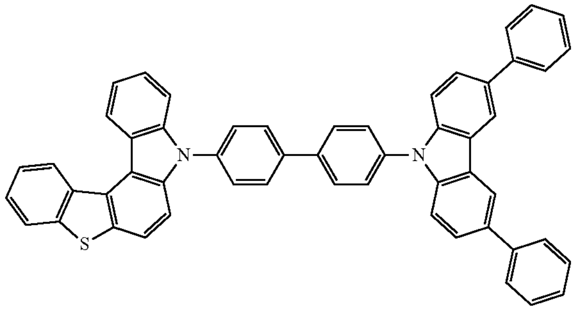

-continued
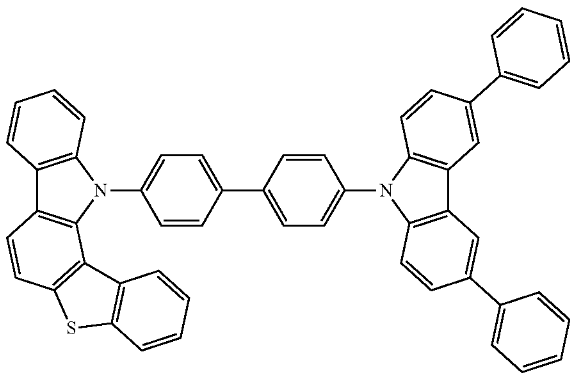
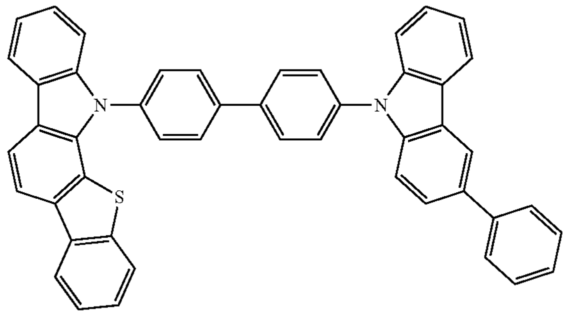
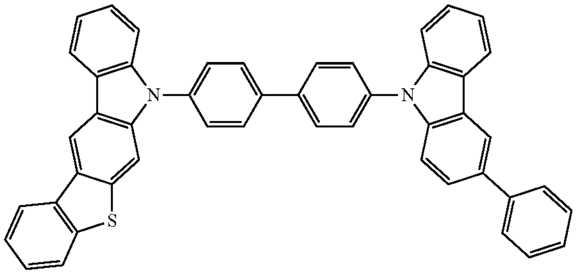
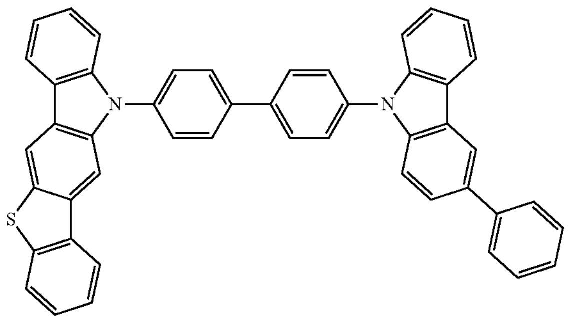
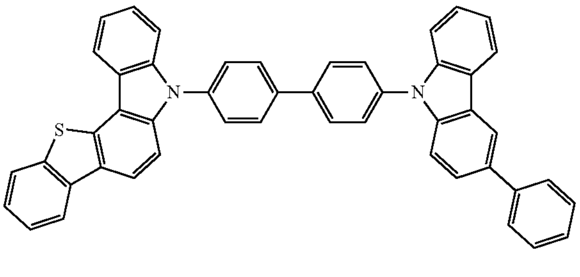
-continued
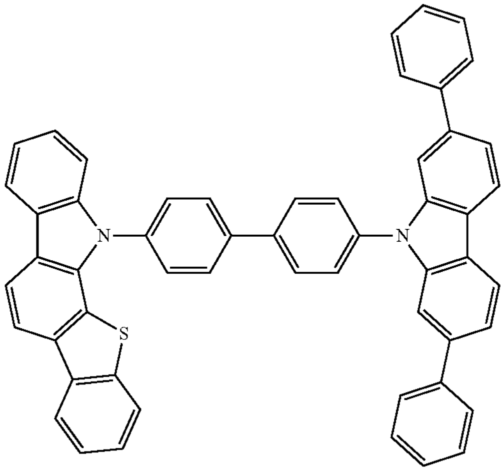
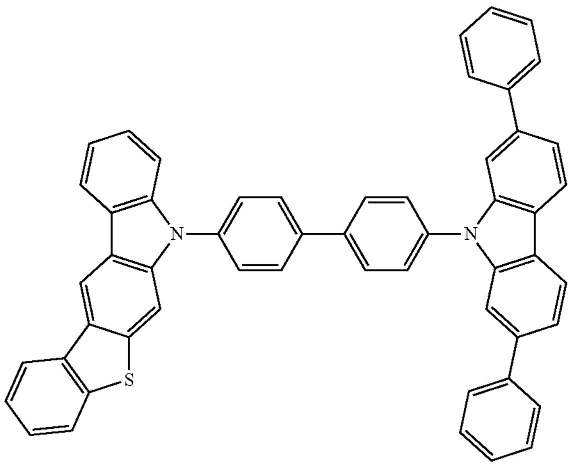
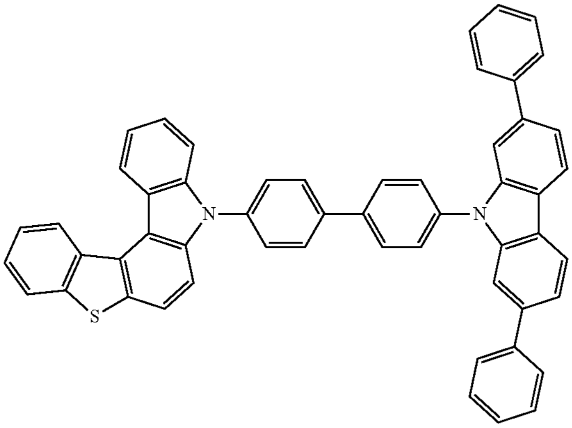

-continued
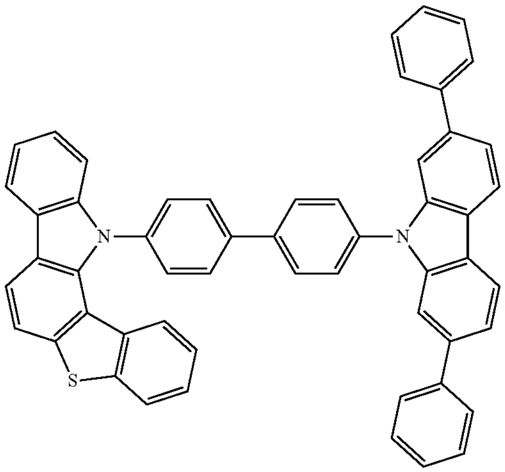
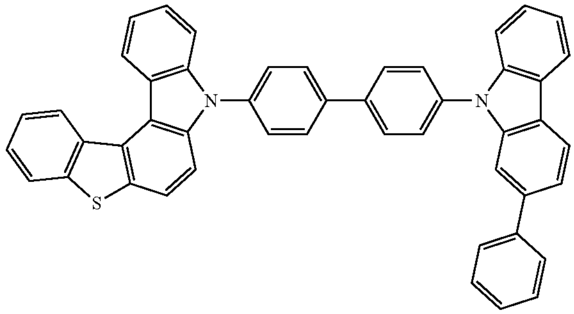
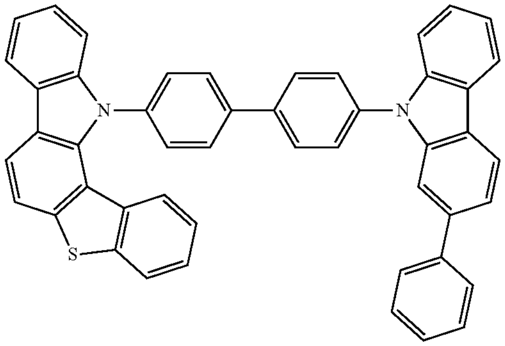
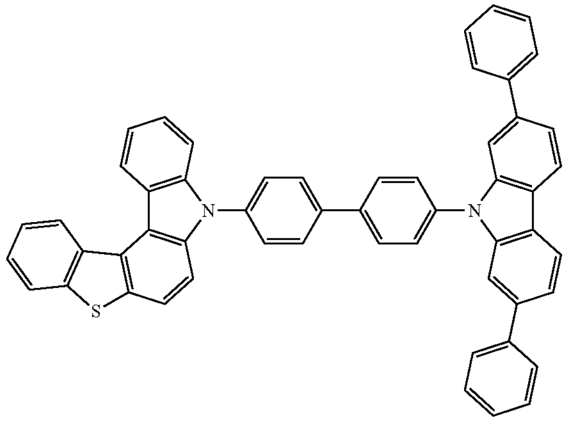
-continued
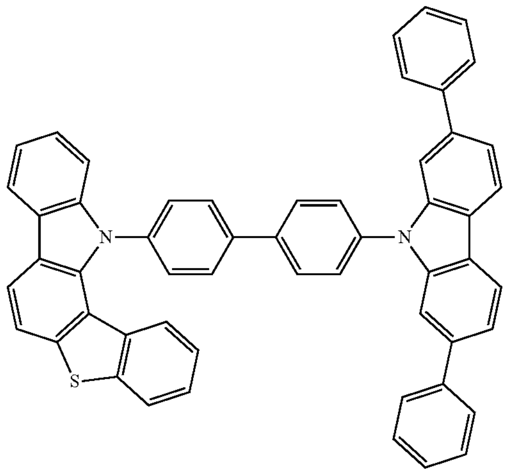
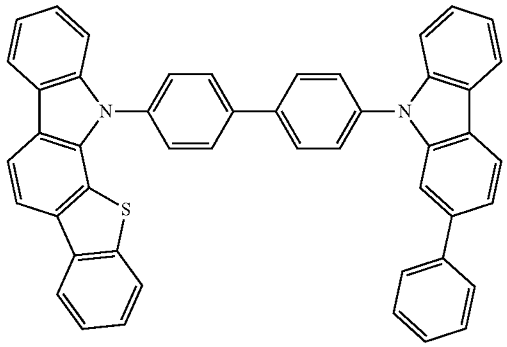
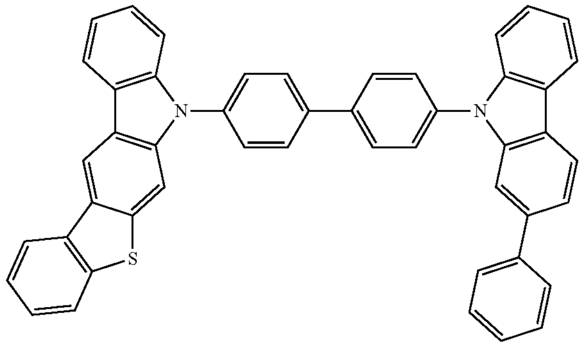
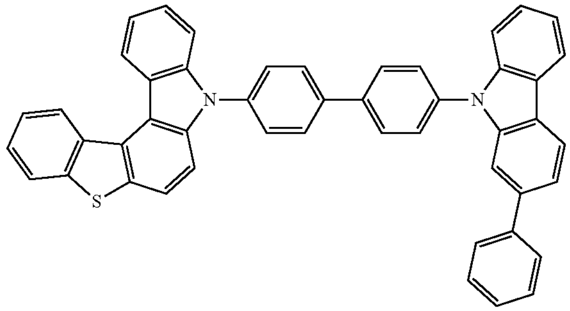

-continued
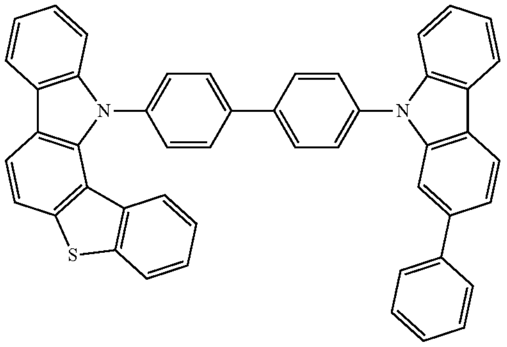
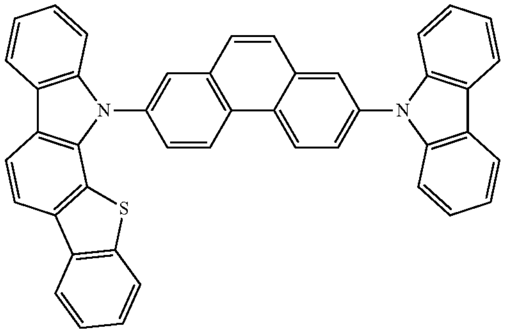
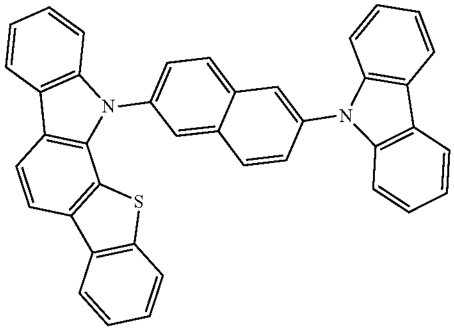
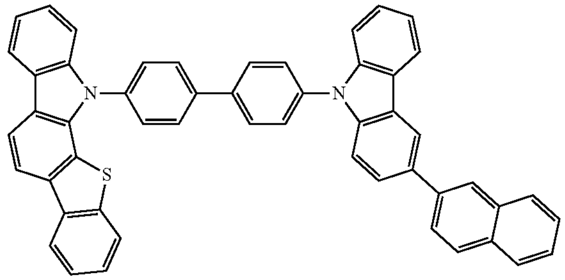
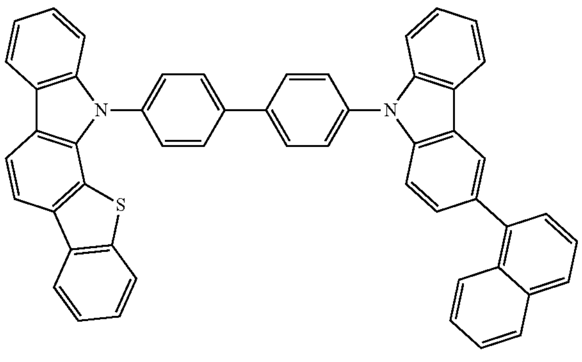
-continued
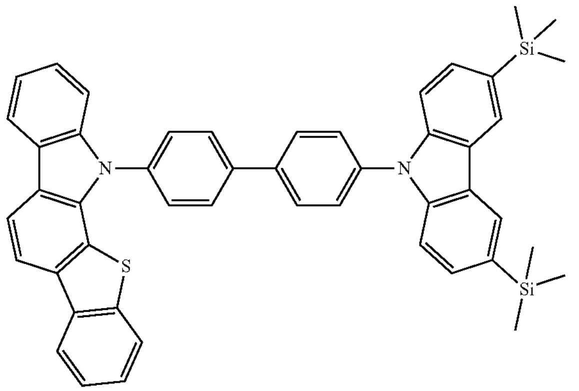
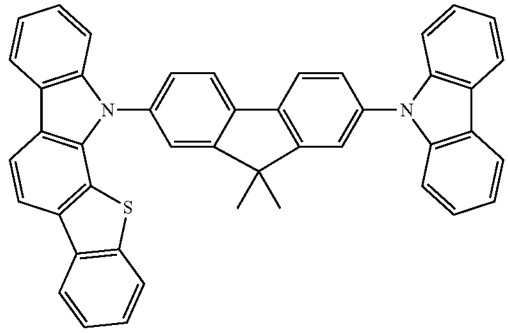
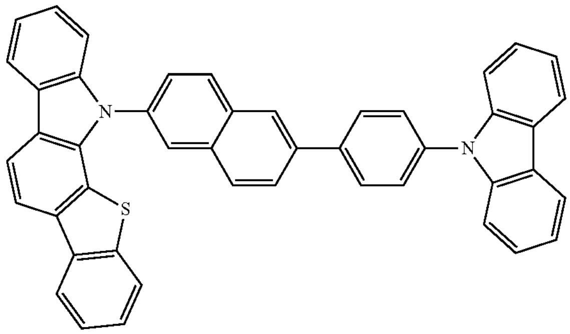
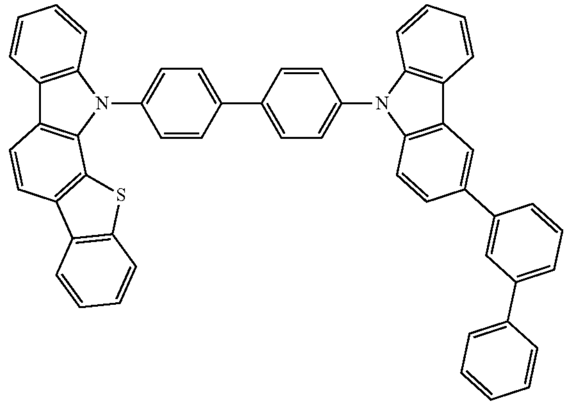

-continued
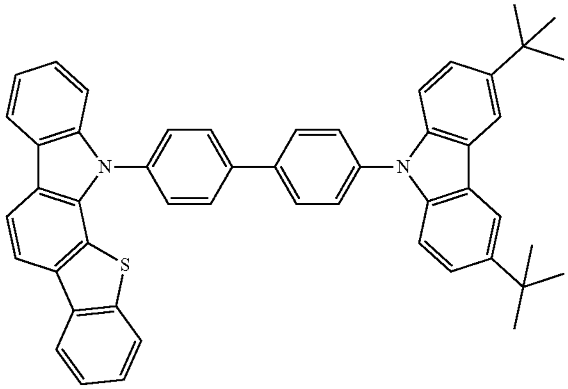
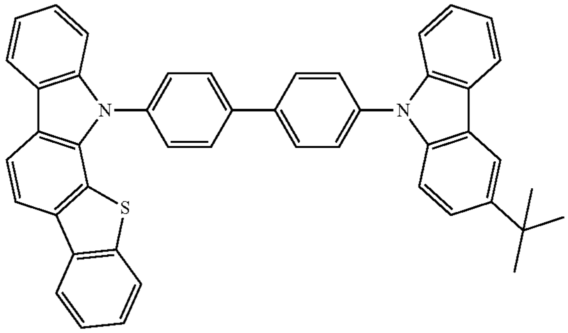
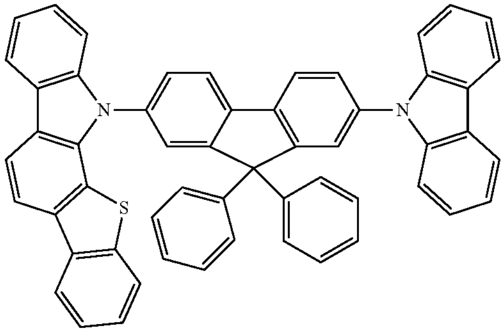
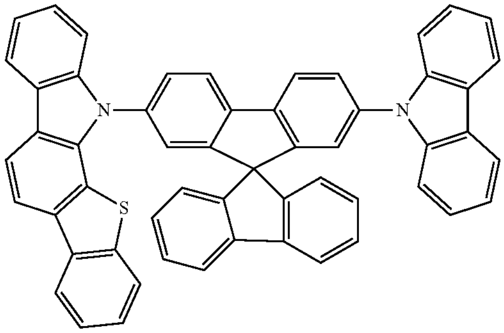
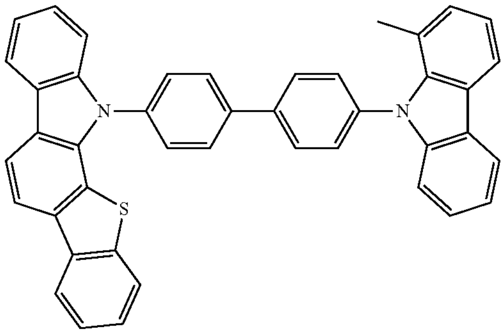
-continued
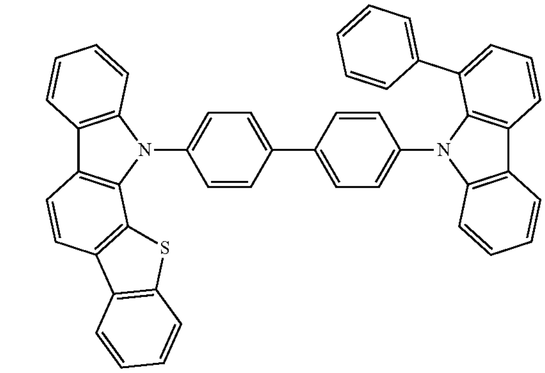
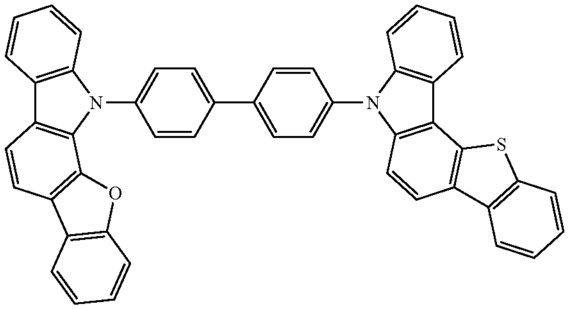
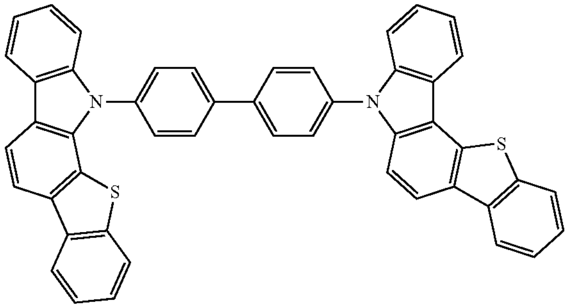
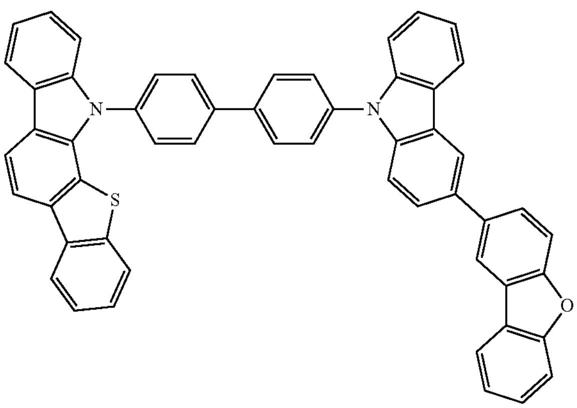

-continued
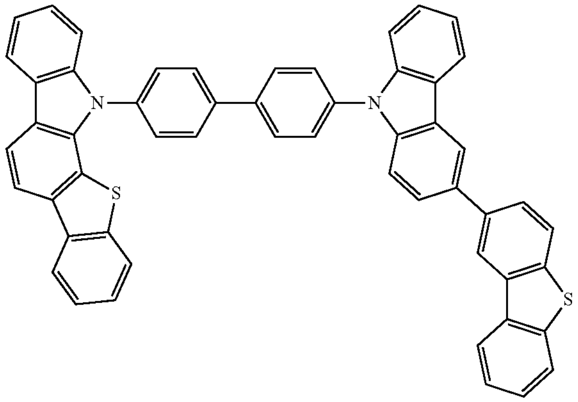
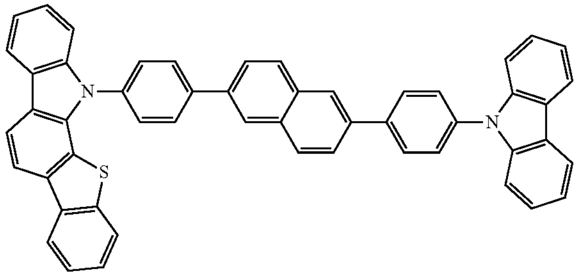
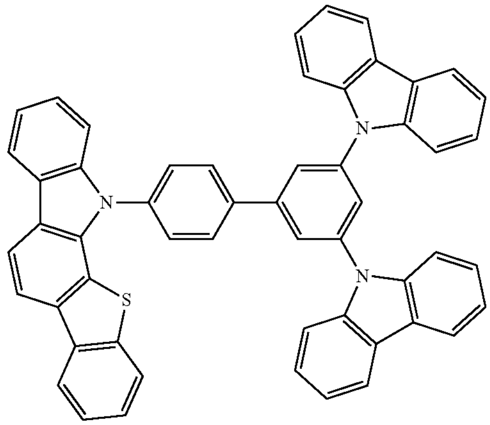
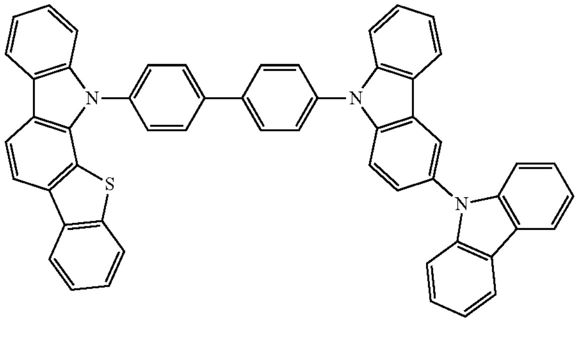
-continued
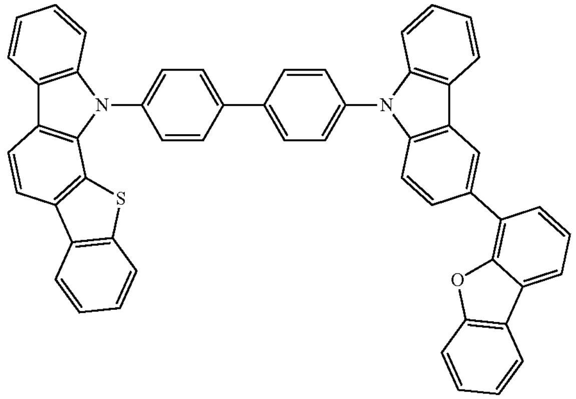
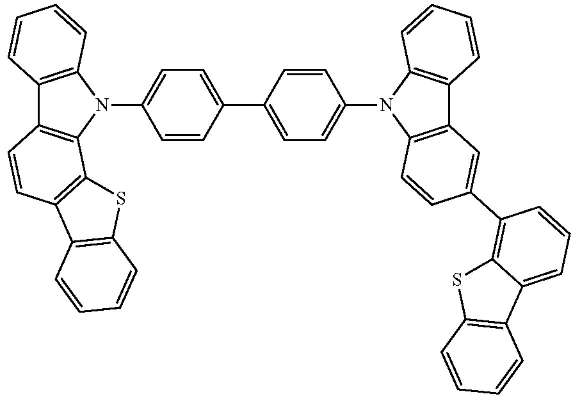
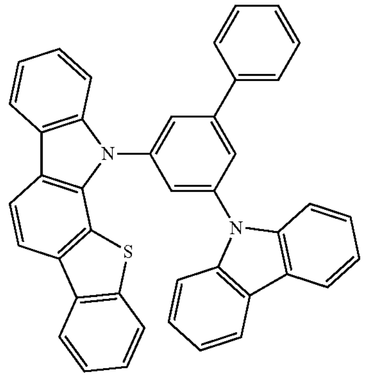
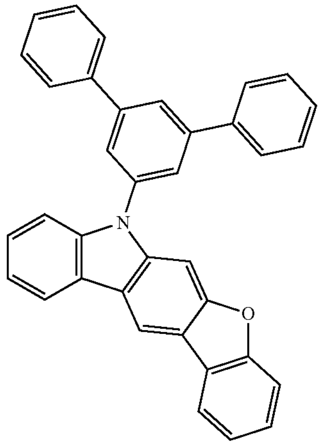

-continued

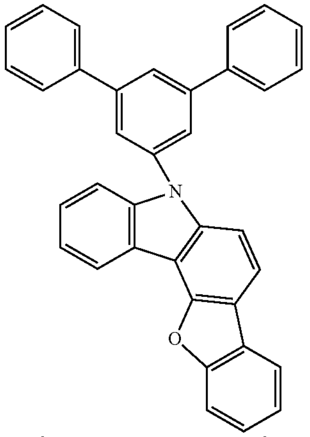

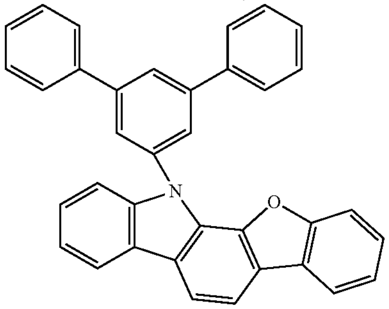

Second Compound

The emitting layer of the exemplary embodiment contains a second compound represented by a formula (2) below.

The second compound of the exemplary embodiment may be a thermally activated delayed fluorescent compound or a compound exhibiting no thermally activated delayed fluorescence.

The second compound of the exemplary embodiment is preferably a compound exhibiting no thermally activated delayed fluorescence.

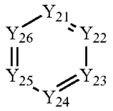

(2)

$$*—L_{21}—(L_{22}—R_B)_{n2}$$

(2A)

In the formula (2):

$Y_{21}$ to $Y_{26}$ are each independently a nitrogen atom or $CR_A$, and at least one of $Y_{21}$ to $Y_{26}$ is a nitrogen atom;

$R_A$ is a hydrogen atom, a substituent or a group represented by the formula (2A), or at least one combination of adjacent ones of $R_A$ are bonded to each other to form a ring;

$R_B$ is a substituent;

when a plurality of $R_B$ are present, the plurality of $R_B$ are the same or different;

* represents a bonding position to a carbon atom in a six-membered ring in the formula (2);

$L_{21}$ is a single bond, a substituted or unsubstituted arylene group having 6 to 22 ring carbon atoms, a trivalent, tetravalent, pentavalent, or hexavalent group derived from the arylene group, a substituted or unsubstituted divalent heterocyclic group having 5 to 22 ring atoms, a trivalent, tetravalent, pentavalent, or hexavalent group derived from the heterocyclic group, or a divalent group formed by bonding two groups selected from the group consisting of a substituted or unsubstituted arylene group having 6 to 22 ring carbon atoms and a substituted or unsubstituted divalent heterocyclic group having 5 to 22 ring atoms, a trivalent, tetravalent, pentavalent, or hexavalent group derived from the divalent group;

$L_{22}$ is a single bond, a substituted or unsubstituted arylene group having 6 to 22 ring carbon atoms, a substituted or unsubstituted divalent heterocyclic group having 5 to 22 ring atoms, n2 is 1, 2, 3, 4, or 5;

when $L_{21}$ is a single bond, n2 is 1, and $L_{22}$ is bonded to a carbon atom in the six-membered ring in the formula (2);

when a plurality of $L_{22}$ are present, the plurality of $L_{22}$ are the same or different;

$R_A$ and $R_B$ as a substituent are each independently a halogen atom, a cyano group, a substituted or unsubstituted aryl group having 6 to 50 ring carbon atoms, a substituted or unsubstituted heterocyclic group having 5 to 50 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, a group represented by $—N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group a substituted boryl group, or a substituted or unsubstituted arylthio group having 6 to 30 ring carbon atoms, and Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

Two Rz in $—N(Rz)_2$ are mutually the same or different.

A substituent for a "substituted or unsubstituted" group as $L_{21}$, $L_{22}$, $R_A$ and $R_B$ in the formula (2) are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, a group represented by —N(Rz)$_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group a substituted boryl group, or a substituted or unsubstituted arylthio group having 6 to 30 ring carbon atoms; and Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

Two Rz in —N(Rz)$_2$ are mutually the same or different.

As $L_{21}$, "a trivalent group derived from the arylene group" is a group obtained by removing one hydrogen atom from the arylene group. "A tetravalent group derived from the arylene group" is a group obtained by removing two hydrogen atoms from the arylene group. "A pentavalent group derived from the arylene group" is a group obtained by removing three hydrogen atoms from the arylene group. "A hexavalent group derived from the arylene group" is a group obtained by removing four hydrogen atoms from the arylene group.

The same applies to "a trivalent group derived from the divalent heterocyclic group", "a tetravalent group derived from the divalent heterocyclic group", "a pentavalent group derived from the divalent heterocyclic group", and "a hexavalent group derived from the divalent heterocyclic group".

A bonding form of the group represented by the formula (2A) is determined depending on a value of n2.

The bonding form of the group represented by the formula (2A) in which n2 is 1 is represented by a formula (2A-1) below. In this case, $L_{21}$ is, for instance, an "arylene group".

The bonding form of the group represented by the formula (2A) in which n2 is 2 is represented by a formula (2A-2). In this case, $L_{21}$ is, for instance, "a trivalent group derived from the arylene group".

The bonding form of the group represented by the formula (2A) in which n2 is 3 is represented by a formula (2A-3). In this case, $L_{21}$ is, for instance, "a tetravalent group derived from the arylene group".

The bonding form of the group represented by the formula (2A) in which n2 is 4 is represented by a formula (2A-4). In this case, $L_{21}$ is, for instance, "a pentavalent group derived from the arylene group".

The bonding form of the group represented by the formula (2A) in which n2 is 5 is represented by a formula (2A-5). In this case, $L_{21}$ is, for instance, "a hexavalent group derived from the arylene group".

In the formulae (2A-1) to (2A-5), * represents a bonding position to a carbon atom in a six-membered ring in the formula (2).

(2A-1)

$*—L_{21}—L_{22}—R_B$ (2A-2)

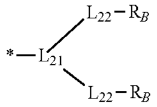

-continued (2A-3)

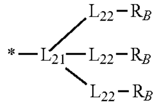

(2A-4)

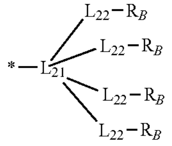

(2A-5)

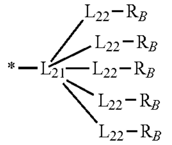

The bonding form of the group represented by the formula (2A) in which n2 is 1 and $L_{21}$ is "a divalent group formed by bonding two groups of a substituted or unsubstituted arylene group $L_{211}$ having 6 to 22 ring carbon atoms and a substituted or unsubstituted divalent heterocyclic group $L_{212}$ having 5 to 22 ring atoms" is represented by a formula (2A-6).

The bonding form of the group represented by the formula (2A) in which n2 is 2 and $L_{21}$ is "a trivalent group formed by bonding two groups of the arylene group $L_{211}$ and the divalent heterocyclic group $L_{212}$" is represented by a formula (2A-7).

The bonding form of the group represented by the formula (2A) in which n2 is 3 and $L_{21}$ is "a tetravalent group formed by bonding two groups of the arylene group $L_{211}$ and the divalent heterocyclic group $L_{212}$" is represented by a formula (2A-8).

The bonding form of the group represented by the formula (2A) in which n2 is 4 and $L_{21}$ is "a pentavalent group formed by bonding two groups of the arylene group $L_{211}$ and the divalent heterocyclic group $L_{212}$" is represented by a formula (2A-9).

The bonding form of the group represented by the formula (2A) in which n2 is 5 and $L_{21}$ is "a hexavalent group formed by bonding two groups of the arylene group $L_{211}$ and the divalent heterocyclic group $L_{212}$" is represented by a formula (2A-10).

In the formulae (2A-6) to (2A-10), * represents a bonding position to a carbon atom in a six-membered ring in the formula (2).

(2A-6)

$*—L_{211}—L_{212}—L_{22}—R_B$ (2A-7)

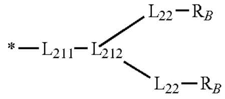

(2A-8)

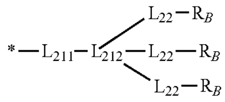

-continued (2A-9)

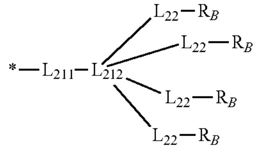

(2A-10)

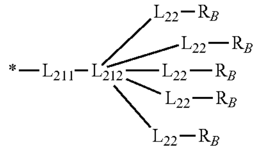

In the second compound of the exemplary embodiment, the formula (2) is preferably represented by one of formulae (21) to (23).

(21)

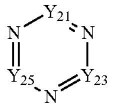

(22)

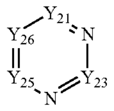

(23)

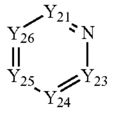

In the formulae (21) to (23), $Y_{21}$ and $Y_{23}$ to $Y_{26}$ are $CR_A$. $R_A$ each independently represents the same as $R_A$ defined when $Y_{21}$ to $Y_{26}$ are $CR_A$ in the formula (2).

In the second compound of the exemplary embodiment, the formula (2) is preferably the formula (21).

In the second compound of the exemplary embodiment, it is preferable that at least one of $Y_{21}$ to $Y_{26}$ is $CR_A$ and at least one $R_A$ is the group represented by the formula (2A).

In the second compound of the exemplary embodiment, it is preferable that at least one of $Y_{21}$ to $Y_{26}$ is $CR_A$, at least one $R_A$ is the group represented by the formula (2A), and $R_B$ in the formula (2A) is a substituted or unsubstituted fused aryl group having 10 to 50 ring carbon atoms or a substituted or unsubstituted fused heterocyclic group having 9 to 50 ring atoms.

In the second compound of the exemplary embodiment, it is more preferable that $R_B$ in the formula (2A) is a substituted or unsubstituted fused aryl group having 10 to 50 ring carbon atoms or a substituted or unsubstituted fused heterocyclic group having 13 to 50 ring atoms.

The "fused aryl group having 10 to 50 ring carbon atoms" is an aryl group having 10 to 50 ring carbon atoms and having a partial structure of two rings sharing one side. It should be noted that the partial structure of two rings sharing one side may be present in plural number.

The "fused heterocyclic group having 9 to 50 ring atoms" is a heterocyclic group having 9 to 50 ring atoms and having a partial structure of two rings sharing one side. It should be noted that the partial structure of two rings sharing one side may be present in plural number.

In the second compound of the exemplary embodiment, $R_B$ is preferably any one of groups represented by formulae (c1) to (c9).

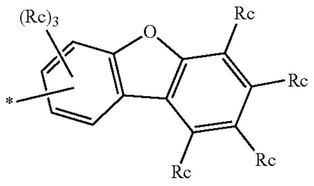

(c1)

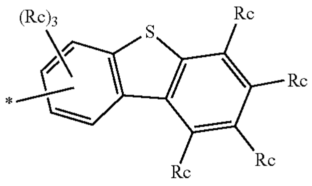

(c2)

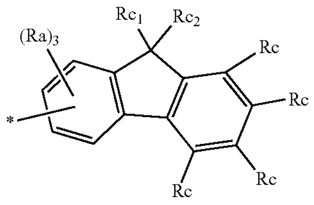

(c3)

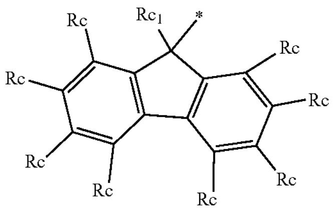

(c4)

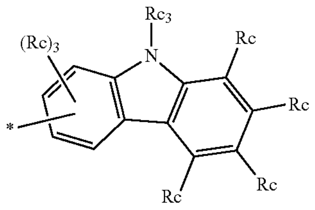

(c5)

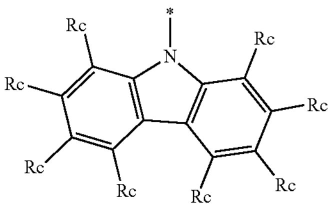

(c6)

-continued

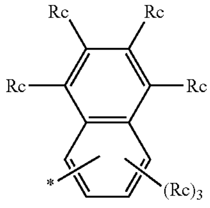

(c7)

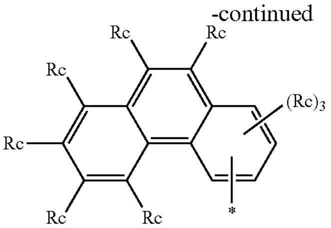

(c8)

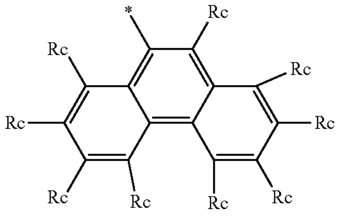

(c9)

In the formulae (c1) to (c9), Rc is a hydrogen atom or a substituent, or at least one pair of adjacent ones of Rc are bonded to each other to form a ring, a plurality of Rc being mutually the same or different, $Rc_1$ and $Rc_2$ are each independently a hydrogen atom or a substituent, or a pair of $Rc_1$ and $Rc_2$ are bonded to each other to form a ring, $Rc_3$ is a hydrogen atom or a substituent, and when Rc, $Rc_1$, $Rc_2$ and $Rc_3$ are each a substituent, the substituent represents the same as the substituent for a "substituted or unsubstituted" group as $R_B$ in the formula (2).

In the formulae (c1) to (c9), Rc is preferably a hydrogen atom, a substituted or unsubstituted aryl group having 6 to 30 ring carbon atoms, or a substituted or unsubstituted alkyl group having 1 to 30 carbon atoms, more preferably a hydrogen atom.

In the formulae (c3) to (c4), it is preferable that $Rc_1$ and $Rc_2$ are each independently a substituted or unsubstituted aryl group having 6 to 30 ring carbon atoms, or a substituted or unsubstituted alkyl group having 1 to 30 carbon atoms, or a pair of $Rc_1$ and $Rc_2$ are bonded to each other to form a ring.

In the formula (c5), $Rc_3$ is preferably a substituted or unsubstituted aryl group having 6 to 30 ring carbon atoms, a substituted or unsubstituted alkyl group having 1 to 30 carbon atoms, or a substituted or unsubstituted heterocyclic group having 5 to 30 ring atoms.

In the second compound of the exemplary embodiment, $R_B$ is preferably any one of groups represented by the formulae (c1) to (c6).

In the second compound of the exemplary embodiment, $L_{21}$ is preferably a single bond, or a divalent, trivalent, tetravalent, pentavalent or hexavalent group derived from any one group selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, a substituted or unsubstituted fluorenyl group, a substituted or unsubstituted dibenzofuranyl group, a substituted or unsubstituted dibenzothienyl group, and a substituted or unsubstituted carbazolyl group.

In the second compound of the exemplary embodiment, $L_{21}$ is more preferably a single bond, or a divalent, trivalent, tetravalent, pentavalent or hexavalent group derived from any one group selected from the group consisting of an unsubstituted phenyl group, an unsubstituted biphenyl group, an unsubstituted naphthyl group, an unsubstituted phenanthryl group, an unsubstituted terphenyl group, an unsubstituted fluorenyl group, an unsubstituted dibenzofuranyl group, an unsubstituted dibenzothienyl group, and an unsubstituted carbazolyl group.

In the second compound of the exemplary embodiment, $L_{22}$ is preferably a single bond, or a divalent group derived from any one group selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, a substituted or unsubstituted fluorenyl group, a substituted or unsubstituted dibenzofuranyl group, a substituted or unsubstituted dibenzothienyl group, and a substituted or unsubstituted carbazolyl group.

In the second compound of the exemplary embodiment, $L_{22}$ is more preferably a single bond, or a divalent group derived from any one group selected from the group consisting of an unsubstituted phenyl group, an unsubstituted biphenyl group, an unsubstituted naphthyl group, an unsubstituted phenanthryl group, an unsubstituted terphenyl group, an unsubstituted fluorenyl group, an unsubstituted dibenzofuranyl group, an unsubstituted dibenzothienyl group, and an unsubstituted carbazolyl group.

Manufacturing Method of Second Compound

The second compound of the exemplary embodiment can be manufactured by a known method.

Specific Examples of Second Compound

Specific examples of the second compound of the exemplary embodiment include, for example, the following compounds. However, the invention is not limited to the specific examples of the compounds.

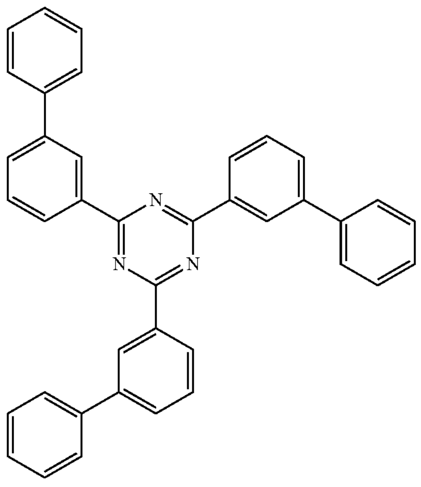

-continued
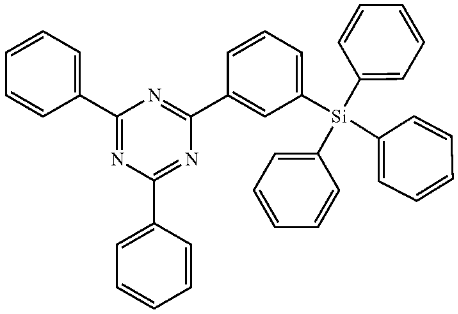
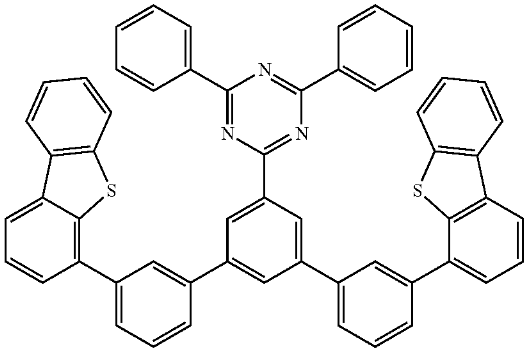
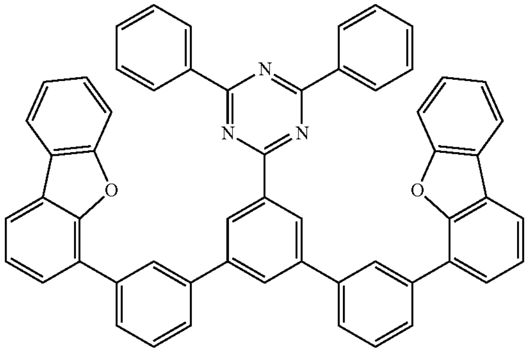
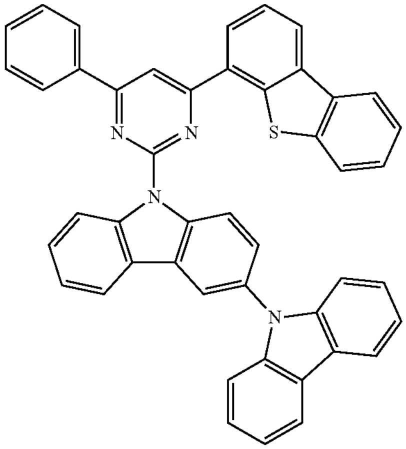
-continued
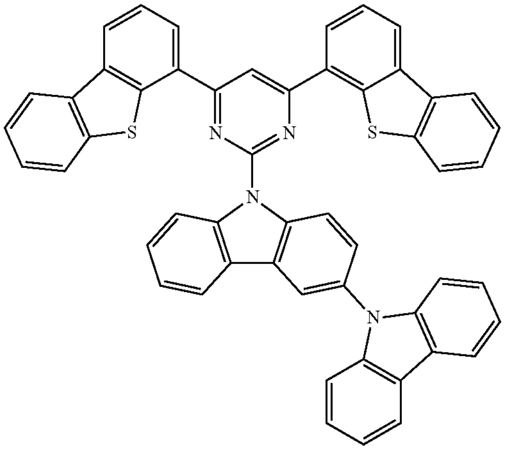
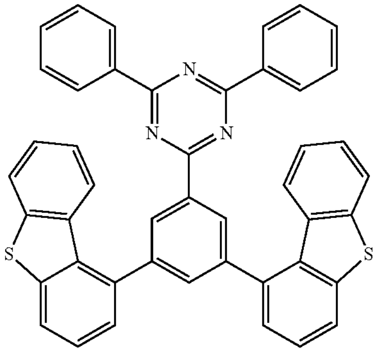
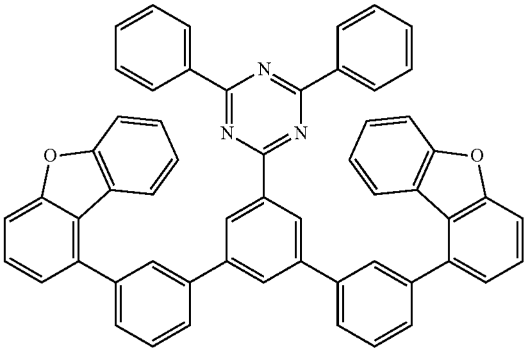
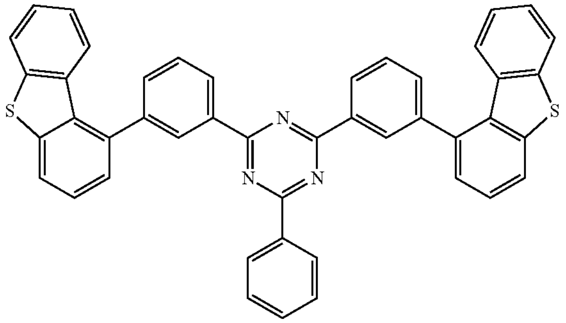

-continued
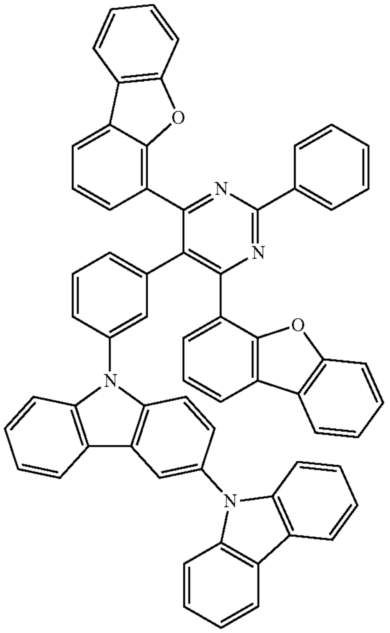
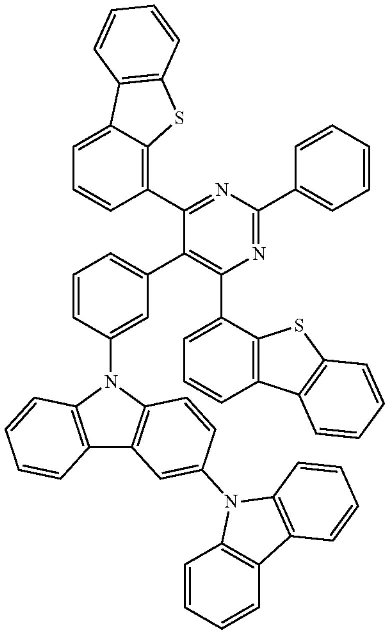
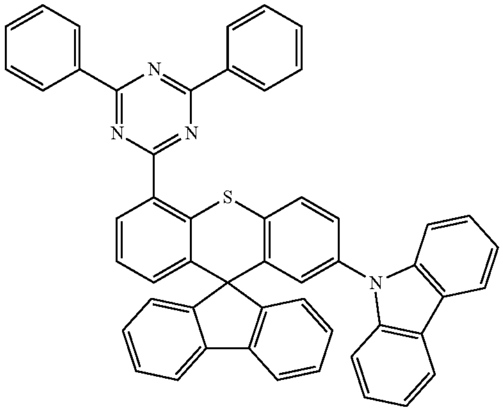
-continued
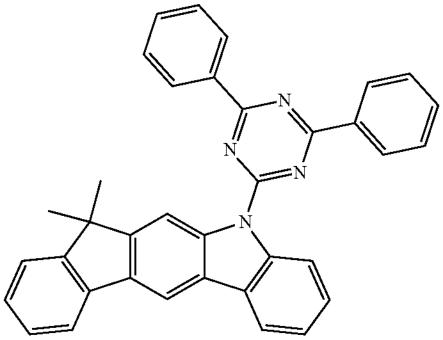
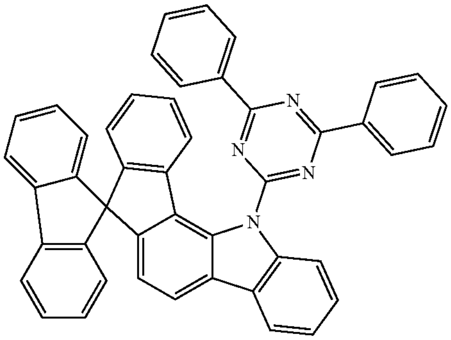
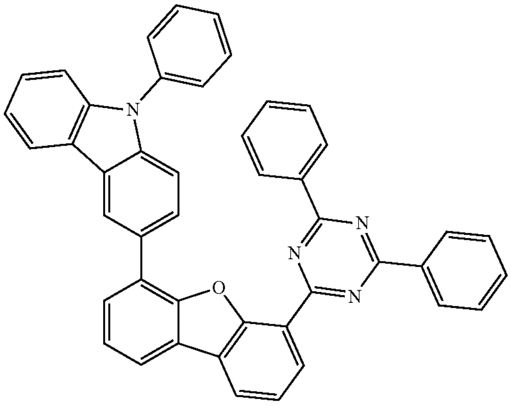
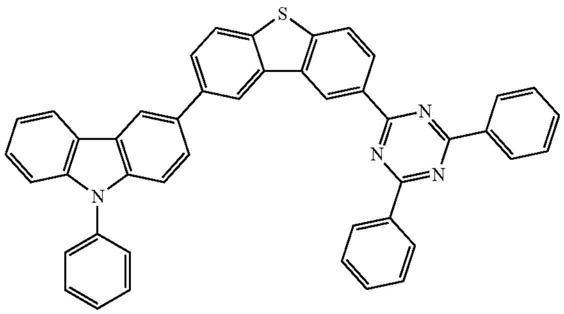

-continued
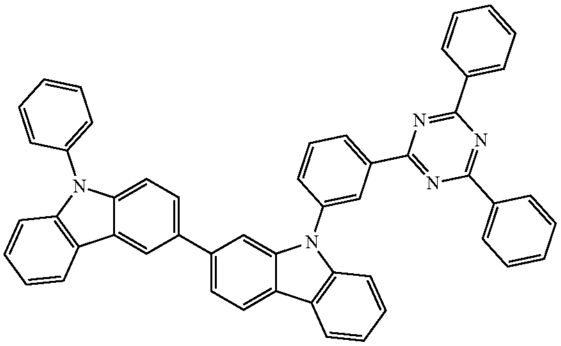
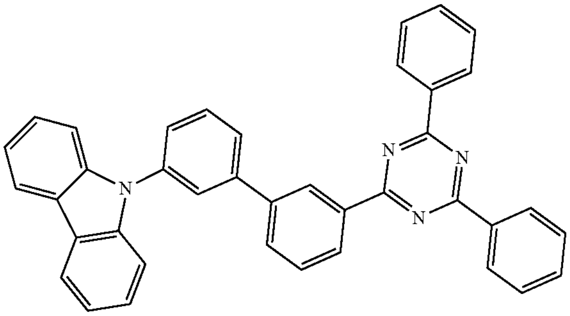
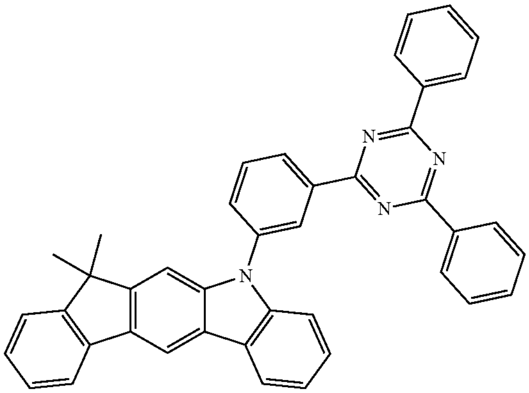
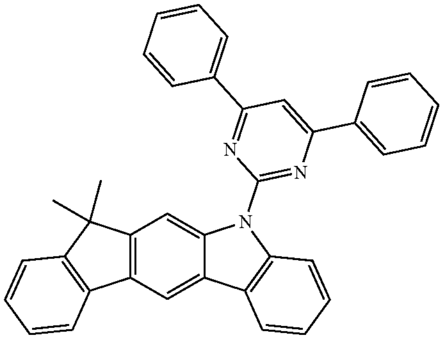
-continued
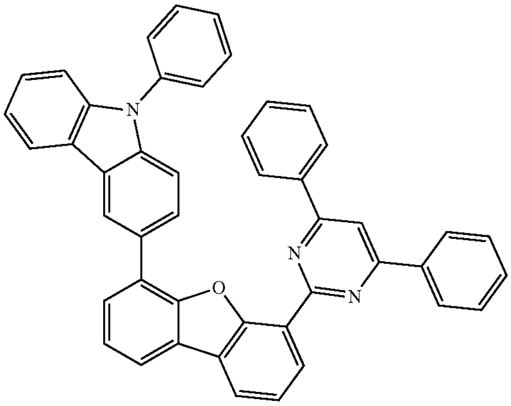
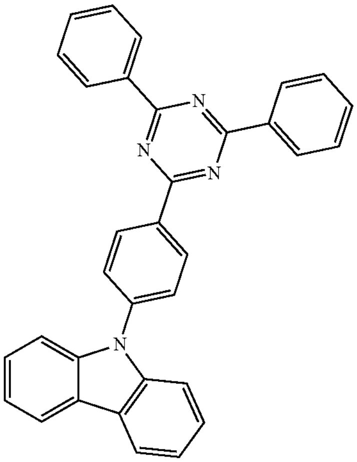
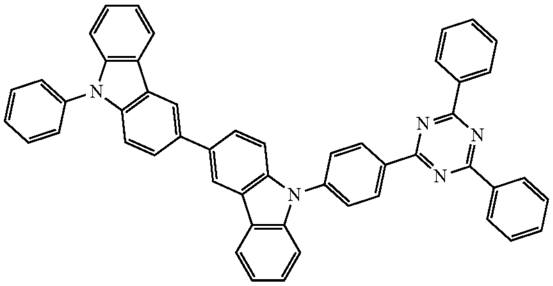
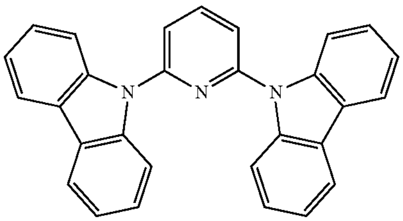

-continued
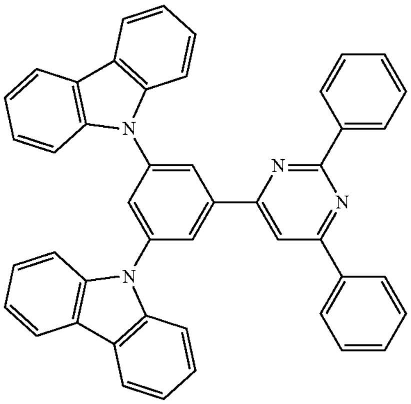
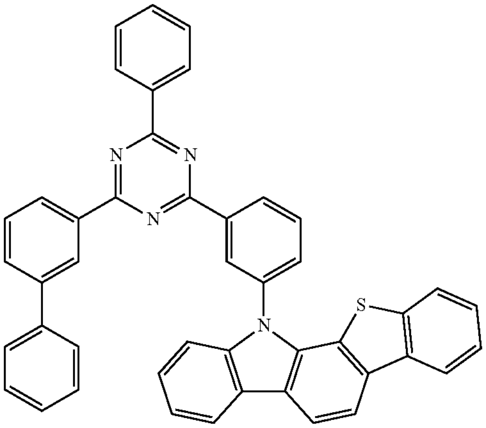
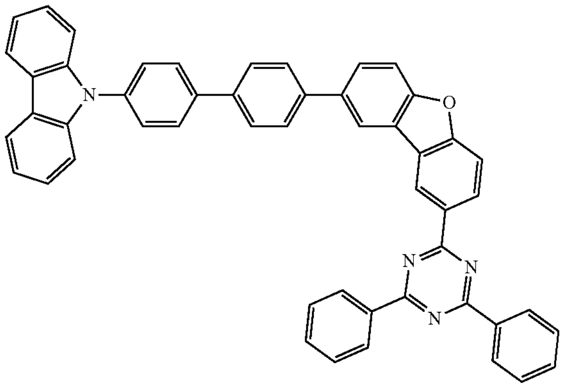
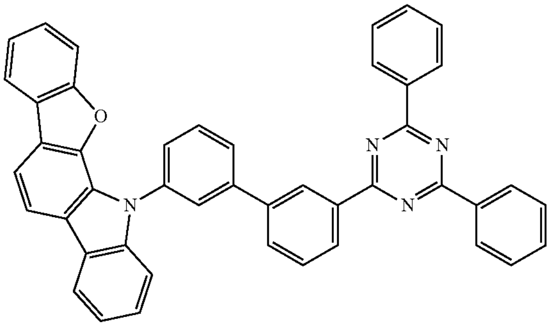
-continued
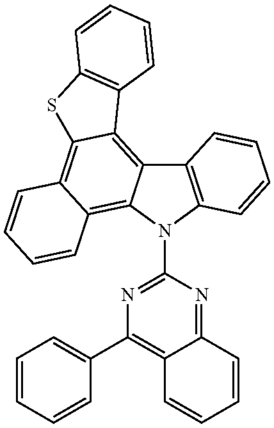
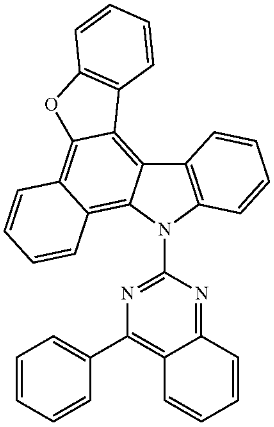
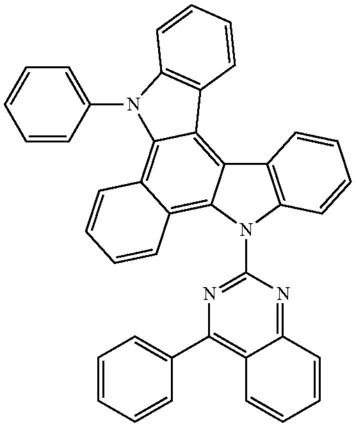

-continued
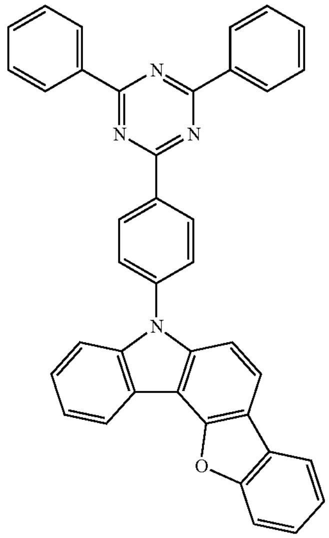
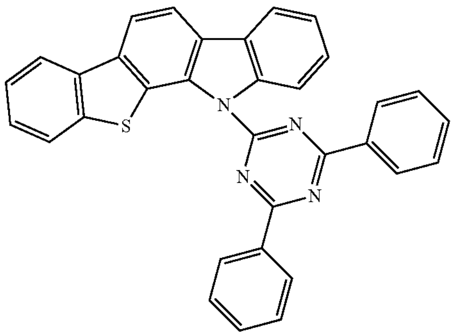
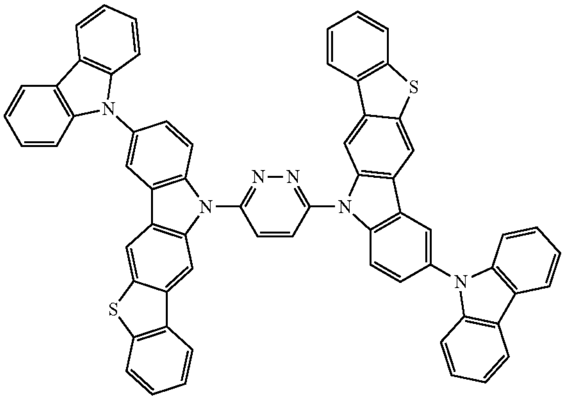
-continued
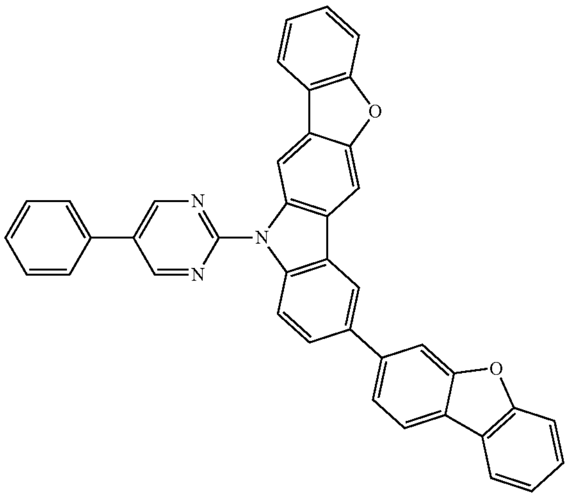
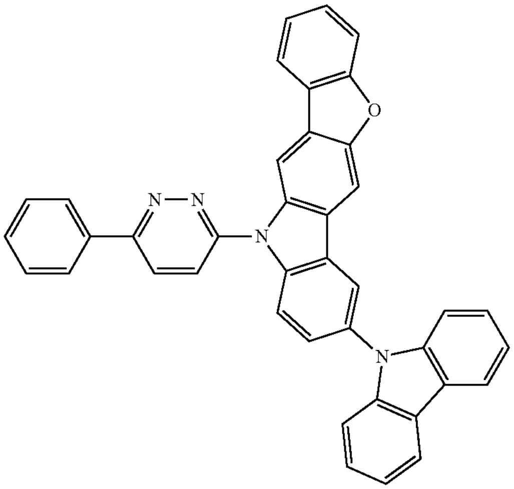
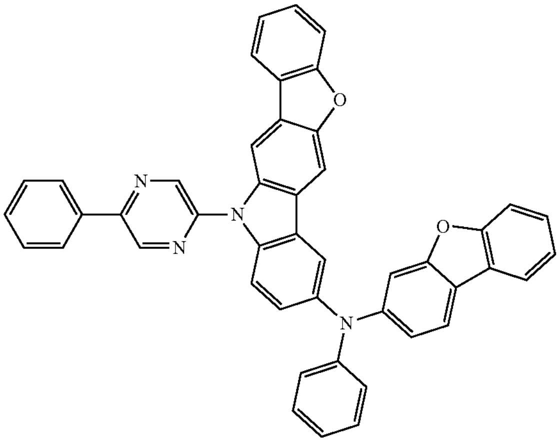

-continued
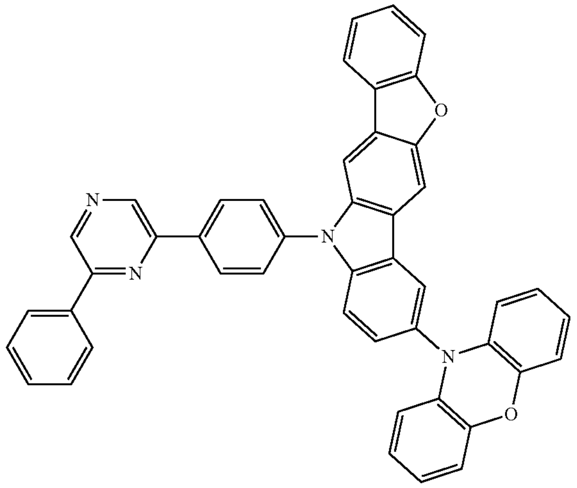
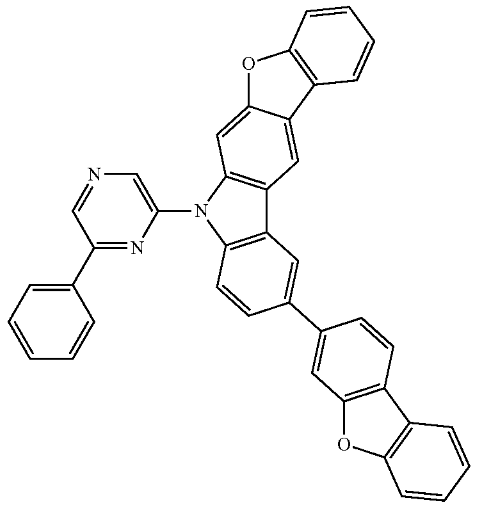
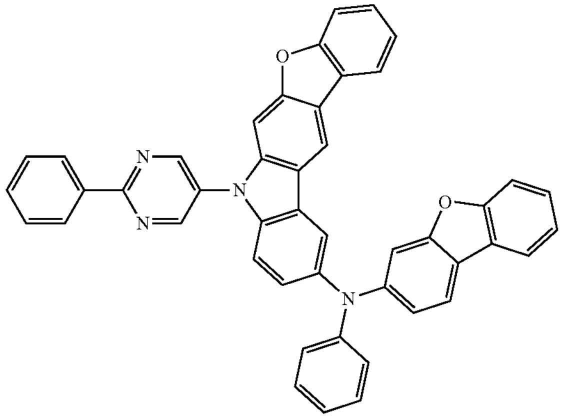
-continued
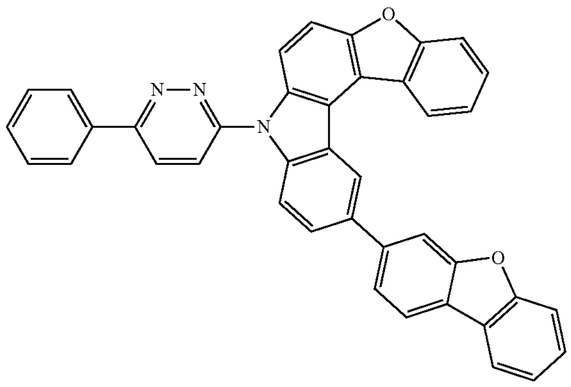
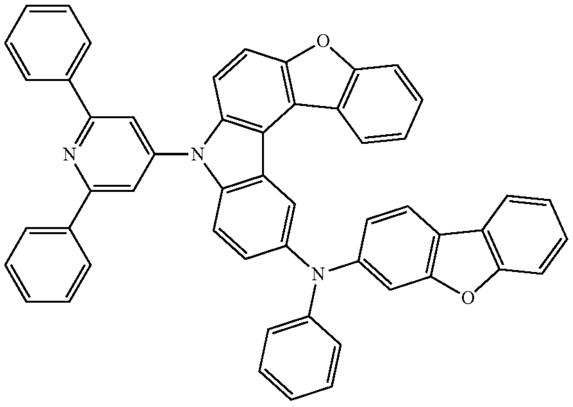
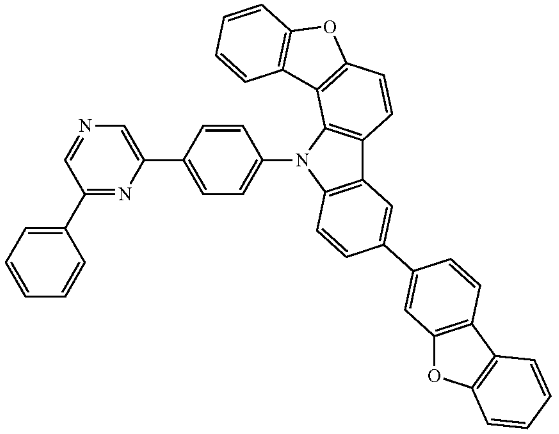
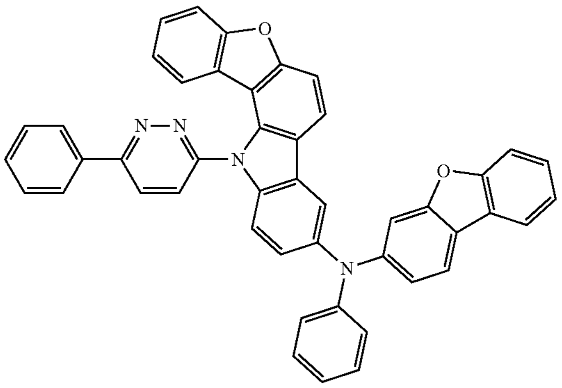

-continued
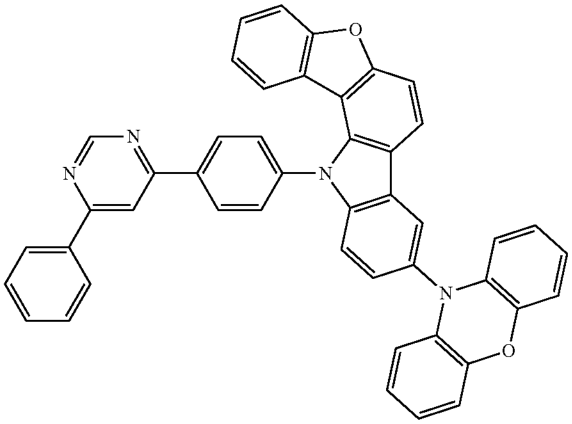
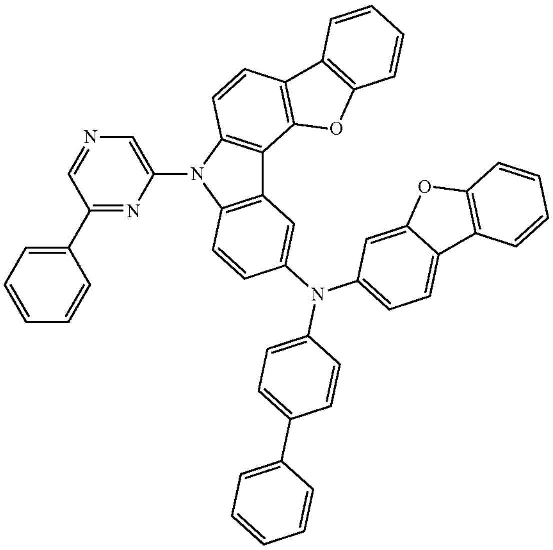
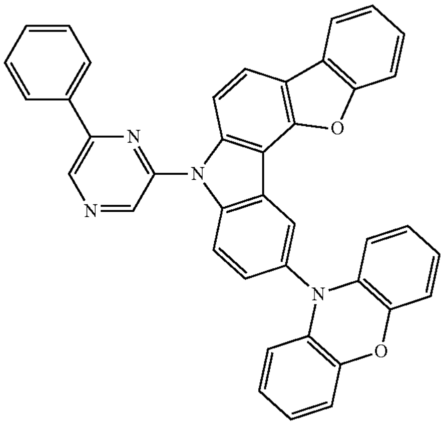
-continued
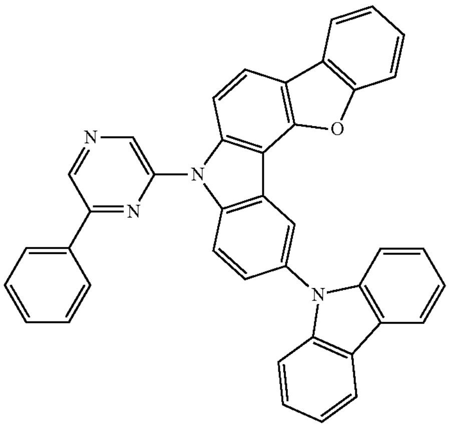
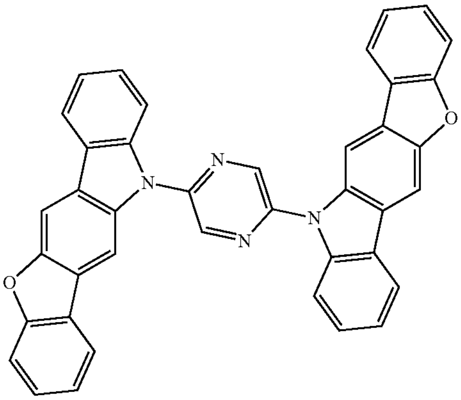
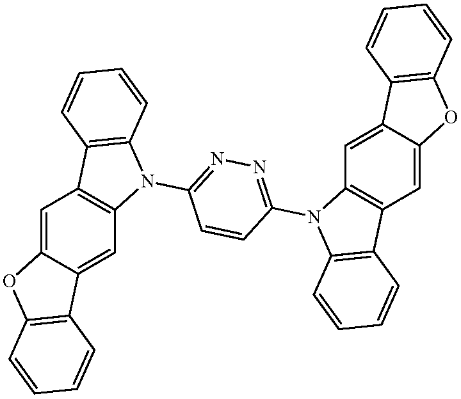
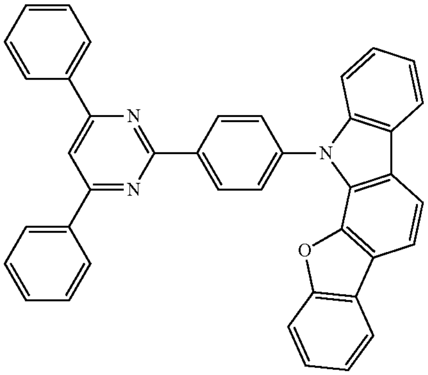

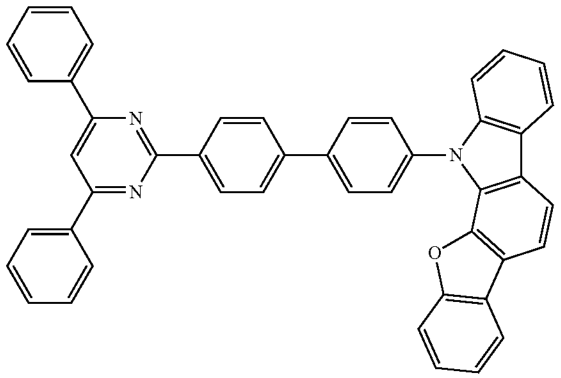
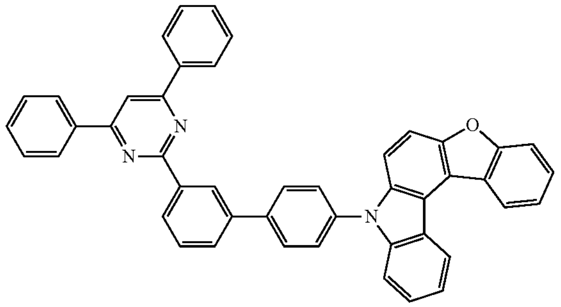
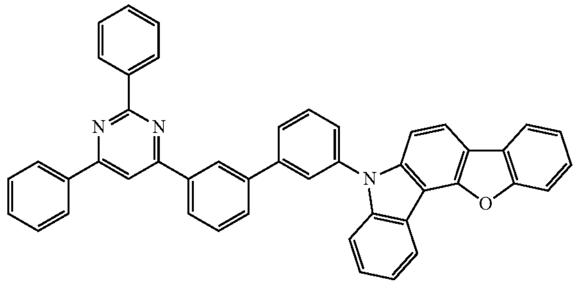
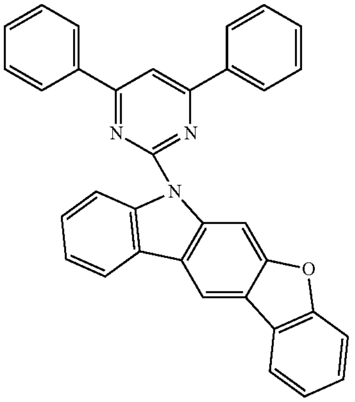
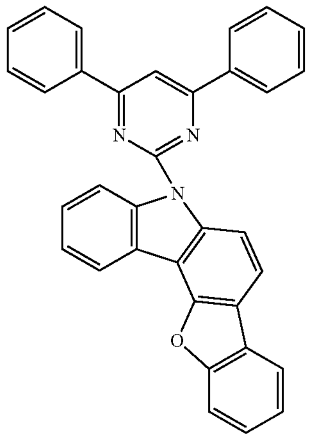
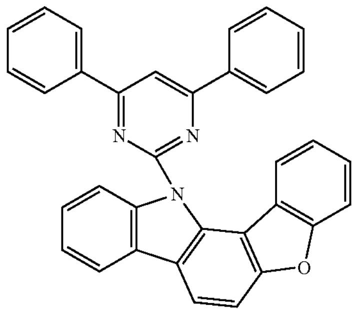
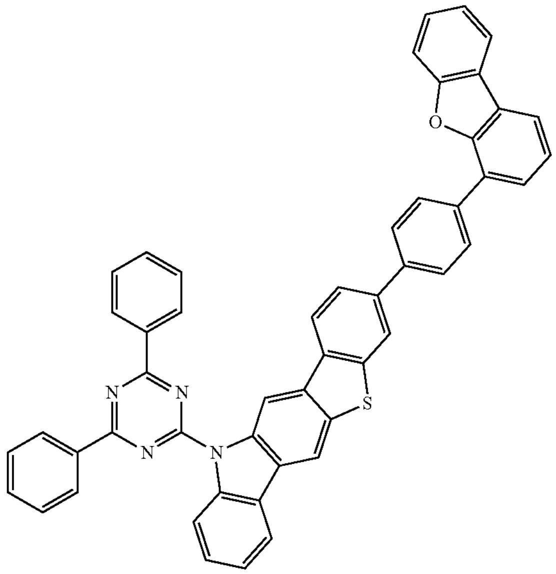
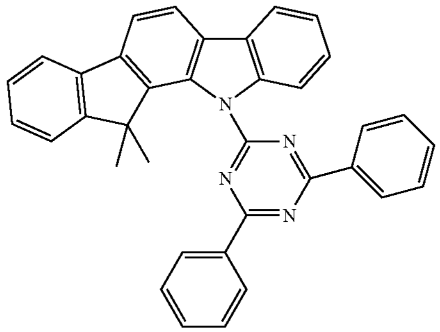

-continued

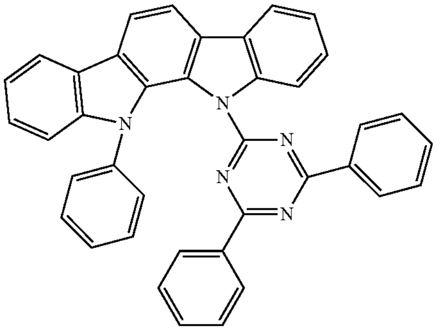

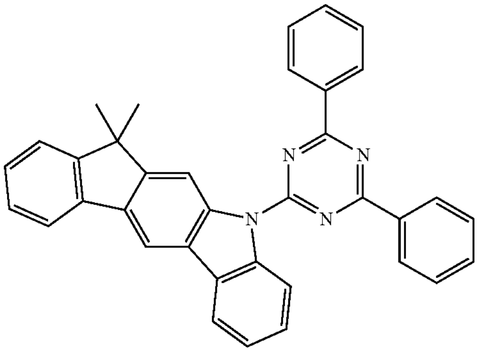

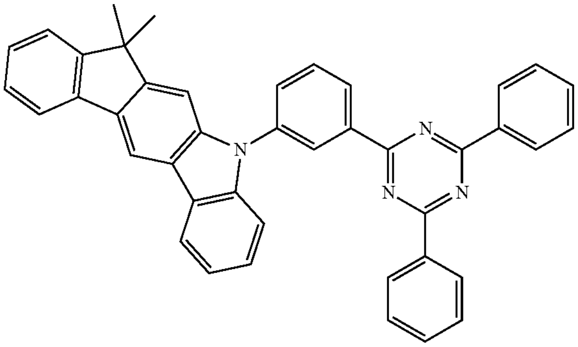

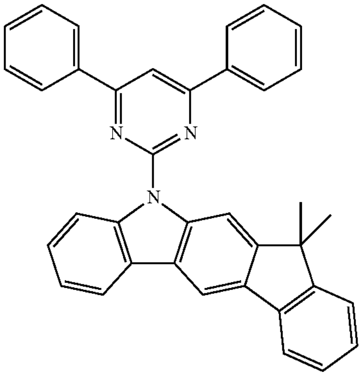

-continued

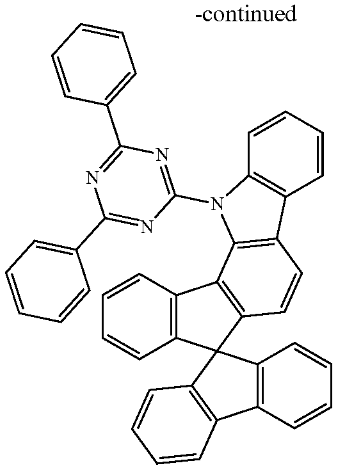

Third Compound

The emitting layer of the exemplary embodiment includes a third compound that emits delayed fluorescence.

Delayed Fluorescence

Delayed fluorescence is explained in "Yuki Hando-tai no Debaisu Bussei (Device Physics of Organic Semiconductors)" (edited by ADACHI, Chihaya, published by Kodansha, on pages 261-268). This document describes that, if an energy difference $\Delta E_{13}$ of a fluorescent material between a singlet state and a triplet state is reducible, a reverse energy transfer from the triplet state to the singlet state, which usually occurs at a low transition probability, would occur at a high efficiency to express thermally activated delayed fluorescence (TADF). Further, a mechanism of generating delayed fluorescence is explained in FIG. 10.38 in the document. The third compound of the exemplary embodiment is preferably a compound exhibiting thermally activated delayed fluorescence generated by such a mechanism.

In general, emission of delayed fluorescence can be confirmed by measuring the transient PL (Photo Luminescence).

The behavior of delayed fluorescence can also be analyzed based on the decay curve obtained from the transient PL measurement. The transient PL measurement is a method of irradiating a sample with a pulse laser to excite the sample, and measuring the decay behavior (transient characteristics) of PL emission after the irradiation is stopped. PL emission in TADF materials is classified into a light emission component from a singlet exciton generated by the first PL excitation and a light emission component from a singlet exciton generated via a triplet exciton. The lifetime of the singlet exciton generated by the first PL excitation is on the order of nanoseconds and is very short. Therefore, light emission from the singlet exciton rapidly attenuates after irradiation with the pulse laser.

On the other hand, the delayed fluorescence is gradually attenuated due to light emission from a singlet exciton generated via a triplet exciton having a long lifetime. As described above, there is a large temporal difference between the light emission from the singlet exciton generated by the first PL excitation and the light emission from the singlet exciton generated via the triplet exciton. Therefore, the luminous intensity derived from delayed fluorescence can be determined.

Figure 2:
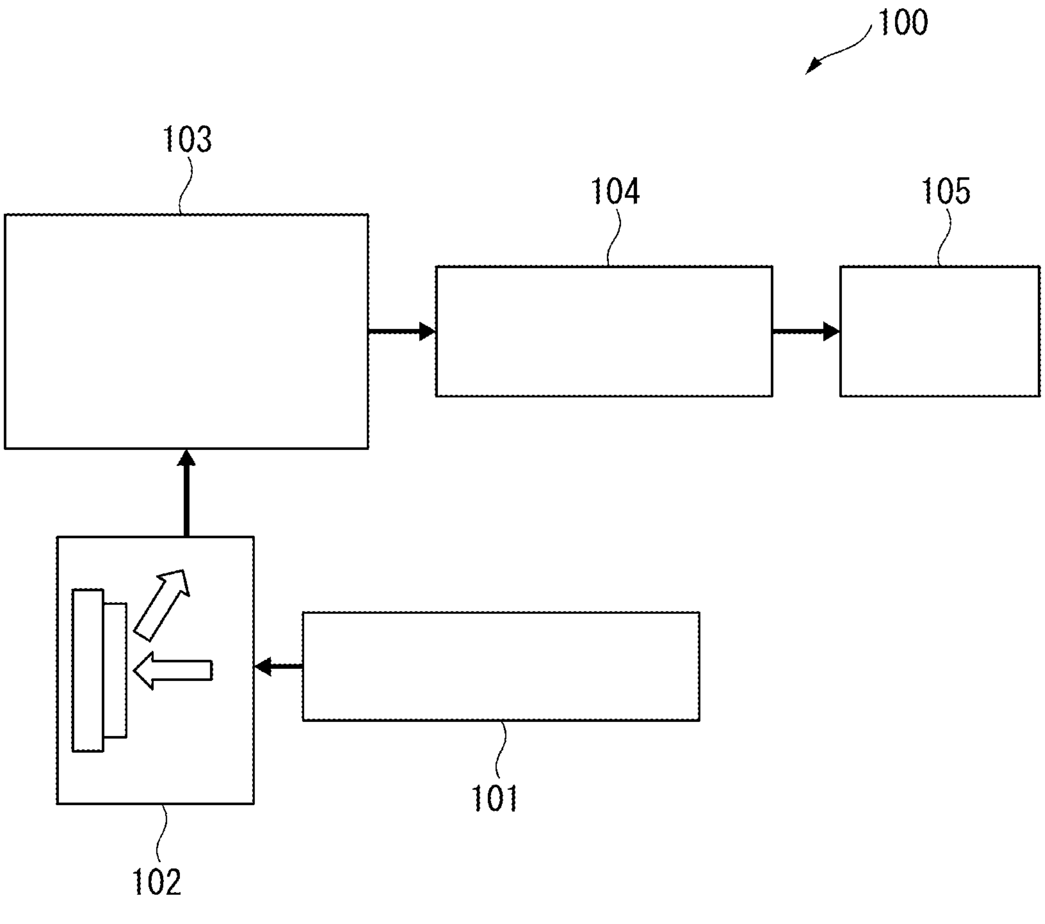

FIG. 2 shows a schematic diagram of an exemplary device for measuring the transient PL.

An example of a method of measuring a transient PL using FIG. 2 and an example of behavior analysis of delayed fluorescence will be described.

A transient PL measuring device 100 in FIG. 2 includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by doping a host material with a doping material at a concentration of 12 mass % and forming a thin film on a quartz substrate.

The thin film sample housed in the sample chamber 102 is irradiated with the pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above from a reference compound H1 as the host material and a reference compound D1 as the doping material and was measured in terms of the transient PL.

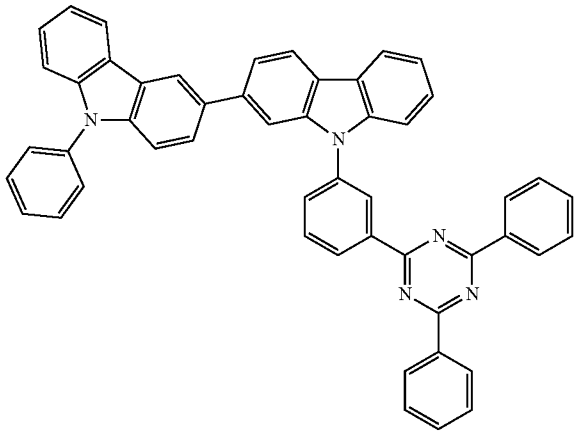

Reference Compound H1

-continued

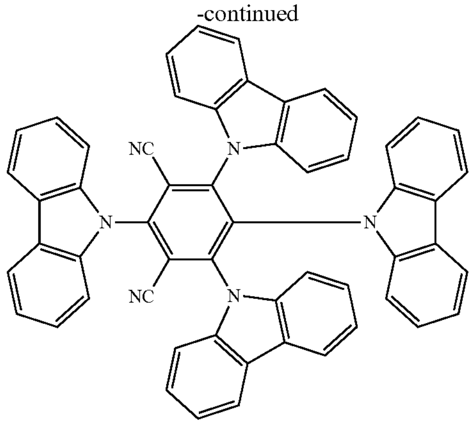

Reference Compound D1

The decay curve was analyzed with respect to the above thin film sample A and a thin film sample B. The thin film sample B was manufactured in the same manner as described above from a reference compound H2 as the host material and the reference compound D1 as the doping material.

Figure 3:
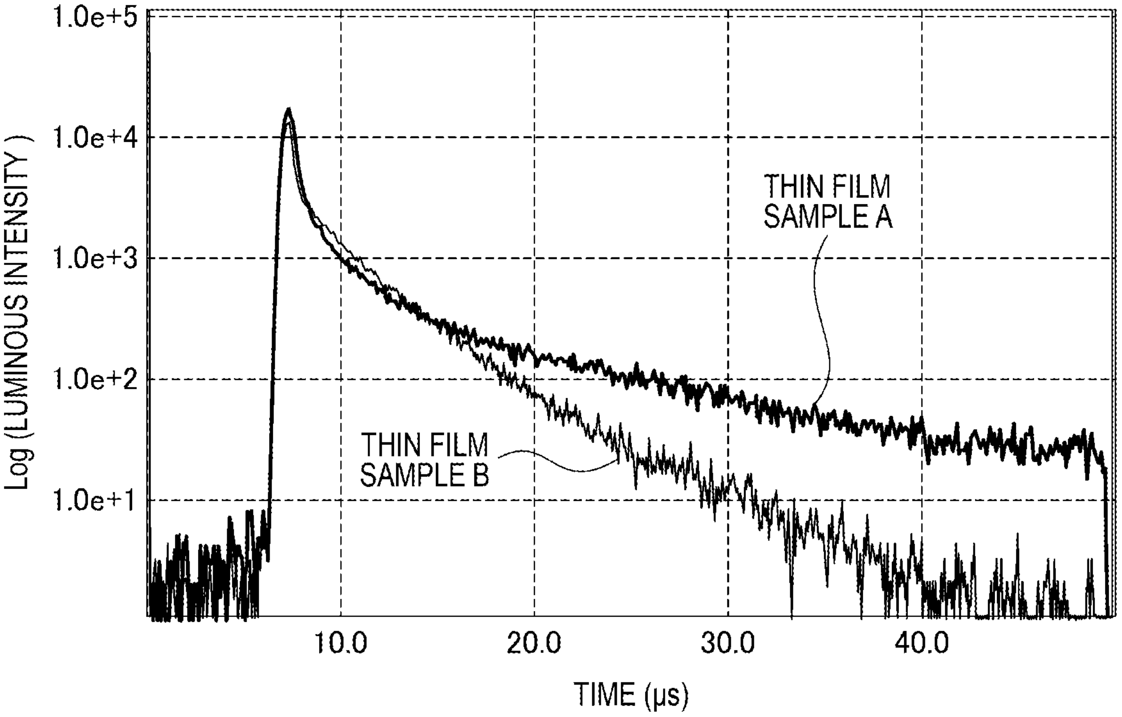
FIG. 3 shows an example of a decay curve of the transient PL.

FIG. 3 shows decay curves obtained from transient PL obtained by measuring the thin film samples A and B.

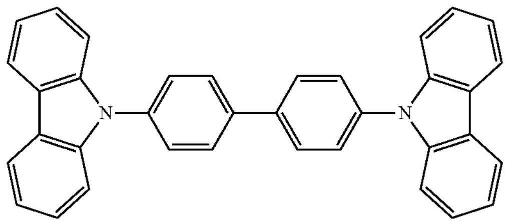

Reference Compound H2

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

Specifically, Prompt emission and Delay emission are present as emission from the delayed fluorescent material. Prompt emission is observed promptly when the excited state is achieved by exciting the compound of the exemplary embodiment with a pulse beam (i.e., a beam emitted from a pulse laser) having a wavelength absorbable by the delayed fluorescent material. Delay emission is observed not promptly when the excited state is achieved but after the excited state is achieved.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

Herein, a sample manufactured by a method shown below is used for measuring delayed fluorescence of the third compound. For instance, the third compound is dissolved in toluene to prepare a dilute solution with an absorbance of 0.05 or less at the excitation wavelength to eliminate the contribution of self-absorption. In order to prevent quenching due to oxygen, the sample solution is frozen and degassed and then sealed in a cell with a lid under an argon atmosphere to obtain an oxygen-free sample solution saturated with argon.

The fluorescence spectrum of the sample solution is measured with a spectrofluorometer FP-8600 (manufactured by JASCO Corporation), and the fluorescence spectrum of a 9,10-diphenylanthracene ethanol solution is measured under the same conditions. Using the fluorescence area intensities of both spectra, the total fluorescence quantum yield is calculated by an equation (1) in Morris et al. J. Phys. Chem. 80 (1976) 969.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

In the exemplary embodiment, provided that an amount of Prompt emission of a measurement target compound (third compound) is denoted by $X_P$ and the amount of Delay emission is denoted by $X_D$, a value of $X_D/X_P$ is preferably 0.05 or more.

The amounts of Prompt emission and Delay emission and a ratio of the amounts thereof in compounds other than the third compound herein are measured in the same manner as those of the third compound.

Examples of the third compound include, for example, a compound represented by a formula (31) below.

(31)

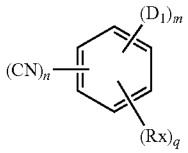

In the formula (31):

n is 1, 2, 3 or 4, m is 1, 2, 3, or 4, q is 0, 1, 2, 3, or 4, m+n+q=6 is satisfied, CN is a cyano group, $D_1$ is a group represented by a formula (3a), a formula (3b) or a formula (3c) below, when a plurality of $D_1$ are present, the plurality of $D_1$ are mutually the same or different, Rx is a hydrogen atom or a substituent, or a pair of adjacent ones of Rx are bonded to each other to form a ring, and when a plurality of Rx are present, the plurality of Rx are mutually the same or different, Rx as a substituent are each independently a halogen atom, a substituted or unsubstituted aryl group having 6 to 30 ring carbon atoms, a substituted or unsubstituted heterocyclic group having 5 to 30 ring atoms, a substituted or unsubstituted amino group, a substituted or unsubstituted carbonyl group, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkylsilyl group having 3 to 30 carbon atoms, or a substituted or unsubstituted arylsilyl group having 6 to 60 ring carbon atoms, and CN, $D_1$ and Rx are each bonded to a carbon atom of a six-membered ring.

(3a)

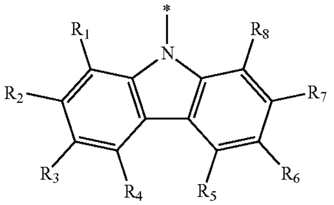

In the formula (3a), $R_1$ to $R_8$ are each independently a hydrogen atom or a substituent, or at least one pair of a pair of $R_1$ and $R_2$, a pair of $R_2$ and $R_3$, a pair of $R_3$ and $R_4$, a pair of $R_5$ and $R_6$, a pair of $R_6$ and $R_7$, or a pair of $R_7$ and $R_8$ are bonded to each other to form a ring;

$R_1$ to $R_8$ as a substituent are each independently a halogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 6 to 60 ring carbon atoms, a hydroxy group, a substituted or unsubstituted alkoxy group having 1 to 30 carbon atoms, a substituted or unsubstituted alkoxy halide group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms; and

* represents a bonding position to a carbon atom in a benzene ring in the formula (31).

(3b)

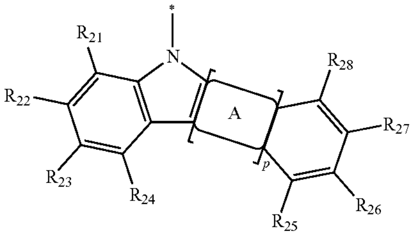

In the formula (3b):

$R_{21}$ to $R_{28}$ are each independently a hydrogen atom or a substituent, or at least one pair of a pair of $R_{21}$ and $R_{22}$, a pair of $R_{22}$ and $R_{23}$, a pair of $R_{23}$ and $R_{24}$, a pair of $R_{25}$ and $R_{26}$, a pair of $R_{26}$ and $R_{27}$, or a pair of $R_{27}$ and $R_{28}$ are bonded to each other to form a ring;

$R_{21}$ to $R_{28}$ as a substituent each independently represent the same as $R_1$ to $R_8$ in the formula (3a);

A represents a cyclic structure represented by a formula (331) or (312), the cyclic structure A is fused at any positions with adjacent cyclic structures;

p is 1, 2, 3, or 4, when p is 2, 3, or 4, a plurality of cyclic structures A are mutually the same or different; and

* represents a bonding position to a carbon atom in a benzene ring in the formula (31).

(3c)

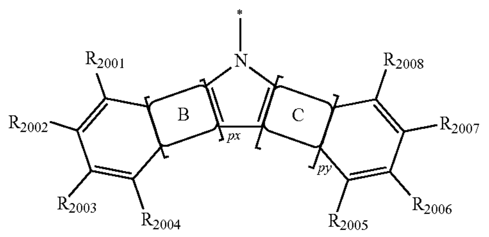

In the formula (3c):

$R_{2001}$ to $R_{2008}$ are each independently a hydrogen atom or a substituent, or at least one pair of a pair of $R_{2001}$ and $R_{2002}$, a pair of $R_{2002}$ and $R_{2003}$, a pair of $R_{2003}$ and $R_{2004}$, a pair of $R_{2005}$ and $R_{2008}$, a pair of $R_{2008}$ and $R_{2007}$, or a pair of $R_{2007}$ and $R_{2008}$ are bonded to each other to form a ring;

$R_{2001}$ to $R_{2008}$ as a substituent each independently represent the same as $R_1$ to $R_8$ as a substituent in the formula (3a);

B represents a cyclic structure represented by the formula (331) or (312), the cyclic structure B is fused at any positions with adjacent cyclic structures;

px is 1, 2, 3, or 4, when px is 2, 3, or 4, a plurality of cyclic structures B are mutually the same or different;

C represents a cyclic structure represented by the formula (331) or (312), the cyclic structure C is fused at any positions with adjacent cyclic structures;

py is 1, 2, 3, or 4, when py is 2, 3, or 4, a plurality of cyclic structures C are mutually the same or different; and

* represents a bonding position to a carbon atom in a benzene ring in the formula (31).

(311)

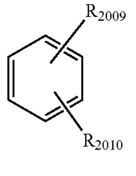

(312)

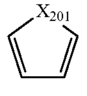

In the formula (311), $R_{2009}$ and $R_{2010}$ are each independently a hydrogen atom, or a substituent, or bonded to a part of an adjacent cyclic structure to form a ring, or a pair of $R_{2009}$ and $R_{2010}$ are mutually bonded to form a ring.

In the formula (312): $X_{201}$ is $CR_{2011}R_{2012}$, $NR_{2013}$, a sulfur atom, or an oxygen atom, $R_{2011}$, $R_{2012}$ and $R_{2013}$ are each independently a hydrogen atom or a substituent, or $R_{2011}$ and $R_{2012}$ are mutually bonded to form a ring.

$R_{2009}$, $R_{2010}$, $R_{2011}$, $R_{2012}$ and $R_{2013}$ as a substituent each independently represent the same as $R_1$ to $R_8$ as a substituent in the formula (3a).

In the formula (311), $R_{2009}$ and $R_{2010}$ are each independently bonded to a part of an adjacent cyclic structure to form a ring, which specifically means any of (I) to (IV) below.

In the formula (331), a pair of $R_{2009}$ and $R_{2010}$ are mutually bonded to form a ring, which specifically means (V) below.

(I) When the cyclic structures represented by the formula (311) are adjacent to each other, between two adjacent rings, at least one pair of the following are mutually bonded to form a ring: $R_{2009}$ of one of the rings and $R_{2009}$ of the other of the rings; $R_{2009}$ of one of the rings and $R_{2010}$ of the other of the rings; or $R_{2010}$ of one of the rings and $R_{2010}$ of the other of the rings.

(II) When the cyclic structure represented by the formula (311) and the benzene ring having $R_{25}$ to $R_{28}$ in the formula (3b) are adjacent to each other, between two adjacent rings, at least one pair of the following are mutually bonded to form a ring: $R_{2009}$ of one of the rings and $R_{25}$ of the other of the rings; $R_{2009}$ of one of the rings and $R_{28}$ of the other of the rings; $R_{2010}$ of one of the rings and $R_{25}$ of the other of the rings; or $R_{2010}$ of one of the rings and $R_{28}$ of the other of the rings.

(III) When the cyclic structure represented by the formula (311) and the benzene ring having $R_{2001}$ to $R_{2004}$ in the formula (3c) are adjacent to each other, between two adjacent rings, at least one pair of the following are mutually bonded to form a ring: $R_{2009}$ of one of the rings and $R_{2001}$ of the other of the rings; $R_{2009}$ of one of the rings and $R_{2004}$ of the other of the rings; $R_{2010}$ of one of the rings and $R_{2001}$ of the other of the rings; or $R_{2010}$ of one of the rings and $R_{2004}$ of the other of the rings.

(IV) When the cyclic structure represented by the formula (311) and the benzene ring having $R_{2005}$ to $R_{2008}$ in the formula (3c) are adjacent to each other, between two adjacent rings, at least one pair of the following are mutually bonded to form a ring: $R_{2009}$ of one of the rings and $R_{2005}$ of the other of the rings; $R_{2009}$ of one of the rings and $R_{2008}$ of the other of the rings; $R_{2010}$ of one of the rings and $R_{2005}$ of the other of the rings; or $R_{2010}$ of one of the rings and $R_{2008}$ of the other of the rings.

(V) A pair of $R_{2009}$ and $R_{2010}$ of the cyclic structure represented by the formula (311) are mutually bonded to form a ring. In other words, (V) means that the pair of $R_{2009}$ and $R_{2010}$ bonded to the same ring are mutually bonded to form a ring.

In the third compound of the exemplary embodiment, Rx is each independently a hydrogen atom, an unsubstituted aryl group having 6 to 30 ring carbon atoms, an unsubstituted heterocyclic group having 5 to 30 ring atoms, or an unsubstituted alkyl group having 1 to 30 carbon atoms.

When Rx is an unsubstituted heterocyclic group having 5 to 30 ring atoms, Rx as an unsubstituted heterocyclic group having 5 to 30 ring atoms is preferably a pyridyl group, pyrimidinyl group, triazinyl group, dibenzofuranyl group, or dibenzothienyl group.

Herein, a triazinyl group refers to a group obtained by excluding one hydrogen atom from 1,3,5-triazine, 1,2,4-triazine, or 1,2,3-triazine.

A triazinyl group is preferably a group obtained by excluding one hydrogen atom from 1,3,5-triazine.

In the third compound of the exemplary embodiment, it is more preferable that Rx is each independently a hydrogen atom, an unsubstituted aryl group having 6 to 30 ring carbon atoms, an unsubstituted dibenzofuranyl group, or an unsubstituted dibenzothienyl group.

In the third compound of the exemplary embodiment, Rx is further preferably a hydrogen atom.

In the third compound of the exemplary embodiment, it is preferable that $R_1$ to $R_8$, $R_{21}$ to $R_{28}$, $R_{2001}$ to $R_{2008}$, $R_{2009}$ to $R_{2010}$, and $R_{2011}$ to $R_{2013}$ as a substituent are each independently an unsubstituted aryl group having 6 to 30 ring carbon atoms, an unsubstituted heterocyclic group having 5 to 30 ring atoms, or an unsubstituted alkyl group having 1 to 30 carbon atoms.

In the third compound of the exemplary embodiment, $D_1$ is preferably any one of groups represented by formulae (D-21) to (D-27) below.

(D-21)

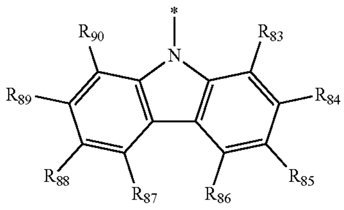

(D-22)

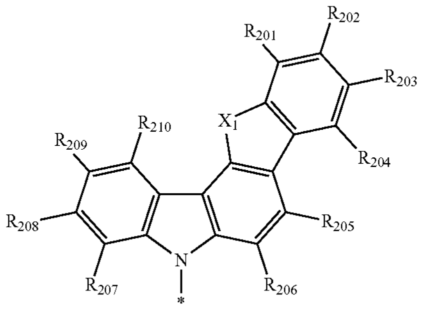

(D-23)

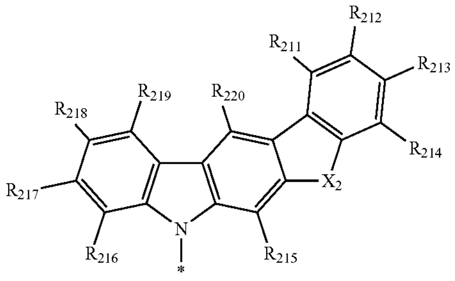

(D-24)

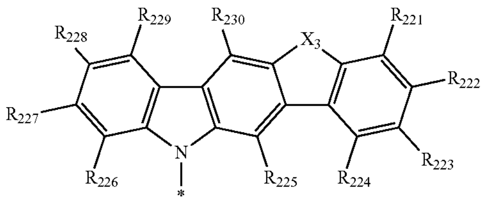

-continued (D-25)

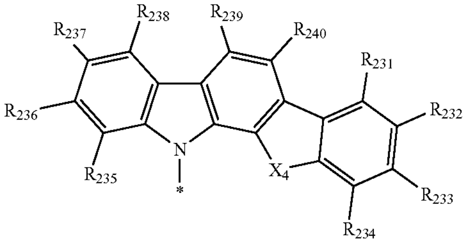

(D-26)

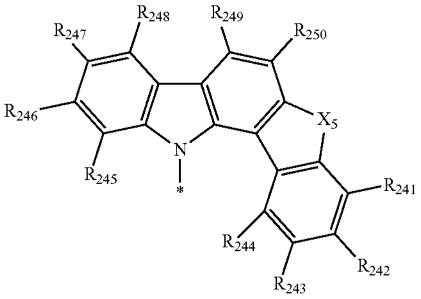

(D-27)

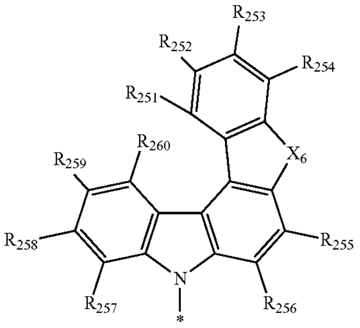

In the formula (D-21), $R_{83}$ to $R_{90}$ are each independently a hydrogen atom or a substituent.

In the formulae (D-22) to (D-27), $X_1$ to $X_6$ are each independently an oxygen atom, a sulfur atom, or $CR_{151}R_{152}$;

$R_{151}$ and $R_{152}$ are each independently a hydrogen atom or a substituent, or $R_{151}$ and $R_{152}$ are bonded to each other to form a ring;

$R_{201}$ to $R_{260}$ are each independently a hydrogen atom or a substituent, or at least one pair of a pair of $R_{201}$ and $R_{202}$, a pair of $R_{202}$ and $R_{203}$, a pair of $R_{203}$ and $R_{204}$, a pair of $R_{205}$ and $R_{206}$, a pair of $R_{207}$ and $R_{208}$, a pair of $R_{208}$ and $R_{209}$, a pair of $R_{209}$ and $R_{210}$, a pair of $R_{211}$ and $R_{212}$, a pair of $R_{212}$ and $R_{213}$, a pair of $R_{213}$ and $R_{214}$, a pair of $R_{216}$ and $R_{217}$, a pair of $R_{217}$ and $R_{218}$, a pair of $R_{218}$ and $R_{219}$, a pair of $R_{221}$ and $R_{222}$, a pair of $R_{222}$ and $R_{223}$, a pair of $R_{223}$ and $R_{224}$, a pair of $R_{226}$ and $R_{227}$, a pair of $R_{227}$ and $R_{228}$, a pair of $R_{228}$ and $R_{229}$, a pair of $R_{231}$ and $R_{232}$, a pair of $R_{232}$ and $R_{233}$, a pair of $R_{233}$ and $R_{234}$, a pair of $R_{235}$ and $R_{236}$, a pair of $R_{236}$ and $R_{237}$, a pair of $R_{237}$ and $R_{238}$, a pair of $R_{239}$ and $R_{240}$, a pair of $R_{241}$ and $R_{242}$, a pair of $R_{242}$ and $R_{243}$, a pair of $R_{243}$ and $R_{244}$, a pair of $R_{245}$ and $R_{246}$, a pair of $R_{246}$ and $R_{247}$, a pair of $R_{247}$ and $R_{248}$, a pair of $R_{249}$ and $R_{250}$, a pair of $R_{251}$ and $R_{252}$, a pair of $R_{252}$ and $R_{253}$, a pair of $R_{253}$ and $R_{254}$, a pair of $R_{255}$ and $R_{256}$, a pair of $R_{257}$ and $R_{258}$, a pair of $R_{258}$ and $R_{259}$, a pair of $R_{259}$ and $R_{260}$ are bonded to each other to form a ring, $R_{83}$ to $R_{90}$, $R_{151}$, $R_{152}$ and $R_{201}$ to $R_{260}$ as a substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted cycloalkyl group having 3 to 8 ring carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a thiol group, a substituted or unsubstituted alkylthio group having 1 to 6 carbon atoms, or a substituted or unsubstituted arylthio group having 6 to 14 ring carbon atoms; and

* represents a bonding position to a carbon atom in a benzene ring in the formula (31).

In the third compound of the exemplary embodiment, $D_1$ is also more preferably a group represented by the formula (D-21), the formula (D-23) or a formula (D-24).

In the third compound of the exemplary embodiment, $D_1$ is also further preferably a group represented by the formula (D-21) or (D-23).

In the third compound of the exemplary embodiment, it is preferable that $R_{83}$ to $R_{90}$, $R_{201}$ to $R_{260}$, $R_{151}$ and $R_{152}$ are each independently a hydrogen atom, an unsubstituted aryl group having 6 to 14 ring carbon atoms, an unsubstituted heterocyclic group having 5 to 14 ring atoms, or an unsubstituted alkyl group having 1 to 6 carbon atoms.

In the third compound of the exemplary embodiment, $R_{83}$ to $R_{90}$ and $R_{201}$ to $R_{260}$ are preferably hydrogen atoms.

In the third compound of the exemplary embodiment, it is preferable that $R_{151}$ and $R_{152}$ are each independently an unsubstituted aryl group having 6 to 14 ring carbon atoms, an unsubstituted heterocyclic group having 5 to 14 ring atoms, or an unsubstituted alkyl group having 1 to 6 carbon atoms.

Examples of the third compound include, for example, a compound represented by a formula (32) below.

(32)

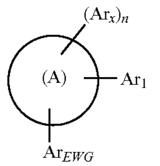

In the formula (32), $Ar_1$ is any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by formulae (1a) to (1j) below;

$Ar_{EWG}$ is a substituted or unsubstituted heteroaryl group having 5 to 30 ring atoms that comprises one or more nitrogen atoms in a ring, or an aryl group having 6 to 30 ring carbon atoms that is substituted with one or more cyano groups;

$Ar_X$ are each independently a hydrogen atom or a substituent, $Ar_X$ as the substituent being any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by formulae (1a) to (1j) below;

n is 0, 1, 2, 3, 4, or 5;

when n is 2, 3, 4, or 5, a plurality of $Ar_X$ are mutually the same or different;

a ring (A) is a substituted or unsubstituted aromatic hydrocarbon ring or a substituted or unsubstituted heterocycle;

the ring (A) is a five-membered ring, a six-membered ring, or a seven-membered ring;

$Ar_{EWG}$, $Ar_1$ and $Ar_X$ are respectively bonded to elements forming the ring (A); and at least one of $Ar_1$ or $Ar_X$ is any one group selected from the group consisting of groups represented by the formulae (1a) to (1j).

(1a)

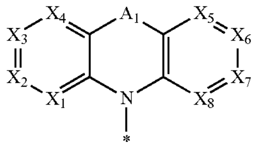

(1b)

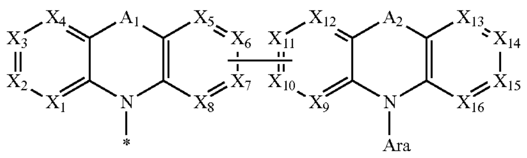

(1c)

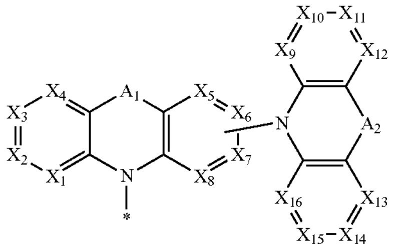

(1d)

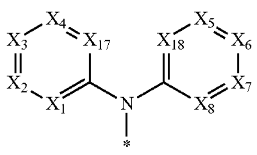

-continued (1e)

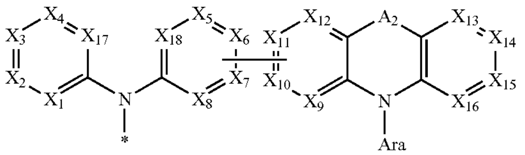

(1f)

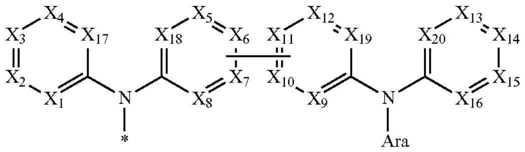

(1g)

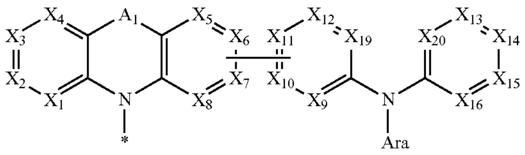

(1h)

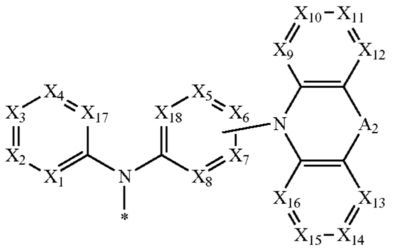

(1i)

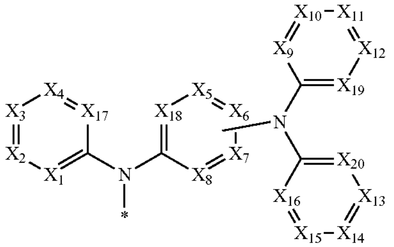

(1j)

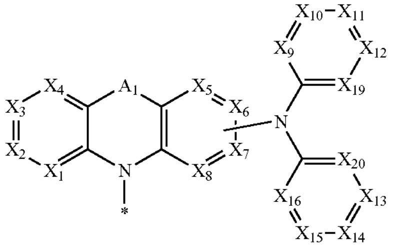

In the formulae (1a) to (1j), $X_1$ to $X_{20}$ are each independently a nitrogen atom (N) or a carbon atom bonded with $R_{A1}$ (C—$R_{A1}$).

In the formula (1b), one of $X_5$ to $X_8$ is a carbon atom bonded with one of $X_9$ to $X_{12}$, and one of $X_9$ to $X_{12}$ is a carbon atom bonded with one of $X_5$ to $X_8$.

In the formula (1c), one of $X_5$ to $X_8$ is a carbon atom bonded with a nitrogen atom in a ring including $A_2$.

In the formula (1e), one of $X_5$ to $X_8$ and $X_{18}$ is a carbon atom bonded with one of $X_9$ to $X_{12}$, and one of $X_9$ to $X_{12}$ is a carbon atom bonded with one of $X_5$ to $X_8$ and $X_{18}$.

In the formula (1f), one of $X_5$ to $X_8$ and $X_{18}$ is a carbon atom bonded with one of $X_9$ to $X_{12}$ and $X_{19}$ and one of $X_9$ to $X_{12}$ and $X_{19}$ is a carbon atom bonded with one of $X_5$ to $X_8$ and $X_{18}$.

In the formula (1g), one of $X_5$ to $X_8$ is a carbon atom bonded with one of $X_9$ to $X_{12}$ and $X_{19}$, and one of $X_9$ to $X_{12}$ and $X_{19}$ is a carbon atom bonded with one of $X_5$ to $X_8$.

In the formula (1h), one of $X_5$ to $X_8$ and $X_{18}$ is a carbon atom bonded with a nitrogen atom in a ring including $A_2$.

In the formula (1i), one of $X_5$ to $X_8$ and $X_{18}$ is a carbon atom bonded with a nitrogen atom connecting a ring including $X_9$ to $X_{12}$ and $X_{19}$ with a ring including $X_{13}$ to $X_{16}$ and $X_{20}$.

In the formula (1j), one of $X_5$ to $X_5$ is a carbon atom bonded with a nitrogen atom connecting a ring including $X_9$ to $X_{12}$ and $X_{19}$ and a ring including $X_{13}$ to $X_{16}$ and $X_{20}$.

$R_{A1}$ is each independently a hydrogen atom or a substituent, or at least one pair of pairs of a plurality of $R_{A1}$ are mutually directly bonded to form a ring or are bonded through a hetero atom to form a ring.

$R_{A1}$ as the substituent is any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

A plurality of $R_{A1}$ as substituents are mutually the same or different.

In the formulae (1a) to (1j), * represents a bonding position to the ring (A).

In the formulae (1a) to (1j), $A_1$ and $A_2$ are each independently a single bond, an oxygen atom (O), a sulfur atom (S), $C(R_{2021})(R_{2022})$, $Si(R_{2023})(R_{2024})$, C(═O), S(═O), $SO_2$, or $N(R_{2025})$. $R_{2021}$ to $R_{2025}$ are each independently a hydrogen atom or a substituent, and $R_{2021}$ to $R_{2025}$ as the substituents are each independently any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group.

In the formulae (1a) to (1j), Ara is any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, and a substituted silyl group.

In the formula (1a), when $X_1$ to $X_8$ are a carbon atom bonded with $R_{A1}$ (C—$R_{A1}$), a plurality of $R_{A1}$ preferably form no ring.

In the formulae (1a) to (1j), Ara is preferably a substituted or unsubstituted aryl group having 6 to 30 ring carbon atoms, or a substituted or unsubstituted heteroaryl group having 5 to 30 ring atoms.

The formula (1a) is represented by a formula (1aa) below when $A_1$ is a single bond, represented by a formula (1 ab) below when $A_1$ is an oxygen atom, represented by a formula (1 ac) below when $A_1$ is a sulfur atom, represented by a formula (1 ad) below when $A_1$ is $C(R_{2021})(R_{2022})$, represented by a formula (1 ae) below when $A_1$ is $Si(R_{2023})(R_{2024})$, represented by a formula (1af) below when $A_1$ is C(═O), represented by a formula (1 ag) below when $A_1$ is S(═O), represented by a formula (1 ah) below when $A_1$ is $SO_2$, and represented by a formula (1ai) below when $A_1$ is $N(R_{2025})$. In the formulae (1aa) to (1aj), $X_1$ to $X_8$ and $R_{2021}$ to $R_{2025}$ represent the same as described above. Also in the formulae (1b), (1c), (1e), (1g) to (1j), connection between rings by $A_1$ and $A_2$ is the same as that in the formulae (1aa) to (1ai). In the formula (1aa), when $X_1$ to $X_8$ are a carbon atom bonded with $R_{A1}$ ($C—R_{A1}$), a plurality of $R_{A1}$ as substituents preferably form no ring.

(1aa)

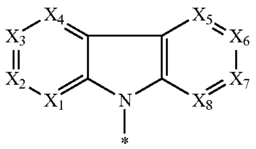

(1ab)

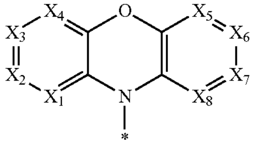

(1ac)

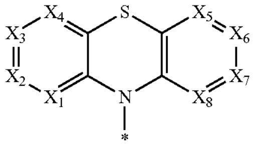

(1ad)

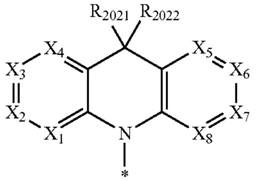

(1ae)

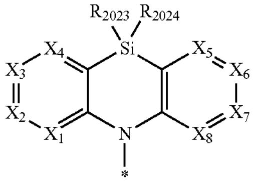

(1af)

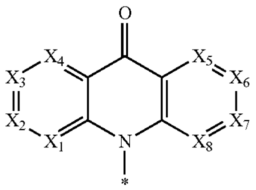

-continued (1ag)

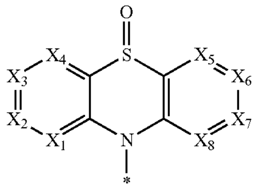

(1ah)

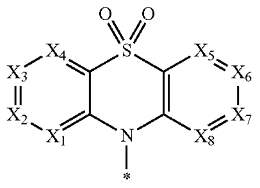

(1ai)

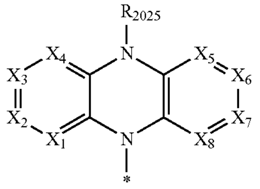

The third compound is preferably represented by the formula (221).

(221)

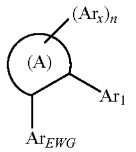

In the formula (221), $Ar_1$, $Ar_{EWG}$, $Ar_x$, n and a ring (A) respectively represent the same as $Ar_1$, $Ar_{EWG}$, $Ar_x$, n and the ring (A) in a formula (32).

The third compound is also preferably represented by a formula (222) below.

(222)

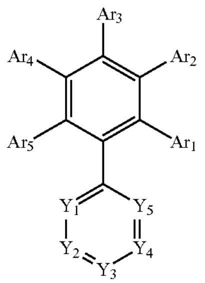

In the formula (222):

$Y_1$ to $Y_5$ are each independently a nitrogen atom (N), carbon atom bonded with a cyano group (C—CN) or carbon atom bonded with $R_{A2}$ ($C—R_{A2}$);

at least one of $Y_1$ to $Y_5$ is N or C—CN. a plurality of $R_{A2}$ are mutually the same or different. $R_{A2}$ is each independently a hydrogen atom or a substituent, and $R_{A2}$ as the substituent is any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; and a plurality of $R_{A2}$ are mutually the same or different.

In the formula (222), $Ar_1$ represents the same as $Ar_1$ in the formula (32).

In the formula (222), $Ar_2$ to $Ar_5$ are each independently a hydrogen atom or a substituent, $Ar_2$ to $Ar_5$ as the substituents each independently being any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, a carboxy group, and groups represented by formulae (1a) to (1c).

In the formula (222), at least one of $Ar_1$ to $Ar_5$ is any one group selected from the group consisting of the groups represented by the formulae (1a) to (1c).

The third compound is also preferably a compound represented by a formula (11aa) below, a formula (11bb) below, or a formula (11cc) below.

(11aa)

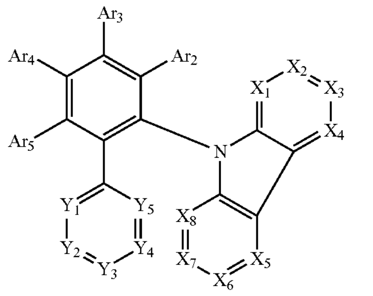

(11bb)

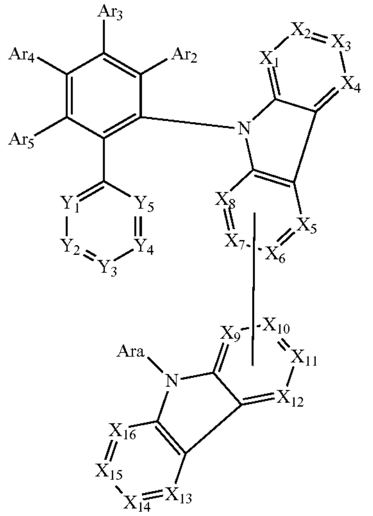

-continued (11cc)

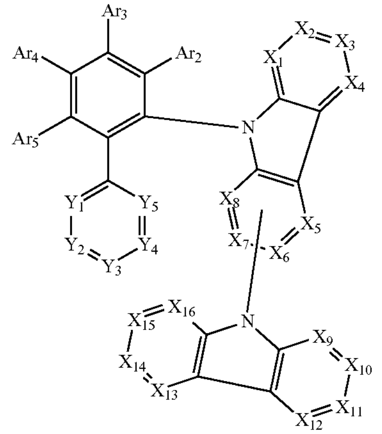

In the formulae (11aa), (11bb), and (11cc), $Y_1$ to $Y_5$, $R_{A2}$, $Ar_2$ to $Ar_5$, $X_1$ to $X_{16}$, $R_{A1}$, and Ara represent the same as above-described $Y_1$ to $Y_5$, $R_{A2}$, $Ar_2$ to $Ar_5$, $X_1$ to $X_{16}$, $R_{A1}$, and Ara, respectively.

Examples of the third compound include, for example, a compound represented by a formula (23) below.

(23)

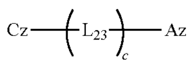

In the formula (23): Az is a cyclic structure selected from the group consisting of a substituted or unsubstituted pyridine ring, a substituted or unsubstituted pyrimidine ring, a substituted or unsubstituted triazine ring; and a substituted or unsubstituted pyrazine ring;

c is 0, 1, 2, 3, 4 or 5;

when c is 0, Cz and Az are bonded to each other with a single bond;

when c is 1, 2, 3, 4 or 5, $L_{23}$ is a linking group selected from the group consisting of a substituted or unsubstituted arylene group having 6 to 30 ring carbon atoms, and a substituted or unsubstituted heteroarylene group having 5 to 30 ring atoms;

when c is 2, 3, 4, or 5, a plurality of $L_{23}$ are mutually the same or different;

the plurality of $L_{23}$ are bonded to each other to form a ring, or are not bonded to form no ring; and Cz is represented by a formula (23a) below.

(23a)

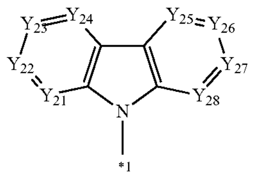

In the formula (23a): $Y_{21}$ to $Y_{28}$ are each independently a nitrogen atom or $CR_{A3}$;

$R_{A3}$ are each independently a hydrogen atom or a substituent, or at least one pair of pairs of a plurality of $R_{A3}$ are mutually bonded to form a ring;

$R_{A3}$ as the substituent is each independently any one group selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

a plurality of $R_{A3}$ are mutually the same or different;

*1 represents a bonding position with a carbon atom in a structure of a linking group represented by $L_{23}$ or a bonding position with a carbon atom in a cyclic structure represented by Az; and $Y_{21}$ to $Y_{28}$ are also preferably $CR_{A3}$;

c in the formula (23) is preferably 0 or 1.

Cz is also preferably represented by a formula (23b) below, a formula (23c) below, or a formula (23d) below.

(23b)

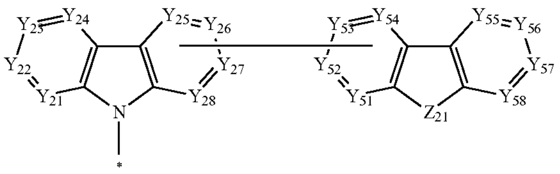

(23c)

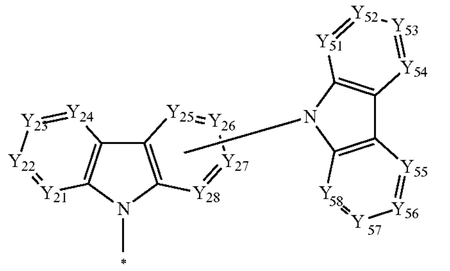

(23d)

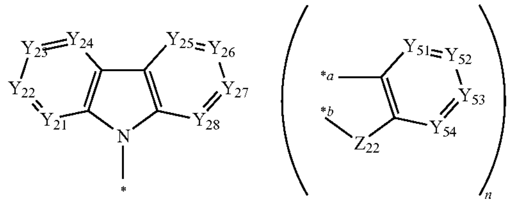

In the formulae (23b), (23c), and (23d), $Y_{21}$ to $Y_{28}$ and $Y_{51}$ to $Y_{58}$ are each independently a nitrogen atom or $CR_{A4}$.

In the formula (23b), at least one of $Y_{25}$ to $Y_{28}$ is a carbon atom bonded with one of $Y_{51}$ to $Y_{54}$, and at least one of $Y_{51}$ to $Y_{54}$ is a carbon atom bonded with one of $Y_{25}$ to $Y_{28}$.

In the formula (23c), at least one of $Y_{25}$ to $Y_{28}$ is a carbon atom bonded to a nitrogen atom in a five-membered ring of a nitrogen-containing fused ring including $Y_{51}$ to $Y_{58}$.

In the formula (23d): *a and *b each represent a bonding position to one of $Y_{21}$ to $Y_{28}$; at least one of $Y_{25}$ to $Y_{28}$ is the bonding position represented by *a; at least one of $Y_{25}$ to $Y_{28}$ is the bonding position represented by *b; and n is 1, 2, 3 or 4.

$R_{A4}$ are each independently a hydrogen atom or a substituent, or at least one pair of pairs of a plurality of $R_{A4}$ are mutually bonded to form a ring.

$R_{A4}$ as a substituent is each independently any one substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

a plurality of $R_{A4}$ are mutually the same or different;

$Z_{21}$ and $Z_{22}$ are each independently any one selected from the group consisting of an oxygen atom, a sulfur atom, $NR_{45}$ and $CR_{46}R4_{7}$;

$R_{45}$ is a hydrogen atom or a substituent;

$R_{46}$ and $R_{47}$ are each independently a hydrogen atom or a substituent, or a pair of $R_{46}$ and $R_{47}$ are mutually bonded to form a ring;

$R_{45}$, $R_{46}$, and $R_{47}$ as a substituent are each independently any one substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

a plurality of $R_{45}$ are mutually the same or different;

a plurality of $R_{46}$ are mutually the same or different;

a plurality of $R_{47}$ are mutually the same or different; and

* represents a bonding position to a carbon atom in a cyclic structure represented by Az.

$Z_{21}$ is preferably $NR_{45}$.

When $Z_{21}$ is $NR_{45}$, $R_{45}$ is preferably a substituted or unsubstituted aryl group having 6 to 30 ring carbon atoms.

$Z_{22}$ is preferably $NR_{45}$.

When $Z_{22}$ is $NR_{45}$, $R_{45}$ is preferably a substituted or unsubstituted aryl group having 6 to 30 ring carbon atoms.

$Y_{51}$ to $Y_{58}$ are preferably $CR_{A4}$, provided that at least one of $Y_{51}$ to $Y_{58}$ is a carbon atom bonded to a cyclic structure represented by the formula (23a).

Cz is also preferably represented by the formula (23d) in which n is 1.

Az is preferably a cyclic structure selected from the group consisting of a substituted or unsubstituted pyrimidine ring and a substituted or unsubstituted triazine ring.

Az is a cyclic structure selected from the group consisting of a substituted pyrimidine ring and a substituted triazine ring, in which a substituent of each of the substituted pyrimidine ring and the substituted triazine ring is more preferably a group selected from the group consisting of a substituted or unsubstituted aryl group having 6 to 30 ring carbon atoms and a substituted or unsubstituted heteroaryl group having 5 to 30 ring atoms, further preferably a substituted or unsubstituted aryl group having 6 to 30 ring carbon atoms.

When the pyrimidine ring and the triazine ring as Az have a substituted or unsubstituted aryl group as a substituent, the aryl group preferably has 6 to 20 ring carbon atoms, more preferably 6 to 14 ring carbon atoms, further preferably 6 to 12 ring carbon atoms.

When Az has a substituted or unsubstituted aryl group as a substituent, the substituent is preferably any substituent selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably any substituent selected from the group consisting of a substituted or unsubstituted phenyl group, a substituted or unsubstituted biphenyl group, and a substituted or unsubstituted naphthyl group.

When Az has a substituted or unsubstituted heteroaryl group as a substituent, the substituent is preferably any substituent selected from the group consisting of a substituted or unsubstituted carbazolyl group, a substituted or unsubstituted dibenzofuranyl group, and a substituted or unsubstituted dibenzothienyl group.

$R_{44}$ is each independently a hydrogen atom or a substituent. $R_{44}$ as a substituent is preferably each independently a substituent selected from the group consisting of a substituted or unsubstituted aryl group having 6 to 30 ring carbon atoms and a substituted or unsubstituted heteroaryl group having 5 to 30 ring atoms.

When $R_{44}$ as a substituent is each a substituted or unsubstituted aryl group having 6 to 30 ring carbon atoms, $R_{44}$ as a substituent is each preferably a substituent selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably a substituent selected from the group consisting of a substituted or unsubstituted phenyl group, a substituted or unsubstituted biphenyl group, and a substituted or unsubstituted naphthyl group.

When $R_{44}$ as a substituent is a substituted or unsubstituted heteroaryl group having 5 to 30 ring atoms, $R_{44}$ as a substituent is preferably a substituent selected from the group consisting of a substituted or unsubstituted carbazolyl group, a substituted or unsubstituted dibenzofuranyl group, and a substituted or unsubstituted dibenzothienyl group.

$R_{45}$, $R_{46}$, $R_{47}$ as substituents are preferably each independently a substituent selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms.

Manufacturing Method of Third Compound of Exemplary Embodiment

The third compound according to the exemplary embodiment can be manufactured by a known method.

Specific Examples of Third Compound

Specific examples of the third compound of the exemplary embodiment include, for example, the following compounds. However, the invention is not limited to the specific examples of the compounds.

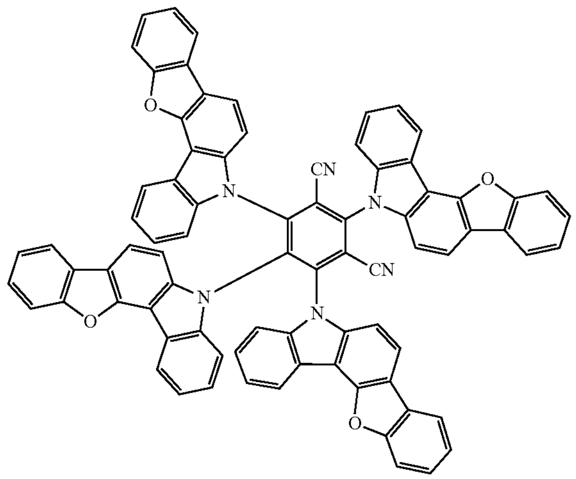

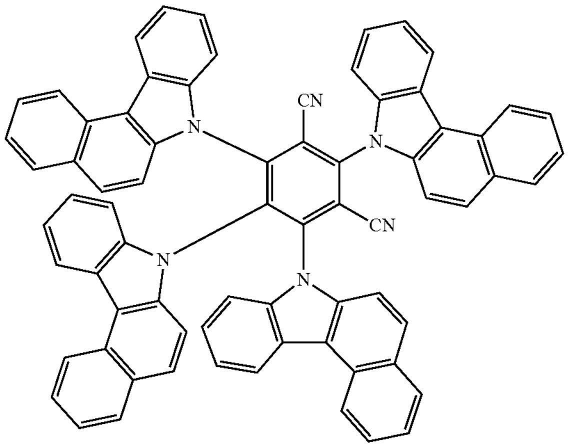

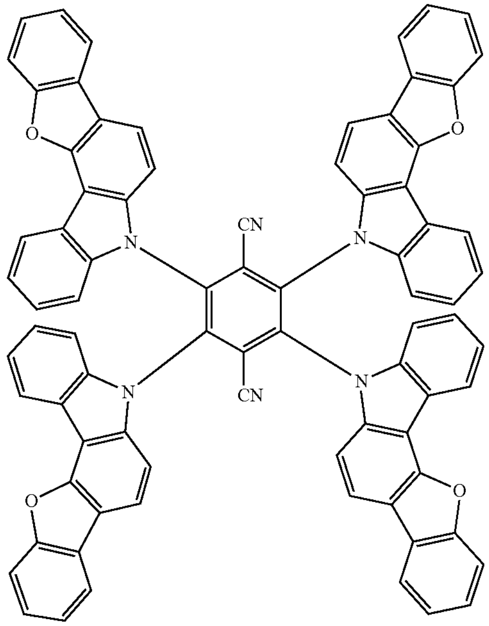

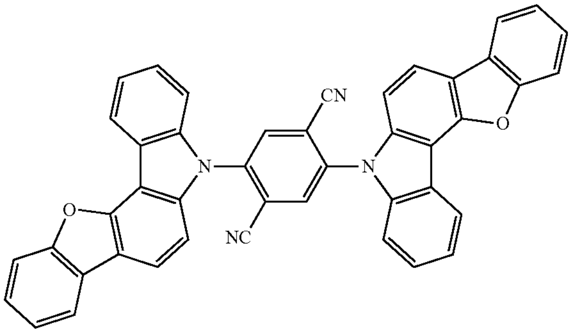
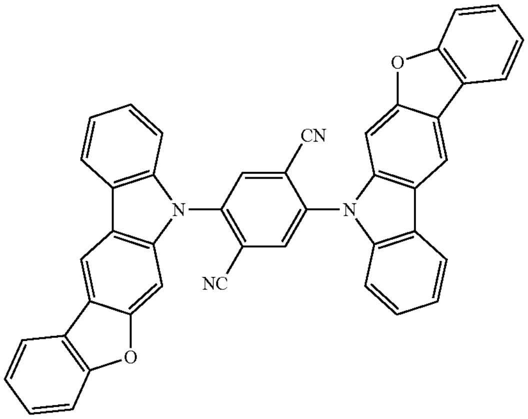
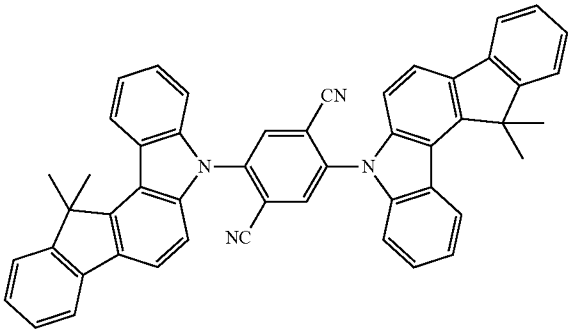
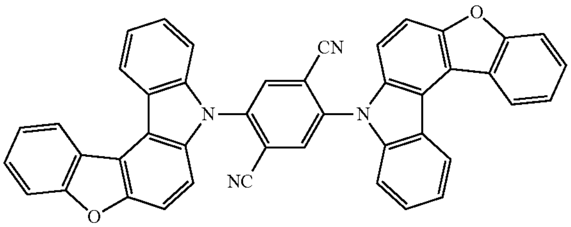
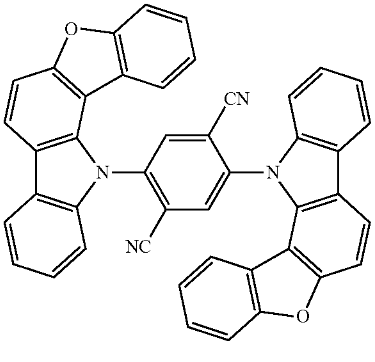
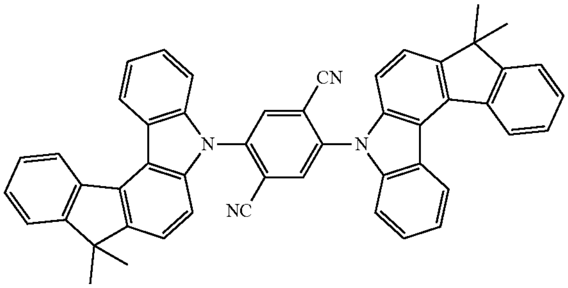
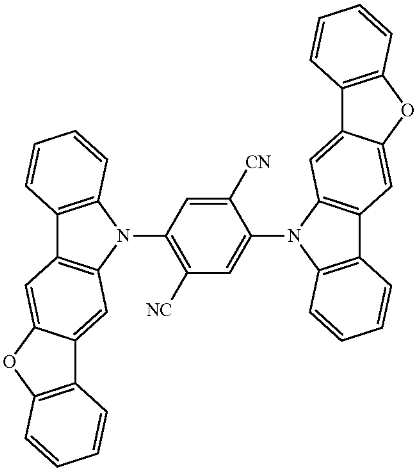
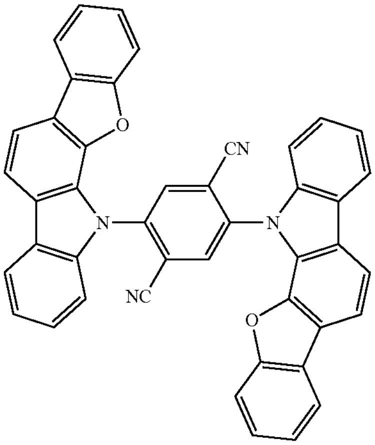
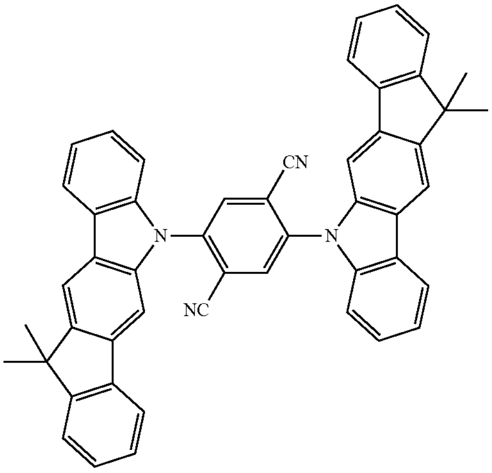

-continued
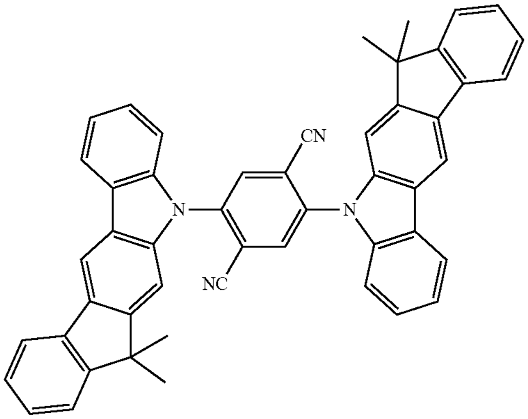
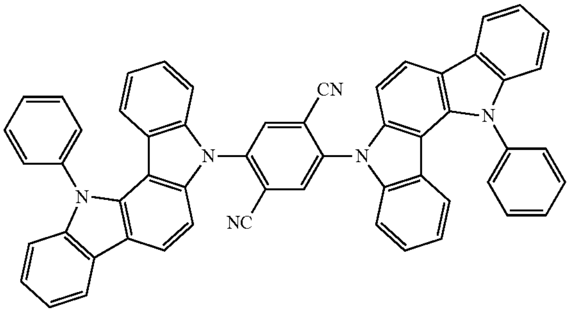
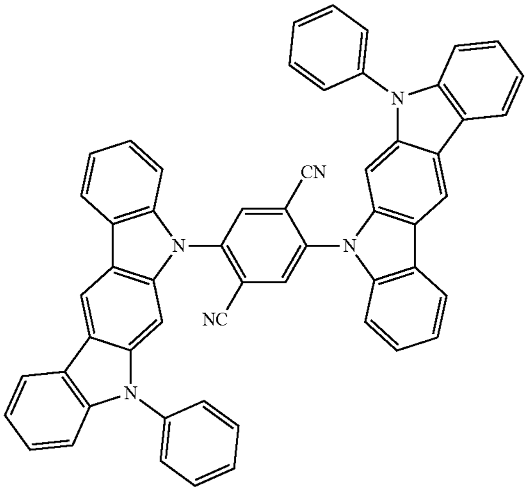
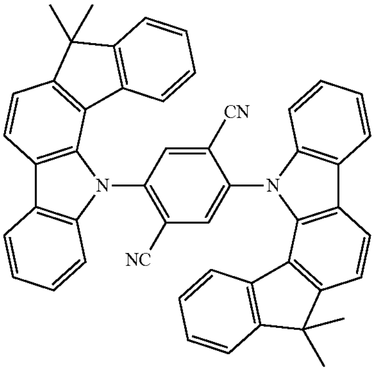
-continued
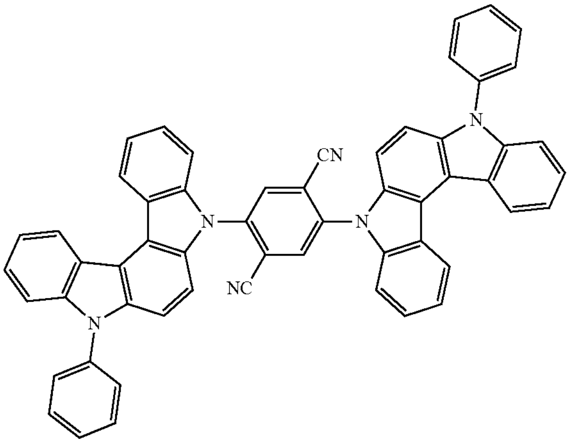
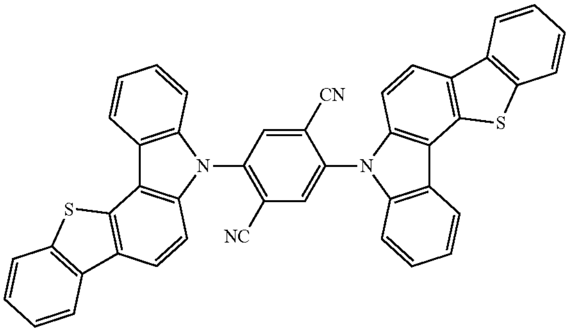
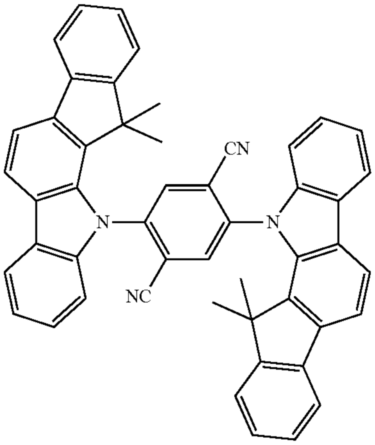
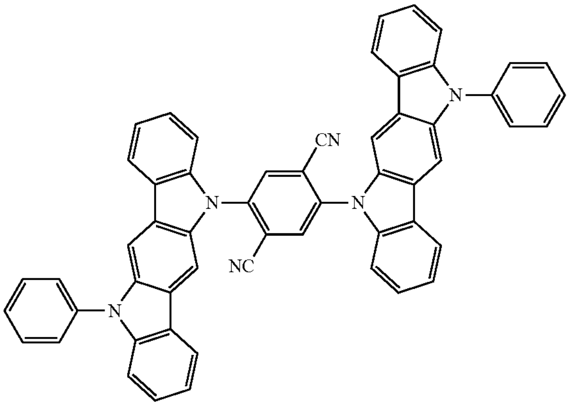

-continued
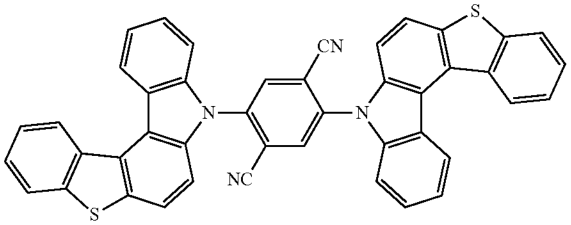
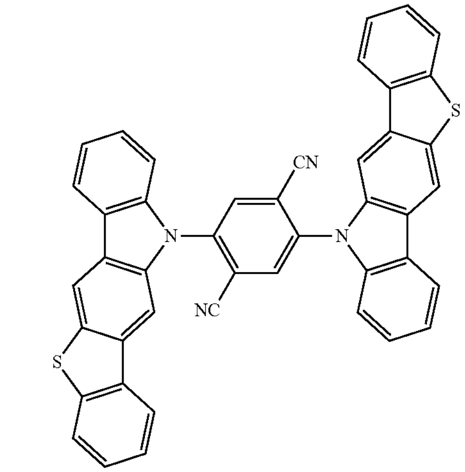
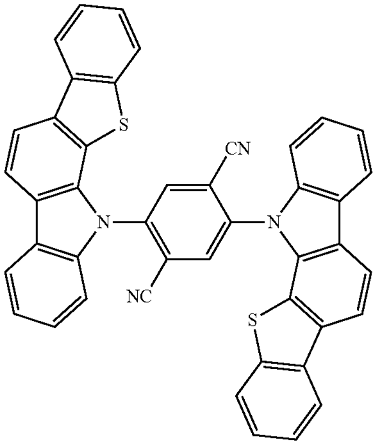
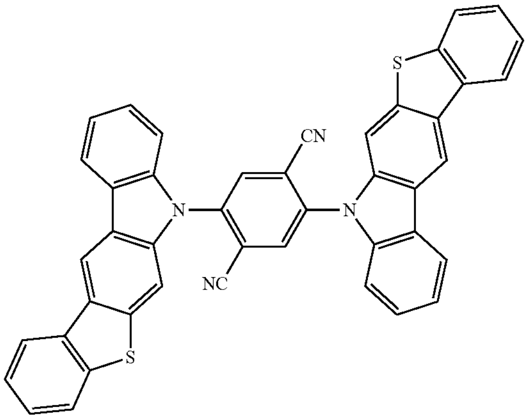
-continued
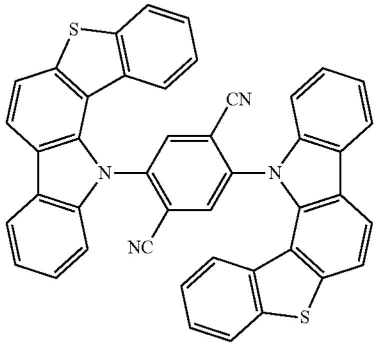
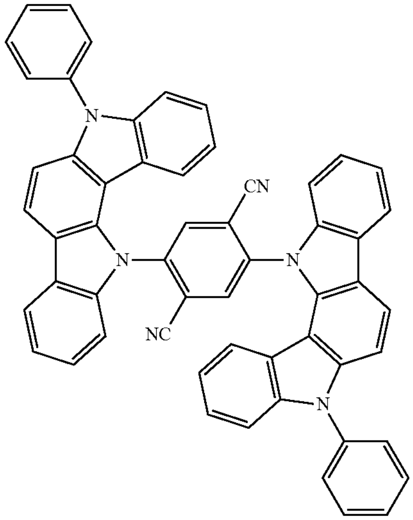
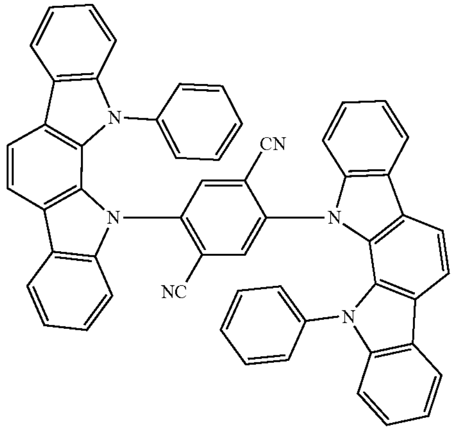
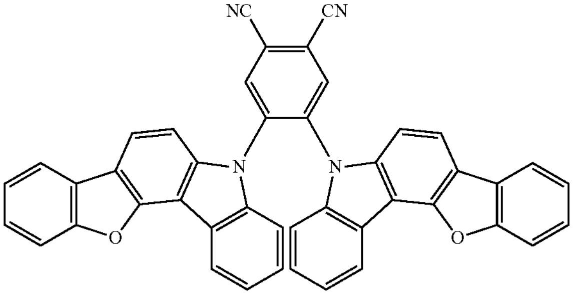

-continued
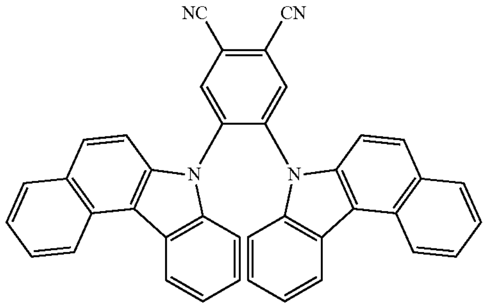
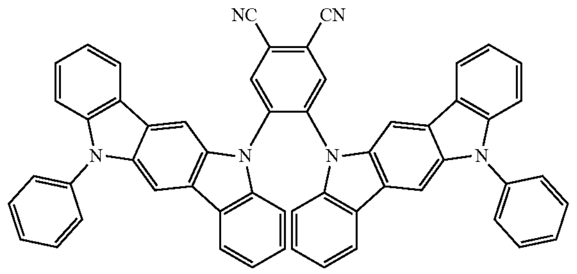
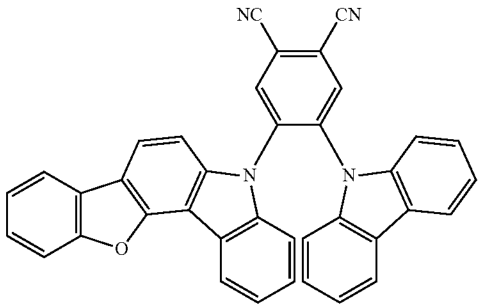
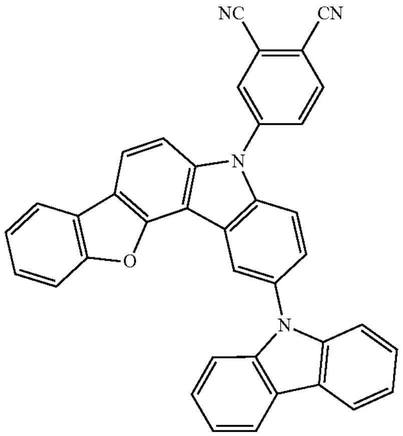
-continued
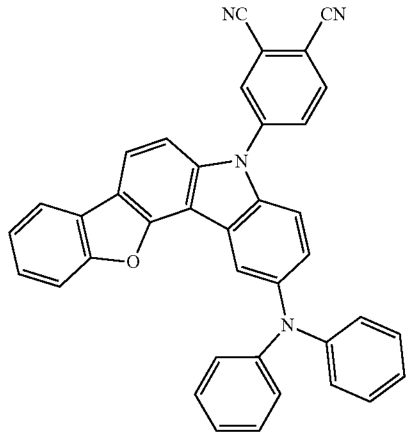
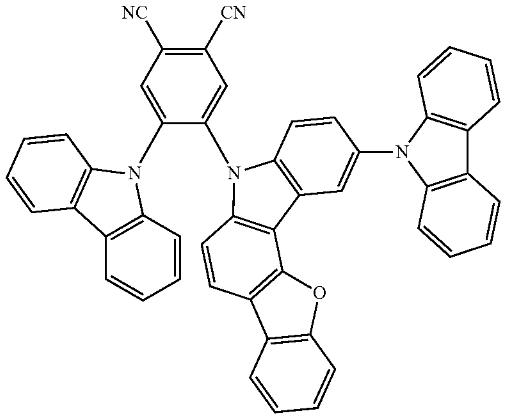
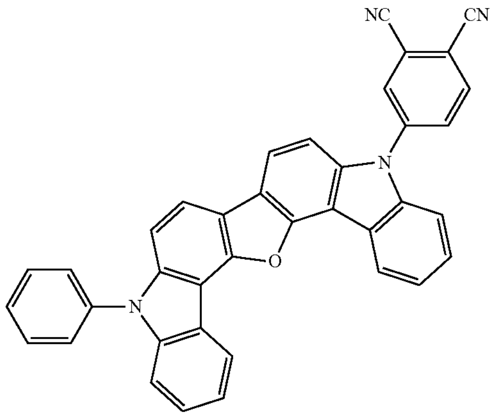
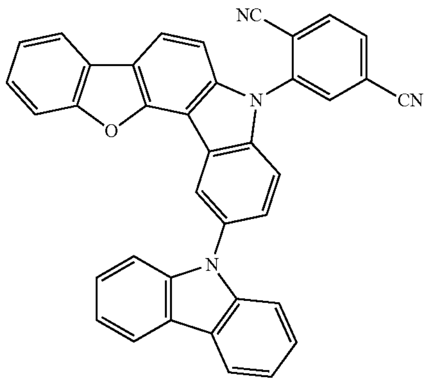

-continued
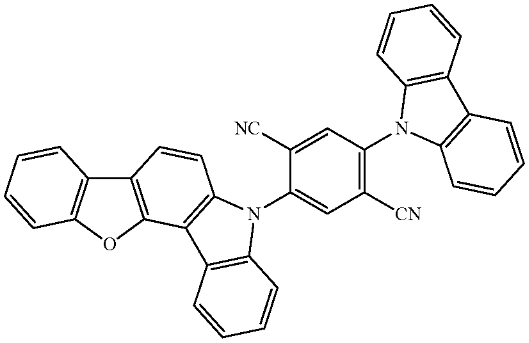
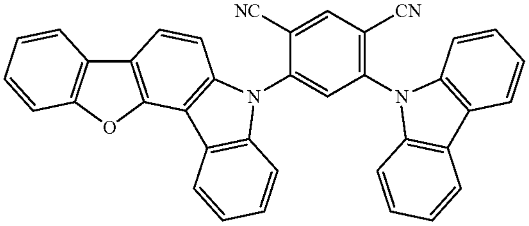
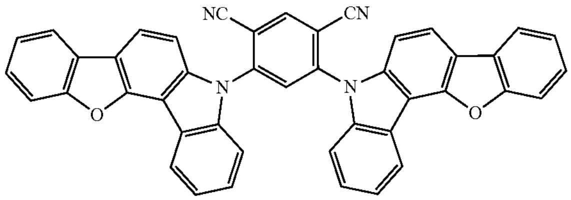
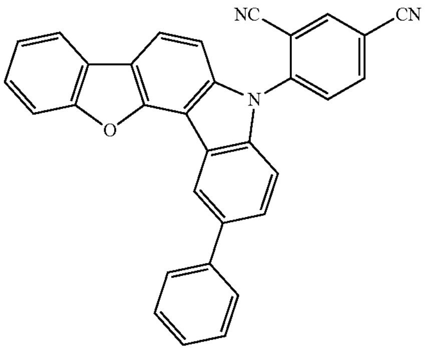
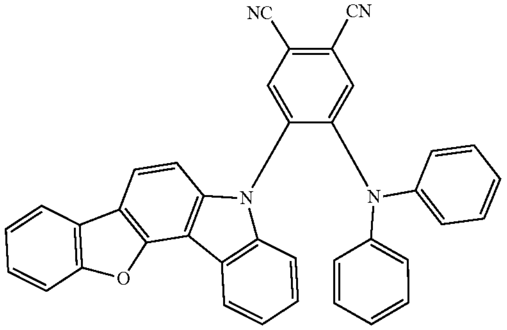
-continued
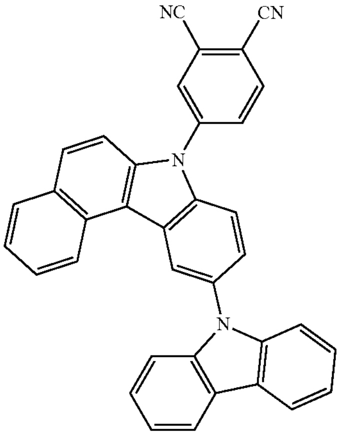
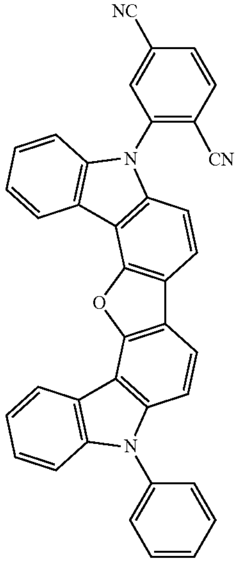
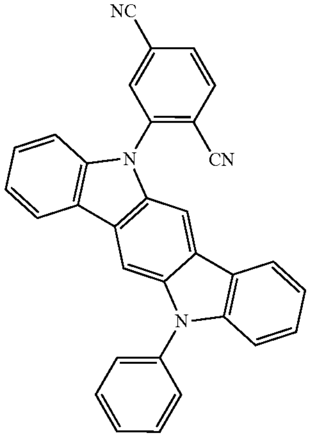

-continued
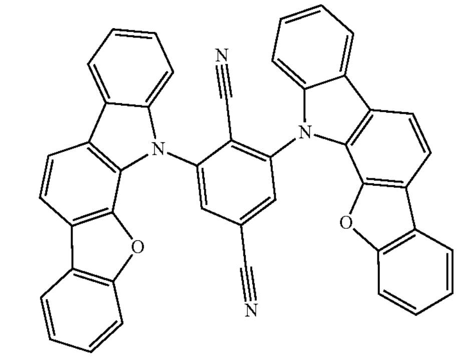
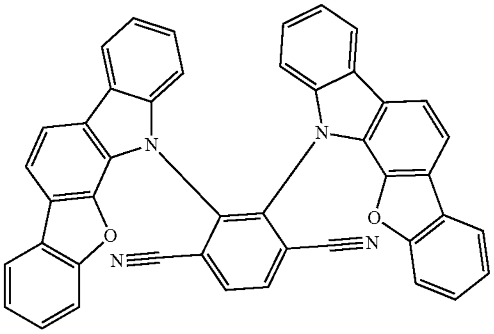
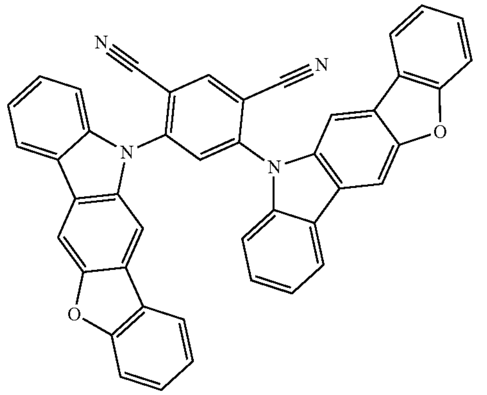
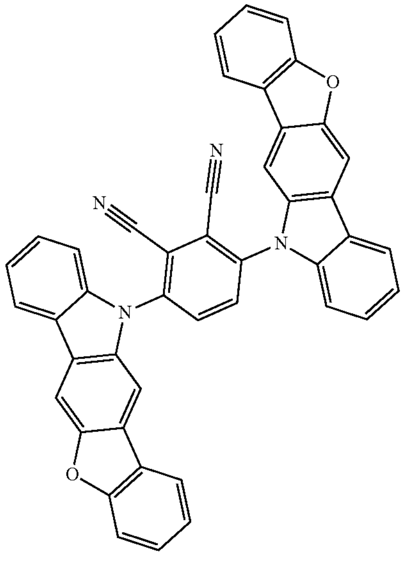
-continued
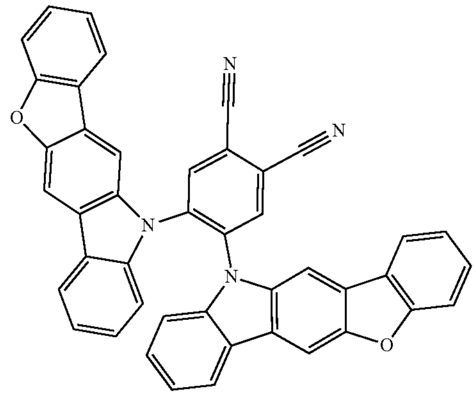
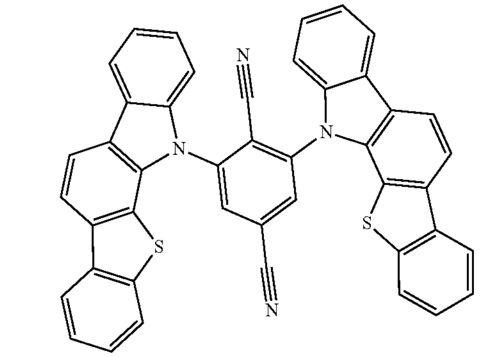
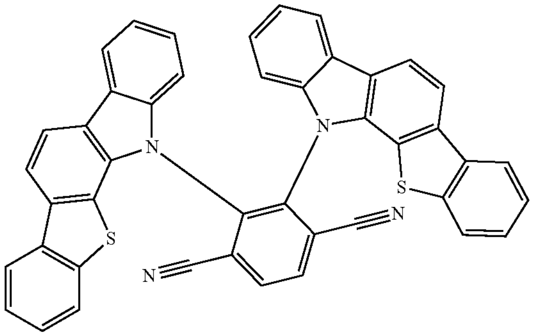
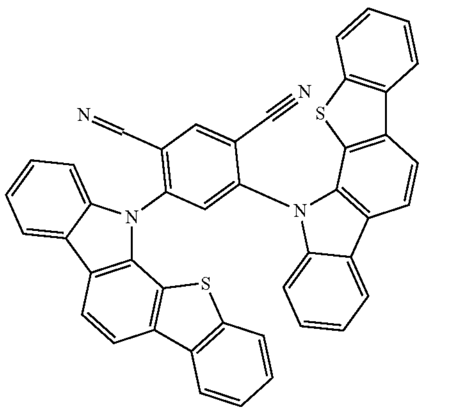

-continued
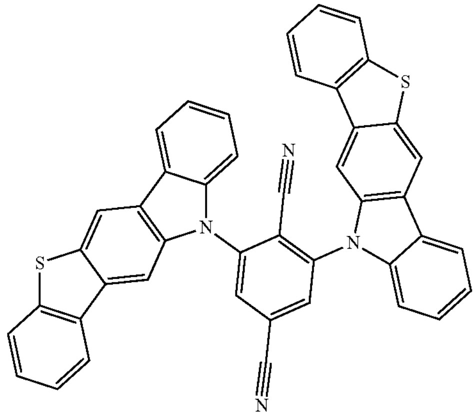
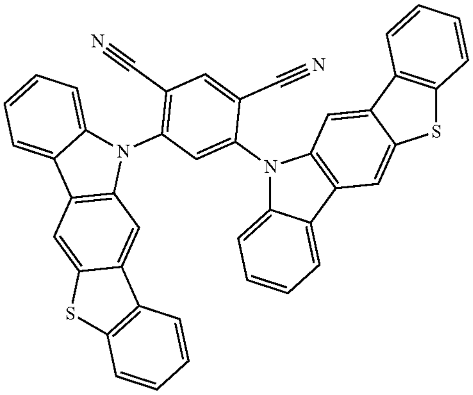
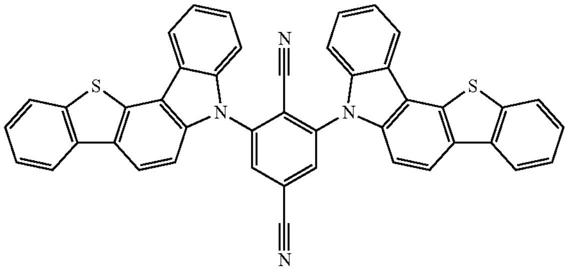
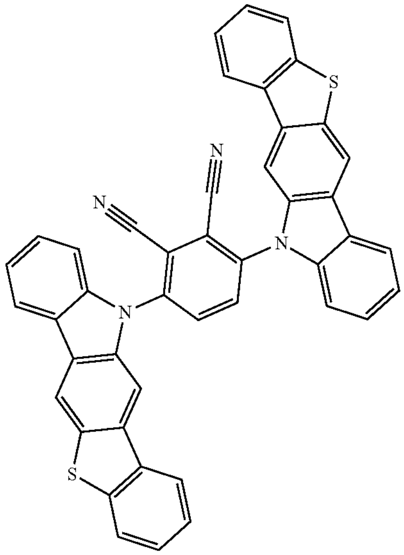
-continued
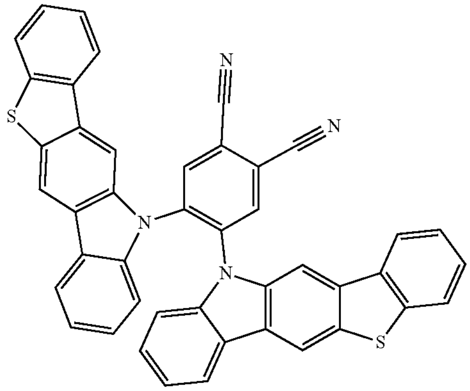
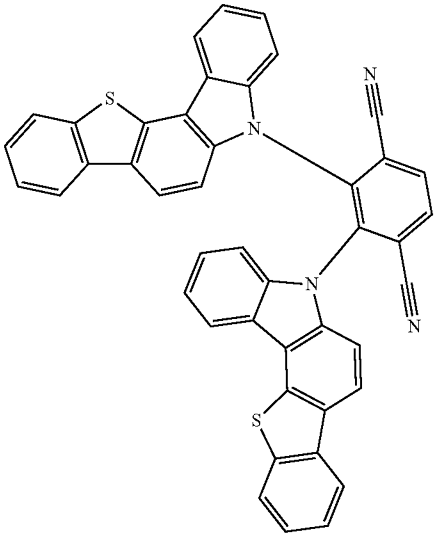
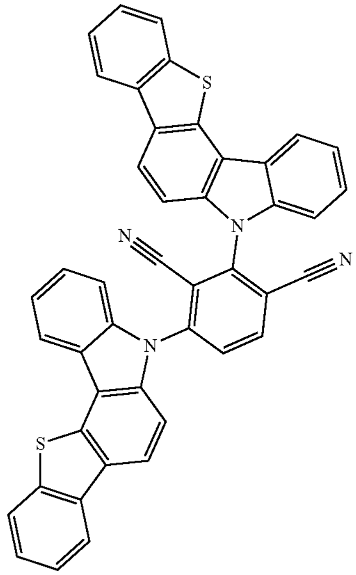

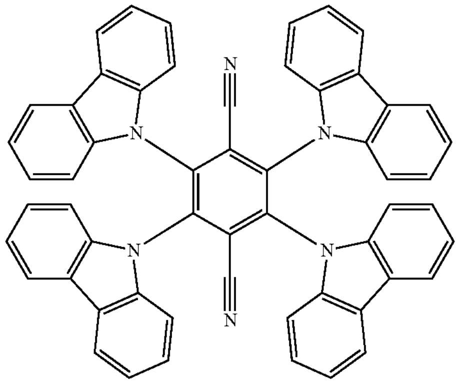
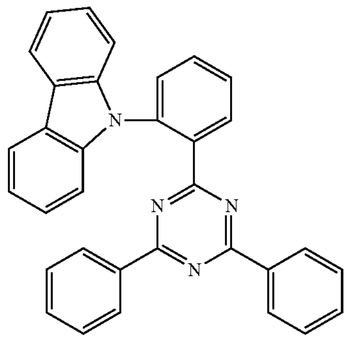
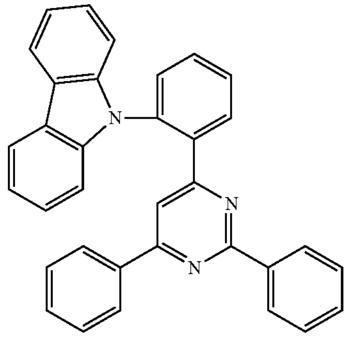
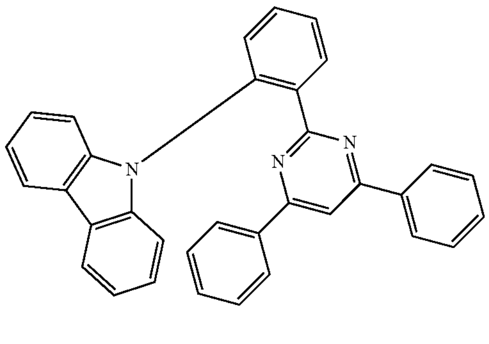
-continued
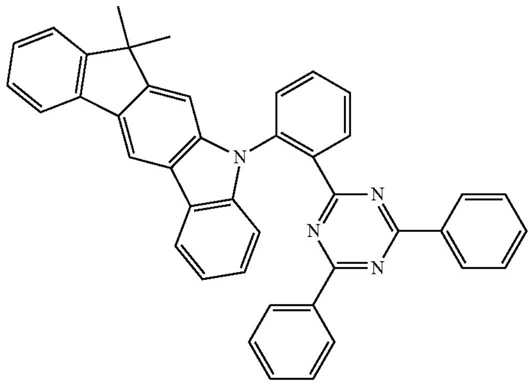
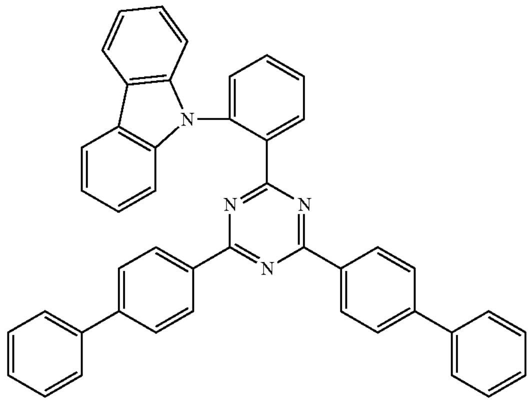
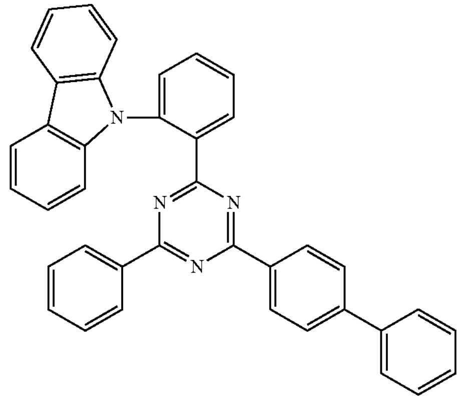
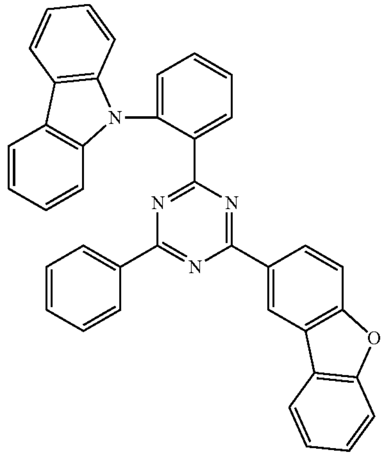

-continued
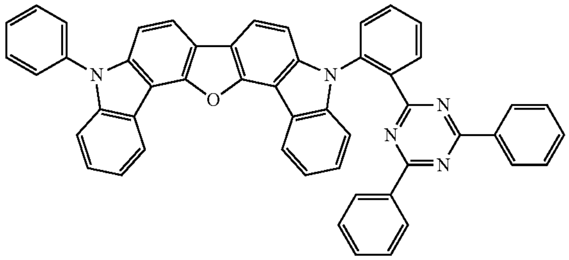
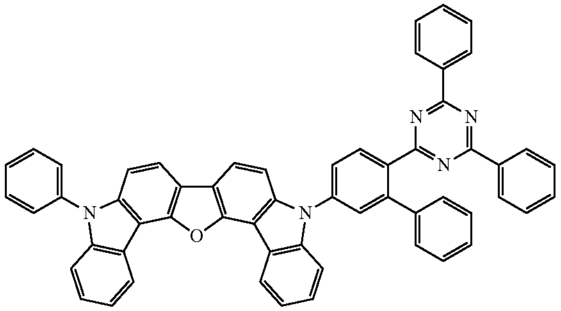
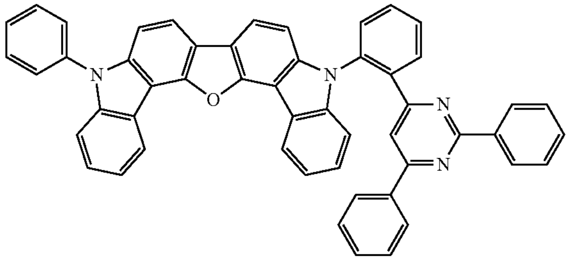
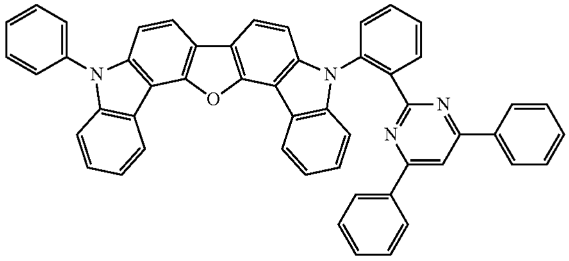
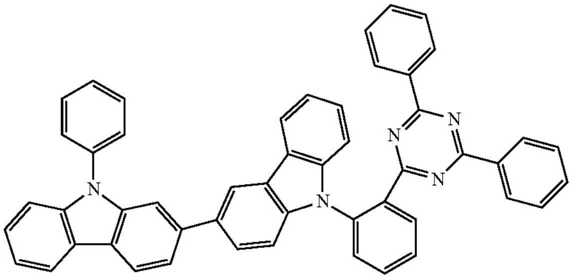
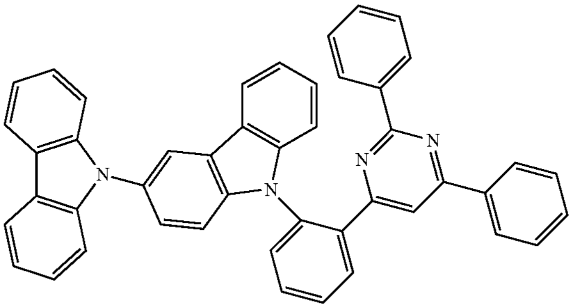
-continued
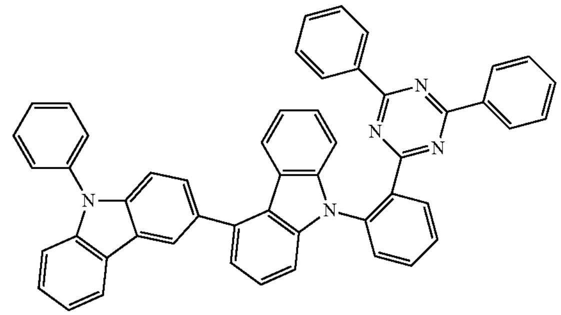
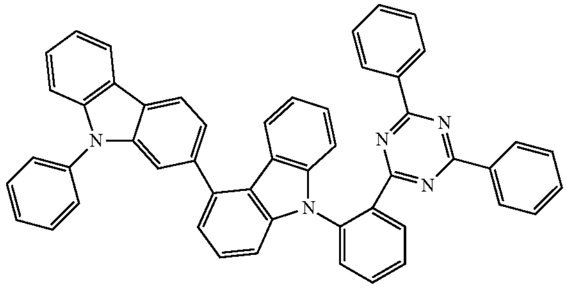
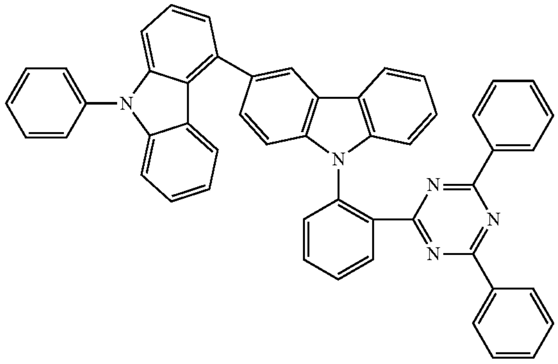
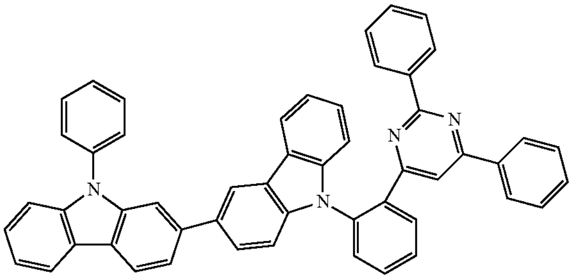
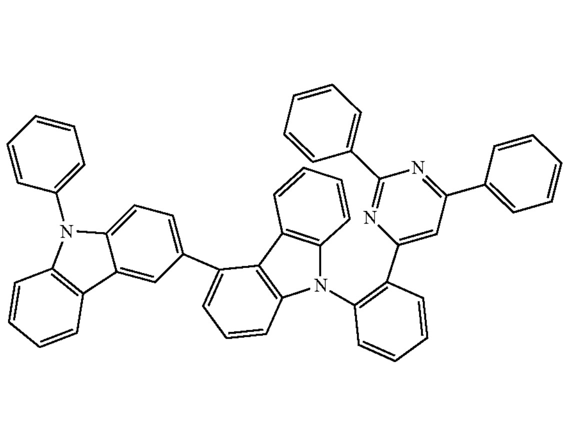

-continued
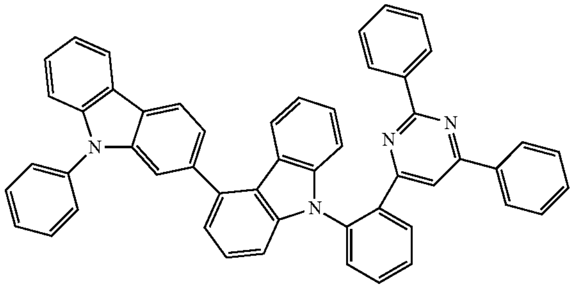
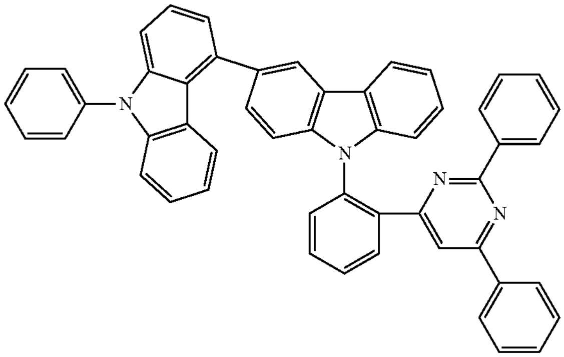
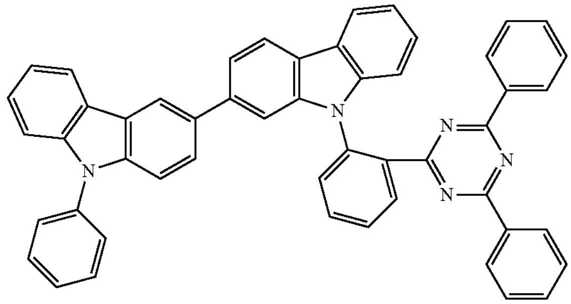
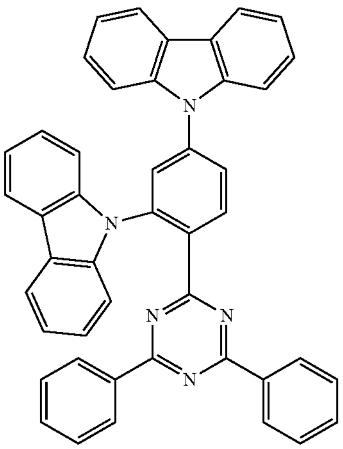
-continued
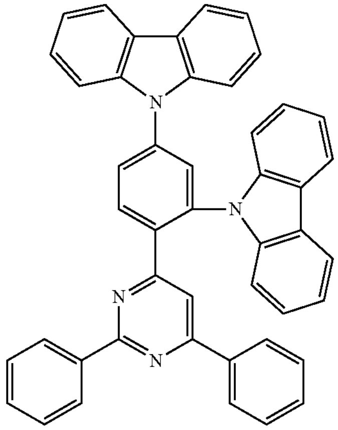
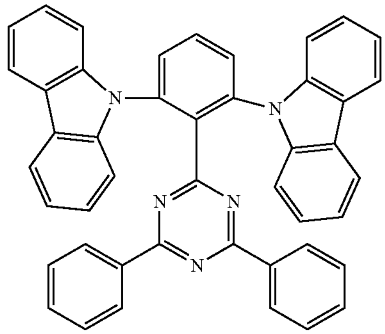
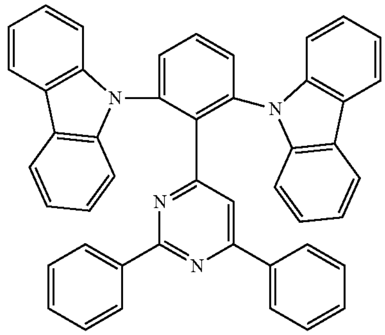
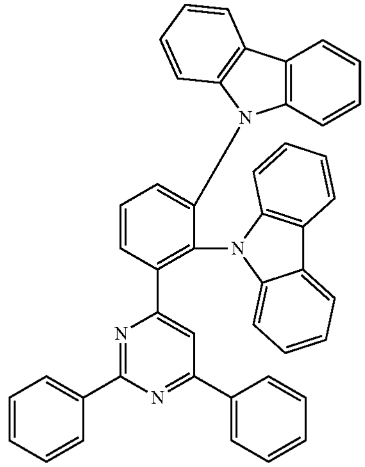

-continued
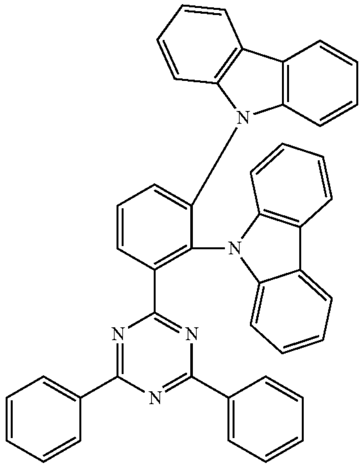
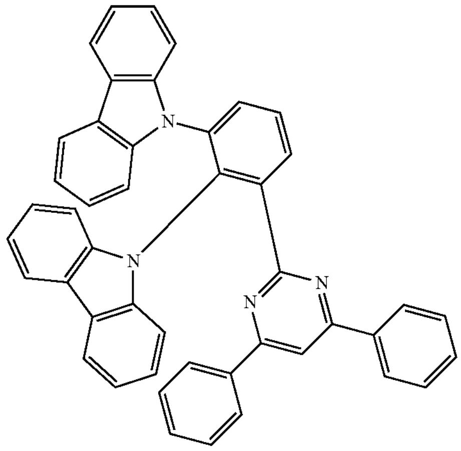
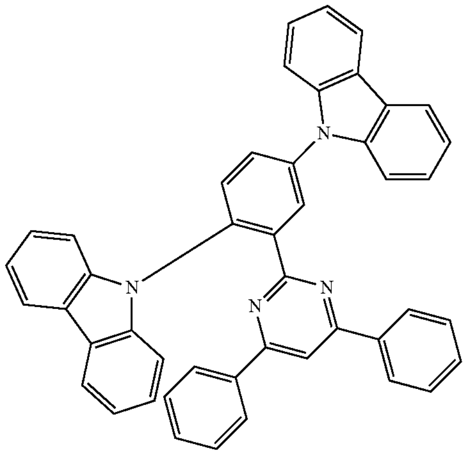
-continued
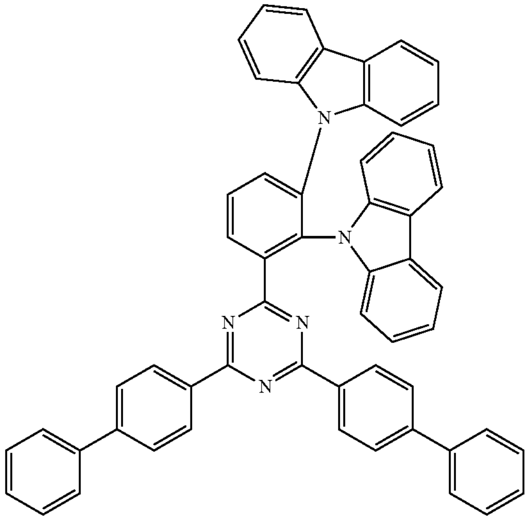
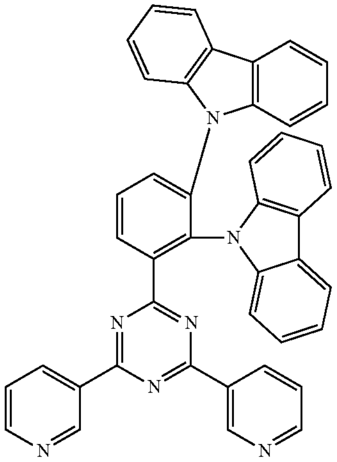
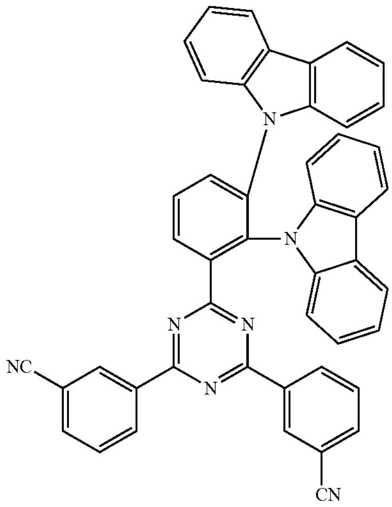

-continued
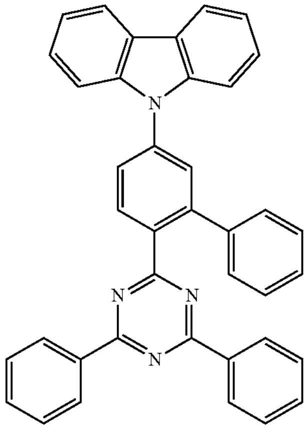
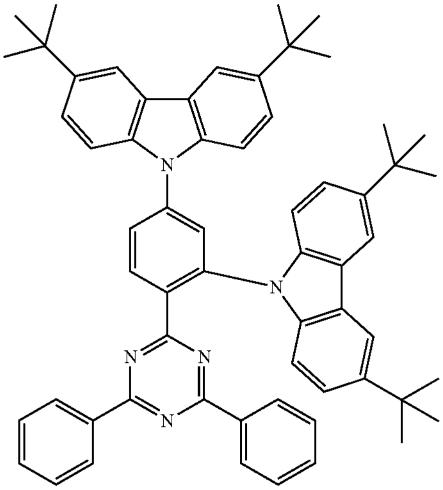
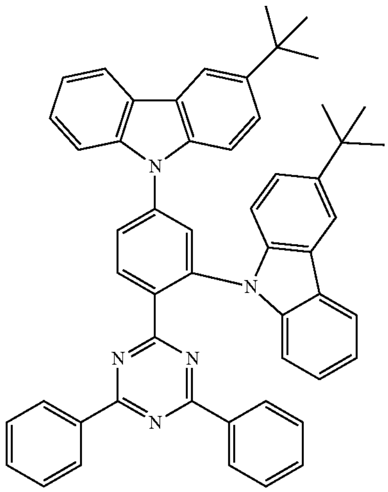
-continued
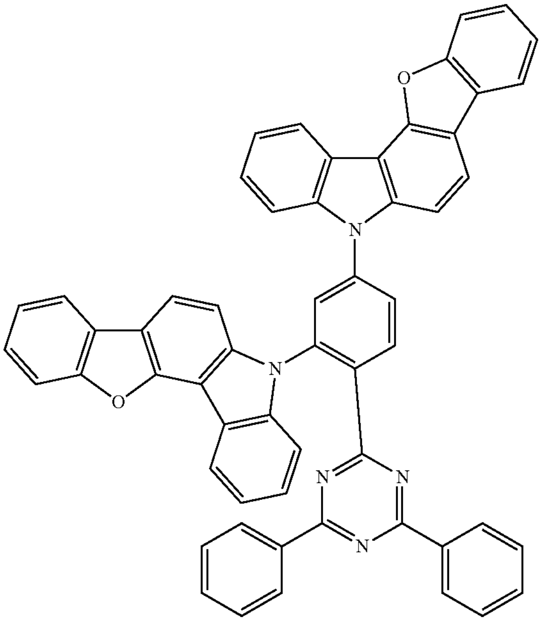
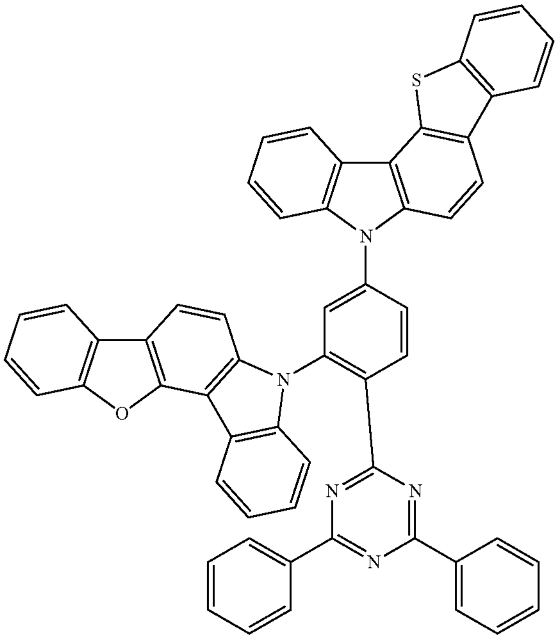

-continued
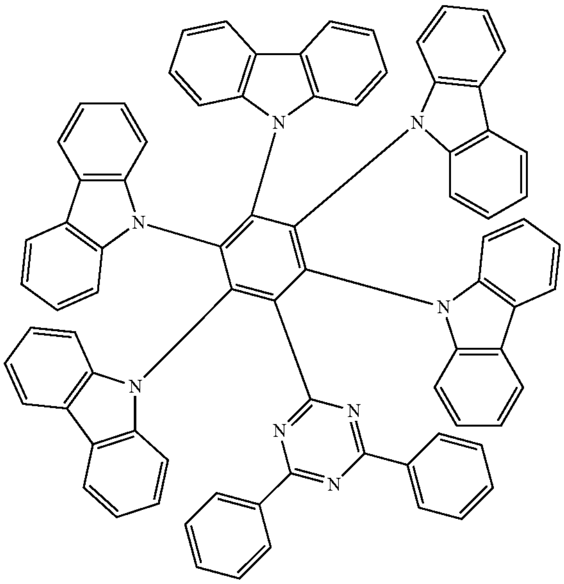
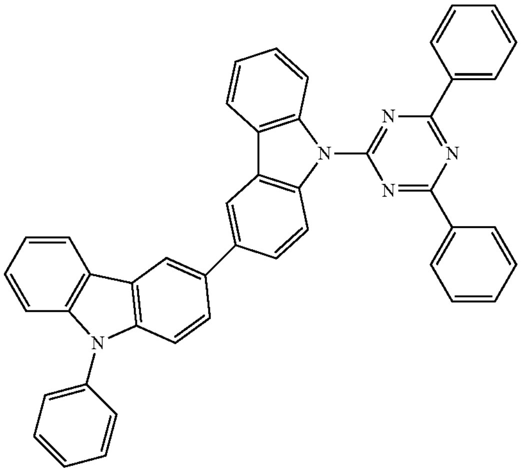
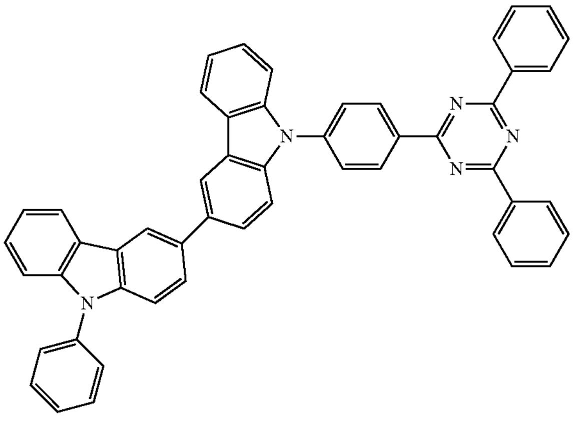
-continued
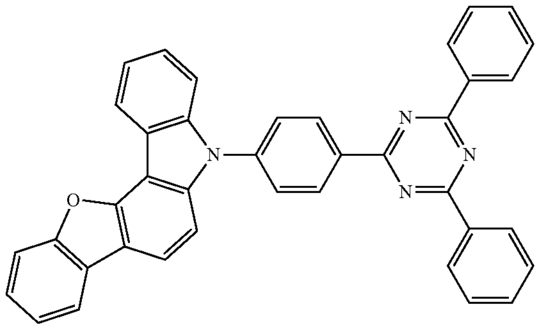
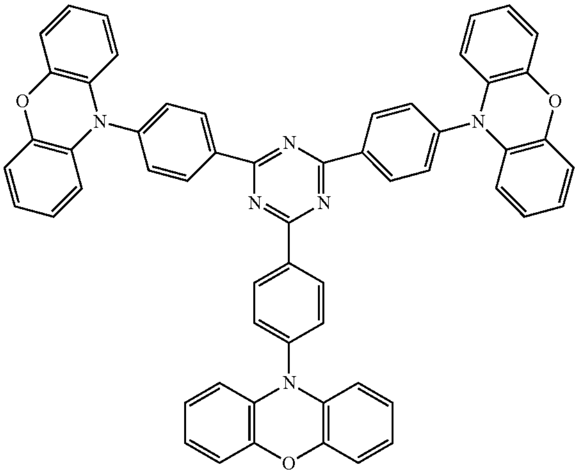
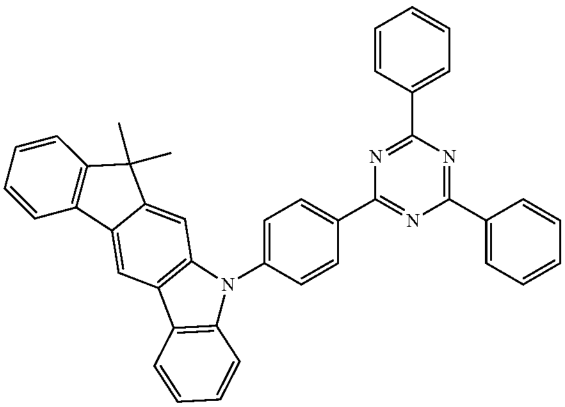
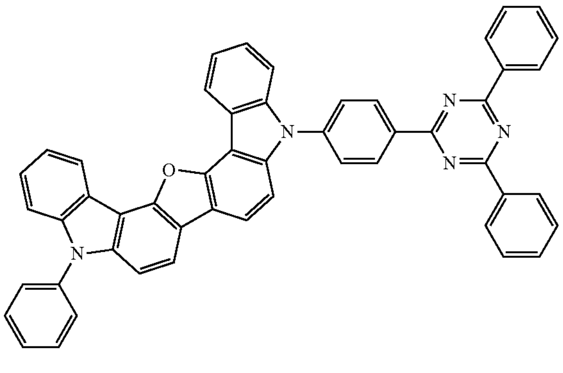

-continued
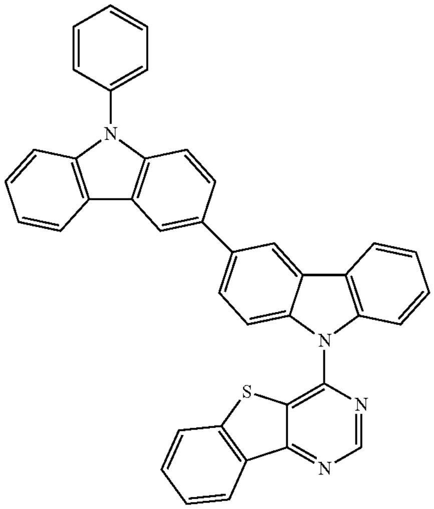
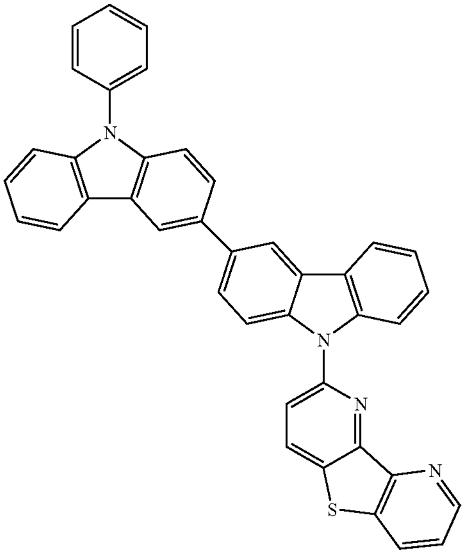
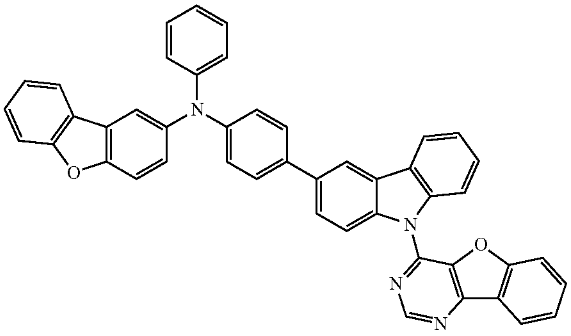
-continued
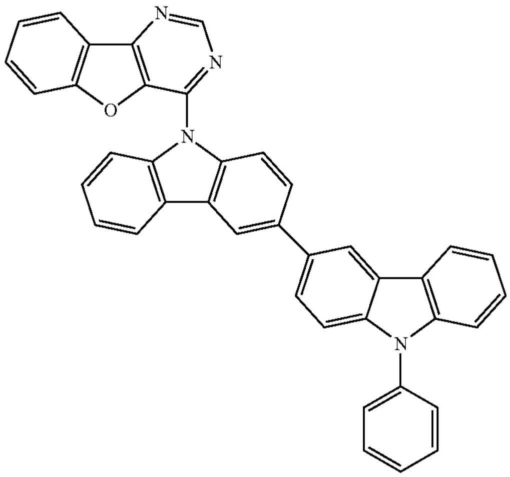
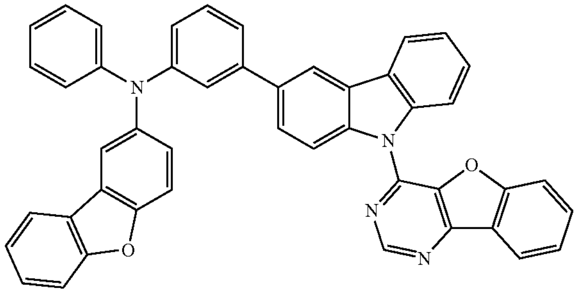
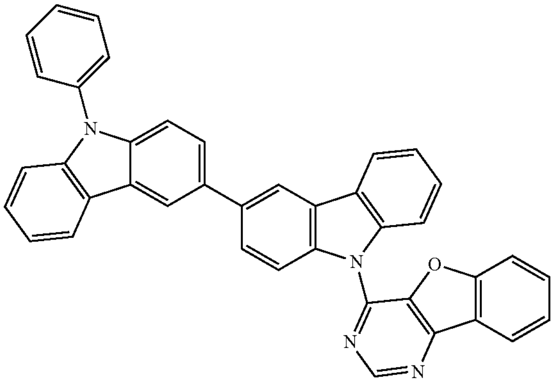

-continued
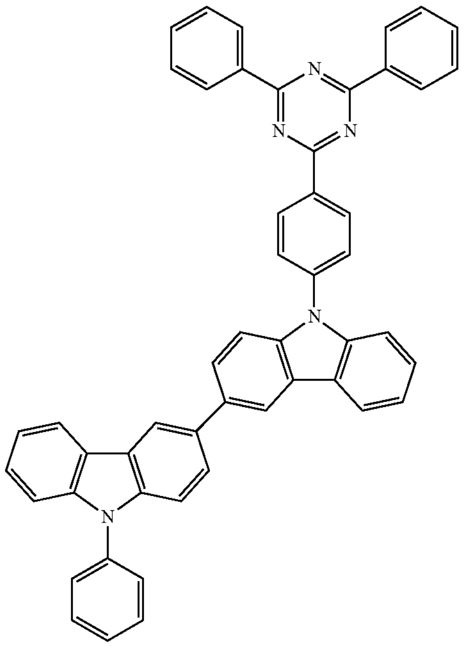
-continued
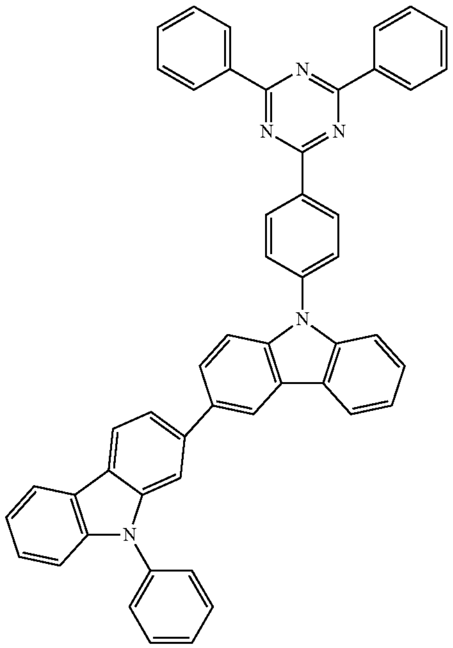
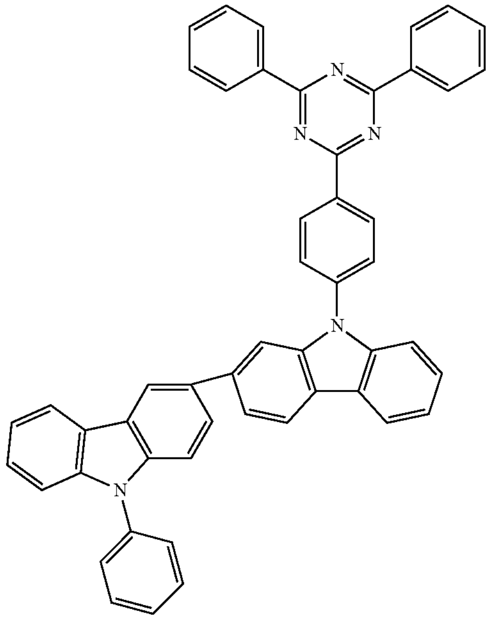
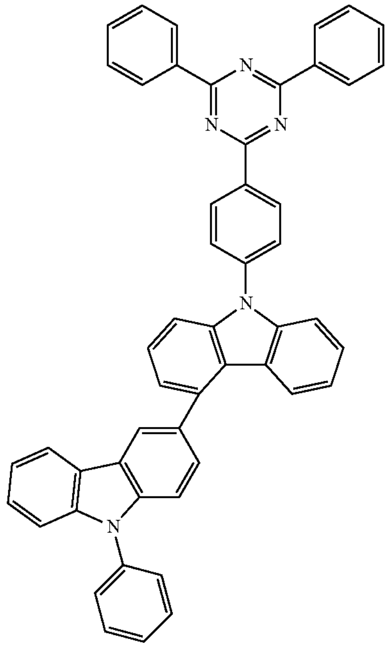

-continued
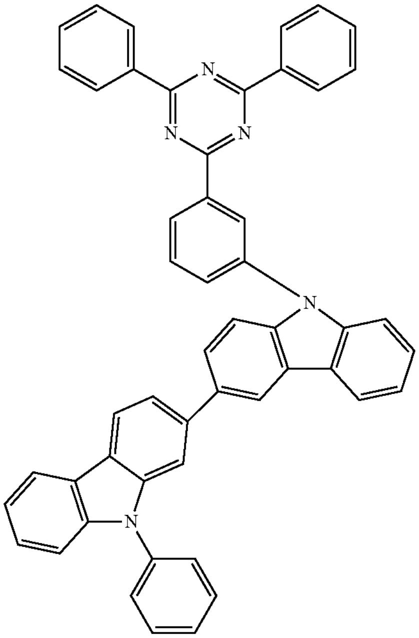
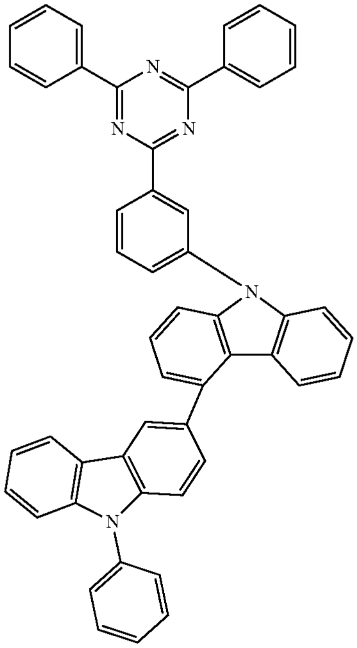
-continued
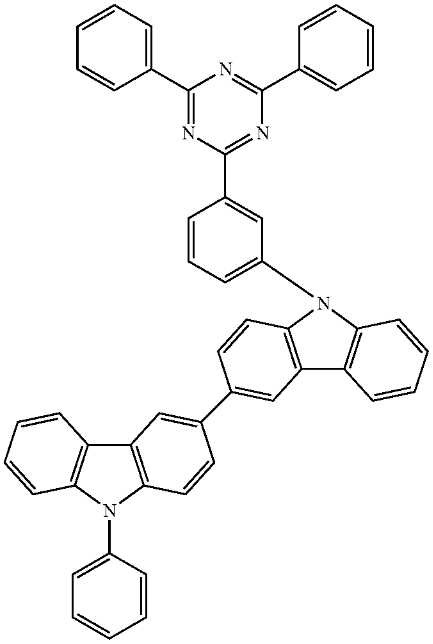
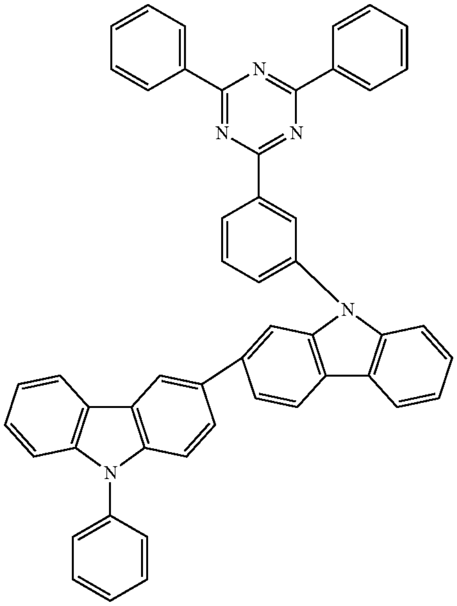

-continued
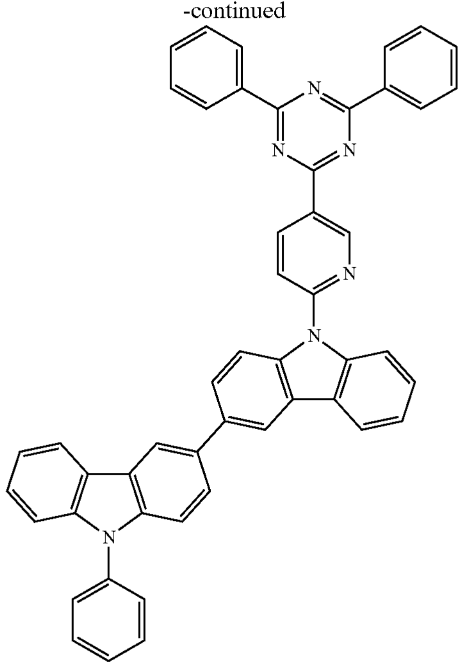
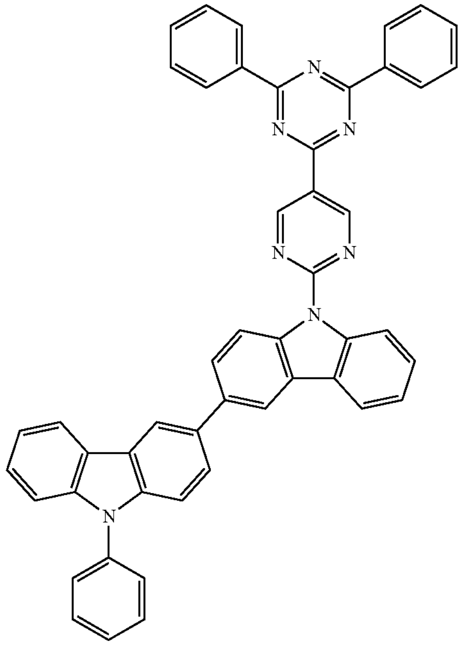
-continued
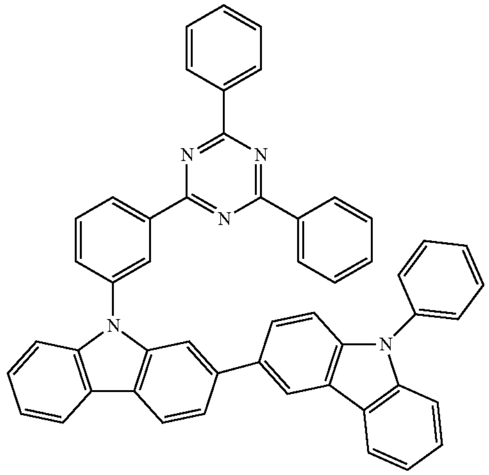
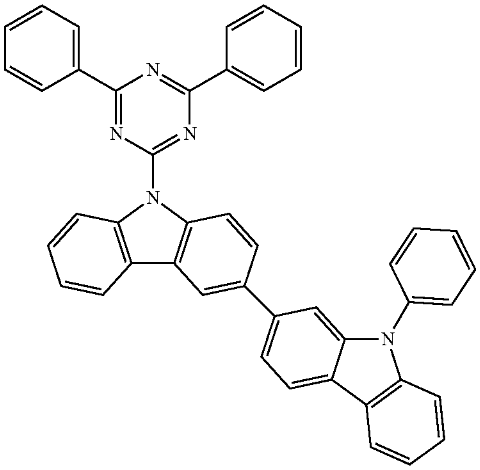
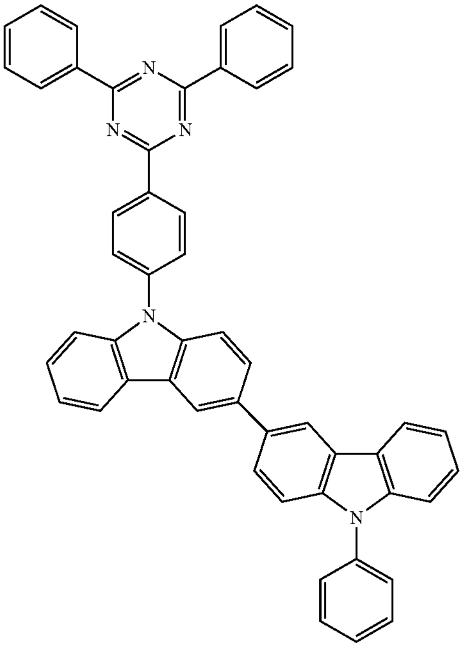

-continued

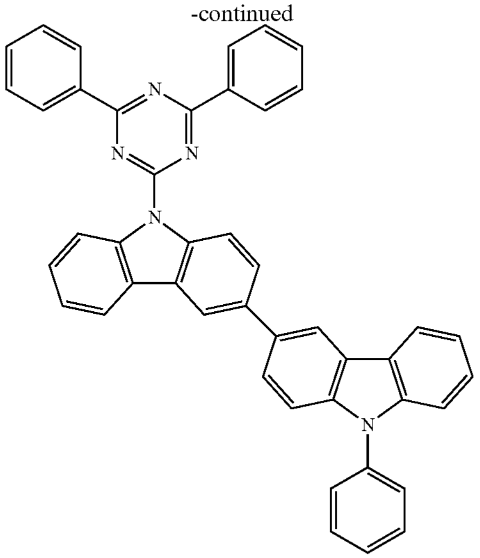

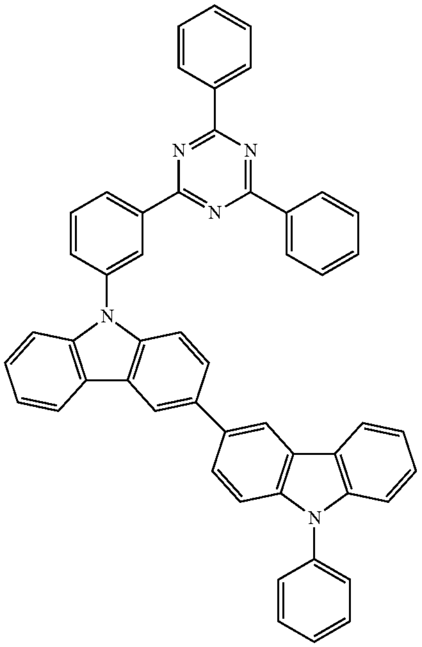

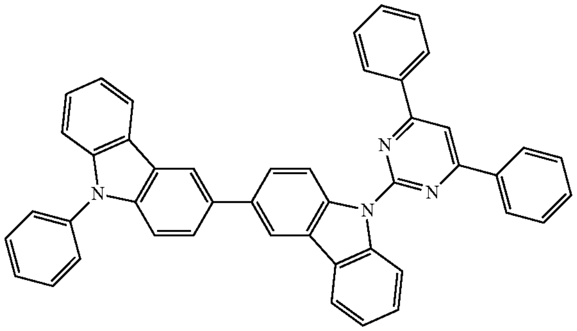

Fourth Compound

The emitting layer of the exemplary embodiment preferably contains the fourth compound that fluoresces.

The fourth compound of the exemplary embodiment is not a phosphorescent metal complex. The fourth compound of the exemplary embodiment is preferably not a heavy metal complex. The fourth compound of the exemplary embodiment is preferably not a metal complex.

The fourth compound of the exemplary embodiment is preferably a compound exhibiting no thermally activated delayed fluorescence.

A fluorescent material is usable as the fourth compound of the exemplary embodiment. Specific examples of the fluorescent material include a bisarylaminonaphthalene derivative, aryl-substituted naphthalene derivative, bisarylaminoanthracene derivative, aryl-substituted anthracene derivative, bisarylaminopyrene derivative, aryl-substituted pyrene derivative, bisarylamino chrysene derivative, aryl-substituted chrysene derivative, bisarylaminofluoranthene derivative, aryl-substituted fluoranthene derivative, indenoperylene derivative, acenaphthofluoranthene derivative, compound including a boron atom, pyromethene boron complex compound, compound having a pyromethene skeleton, metal complex of the compound having a pyromethene skeleton, diketopyrrolopyrrole derivative, perylene derivative, and naphthacene derivative.

Compound Represented by Formula (20)

In the exemplary embodiment, the fourth compound is preferably a compound represented by a formula (20).

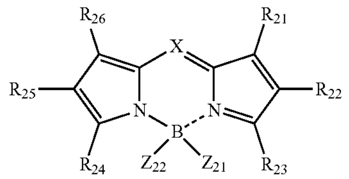

(20)

In the formula (20):

X is a nitrogen atom, or a carbon atom bonded to Y;

Y is a hydrogen atom or a substituent;

$R_{21}$ to $R_{26}$ are each independently a hydrogen atom or a substituent, or at least one of a pair of $R_{21}$ and $R_{22}$, a pair of $R_{22}$ and $R_{23}$, a pair of $R_{24}$ and $R_{25}$, or a pair of $R_{25}$ and $R_{26}$ are mutually bonded to form a ring;

Y and $R_{21}$ to $R_{26}$ as a substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group a cyano group, a substituted or unsubstituted silyl group, and a substituted or unsubstituted siloxanyl group;

$Z_{21}$ and $Z_{22}$ are each independently a substituent, or are mutually bonded to form a ring; and $Z_{21}$ and $Z_{22}$ as a substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

When the fourth compound is a fluorescent compound, the main peak wavelength of the fourth compound is preferably in a range from 400 nm to 700 nm.

Herein, the main peak wavelength means a peak wavelength of an fluorescence spectrum exhibiting a maximum luminous intensity among fluorescence spectra measured in a toluene solution in which a measurement target compound is dissolved at a concentration ranging from $10^{-6}$ mol/l to $10^{-5}$ mol/l. A spectrophotofluorometer (F-7000 manufactured by Hitachi High-Tech Science Corporation) is used as a measurement device.

The fourth compound preferably exhibits red or green light emission.

Herein, the red light emission refers to light emission whose main peak wavelength of fluorescence spectrum is in a range from 600 nm to 660 nm.

When the fourth compound is a red fluorescent compound, the main peak wavelength of the fourth compound is preferably in a range from 600 nm to 660 nm, more preferably in a range from 600 nm to 640 nm, further preferably in a range from 610 nm to 630 nm.

Herein, the green light emission refers to light emission whose main peak wavelength of fluorescence spectrum is in a range from 500 nm to 560 nm.

When the fourth compound is a green fluorescent compound, the main peak wavelength of the fourth compound is preferably in a range from 500 nm to 560 nm, more preferably in a range from 500 nm to 540 nm, further preferably in a range from 510 nm to 540 nm.

Herein, the blue light emission refers to a light emission in which a main peak wavelength of fluorescence spectrum is in a range from 430 nm to 480 nm.

When the fourth compound is a blue fluorescent compound, the main peak wavelength of the fourth compound is preferably in a range from 430 nm to 480 nm, more preferably in a range from 440 nm to 480 nm.

A main peak wavelength of light from an organic EL device is measured as follows.

Voltage is applied on the organic EL devices such that a current density becomes 10 mA/$cm^2$, where spectral radiance spectrum is measured by a spectroradiometer CS-2000 (manufactured by Konica Minolta, Inc.).

A peak wavelength of an emission spectrum, at which the luminous intensity of the resultant spectral radiance spectrum is at the maximum, is measured and defined as the main peak wavelength (unit: nm).

Manufacturing Method of Fourth Compound

The fourth compound can be manufactured by a known method.

Specific Examples of Fourth Compound

Specific examples of the fourth compound (compound represented by the formula (20)) according to the exemplary embodiment are shown below. However, the invention is not limited to the specific examples of the compounds.

A coordinate bond between a boron atom and a nitrogen atom in a pyrromethene skeleton is shown by various means such as a solid line, a broken line, an arrow, and omission. Herein, the coordinate bond is shown by a solid line or a broken line, or the description of the coordinate bond is omitted.

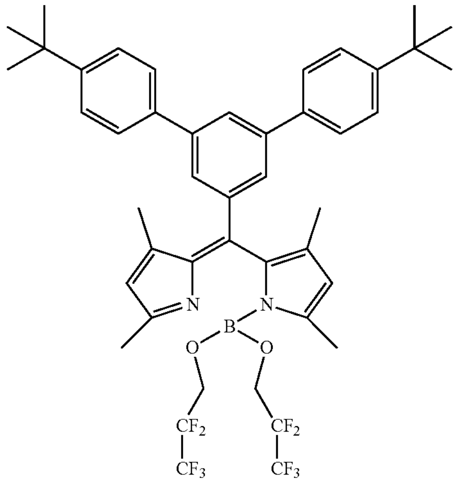

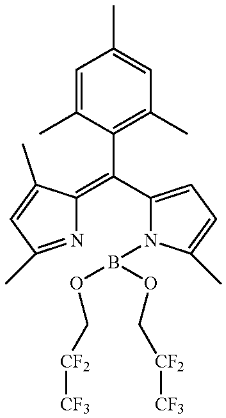

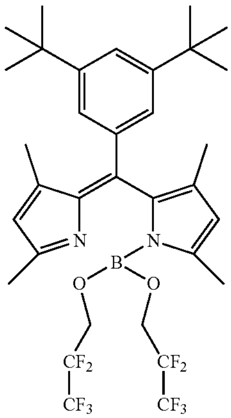

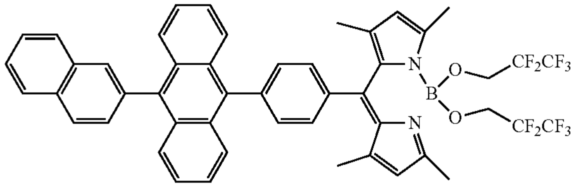

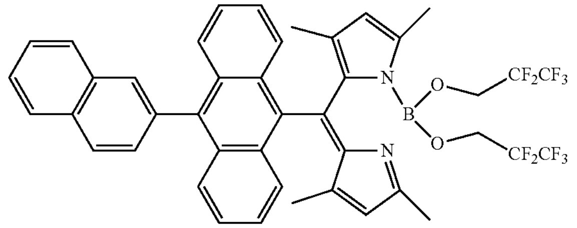

-continued
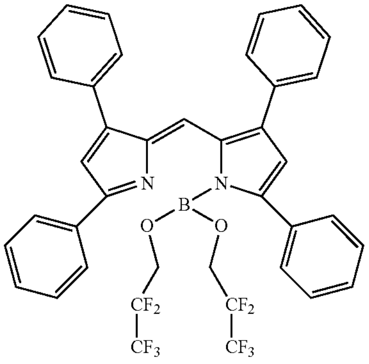
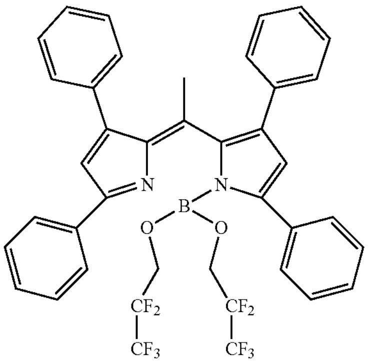
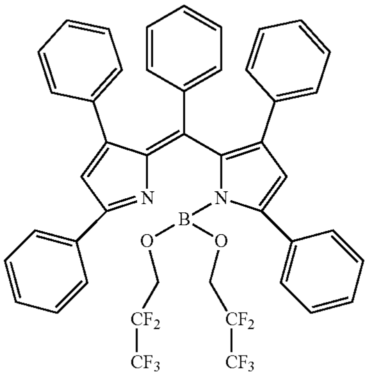
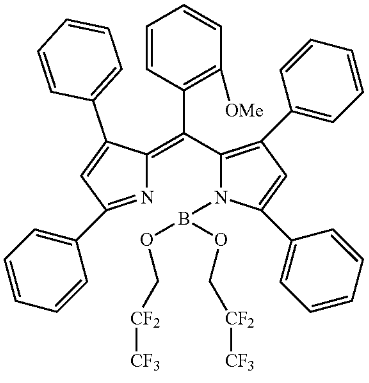
-continued
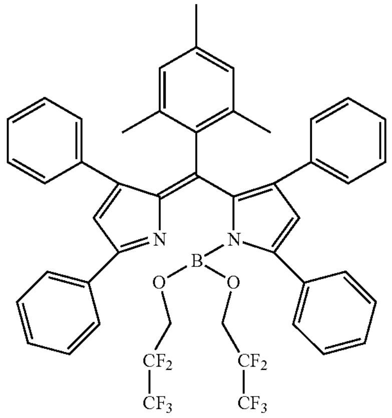
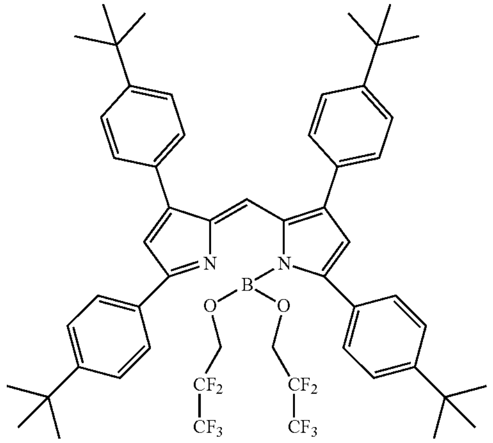
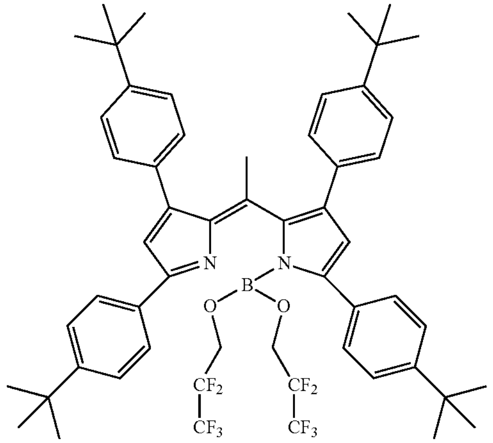
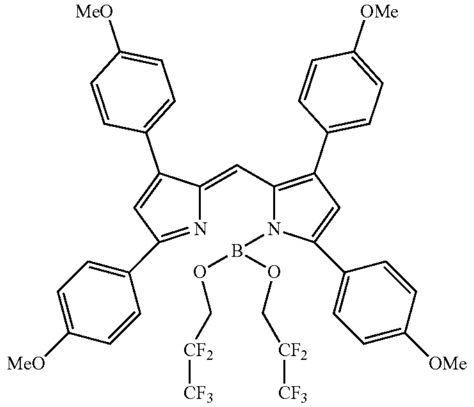

-continued
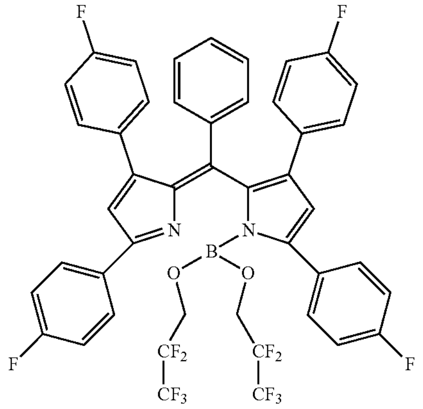
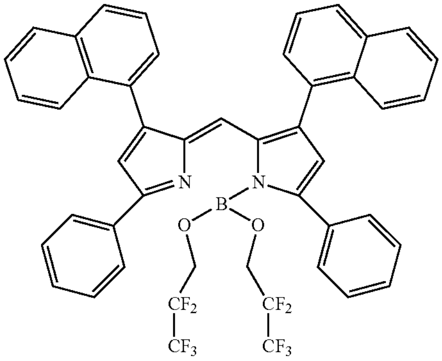
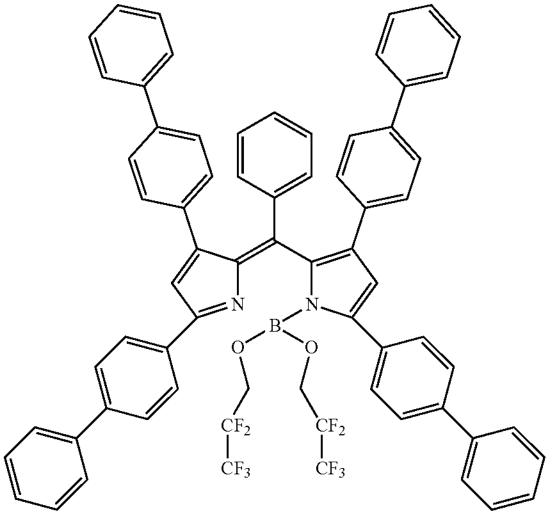
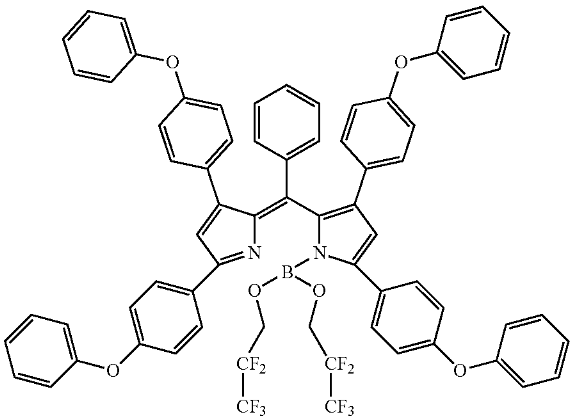
-continued
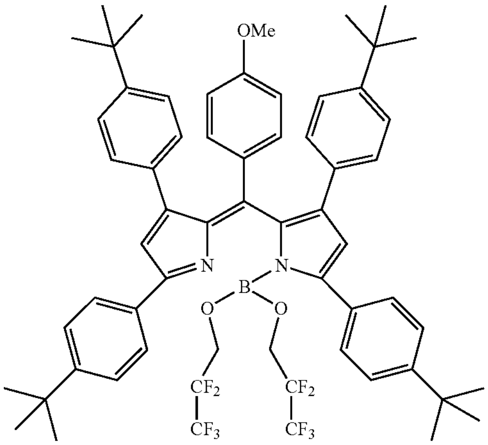
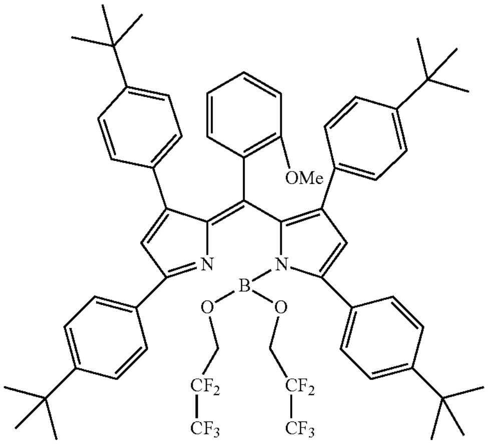
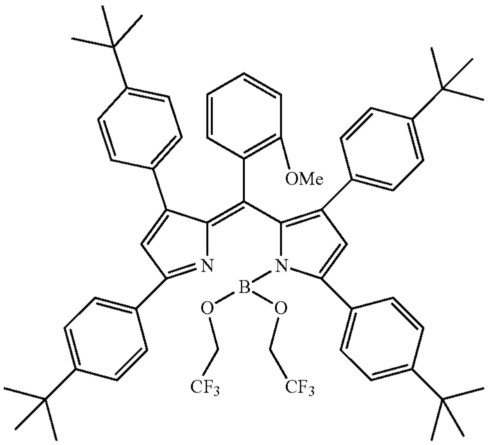

-continued
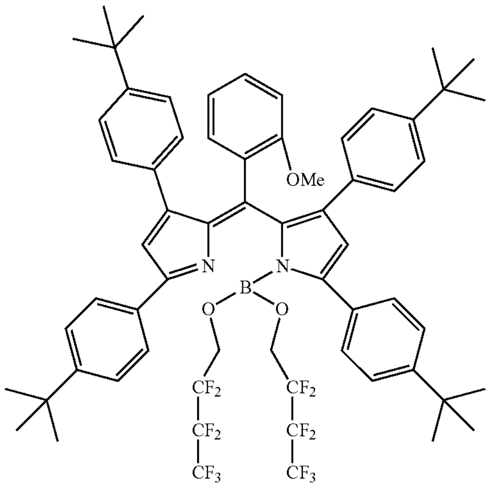
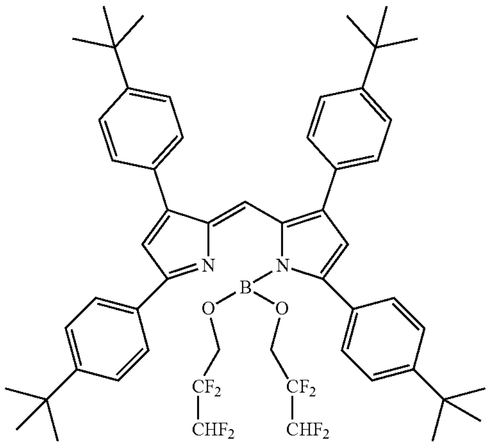
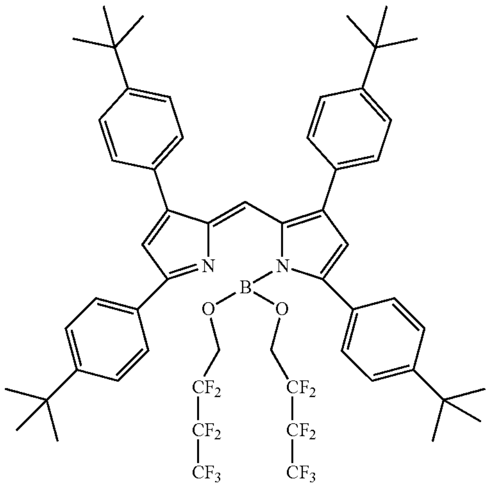
-continued
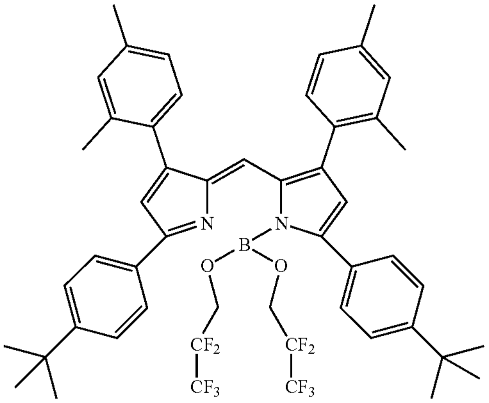
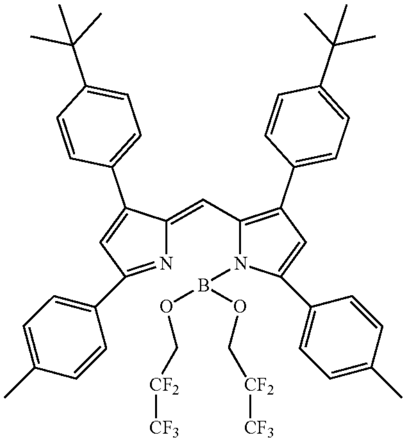
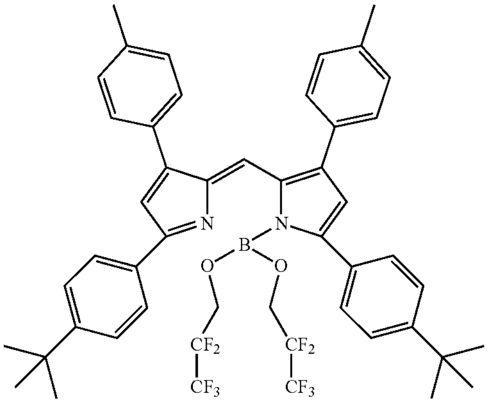
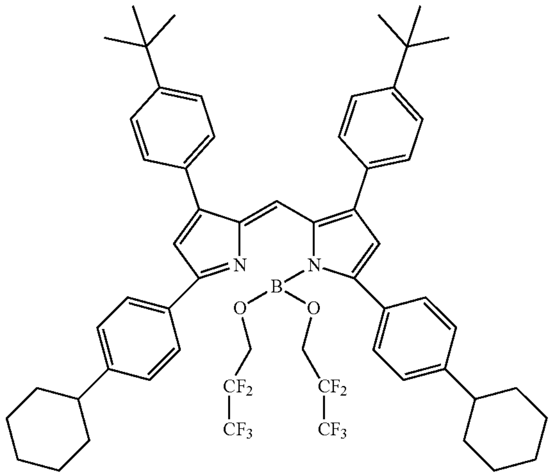

-continued
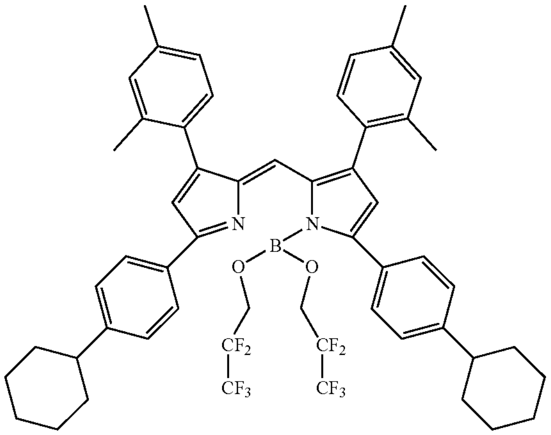
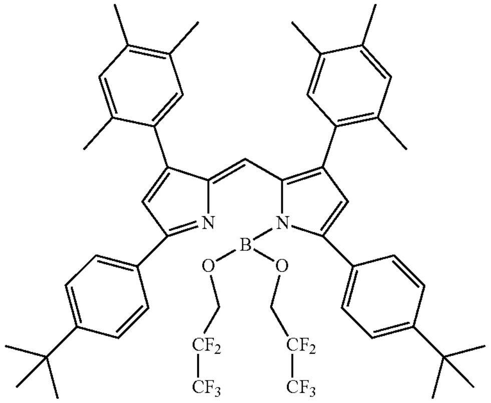
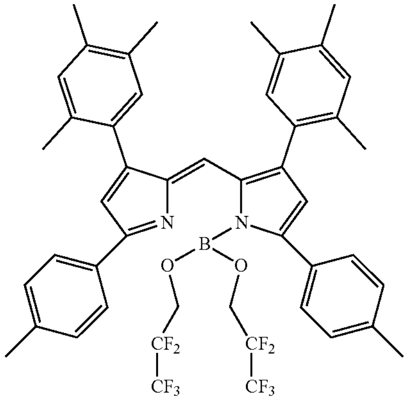
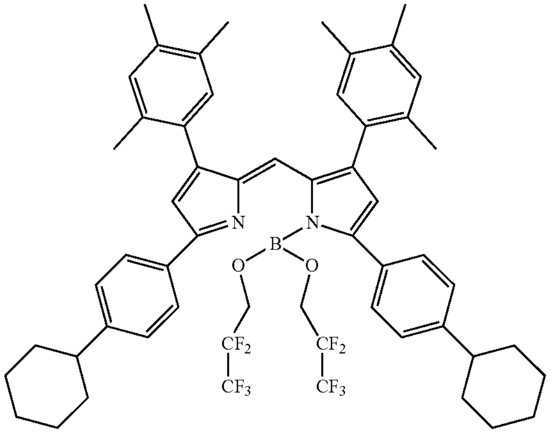
-continued
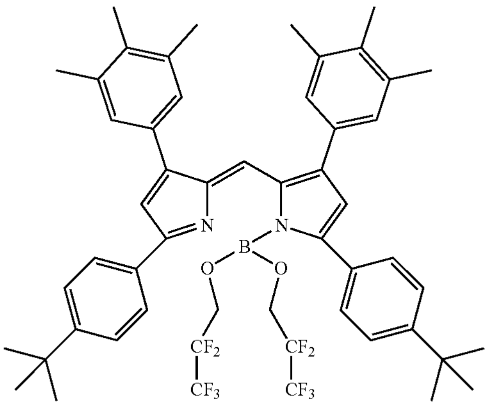
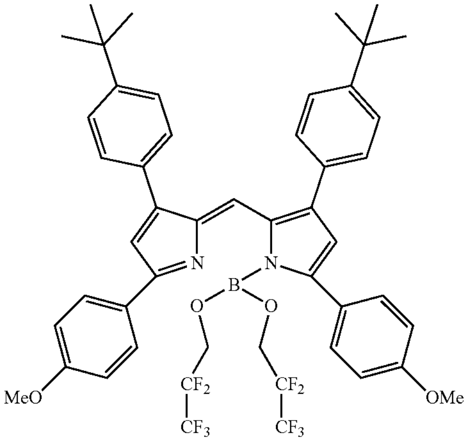
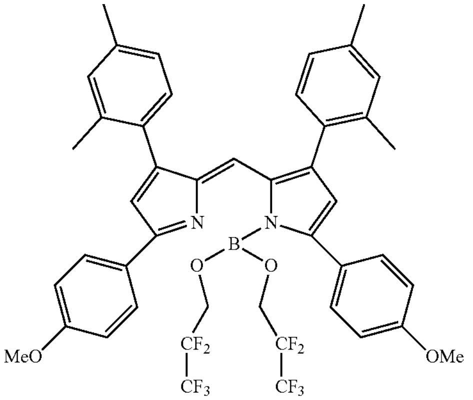
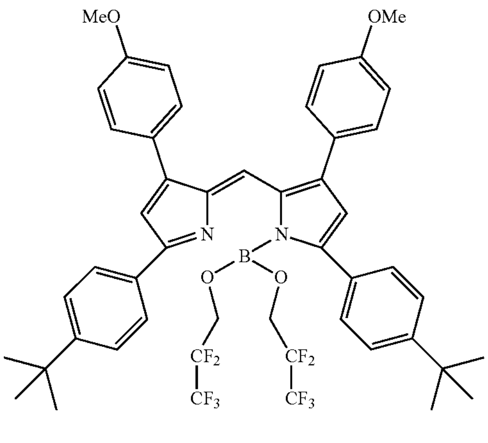

-continued
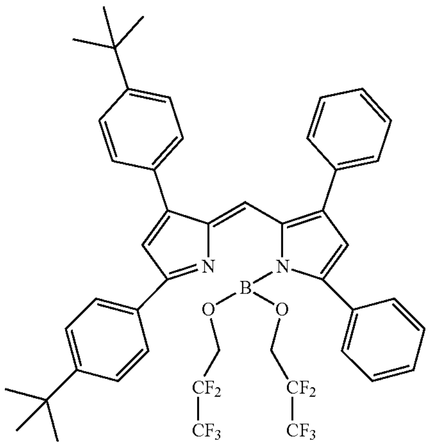
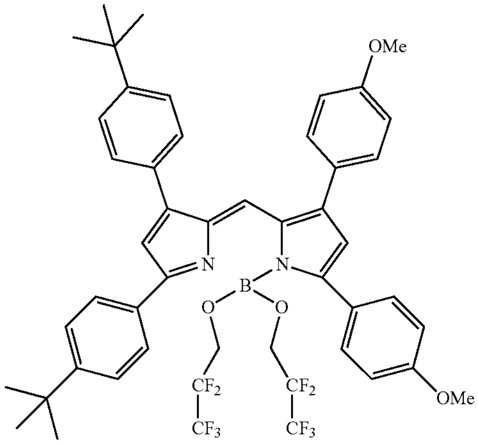
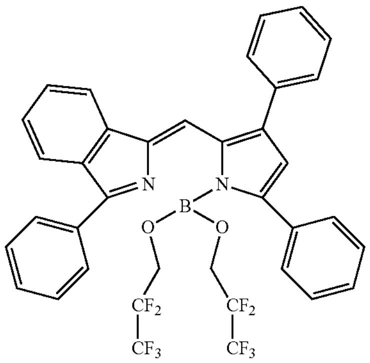
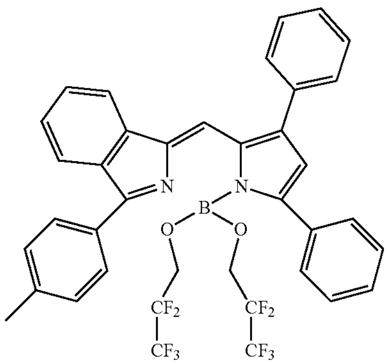
-continued
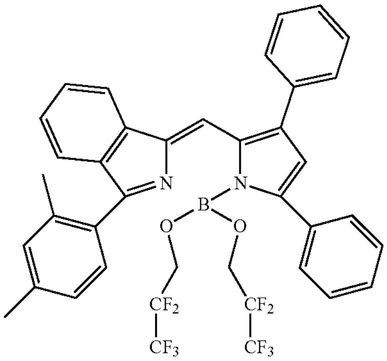
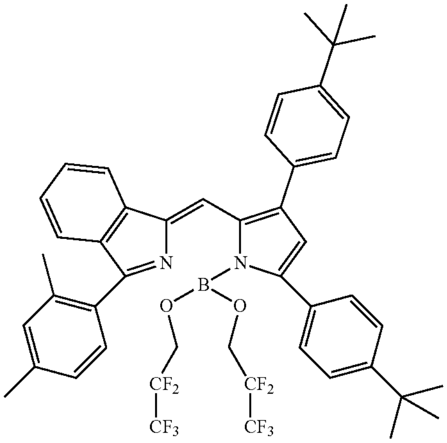
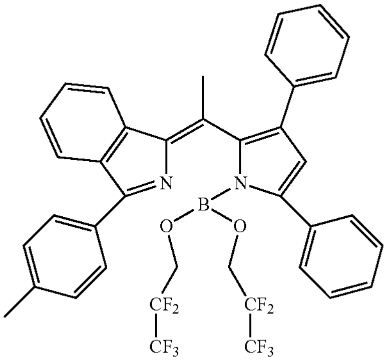
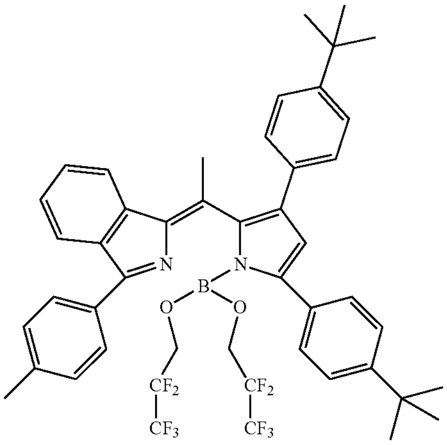

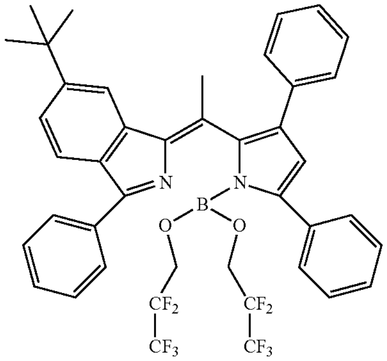
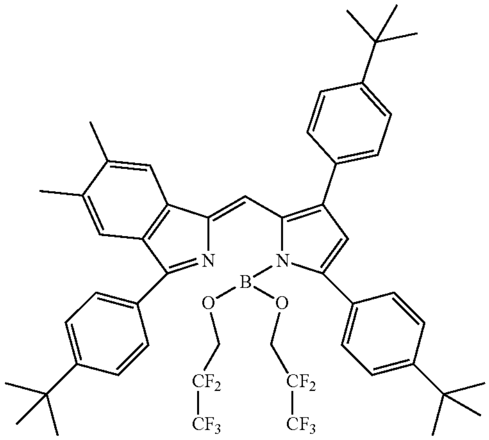
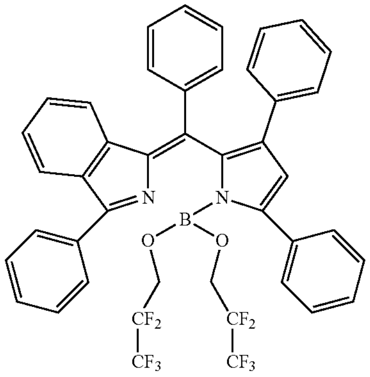
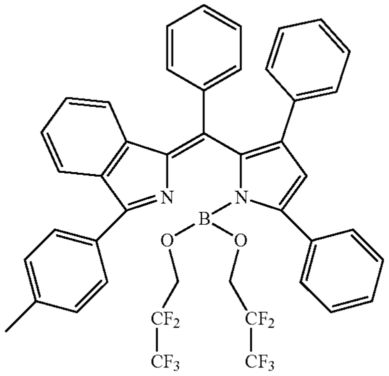
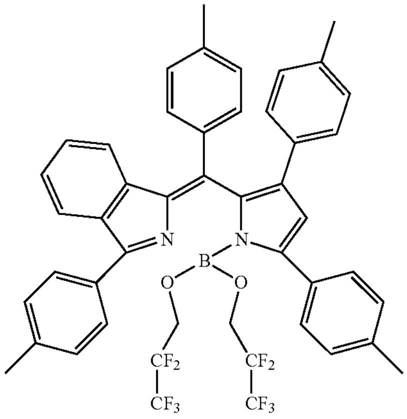
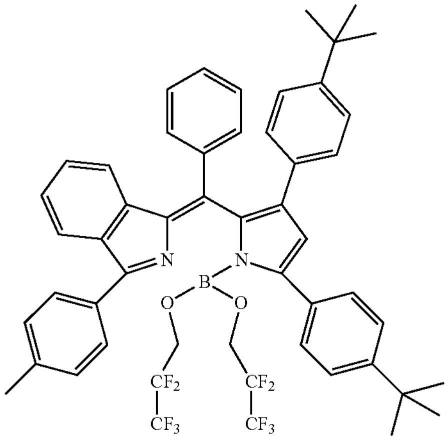
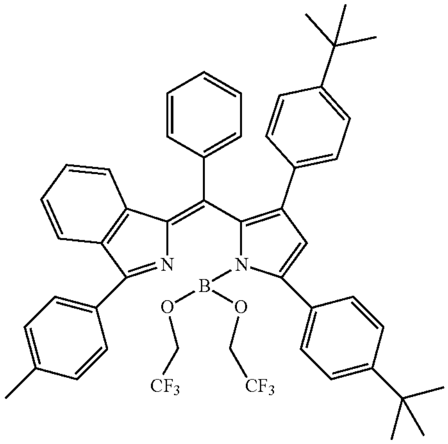

-continued
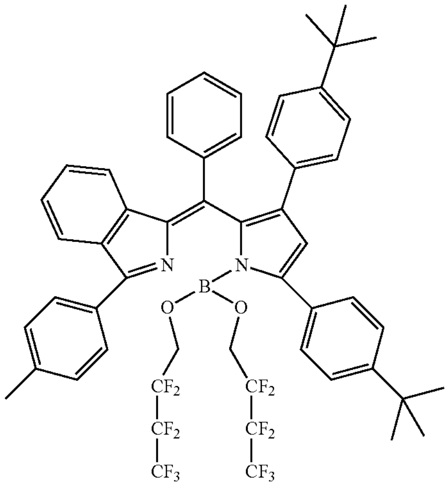
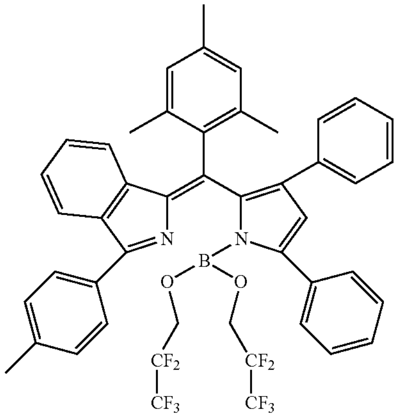
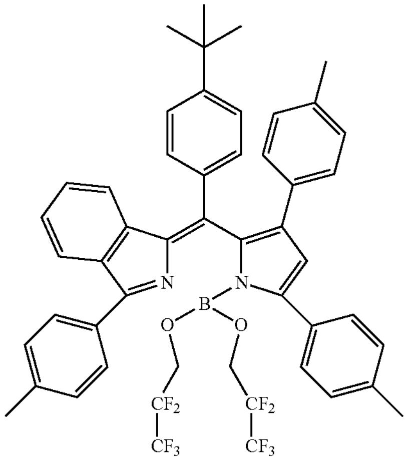
-continued
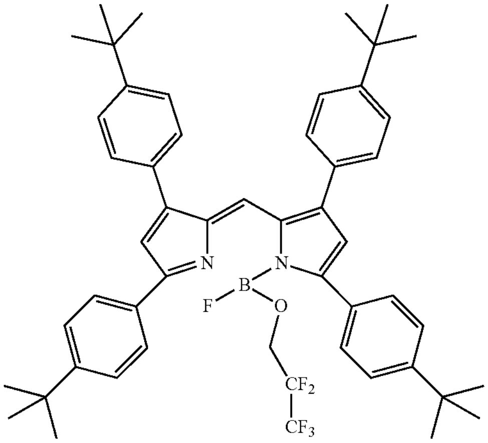
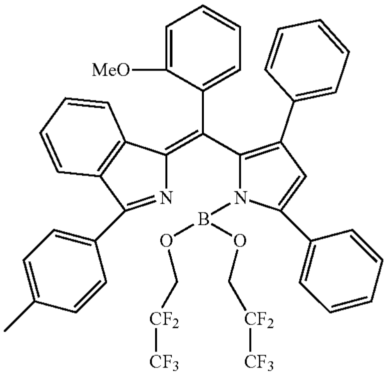
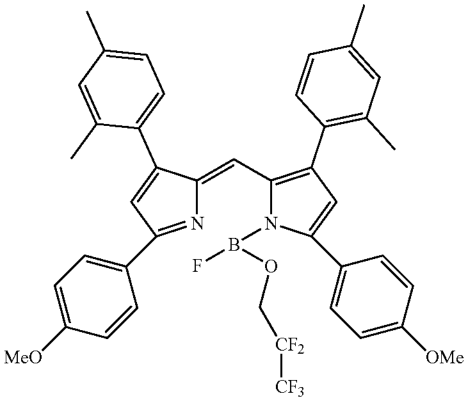
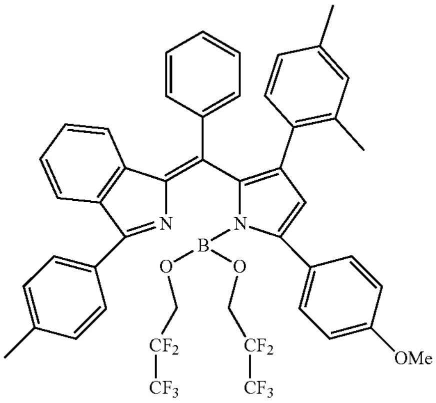

-continued
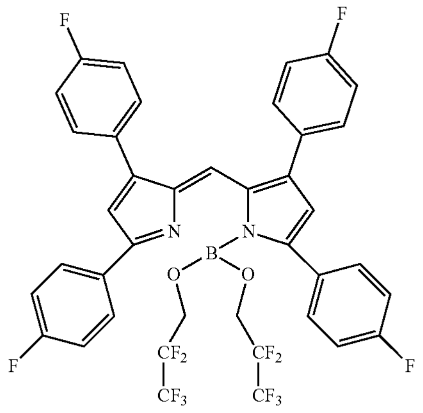
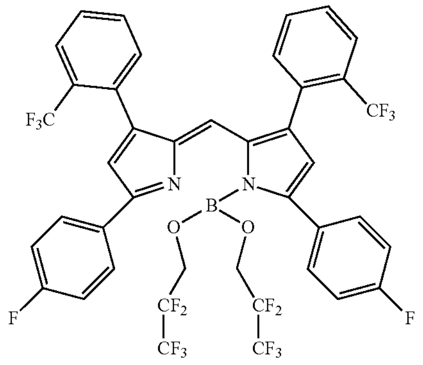
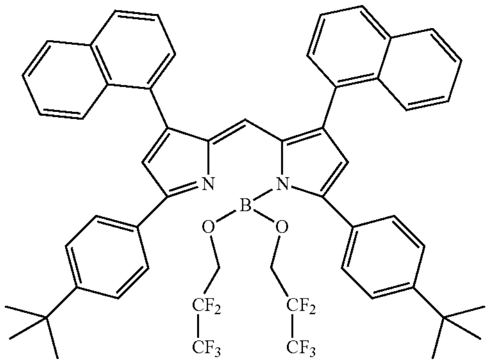
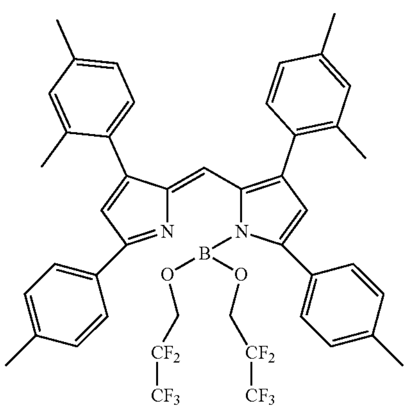
-continued
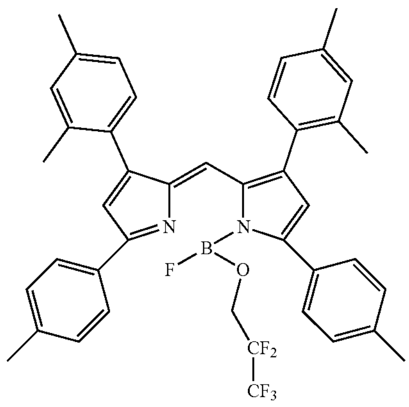
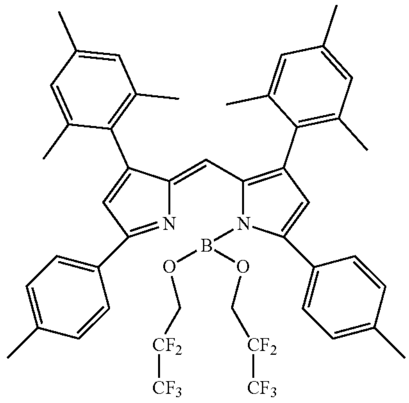
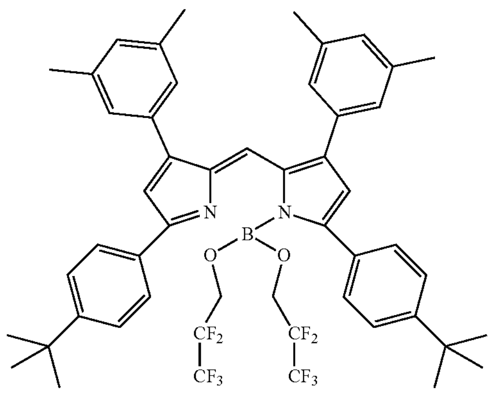
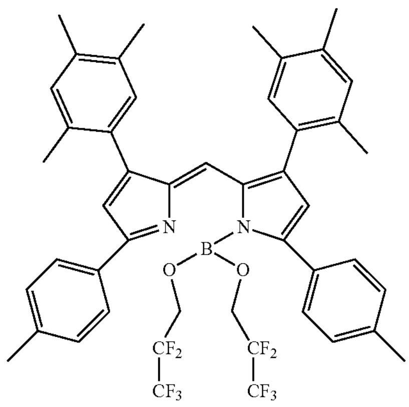

-continued
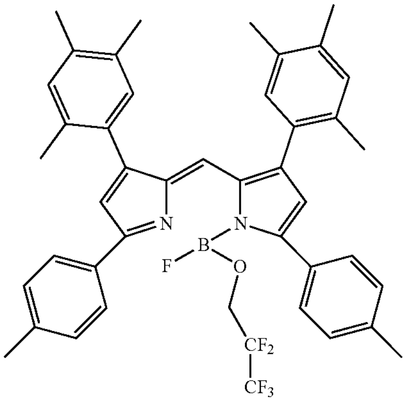
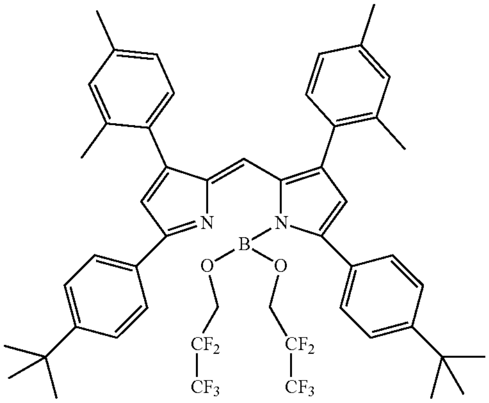
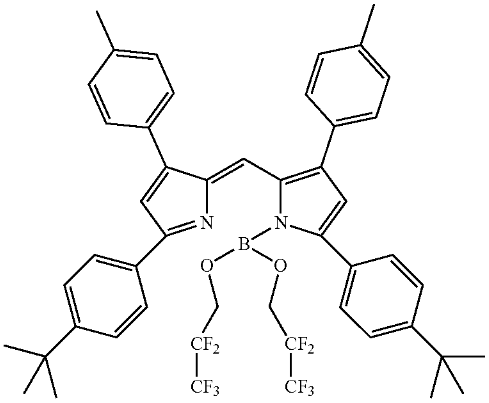
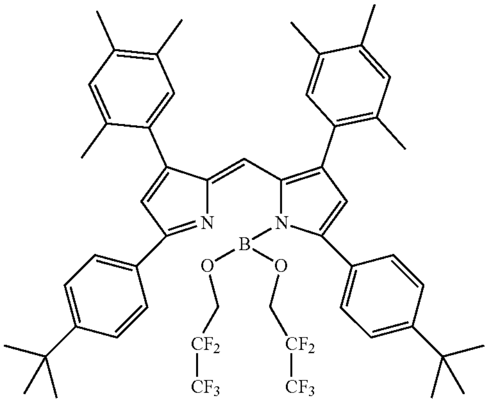
-continued
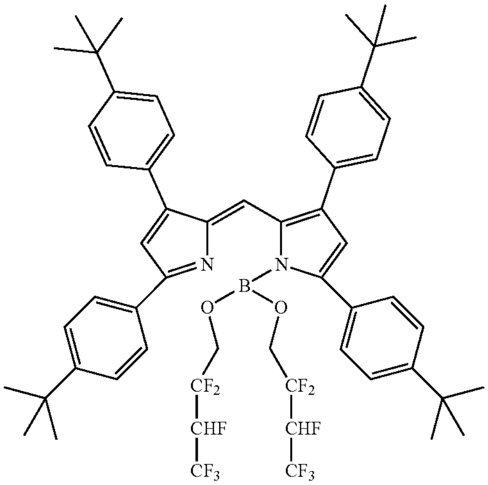
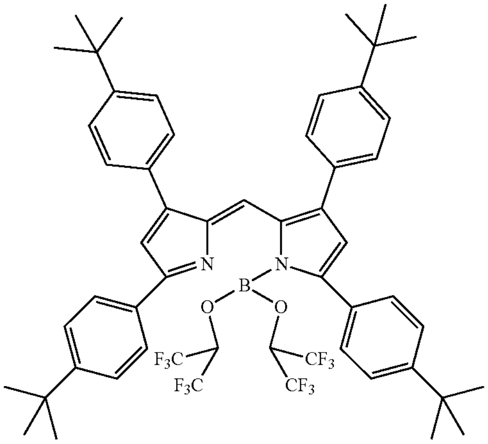
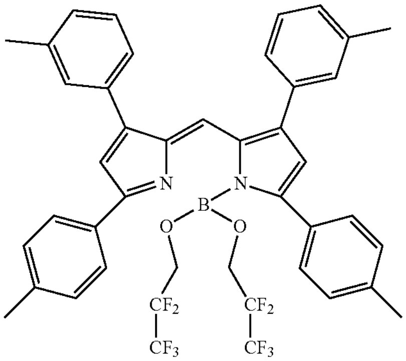

-continued
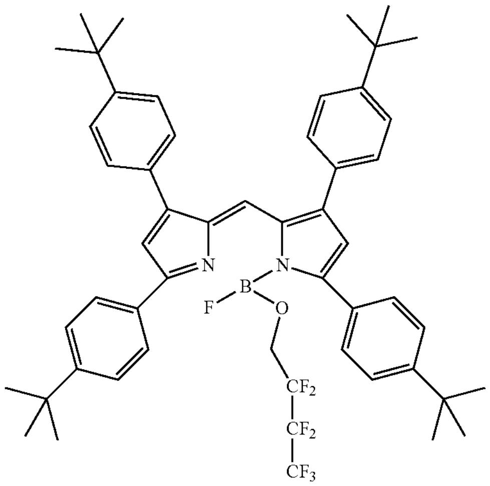
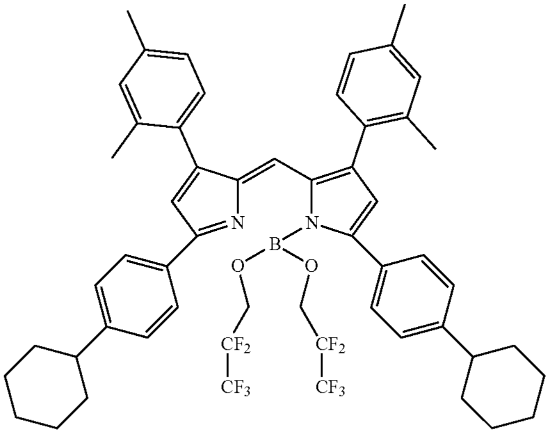
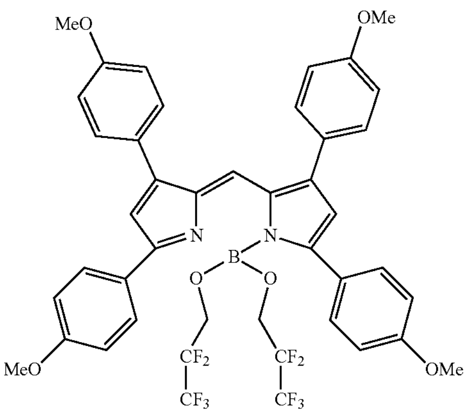
-continued
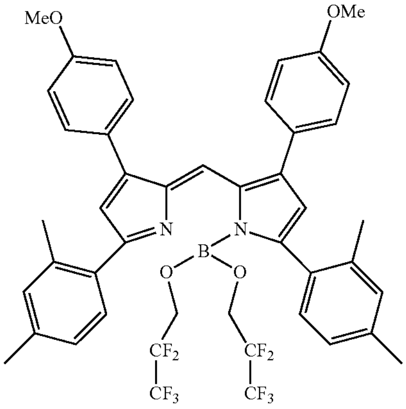
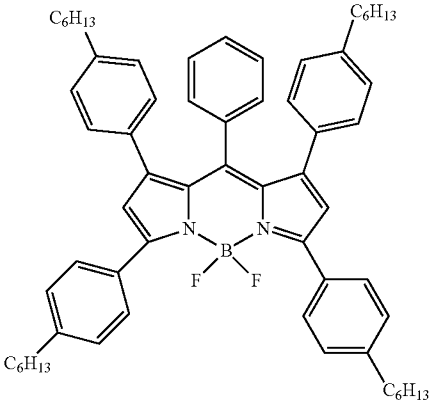
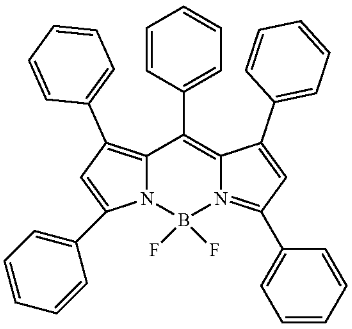
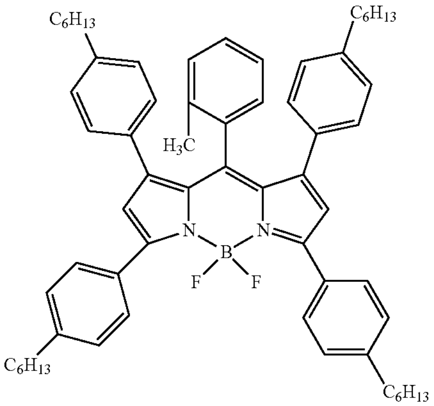

-continued
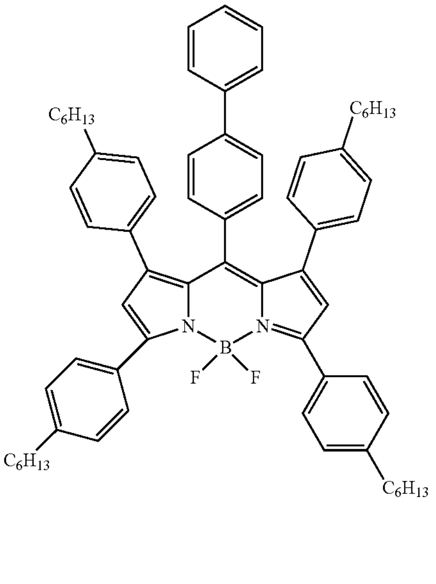
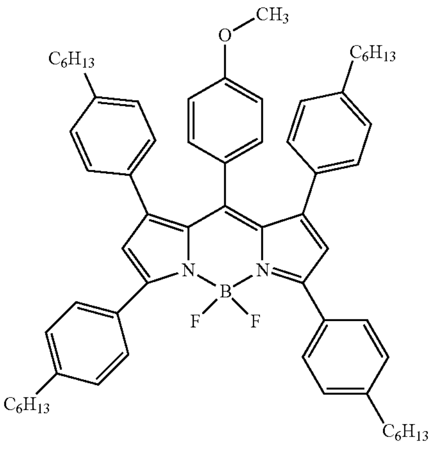
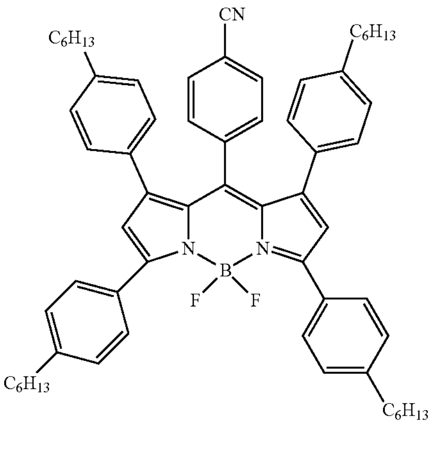
-continued
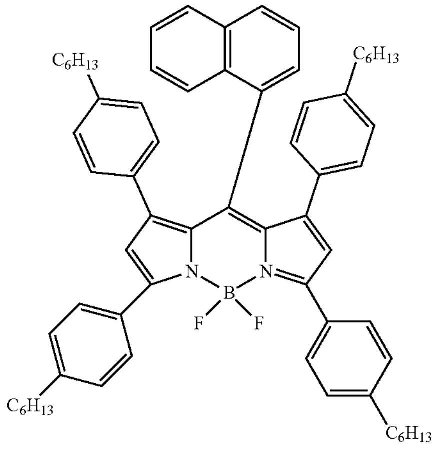
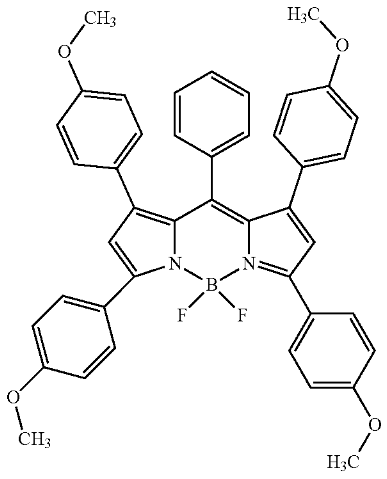
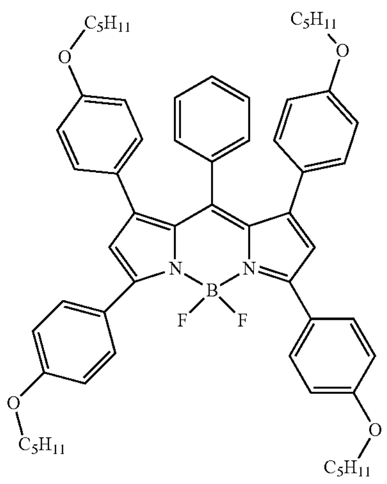

-continued
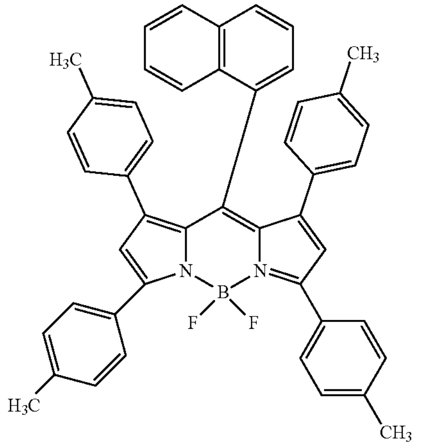
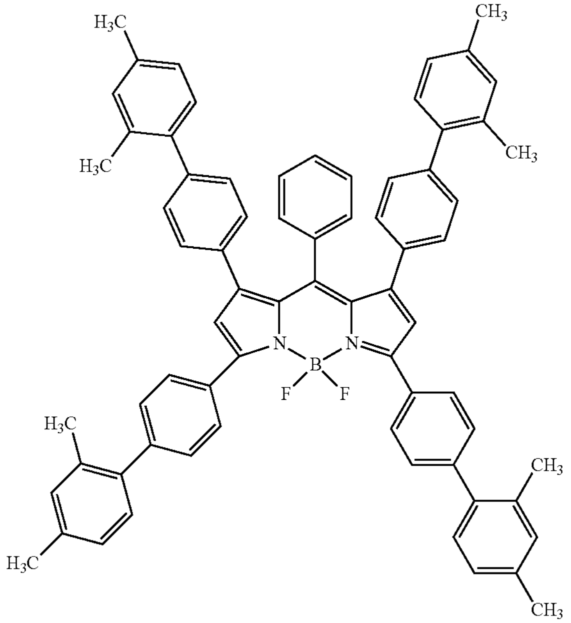
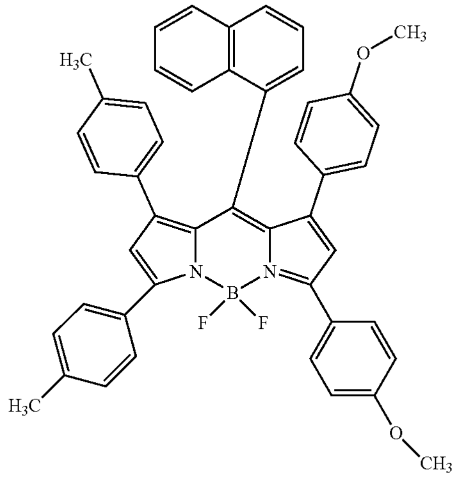
-continued
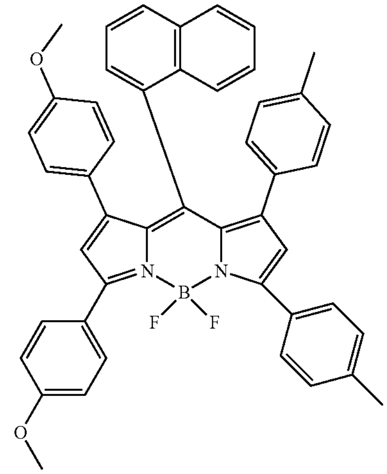
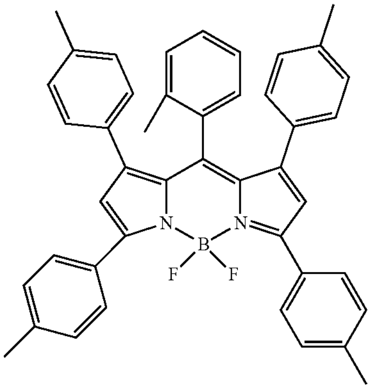
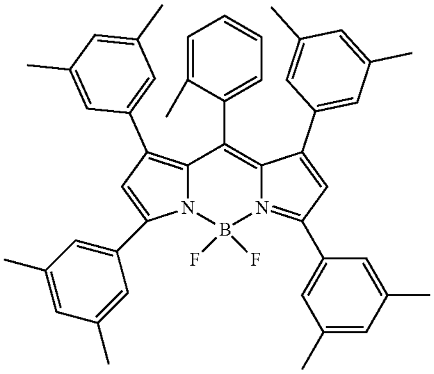
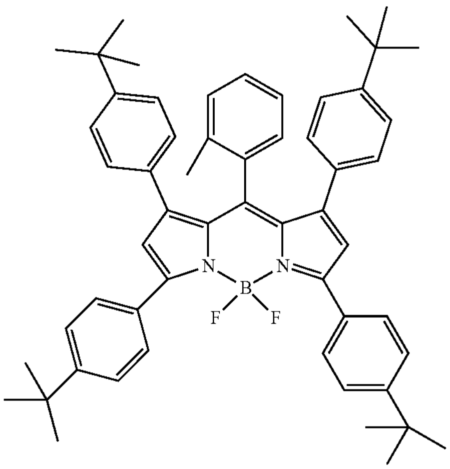

-continued
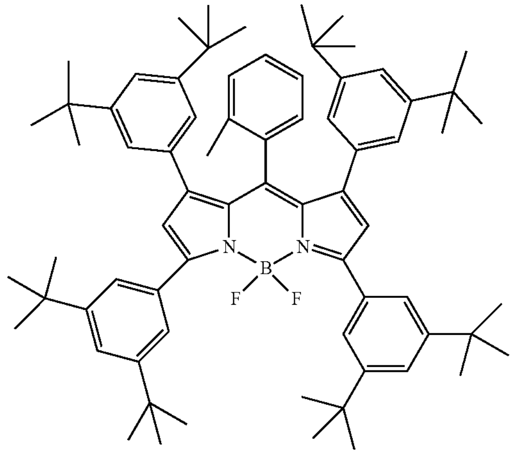
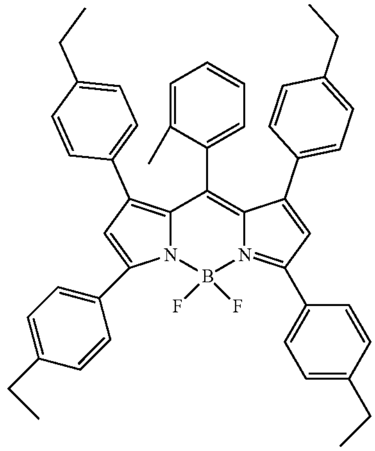
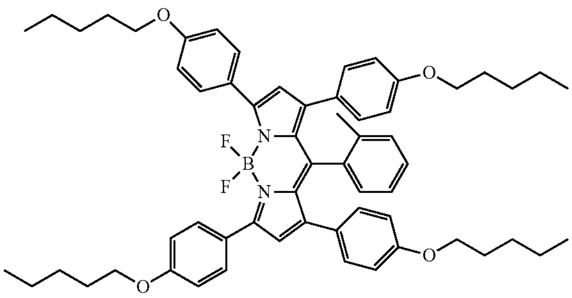
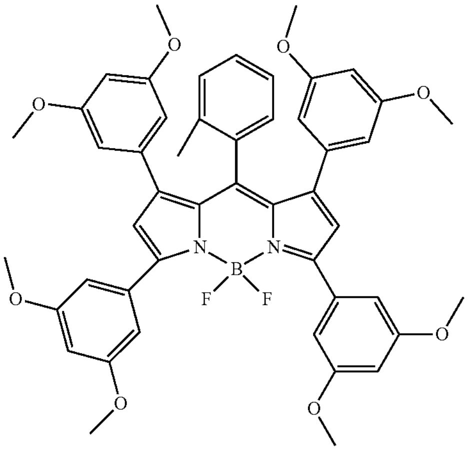
-continued
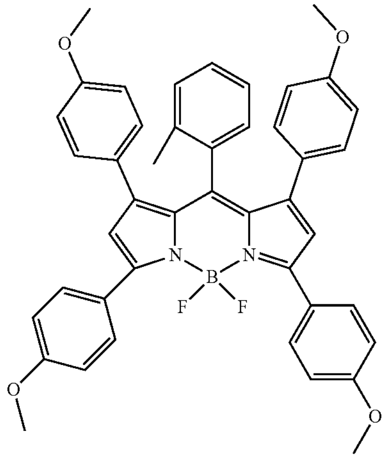
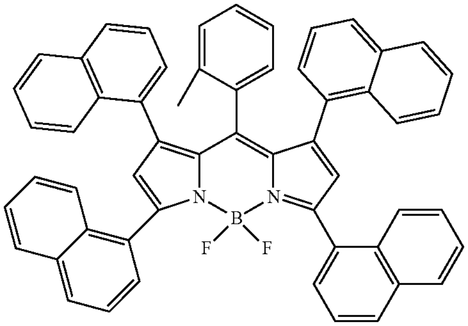
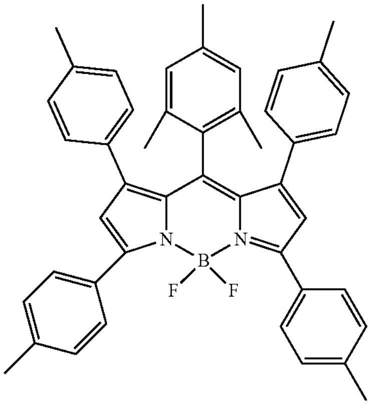
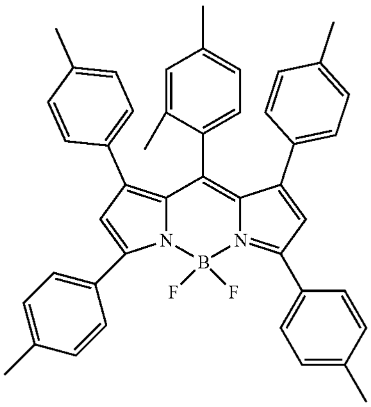

-continued
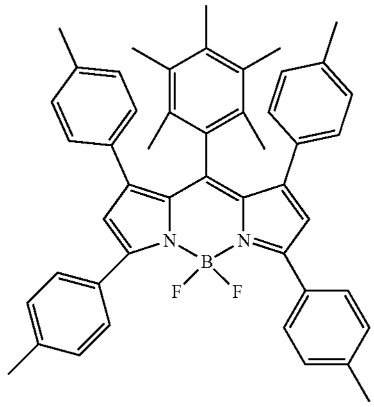
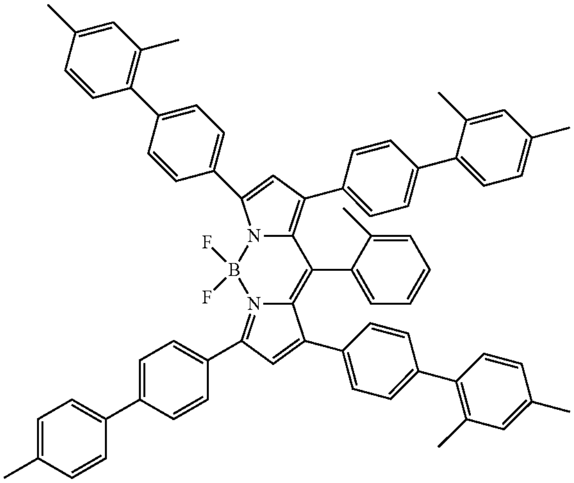
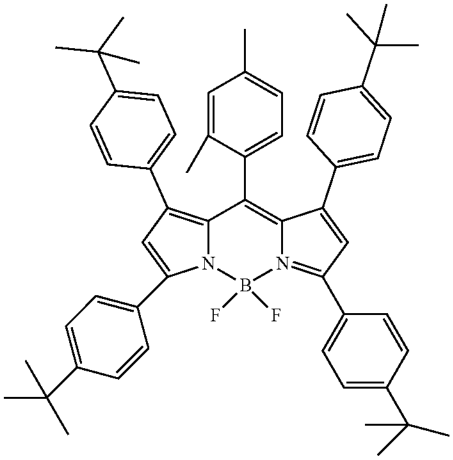
-continued
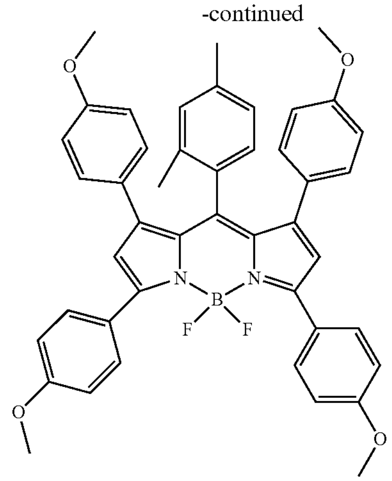
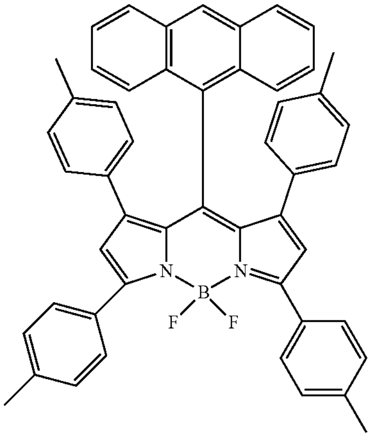
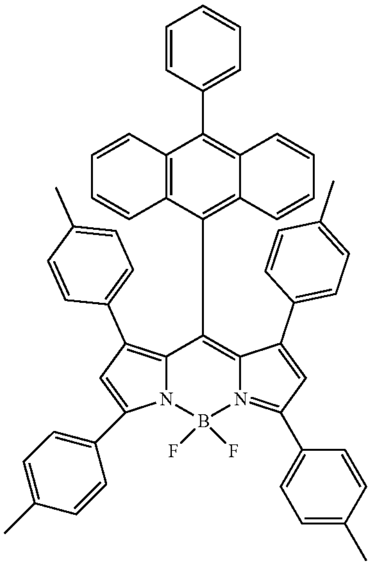

-continued
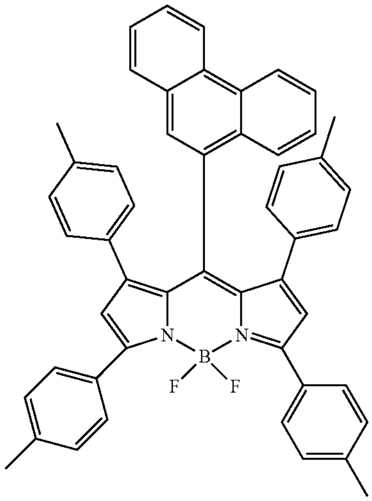
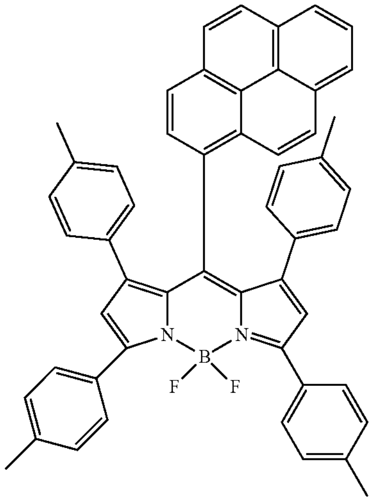
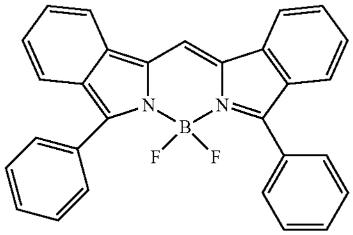
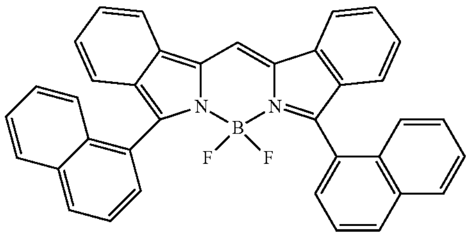
-continued
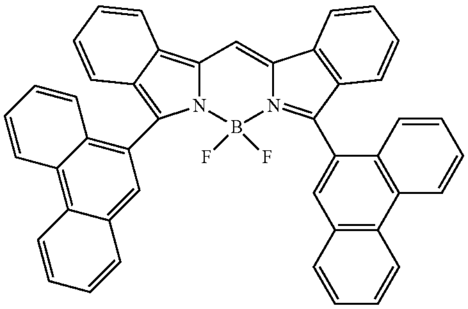
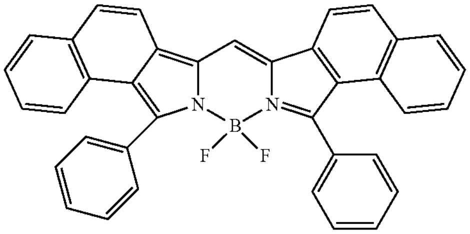
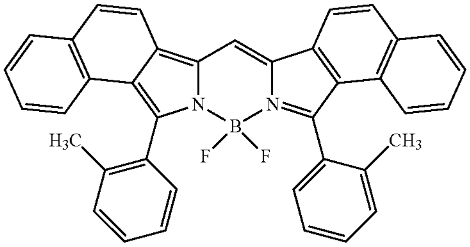
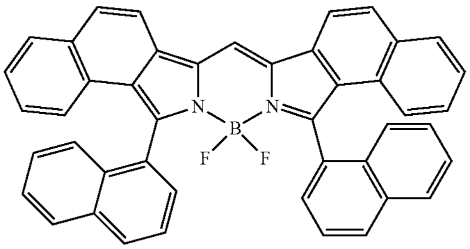
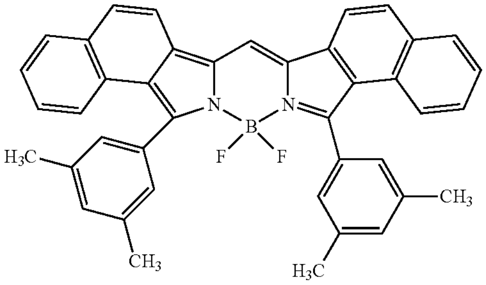
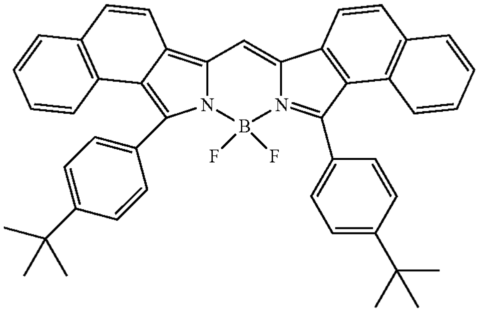

-continued

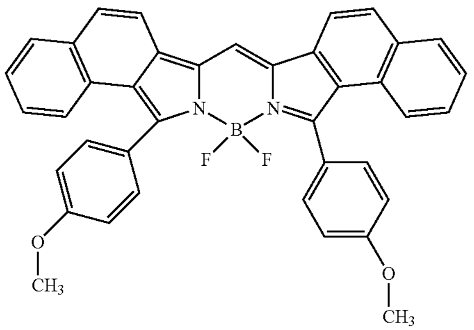

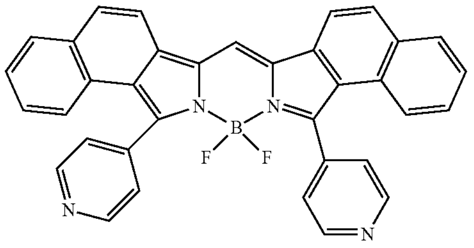

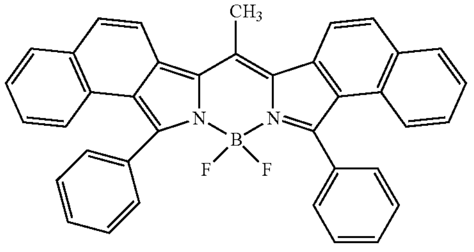

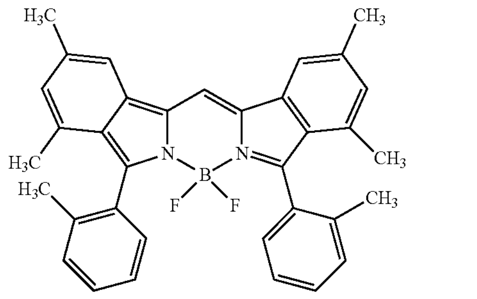

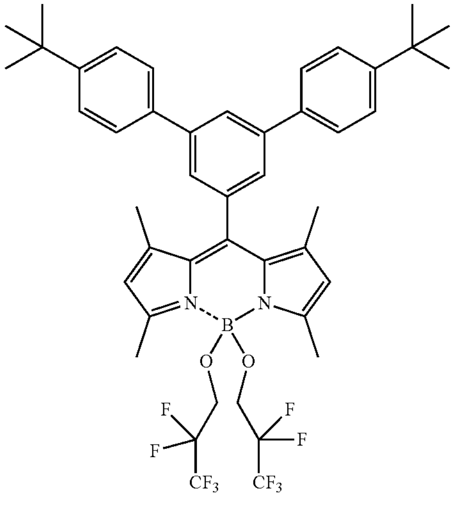

-continued

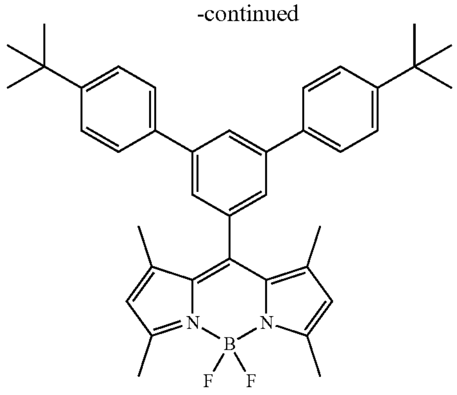

Relationship between First Compound, Second Compound, Third Compound, and Fourth Compound in Emitting Layer In the organic EL device of the exemplary embodiment, a singlet energy $S_1$(M1) of the first compound and a singlet energy $S_1$(M3) of the third compound satisfy a relationship of a numerical formula (Numerical Formula 1) below.

Further, a singlet energy $S_1$(M2) of the second compound and a singlet energy $S_1$(M3) of the third compound satisfy a relationship of a numerical formula (Numerical Formula 2) below.

$$S_1(M1)>S_1(M3) \quad \text{(Numerical Formula 1)}$$

$$S_1(M2)>S_1(M3) \quad \text{(Numerical Formula 2)}$$

In the organic EL device according to the exemplary embodiment, an energy gap $T_{77K}$(M1) at 77K of the first compound and an energy gap $T_{77K}$(M3) at 77K of the third compound preferably satisfy a relationship of a numerical formula (Numerical Formula 1a) below.

Further, an energy gap $T_{77K}$(M2) at 77K of the second compound and the energy gap $T_{77K}$(M3) at 77K of the third compound preferably satisfy a relationship of a numerical formula (Numerical Formula 2b) below.

$$T_{77K}(M1)>T_{77K}(M3) \quad \text{(Numerical Formula 1a)}$$

$$T_{77K}(M2)>T_{77K}(M3) \quad \text{(Numerical Formula 2a)}$$

In the organic EL device of the exemplary embodiment, the emitting layer preferably further contains a fluorescent fourth compound. In this arrangement, the singlet energy $S_1$(M3) of the third compound and a singlet energy $S_1$(M4) of the fourth compound preferably satisfy a relationship of a numerical formula (Numerical Formula 3) below.

$$S_1(M3)>S_1(M4) \quad \text{(Numerical Formula 3).}$$

The singlet energy $S_1$(M1) of the first compound and the singlet energy $S_1$(M4) of the fourth compound preferably satisfy a relationship of a numerical formula (Numerical Formula 4) below.

The singlet energy $S_1$(M2) of the second compound and the singlet energy $S_1$(M4) of the fourth compound preferably satisfy a relationship of a numerical formula (Numerical Formula 5) below.

$$S_1(M1)>S_1(M4) \quad \text{(Numerical Formula 4)}$$

$$S_1(M2)>S_1(M4) \quad \text{(Numerical Formula 5)}$$

The singlet energy $S_1$(M1) of the first compound, the singlet energy $S_1$(M3) of the third compound, and the singlet energy $S_1$(M4) of the fourth compound preferably satisfy a relationship of a numerical formula (Numerical Formula 6) below.

$$S_1(M1)>S_1(M3)>S_1(M4) \quad \text{(Numerical Formula 6)}$$

The singlet energy $S_1$(M2) of the second compound, the singlet energy $S_1$(M3) of the third compound, and the singlet energy $S_1$(M4) of the fourth compound preferably satisfy a relationship of a numerical formula (Numerical Formula 7) below.

$$S_1(M2)>S_1(M3)>S_1(M4) \quad \text{(Numerical Formula 7)}$$

A magnitude relationship between the singlet energy $S_1$(M1) of the first compound and the singlet energy $S_1$(M2) of the second compound does not matter. Specifically, the singlet energy $S_1$(M1) of the first compound is larger or smaller than the singlet energy $S_1$(M2) of the second compound, or the singlet energy $S_1$(M1) of the first compound is the same as the singlet energy $S_1$(M2) of the second compound.

When the organic EL device of the exemplary embodiment emits light, it is preferable that the first compound and the second compound do not mainly emit light in the emitting layer. Further, it is preferable that the third compound also does not mainly emit light.

When the organic EL device of the exemplary embodiment emits light, it is preferable that the fluorescent fourth compound in the emitting layer mainly emits light.

The organic EL device of the exemplary embodiment preferably emits red light or green light.

Relationship between Triplet Energy and Energy Gap at 77K

Here, a relationship between a triplet energy and an energy gap at 77 [K] will be described. In the exemplary embodiment, the energy gap at 77K is different from a typical triplet energy in some aspects.

The triplet energy is measured as follows. Firstly, a solution in which a compound (measurement target) is dissolved in an appropriate solvent is encapsulated in a quartz glass tube to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. The triplet energy is calculated by a predetermined conversion equation based on a wavelength value at an intersection of the tangent and the abscissa axis.

Here, the thermally activated delayed fluorescent compound among the compounds of the exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. An energy amount is calculated by a conversion equation (F1) below based on a wavelength value $\lambda_{edge}$ [nm] at an intersection of the tangent and the abscissa axis and is defined as an energy gap $T_{77K}$ at 77K.

$$T_{77K}\,[\text{eV}]=1239.85/\lambda\text{edge} \quad \text{Conversion Equation (F1):}$$

The tangent to the rise of the phosphorescence spectrum close to the short-wavelength region is drawn as follows. While moving on a curve of the phosphorescence spectrum from the short-wavelength region to the maximum spectral value closest to the short-wavelength region among the maximum spectral values, a tangent is checked at each point on the curve toward the long-wavelength of the phosphorescence spectrum. An inclination of the tangent is increased along the rise of the curve (i.e., a value of the ordinate axis is increased). A tangent drawn at a point of the maximum inclination (i.e., a tangent at an inflection point) is defined as the tangent to the rise of the phosphorescence spectrum close to the short-wavelength region.

The maximum with peak intensity being 15% or less of the maximum peak intensity of the spectrum is not included in the above-mentioned maximum closest to the short-wavelength region. The tangent drawn at a point of the maximum spectral value being closest to the short-wavelength region and having the maximum inclination is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy $S_1$

A method of measuring a singlet energy $S_1$ with use of a solution (occasionally referred to as a solution method) is exemplified by a method below.

A toluene solution of a measurement target compound at a concentration of 10 μmol/L is prepared and put in a quartz cell. An absorption spectrum (ordinate axis: absorption intensity, abscissa axis: wavelength) of the thus-obtained sample is measured at a normal temperature (300K). A tangent was drawn to the fall of the absorption spectrum close to the long-wavelength region, and a wavelength value fledge (nm) at an intersection of the tangent and the abscissa axis was assigned to a conversion equation (F2) below to calculate the singlet energy.

$$S_1\,[\text{eV}]=1239.85/\lambda\text{edge} \quad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum on the long-wavelength side is drawn as follows. While moving on a curve of the absorption spectrum from the maximum spectral value closest to the long-wavelength side in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength side (except when absorbance is 0.1 or less) is defined as the tangent to the fall of the absorption spectrum on the long-wavelength side.

The maximum absorbance of 0.2 or less is not included in the above-mentioned maximum absorbance on the long-wavelength side.

In the exemplary embodiment, a difference ($S_1$-$T_{77K}$) between the singlet energy $S_1$ and the energy gap $T_{77K}$ at 77K is defined as ΔST.

In the exemplary embodiment, a difference ΔST(M3) between the singlet energy $S_1$(M3) of the third compound and the energy gap $T_{77K}$(M3) at 77K of the third compound is preferably less than 0.3 eV, more preferably less than 0.2 eV, further preferably less than 0.1 eV, more further preferably less than 0.01 eV. In other words, ΔST(M3) preferably satisfies a relationship of one of numerical formulae (Numerical Formula 1A to Numerical Formula 1D) below.

$$\Delta ST(M3)=S_1(M3)-T_{77K}(M3)<0.3\text{ eV} \quad \text{(Numerical Formula 1A)}$$

$$\Delta ST(M3)=S_1(M3)-T_{77K}(M3)<0.2\text{ eV} \quad \text{(Numerical Formula 1B)}$$

$$\Delta ST(M3)=S_1(M3)-T_{77K}(M3)<0.1\text{ eV} \quad \text{(Numerical Formula 1C)}$$

$$\Delta ST(M3)=S_1(M3)-T_{77K}(M3)<0.01\text{ eV} \quad \text{(Numerical Formula 1D)}$$

Film Thickness of Emitting Layer

A film thickness of the emitting layer of the organic EL device in the exemplary embodiment is preferably in a range from 5 nm to 50 nm, more preferably in a range from 7 nm to 50 nm, most preferably in a range from 10 nm to 50 nm. When the film thickness of the emitting layer is 5 nm or more, the formation of the emitting layer and the adjustment of the chromaticity are easy. When the film thickness of the emitting layer is 50 nm or less, an increase in the drive voltage is likely to be reducible.

Content Ratios of Compounds in Emitting Layer

Content ratios of the first, second, third and fourth compounds in the emitting layer preferably fall, for instance, within a range below.

The content ratio of the sum of the first and second compounds in the emitting layer is preferably in a range from 10 mass % to 80 mass %.

The ratio of the content ratio of the first compound to the content ratio of the second compound in the emitting layer is preferably 1:9 to 9:1, more preferably 3:7 to 7:3, further preferably 4:6 to 6:4.

The content ratio of the third compound is preferably in a range from 10 mass % to 80 mass %, more preferably in a range from 10 mass % to 60 mass %, further preferably in a range from 20 mass % to 60 mass %.

The content ratio of the fourth compound is preferably in a range from 0.01 mass % to 10 mass %, more preferably in a range from 0.01 mass % to 5 mass %, further preferably in a range from 0.01 mass % to 1 mass %.

An upper limit of the total of the respective content ratios of the first, second, third, and fourth compounds in the emitting layer is 100 mass %. It should be noted that the emitting layer of the exemplary embodiment may further contain material(s) other than the first, second, third, and fourth compounds.

The emitting layer may include a single type of the first compound or may include two or more types of the first compound. The emitting layer may include a single type of the second compound or may include two or more types of the second compound. The emitting layer may include a single type of the third compound or may include two or more types of the third compound. The emitting layer may include a single type of the fourth compound or may include two or more types of the fourth compound.

Figure 4:
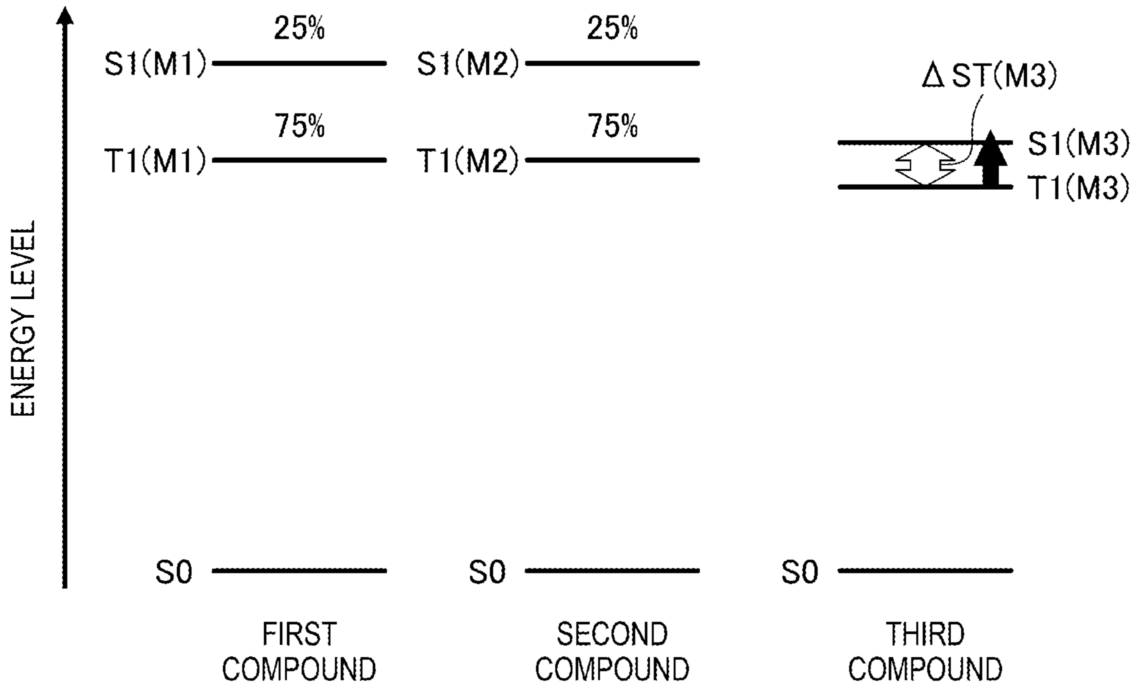
FIG. 4 illustrates a principle of light emission according to exemplary embodiments of the invention.

FIG. 4 illustrates a principle of light emission according to exemplary embodiments of the invention.

In FIG. 4, S0 represents a ground state. S1(M1) represents the lowest singlet state of the first compound. T1(M1) represents the lowest triplet state of the first compound. S1(M2) represents the lowest singlet state of the second compound. T1(M2) represents the lowest triplet state of the second compound. S1(M3) represents the lowest singlet state of the third compound. T1(M3) represents the lowest triplet state of the third compound.

As shown in FIG. 4, when a compound having a small ΔST(M3) is used as the third compound, inverse intersystem crossing from the lowest triplet state T1(M3) to the lowest singlet state S1(M3) can be caused by a heat energy.

The inverse intersystem crossing caused in the third compound enables (i) and (ii), as follows: (i) when the emitting layer includes a fluorescent dopant with the lowest singlet state S1 smaller than the lowest singlet state S1(M3) of the third compound (fluorescent fourth compound in the first exemplary embodiment), light emission from the fluorescent dopant can be observed; (ii) when the emitting layer does not include the fluorescent dopant with the lowest singlet state S1 smaller than the lowest singlet state S1(M3) of the third compound, light emission from the lowest singlet state S1(M3) of the third compound can be observed.

The emitting layer of the first exemplary embodiment corresponds to (i). An emitting layer of a second exemplary embodiment described later corresponds to (ii).

FIG. 5 shows a relationship in energy level and energy transfer between the first compound, the second compound, the third compound, and the fourth compound in the emitting layer of an exemplary organic electroluminescence device according to the first exemplary embodiment. FIG. 5 shows a case where the emitting layer shown in FIG. 4 corresponds to the above (i).

FIG. 5 further shows the lowest singlet state S1(M4) and the lowest triplet state T1(M4) of the fourth compound in addition to the compounds shown in FIG. 4.

A dashed arrow directed from S1(M3) to S1(M4) in FIG. 5 represents Förster energy transfer from the lowest singlet state of the third compound to the fourth compound.

As shown in FIG. 5, when a compound having a small ΔST(M3) is used as the third compound, inverse intersystem crossing from the lowest triplet state T1(M3) to the lowest singlet state S1(M3) can be caused by a heat energy. Subsequently, Förster energy transfer from the lowest singlet state S1(M3) of the third compound to the fourth compound occurs to generate the lowest singlet state S1(M4). Consequently, fluorescence from the lowest singlet state S1(M4) of the fourth compound can be observed. It is inferred that the internal quantum efficiency can be theoretically raised up to 100% also by using delayed fluorescence by the TADF mechanism.

In the organic EL device according to the first exemplary embodiment, the emitting layer includes, together with the third compound that exhibits delayed fluorescence, the first compound having the singlet energy larger than the third compound and the second compound having the singlet energy larger than the third compound, the first and second compound being as the co-matrix, and further includes the fourth compound that fluoresces.

According to the first exemplary embodiment, the organic EL device having higher performance, in particular, capable of improving luminous efficiency can be achieved.

The organic EL device according to the first exemplary embodiment is applicable to an electronic device such as a display device and a light-emitting device.

An arrangement of an organic EL device will be further described below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal having a large work function (specifically, 4.0 eV or more), an alloy, an electrically conductive compound and a mixture thereof are preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, and a mixture thereof, which have a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode irrespective of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance include: an aromatic amine compound, which is a low-molecule organic compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3, 5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N, N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ $cm^2/(V \cdot s)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

When the hole transporting layer includes two or more layers, one of the layers with a larger energy gap is preferably provided closer to the emitting layer. Examples of the material with a larger energy gap include compounds EBL and EBL-2 used in later-described Examples.

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ $cm^2/(V \cdot s)$ or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Further, a high polymer compound is usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the present exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

In the exemplary embodiment, the emitting layer is also preferably formed by using, as a vapor deposition source, a composition containing the first and second compounds. Use of the composition can reduce the number of vapor deposition sources when forming the emitting layer.

Film Thickness

A thickness of each of the organic layers in the organic EL device according to the third exemplary embodiment is not limited except for the above particular description. In general, the thickness preferably ranges from several nanometers to 1 μm because excessively small film thickness is likely to cause defects (e.g. pin holes) and excessively large thickness leads to the necessity of applying high voltage and consequent reduction in efficiency.

Second Exemplary Embodiment

An arrangement of an organic EL device according to a second exemplary embodiment will be further described below. In the description of the second exemplary embodiment, the same components as those in the first exemplary embodiment are denoted by the same reference signs and names to simplify or omit an explanation of the components. In the second exemplary embodiment, any materials and compounds that are not specified may be the same as those in the first exemplary embodiment.

The organic EL device according to the second exemplary embodiment is different from the organic EL device according to the first exemplary embodiment in that the emitting layer of the second exemplary embodiment does not contain the fluorescent dopant with the lowest singlet state 51 (fourth compound that fluoresces in the first exemplary embodiment) smaller than the lowest singlet state S1(M3) of the third compound. Other components are the same as those in the first exemplary embodiment.

That is, in the second exemplary embodiment, the emitting layer includes the first compound represented by the formula (1) and the second compound represented by the formula (2) as the co-matrix, together with the delayed fluorescent third compound, In the organic EL device according to the second exemplary embodiment, the emitting layer does not include the fluorescent dopant with the lowest singlet state S1 (fourth compound that fluoresces in the first exemplary embodiment) smaller than the lowest singlet state S1(M3) of the third compound.

Relationship between First Compound, Second Compound and Third Compound in Emitting Layer The organic EL device according to the second exemplary embodiment is the same as that according to the first exemplary embodiment in the relationship between the singlet energy $S_1$ of the first compound and the singlet energy $S_1$ of the second compound and the singlet energy $S_1$ of the third compound as well as the relationship between the energy gap $T_{77K}$ at 77K of the first compound and the energy gap $T_{77K}$ at 77K of the second compound and the energy gap $T_{77K}$ at 77K of the third compound. That is, $S_1$ and $T_{77K}$ of the first, second, and third compounds according to the second exemplary embodiment satisfy relationships of numerical formulae below (Numerical Formulae 1, 2, 1a, and 2b).

$$S_1(M1)>S_1(M3) \quad \text{(Numerical Formula 1)}$$

$$S_1(M2)>S_1(M3) \quad \text{(Numerical Formula 2)}$$

$$T_{77K}(M1)>T_{77K}(M3) \quad \text{(Numerical Formula 1a)}$$

$$T_{77K}(M2)>T_{77K}(M3) \quad \text{(Numerical Formula 2b)}$$

When the organic EL device of the exemplary embodiment emits light, it is preferable that the first compound and the second compound do not mainly emit light in the emitting layer.

Content Ratios of Compounds in Emitting Layer

Content ratios of the first, second, and third compounds contained in the emitting layer preferably fall, for instance, within a range below.

The content ratio of the sum of the first and second compounds in the emitting layer is preferably in a range from 20 mass % to 90 mass %, more preferably in a range from 40 mass % to 90 mass %, further preferably in a range from 40 mass % to 80 mass %.

The ratio of the content ratio of the first compound to the content ratio of the second compound in the emitting layer is preferably 1:9 to 9:1, more preferably 3:7 to 7:3, further preferably 4:6 to 6:4.

The content ratio of the third compound is preferably in a range from 10 mass % to 80 mass %, more preferably in a range from 10 mass % to 60 mass %, further preferably in a range from 20 mass % to 60 mass %.

An upper limit of the total of the respective content ratios of the first, second, and third compounds in the emitting layer is 100 mass %. It is not excluded that the emitting layer of the exemplary embodiment further contains a material(s) other than the first, second, and third compounds.

The emitting layer may include a single type of the first compound or may include two or more types of the first compound.

The emitting layer may include a single type of the second compound or may include two or more types of the second compound.

The emitting layer may include a single type of the third compound or may include two or more types of the third compound.

In the organic EL device according to the second exemplary embodiment, the emitting layer includes, together with the delayed fluorescent third compound, the first compound having the singlet energy larger than the third compound and the second compound having the singlet energy larger than the third compound, the first and second compound being as the co-matrix.

According to the second exemplary embodiment, the organic EL device with higher performance, in particular, with improved luminous efficiency can be achieved.

The organic EL device according to the second exemplary embodiment is applicable to an electronic device such as a display device and a light-emitting device.

Third Exemplary Embodiment

Composition

A composition that is an exemplary arrangement of the third exemplary embodiment contains the first compound represented by the formula (1) and the second compound represented by the formula (2).

The first compound contained in the composition according to the third exemplary embodiment corresponds to the first compound described in the first exemplary embodiment.

The second compound contained in the composition according to the third exemplary embodiment corresponds to the second compound described in the first exemplary embodiment.

Preferable arrangements of the first and second compounds contained in the composition according to the third exemplary embodiment are the same as those in the first exemplary embodiment, which will be specifically shown below. Preferable Arrangements of First Compound Contained in Composition of Third Exemplary Embodiment In the first compound contained in the composition, A in the formula (1) is preferably a group represented by the formula (a1), (a2), (a3), (a4), or (a6), more preferably a group represented by the formula (a1), (a2), (a3), or (a4), further preferably a group represented by the formula (a1) or (a4), more further preferably a group represented by the formula (a1).

In the first compound contained in the composition, $X_{11}$, $X_{12}$, $X_{13}$, $X_{14}$, $X_{15}$ and $X_{16}$ are preferably oxygen atoms in the formulae (a1), (a2), (a3) (a4), (a5), and (a6).

The first compound contained in the composition is preferably a compound represented by the formula (11), (12), (13), (14), (15), or (16).

In the first compound contained in the composition, it is preferable that: $R_{110}$ to $R_{169}$ in the formulae (a1), (a2), (a3) (a4), (a5), and (a6) are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms; and it is preferable that $R_{11}$ to $R_{16}$ are each independently a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

In the first compound contained in the composition, it is more preferable that in the formulae (a1), (a2), (a3) (a4), (a5), and (a6), $R_{110}$ to $R_{169}$ are each independently a hydrogen atom or a substituted or unsubstituted aryl group having 6 to 30 ring carbon atoms, and $R_{11}$ to $R_{16}$ are each independently a substituted or unsubstituted aryl group having 6 to 30 ring carbon atoms.

In the first compound contained in the composition, it is further preferable that in the formulae (a1), (a2), (a3) (a4), (a5), and (a6), $R_{110}$ to $R_{169}$ are hydrogen atoms, and $R_{11}$ to $R_{16}$ are each independently a substituted or unsubstituted aryl group having 6 to 30 ring carbon atoms.

In the first compound contained in the composition, L in the formula (1) is preferably a single bond, a substituted or unsubstituted arylene group having 6 to 25 ring carbon atoms, or a substituted or unsubstituted divalent heterocyclic group having 5 to 22 ring atoms, more preferably a single bond or a substituted or unsubstituted arylene group having 6 to 25 ring carbon atoms, further preferably a substituted or unsubstituted para-biphenylene group or a substituted or unsubstituted para-terphenylene group. In the first compound contained in the composition, B in the formula (1) is preferably a substituted or unsubstituted aryl group having 6 to 19 ring carbon atoms or a substituted or unsubstituted heterocyclic group having 5 to 19 ring atoms, more preferably any one of the groups represented by the formulae (b1) to (b17), further preferably any one of the groups represented by the formulae (b1) to (b6).

In the first compound contained in the composition, when B in the formula (1) is any one of the groups represented by the formulae (b1) to (b6), at least one pair of adjacent ones of Ra are preferably not bonded to each other.

Specific examples of the first compound contained in the composition according to the third exemplary embodiment are shown in the specific examples of the first compound described in the first exemplary embodiment.

Preferable Arrangements of Second Compound Contained in Composition of Third Exemplary Embodiment The second compound contained in the composition, which is represented by the formula (2), is preferably represented by one of the formulae (21) to (23), more preferably represented by the formula (21).

In the second compound contained in the composition, it is preferable that at least one of $Y_{21}$ to $Y_{26}$ in the formula (2) is $CR_A$ and at least one $R_A$ is the group represented by the formula (2A).

In the second compound contained in the composition, it is more preferable that at least one of $Y_{21}$ to $Y_{26}$ in the formula (2) is $CR_A$, at least one $R_A$ is the group represented by the formula (2A), and $R_B$ in the formula (2A) is a substituted or unsubstituted fused aryl group having 10 to 50 ring carbon atoms or a substituted or unsubstituted fused heterocyclic group having 9 to 50 ring atoms.

In the second compound contained in the composition, $R_B$ in the formula (2A) is preferably any one of the groups represented by the formulae (c1) to (c9), more preferably any one of the groups represented by the formulae (c1) to (c6).

In the second compound contained in the composition, $L_{21}$ in the formula (2A) is preferably a single bond, or a divalent, trivalent, tetravalent, pentavalent or hexavalent group derived from any one group selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, a substituted or unsubstituted fluorenyl group, a substituted or unsubstituted dibenzofuranyl group, a substituted or unsubstituted dibenzothienyl group, and a substituted or unsubstituted carbazolyl group.

In the second compound contained in the composition, $L_{22}$ in the formula (2A) is preferably a single bond, or a divalent group derived from any one group selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, a substituted or unsubstituted fluorenyl group, a substituted or unsubstituted dibenzofuranyl group, a substituted or unsubstituted dibenzothienyl group, and a substituted or unsubstituted carbazolyl group.

The ratio of the content ratio (mass %) of the first compound to the content ratio (mass %) of the second compound in the composition according to the third exemplary embodiment is preferably 1:9 to 9:1, more preferably 3:7 to 7:3, further preferably 4:6 to 6:4.

An upper limit of the total of the respective content ratios of the first and second compounds in the composition according to the third exemplary embodiment is 100 mass %. It is not excluded that the composition of the exemplary embodiment further contains a material(s) other than the first and second compounds.

The composition may include a single type of the first compound or may include two or more types of the first compound.

The composition may include a single type of the second compound or may include two or more types of the second compound.

Specific examples of the second compound contained in the composition according to the third exemplary embodiment are shown in the specific examples of the second compound described in the first exemplary embodiment.

The emitting layer is preferably formed by using, as a vapor deposition source, the composition according to the third exemplary embodiment (composition containing the first and second compounds). For example, the emitting layer according to each of the first and second exemplary embodiments can be formed by using at least the vapor deposition source that is the composition of the third exemplary embodiment and any other compound.

The composition according to the third exemplary embodiment can reduce the number of vapor deposition sources for forming a desired layer (e.g., emitting layer).

The emitting layer with higher performance, in particular, with improved luminous efficiency can be formed by the composition according to the third exemplary embodiment, thus resulting in the organic EL device with improved luminous efficiency.

The composition according to the third exemplary embodiment may further contain an additional compound. When the composition according to the third exemplary embodiment contains the additional compound, the additional compound may be a solid or a liquid.

Fourth Exemplary Embodiment

Organic EL Device

An organic EL device that is an exemplary arrangement according to a fourth exemplary embodiment includes an anode, a cathode, and an emitting layer interposed between the anode and the cathode, in which the emitting layer contains a first compound represented by a formula (11C), a second compound represented by a formula (2), and a third compound that emits delayed fluorescence, a singlet energy $S_1(M1)$ of the first compound and a singlet energy $S_1(M3)$ of the third compound satisfy a relationship of a numerical formula (Numerical Formula 1) below, and a singlet energy $S_1(M2)$ of the second compound and the singlet energy $S_1(M3)$ of the third compound satisfy a relationship of a numerical formula (Numerical Formula 2) below.

$$S_1(M1)>S_1(M3) \quad \text{(Numerical Formula 1)}$$

$$S_1(M2)>S_1(M3) \quad \text{(Numerical Formula 2)}$$

The organic EL device that is an exemplary arrangement according to the fourth exemplary embodiment is an organic EL device in which the first compound represented by the formula (1) in the organic EL device according to the first exemplary embodiment is replaced by the first compound represented by the formula (11C). That is, the organic EL device according to the fourth exemplary embodiment is different from the organic EL element according to the first exemplary embodiment.

Thus, "the first compound represented by the formula (11C)" different from that in the first exemplary embodiment will be mainly explained in the fourth exemplary embodiment, and descriptions on the same arrangements as those in the first exemplary embodiment will be simplified or omitted.

(11C)

A—L—B (c11)

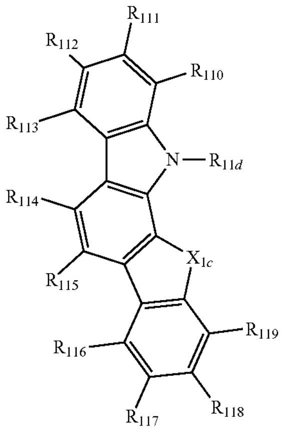

-continued (c12)

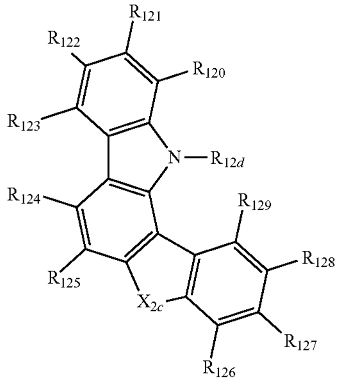

(c13)

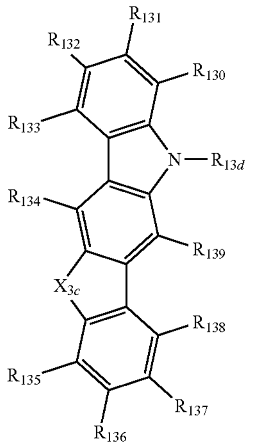

(c14)

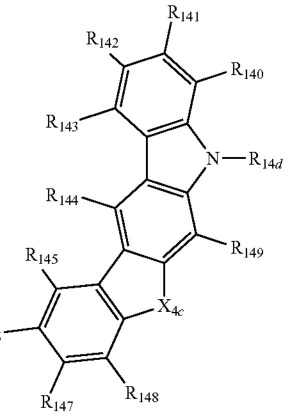

(c15)

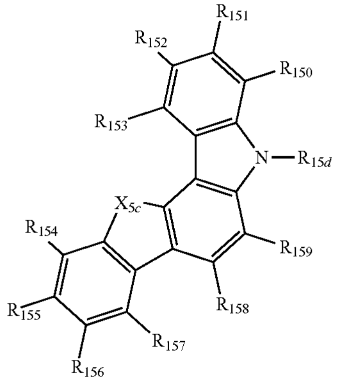

-continued (c16)

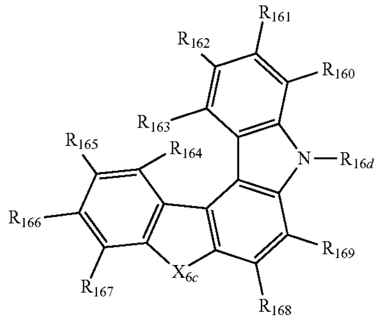

(c17)

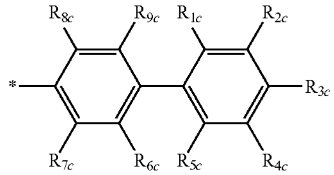

In the formula (11C), A is a group represented by a formula (c11), (c12), (c13) (c14), (c15), or (c16).

In the formula (11C), L represents the same as L in the first compound of the first exemplary embodiment.

In the formula (11C), B is a hydrogen atom, a substituted or unsubstituted aryl group having 6 to 50 ring carbon atoms, or a substituted or unsubstituted heterocyclic group having 5 to 50 ring atoms.

It should be noted that the first compound represented by the formula (11C) does not have a carbonyl group in a molecule.

In the formulae (c11) to (c17):

$R_{11d}$, $R_{12d}$, $R_{13d}$, $R_{14d}$, $R_{15d}$ and $R_{16d}$ are each independently a substituent, the group represented by the formula (c17), or a single bond bonded to L;

$X_{1c}$, $X_{2c}$, $X_{3c}$, $X_{4c}$, $X_{6c}$, and $X_{6c}$ are each independently $CR_{11C}R_{12C}$ or $NR_{13C}$;

$R_{11c}$ and $R_{12C}$ are each independently a hydrogen atom, a substituent, or a single bond bonded to L, or $R_{11C}$ and $R_{12C}$ are mutually bonded to form a ring; and $R_{13C}$ is a substituent, the group represented by the formula (c17), or a single bond bonded to L.

In the formula (c17), $R_{1c}$ to $R_{9c}$ are each independently a hydrogen atom or a substituent, or at least one pair of a pair of $R_{1c}$ and $R_{2c}$, a pair of $R_{2c}$ and $R_{3c}$, a pair of $R_{3c}$ and $R_{4c}$, a pair of $R_{4c}$ and $R_{5c}$, a pair of $R_{6c}$ and $R_{7c}$, or a pair of $R_{8c}$ and $R_{9c}$ are mutually bonded to form a ring, and * is a bonding position to a nitrogen atom bonded to $R_{13C}$ or a bonding position to a nitrogen atom bonded to $R_{11d}$ to $R_{16d}$.

When $X_{1c}$ is $NR_{13C}$, at least one of $R_{13C}$ or $R_{11d}$ is the group represented by the formula (c17). When $X_{1c}$ is $CR_{11C}R_{12C}$, $R_{11d}$ is the group represented by the formula (c17).

When $X_{2c}$ is $NR_{13C}$, at least one of $R_{13C}$ and $R_{12d}$ is the group represented by the formula (c17). When $X_{2c}$ is $CR_{11C}R_{12C}$, $R_{12d}$ is the group represented by the formula (c17).

When $X_{3c}$ is $NR_{13C}$, at least one of $R_{13C}$ and $R_{13d}$ is the group represented by the formula (c17). When $X_{3c}$ is $CR_{11C}R_{12C}$, $R_{13d}$ is the group represented by the formula (c17).

When $X_{4c}$ is $NR_{13C}$, at least one of $R_{13C}$ and $R_{14d}$ is the group represented by the formula (c17). When $X_{4c}$ is $CR_{11C}R_{12C}$, $R_{14d}$ is the group represented by the formula (c17).

When $X_{6c}$ is $NR_{13C}$, at least one of $R_{13C}$ and $R_{15d}$ is the group represented by the formula (c17). When $X_{5c}$ is $CR_{11C}R_{12C}$, $R_{15d}$ is the group represented by the formula (c17).

When $X_{6c}$ is $NR_{13C}$, at least one of $R_{13C}$ and $R_{16d}$ is the group represented by the formula (c17). When $X_{6c}$ is $CR_{11C}R_{12C}$, $R_{16d}$ is the group represented by the formula (c17).

$R_{110}$ to $R_{119}$ are each independently a hydrogen atom, a substituent, or a single bond bonded to L, or at least one pair of a pair of $R_{110}$ and $R_{111}$, a pair of $R_{111}$ and $R_{112}$, a pair of $R_{112}$ and $R_{113}$, a pair of $R_{114}$ and $R_{115}$, a pair of $R_{116}$ and $R_{117}$, a pair of $R_{117}$ and $R_{118}$, or a pair of $R_{118}$ and $R_{119}$ are bonded to each other to form a ring.

One of $R_{110}$ to $R_{119}$, $R_{11d}$, $R_{11C}$, $R_{12C}$, $R_{13C}$, and $R_{1c}$ to $R_{9c}$ is a single bond bonded to L.

When B is a hydrogen atom and L is a linking group, the hydrogen atom as B is bonded to any carbon atom in a six-membered ring being L.

When B is a hydrogen atom and L is a single bond, the hydrogen atom as B is bonded to one of $R_{110}$ to $R_{119}$, $R_{11d}$, $R_{11C}$, $R_{12C}$, $R_{13C}$, and $R_{1c}$ to $R_{9c}$.

$R_{120}$ to $R_{129}$ are each independently a hydrogen atom, a substituent, or a single bond bonded to L, or at least one pair of a pair of $R_{120}$ and $R_{121}$, a pair of $R_{121}$ and $R_{122}$, a pair of $R_{122}$ and $R_{123}$, a pair of $R_{124}$ and $R_{125}$, a pair of $R_{126}$ and $R_{127}$, a pair of $R_{127}$ and $R_{128}$, or a pair of $R_{128}$ and $R_{129}$ are bonded to each other to form a ring.

One of $R_{120}$ to $R_{129}$, $R_{12d}$, $R_{11C}$, $R_{12C}$, $R_{13C}$, and $R_{1c}$ to $R_{9c}$ is a single bond bonded to L.

When B is a hydrogen atom and L is a linking group, the hydrogen atom as B is bonded to any carbon atom in a six-membered ring being L.

When B is a hydrogen atom and L is a single bond, the hydrogen atom as B is bonded to one of $R_{120}$ to $R_{129}$, $R_{12d}$, $R_{11C}$, $R_{12C}$, $R_{13C}$, and $R_{1c}$ to $R_{9c}$.

$R_{130}$ to $R_{139}$ are each independently a hydrogen atom, a substituent, or a single bond bonded to L, or at least one pair of a pair of $R_{130}$ and $R_{131}$, a pair of $R_{131}$ and $R_{132}$, a pair of $R_{132}$ and $R_{133}$, a pair of $R_{135}$ and $R_{136}$, a pair of $R_{136}$ and $R_{137}$, or a pair of $R_{137}$ and $R_{138}$ are bonded to each other to form a ring.

One of $R_{130}$ to $R_{139}$, $R_{13d}$, $R_{11C}$, $R_{12C}$, $R_{13C}$, and $R_{1c}$ to $R_{9c}$ is a single bond bonded to L.

When B is a hydrogen atom and L is a linking group, the hydrogen atom as B is bonded to any carbon atom in a six-membered ring being L.

When B is a hydrogen atom and L is a single bond, the hydrogen atom as B is bonded to one of $R_{130}$ to $R_{139}$, $R_{13d}$, $R_{11C}$, $R_{12C}$, $R_{13C}$, and $R_{1c}$ to $R_{9c}$.

$R_{140}$ to $R_{149}$ are each independently a hydrogen atom, a substituent, or a single bond bonded to L, or at least one pair of a pair of $R_{140}$ and $R_{141}$, a pair of $R_{141}$ and $R_{142}$, a pair of $R_{142}$ and $R_{143}$, a pair of $R_{145}$ and $R_{146}$, a pair of $R_{146}$ and $R_{147}$, or a pair of $R_{147}$ and $R_{148}$ are bonded to each other to form a ring.

One of $R_{140}$ to $R_{149}$, $R_{14d}$, $R_{11C}$, $R_{12C}$, $R_{13C}$, and $R_{1c}$ to $R_{9c}$ is a single bond bonded to L.

When B is a hydrogen atom and L is a linking group, the hydrogen atom as B is bonded to any carbon atom in a six-membered ring being L.

When B is a hydrogen atom and L is a single bond, the hydrogen atom as B is bonded to one of $R_{140}$ to $R_{149}$, $R_{14d}$, $R_{11C}$, $R_{12C}$, $R_{13C}$, and $R_{1c}$ to $R_{9c}$.

$R_{150}$ to $R_{159}$ are each independently a hydrogen atom, a substituent, or a single bond bonded to L, or at least one pair of a pair of $R_{150}$ and $R_{151}$, a pair of $R_{151}$ and $R_{152}$, a pair of $R_{152}$ and $R_{153}$, a pair of $R_{154}$ and $R_{155}$, a pair of $R_{155}$ and $R_{156}$, a pair of $R_{156}$ and $R_{157}$, or a pair of $R_{158}$ and $R_{159}$ are bonded to each other to form a ring.

One of $R_{150}$ to $R_{159}$, $R_{15d}$, $R_{11C}$, $R_{12C}$, $R_{13C}$, and $R_{1c}$ to $R_{9c}$ is a single bond bonded to L.

When B is a hydrogen atom and L is a linking group, the hydrogen atom as B is bonded to any carbon atom in a six-membered ring being L.

When B is a hydrogen atom and L is a single bond, the hydrogen atom as B is bonded to one of $R_{150}$ to $R_{159}$, $R_{15d}$, $R_{11C}$, $R_{12C}$, $R_{13C}$, and $R_{1c}$ to $R_{9c}$.

$R_{160}$ to $R_{169}$ are each independently a hydrogen atom, a substituent, or a single bond bonded to L, or at least one pair of a pair of $R_{160}$ and $R_{161}$, a pair of $R_{161}$ and $R_{162}$, a pair of $R_{162}$ and $R_{163}$, a pair of $R_{164}$ and $R_{165}$, a pair of $R_{165}$ and $R_{166}$, a pair of $R_{166}$ and $R_{167}$, or a pair of $R_{168}$ and $R_{169}$ are bonded to each other to form a ring.

One of $R_{160}$ to $R_{169}$, $R_{16d}$, $R_{11C}$, $R_{12C}$, $R_{13C}$, and $R_{1c}$ to $R_{9c}$ is a single bond bonded to L.

When B is a hydrogen atom and L is a linking group, the hydrogen atom as B is bonded to any carbon atom in a six-membered ring being L.

When B is a hydrogen atom and L is a single bond, the hydrogen atom as B is bonded to one of $R_{160}$ to $R_{169}$, $R_{16d}$, $R_{11C}$, $R_{12C}$, $R_{13C}$, and $R_{1c}$ to $R_{9c}$.

$R_{110}$ to $R_{169}$, $R_{11d}$ to $R_{16d}$, $R_{11C}$ to $R_{13C}$, and $R_{1c}$ to $R_{9c}$ as a substituent each independently represent the same as $R_{110}$ to $R_{169}$ and $R_{11}$ to $R_{16}$ as a substituent in the first compound of the first exemplary embodiment.

(2)

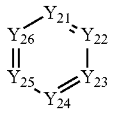

(2A)

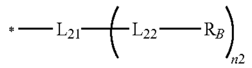

The formula (2) represents the same as the formula (2) of the second compound of the first exemplary embodiment. Accordingly, the description of the formula (2) is omitted.

In the formula (11C), a substituent for "a substituted or unsubstituted" group as $R_{110}$ to $R_{169}$, $R_{11d}$ to $R_{16d}$, $R_{11C}$ to $R_{13C}$, $R_{1c}$ to $R_{9c}$, L and B each independently represent the same as the substituent for "a substituted or unsubstituted" group as $R_{110}$ to $R_{169}$, $R_{11}$ to $R_{16}$, L and B in the formula (1) of the first exemplary embodiment.

Preferable Arrangements of Organic EL Device of Fourth Exemplary Embodiment

The organic EL device that is an exemplary arrangement according to the fourth exemplary embodiment is an organic EL device in which the first compound in the organic EL device according to the first exemplary embodiment is replaced by the first compound represented by the formula (11C).

The preferable embodiments of the organic EL device according to the fourth exemplary embodiment are the same as those according to the first exemplary embodiment except for the structure of the first compound, which will be specifically shown below. In the organic EL device according to the fourth exemplary embodiment, it is preferable that the emitting layer contains a fluorescent fourth compound and the singlet energy $S_1$ (M3) of the third compound and a singlet energy $S_1$(M4) of the fourth compound satisfy a relationship of a numerical formula (Numerical Formula 3) below.

$$S_1(M3)>S_1(M4) \quad \text{(Numerical Formula 3)}$$

In the organic EL device according to the fourth exemplary embodiment, it is preferable that an energy gap $T_{77K}$(M1) at 77K of the first compound and an energy gap $T_{77K}$(M3) at 77K of the third compound satisfy a relationship of a numerical formula (Numerical Formula 1a) below.

It is preferable that an energy gap $T_{77K}$(M2) at 77K of the second compound and the energy gap $T_{77K}$(M3) at 77K of the third compound satisfy a relationship of a numerical formula (Numerical Formula 2b) below.

$$T_{77K}(M1)>T_{77K}(M3) \quad \text{(Numerical Formula 1a)}$$

$$T_{77K}(M2)>T_{77K}(M3) \quad \text{(Numerical Formula 2b)}$$

In the organic EL device according to the fourth exemplary embodiment, A in the formula (11C) is preferably a group represented by the formula (c11), (c12), (c13), (c14), or (c16), more preferably a group represented by the formula (c11), (c12), (c13), or (c14), further preferably a group represented by the formula (c11) or (c14), still further preferably a group represented by the formula (c11).

In the organic EL device according to the fourth exemplary embodiment, A in the formula (11C) is preferably a group represented by any one of formulae (11D) to (22D).

(11D)

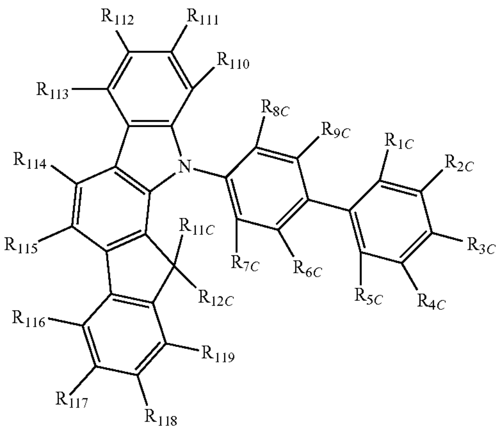

(12D)

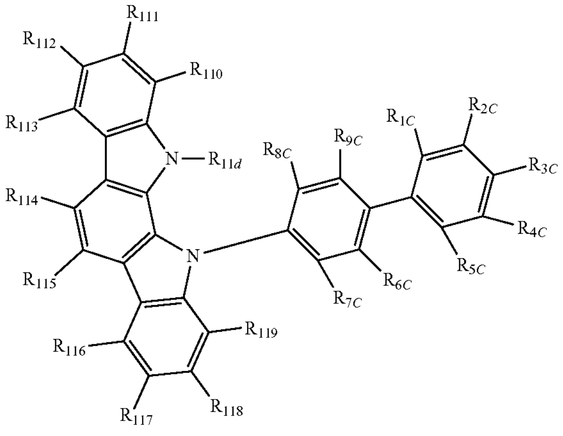

-continued
(13D)
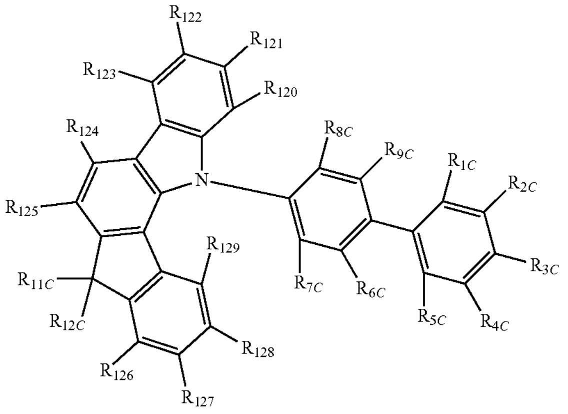
(14D)
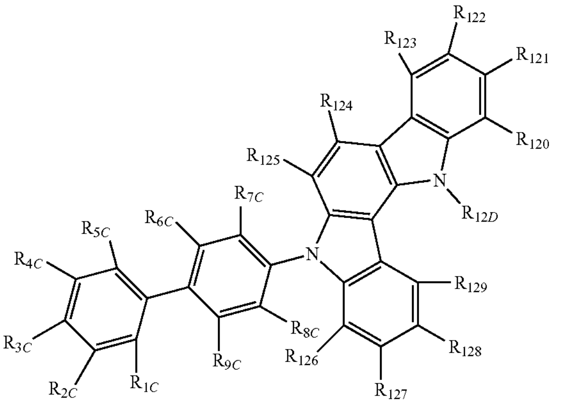
(15D)
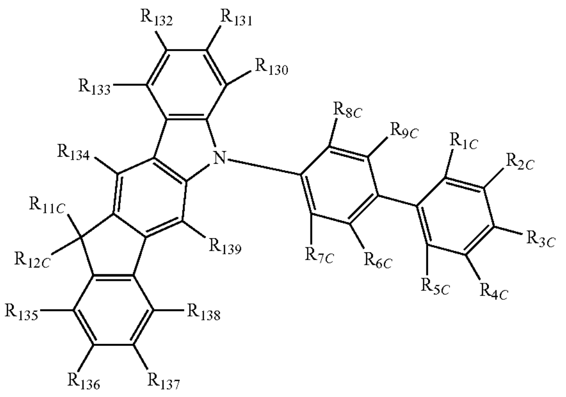
-continued
(16D)
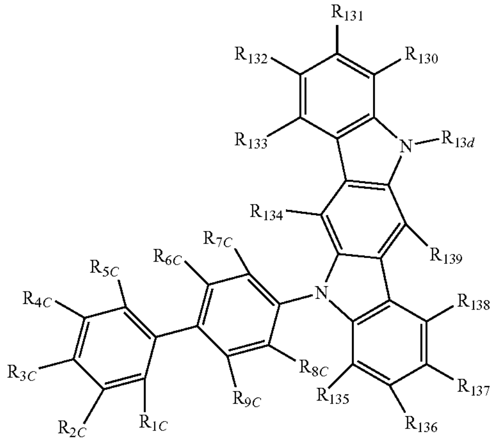
(17D)
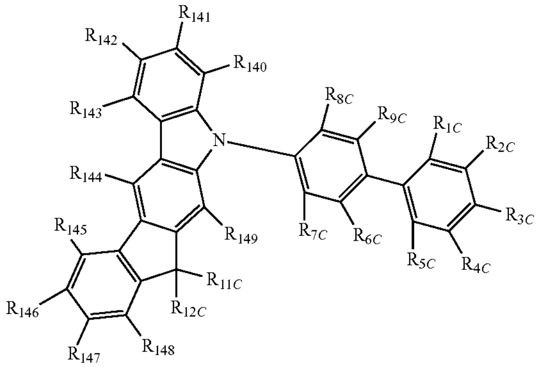
(18D)
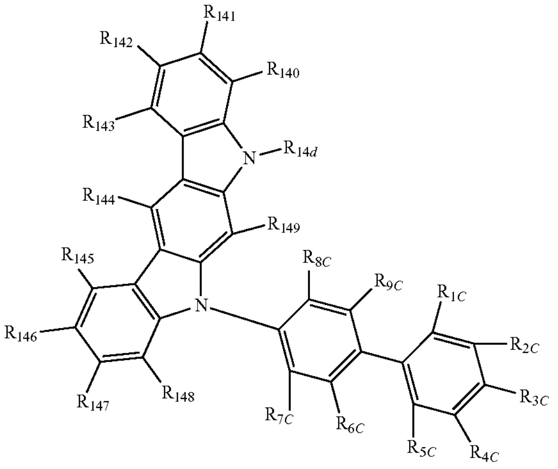

-continued (19D)

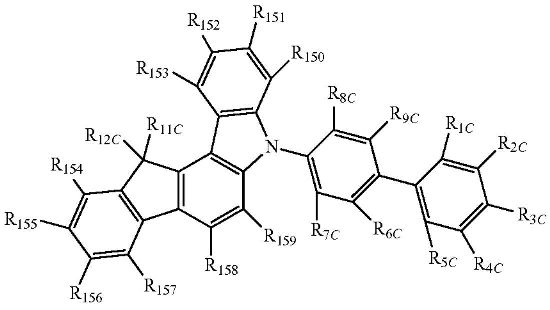

(20D)

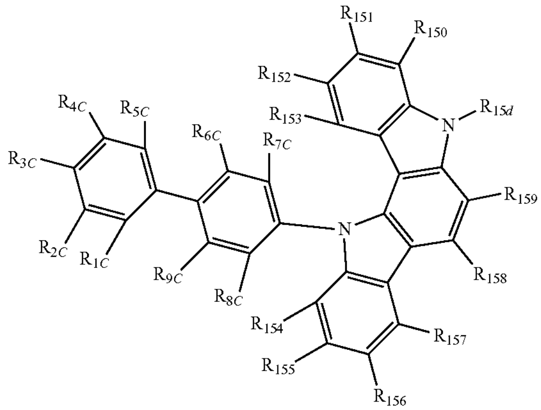

(21D)

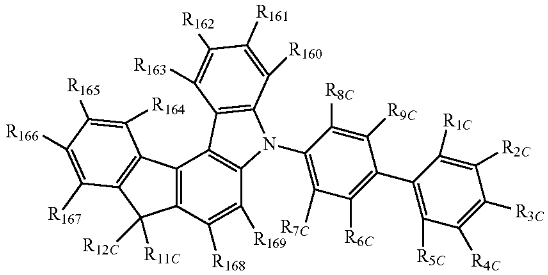

(22D)

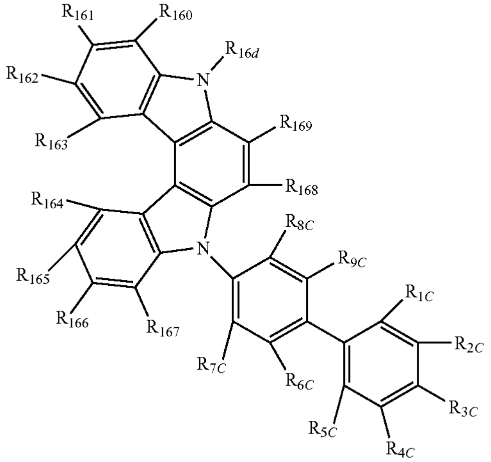

In the formulae (11D) to (22D), $R_{110}$ to $R_{169}$, $R_{11d}$ to $R_{16d}$, $R_{1C}$ to $R_{9C}$, and $R_{11C}$ to $R_{12C}$ each independently represent the same as $R_{110}$ to $R_{169}$, $R_{11d}$ to $R_{16d}$, $R_{1C}$ to $R_{9C}$, and $R_{11C}$ to $R_{12C}$ in the formulae (c11) to (c16).

In the first compound represented by the formula (11C), in the formulae (c11), (c12), (c13), (c14), (c15), and (c16), it is preferable that $R_{110}$ to $R_{169}$, $R_{11d}$ to $R_{16d}$, and $R_{1c}$ to $R_{9c}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms, and $R_{11d}$ to $R_{16d}$ and $R_{11c}$ to $R_{13c}$ are each independently a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

In the first compound represented by the formula (11C), in the formulae (c11), (c12), (c13), (c14), (c15), and (c16), it is more preferable that $R_{110}$ to $R_{169}$, $R_{11d}$ to $R_{16d}$, and $R_{1c}$ to $R_{9c}$ are each independently a hydrogen atom or a substituted or unsubstituted aryl group having 6 to 30 ring carbon atoms, and $R_{11d}$ to $R_{16d}$ and $R_{11c}$ to $R_{13C}$ are each independently a substituted or unsubstituted aryl group having 6 to 30 ring carbon atoms or a substituted or unsubstituted alkyl group having 1 to 30 carbon atoms.

In the first compound represented by the formula (11C), in the formulae (c11), (c12), (c13), (c14), (c15), and (c16), it is further preferable that $R_{110}$ to $R_{169}$, $R_{11d}$ to $R_{16d}$, and $R_{1c}$ to $R_{9c}$ are hydrogen atoms, and $R_{11d}$ to $R_{16d}$ and $R_{11c}$ to $R_{13c}$ are each independently a substituted or unsubstituted aryl group having 6 to 30 ring carbon atoms or a substituted or unsubstituted alkyl group having 1 to 30 carbon atoms.

In the first compound represented by the formula (11C), L in the formula (11C) is preferably a single bond, a substituted or unsubstituted arylene group having 6 to 25 ring carbon atoms, or a substituted or unsubstituted divalent heterocyclic group having 5 to 22 ring atoms, more preferably a single bond or a substituted or unsubstituted arylene group having 6 to 25 ring carbon atoms, further preferably a substituted or unsubstituted para-biphenylene group or a substituted or unsubstituted para-terphenylene group.

In the first compound represented by the formula (11C), B in the formula (11C) is preferably a substituted or unsubstituted aryl group having 6 to 19 ring carbon atoms or a substituted or unsubstituted heterocyclic group having 5 to 19 ring atoms, more preferably any one of the groups represented by the formulae (b1) to (b17) in the first compound of the first exemplary embodiment, further preferably any one of the groups represented by the formulae (b1) to (b6).

In the first compound represented by the formula (11C), when B in the formula (11C) is any one of the groups represented by the formulae (b1) to (b6) in the first compound of the first exemplary embodiment, at least one pair of adjacent ones of Ra are preferably not bonded to each other.

The emitting layer according to the fourth exemplary embodiment is preferably formed by using, as a vapor deposition source, "a composition containing the first compound represented by the formula (11C) and the second compound". For example, the emitting layer according to the fourth exemplary embodiment can be formed by using at least the vapor deposition source that is "the composition containing the first compound represented by the formula (11C) and the second compound" and the third compound.

Using the "composition containing the first compound represented by the formula (11C) and the second compound" can reduce the number of vapor deposition sources for forming a target layer (e.g., emitting layer).

The organic EL device that is an exemplary arrangement of the fourth exemplary embodiment can also achieve higher performance, in particular, improved luminous efficiency.

Examples of the first compound represented by the formula (11C) are as follows.

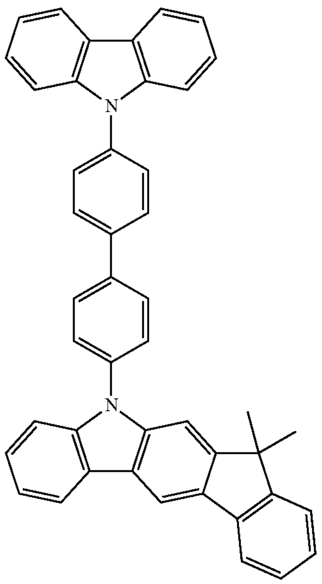

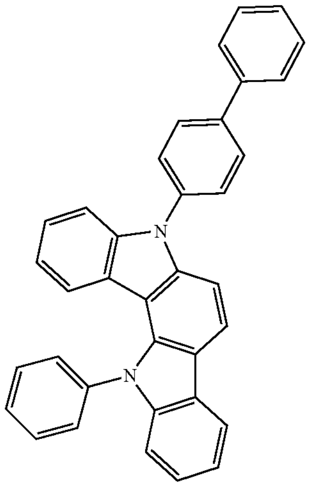

-continued

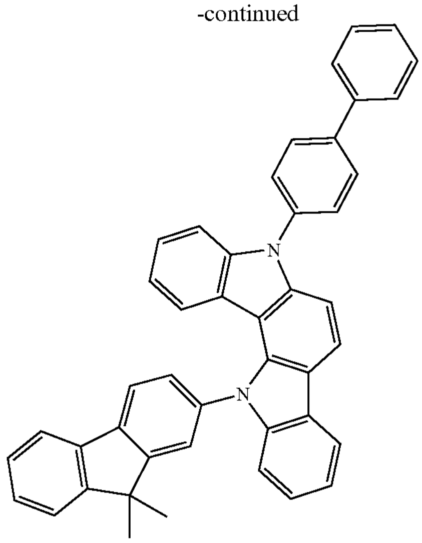

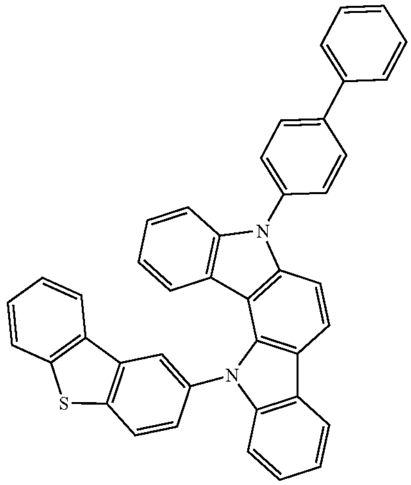 [SMILES: c1ccc(-c2ccc(-n3c4ccccc4c4c3ccc3c5ccccc5n(-c5ccc6sc7ccccc7c6c5)c34)cc2)cc1]

Fifth Exemplary Embodiment

Electronic Device

An electronic device according to the present exemplary embodiment is installed with any one of the organic EL devices according to the above exemplary embodiments. Examples of the electronic device include a display device and a light-emitting device. Examples of the display device include a display component (e.g., an organic EL panel module), TV, mobile phone, tablet and personal computer. Examples of the light-emitting unit include an illuminator and a vehicle light.

Sixth Exemplary Embodiment

Organic-EL-Device Material

An organic-EL-device material according to a sixth exemplary embodiment contains at least the first compound (compound represented by the formula (1)), the second compound (compound represented by the formula (2)), and the third compound that exhibits delayed fluorescence according to the first or second exemplary embodiment.

The organic-EL-device material of the sixth exemplary embodiment can provide an organic EL device with higher performance, in particular, improved luminous efficiency.

The organic-EL-device material according to the sixth exemplary embodiment may further contain an additional compound. When the organic-EL-device material according to the sixth exemplary embodiment further contains the additional compound, the additional compound may be solid or liquid.

Modification of Embodiment(s)

The scope of the invention is not limited by the above-described exemplary embodiments but includes any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the emitting layers satisfies the conditions described in the above exemplary embodiments. The rest of the emitting layers is, for instance, a fluorescent emitting layer or a phosphorescent emitting layer with use of emission caused by electron transfer from the triplet excited state directly to the ground state, in an exemplary embodiment.

When the organic EL device includes a plurality of emitting layers, these emitting layers are mutually adjacently provided, or form a so-called tandem organic EL device, in which a plurality of emitting units are layered via an intermediate layer.

For instance, in an exemplary embodiment, a blocking layer is provided adjacent to at least one of a side near the anode and a side near the cathode of the emitting layer. The blocking layer is preferably provided in contact with the emitting layer to block holes, electrons, excitons or combinations thereof.

For instance, when the blocking layer is provided in contact with the cathode-side of the emitting layer, the blocking layer permits transport of electrons, and blocks holes from reaching a layer provided near the cathode (e.g., the electron transporting layer) beyond the blocking layer. When the organic EL device includes the electron transporting layer, the blocking layer is preferably disposed between the emitting layer and the electron transporting layer.

When the blocking layer is provided in contact with the anode-side of the emitting layer, the blocking layer permits transport of holes, but blocks electrons from reaching a layer provided near the anode (e.g., the hole transporting layer) beyond the blocking layer. When the organic EL device includes the hole transporting layer, the blocking layer is preferably disposed between the emitting layer and the hole transporting layer.

Alternatively, the blocking layer may be provided adjacent to the emitting layer so that the excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

Other Explanations

Herein, numerical ranges represented by "x to y" represents a range whose lower limit is the value (x) recited before "to" and whose upper limit is the value (y) recited after "to."

Rx and Ry are mutually bonded to form a ring, which means herein, for instance, that Rx and Ry contain a carbon atom, a nitrogen atom, an oxygen atom, a sulfur atom or a silicon atom, the atom (a carbon atom, a nitrogen atom, an oxygen atom, a sulfur atom or a silicon atom) contained in Rx and the atom (a carbon atom, a nitrogen atom, an oxygen atom, a sulfur atom or a silicon atom) contained in Ry are mutually bonded via a single bond, a double bond, a triple bond or a divalent linking group to form a ring having 5 or more ring atoms (specifically, a heterocyclic ring or an aromatic hydrocarbon ring). x represents a number, a character or a combination of a number and a character. y represents a number, a character or a combination of a number and a character.

The divalent linking group is not particularly limited and is exemplified by —O—, —CO—, —$CO_2$—, —S—, —SO—, —$SO_2$—, —NH—, —NRa—, and a group obtained by combining two or more linking groups of those.

Specific examples of the heterocyclic ring include a cyclic structure (heterocyclic ring) obtained by removing a bond from a "heteroaryl group $Sub_2$" exemplarily shown in the later-described "Description of Each Substituent in Formula." The heterocyclic ring may have a substituent.

Specific examples of the heterocyclic ring include cyclic structures (heterocyclic rings) obtained by removing a bond from an "aryl group $Sub_1$" exemplarily shown in the later-described "Description of Each Substituent in Formula." The aromatic hydrocarbon ring may have a substituent.

Examples of Ra include a substituted or unsubstituted alkyl group $Sub_3$ having 1 to 30 carbon atoms, a substituted or unsubstituted aryl group $Sub_1$ having 6 to 30 ring carbon atoms, and a substituted or unsubstituted heteroaryl group $Sub_2$ having 5 to 30 ring atoms, which are exemplarily shown in the later-described "Description of Each Substituent in Formula."

Rx and Ry are mutually bonded to form a ring, which means, for instance, that: an atom contained in $Rx_1$ and an atom contained in $Ry_1$ in a molecular structure represented by a formula (E1) below form a ring (cyclic structure) E represented by a formula (E2); an atom contained in $Rx_1$ and an atom contained in $Ry_1$ in a molecular structure represented by a formula (F1) below form a ring (cyclic structure) F represented by a formula (F2); an atom contained in $Rx_1$ and an atom contained in $Ry_1$ in a molecular structure represented by a formula (G1) below form a ring (cyclic structure) G represented by a formula (G2); an atom contained in $Rx_1$ and an atom contained in $Ry_1$ in a molecular structure represented by a formula (H1) below form a ring (cyclic structure) H represented by a formula (H2); and an atom contained in $Rx_1$ and an atom contained in $Ry_1$ in a molecular structure represented by a formula (11) below form a ring (cyclic structure) I represented by a formula (12).

In the formulae (E1) to (I1), * each independently represents a bonding position to another atom in a molecule. Two * in the formula (E1) correspond one-to-one to two * in the formula (E2). Two * in the formula (F1) correspond one-to-one to two * in the formula (F2). Two * in the formula (G1) correspond one-to-one to two * in the formula (G2). Two * in the formula (H1) correspond one-to-one to two * in the formula (H2). Two * in the formula (I1) correspond one-to-one to two * in the formula (I2).

(E1)

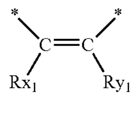

-continued (F1)

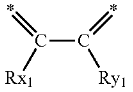

(G1)

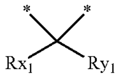

(H1)

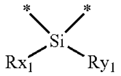

(I1)

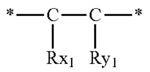

(E2)

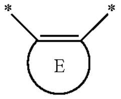

(F2)

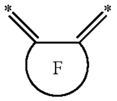

(G2)

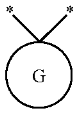

(H2)

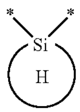

(I2)

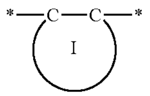

In the molecular structures represented by the respective formulae (E2) to (I2), E to I each represent a cyclic structure (the ring having 5 or more ring atoms). In the formulae (E2) to (I2), * each independently represents a bonding position to another atom in a molecule. Two * in the formula (E2) correspond one-to-one to two * in the formula (E1). Similarly, two * in each of the formulae (F2) to (12) correspond one-to-one to two * in in each of the formulae (F1) to (I1).

For instance, when $Rx_1$ and $Ry_1$ in the formula (E1) are mutually bonded to form the ring E in the formula (E2) and the ring E is an unsubstituted benzene ring, the molecular structure represented by the formula (E1) is a molecular structure represented by a formula (E3) below. Herein, two * in the formula (E3) each independently correspond to two * in the formula (E2) and the formula (E1).

For instance, when $Rx_1$ and $Ry_1$ in the formula (E1) are mutually bonded to form the ring E in the formula (E2) and the ring E is an unsubstituted pyrrole ring, the molecular structure represented by the formula (E1) is a molecular structure represented by a formula (E4) below. Herein, two * in the formula (E4) each independently correspond to two * in the formula (E2) and the formula (E1). In the formulae (E3) and (E4), * each independently represents a bonding position to another atom in a molecule.

(E3)

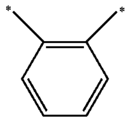

(E4)

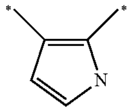

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. Unless specifically described, the same applies to the “ring carbon atoms” described later. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). Atom(s) not forming a ring and atom(s) included in a substituent when the ring is substituted by the substituent are not counted in the number of the ring atoms. Unless specifically described, the same applies to the “ring atoms” described later. For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Description of Each Substituent in Formulae Herein

The aryl group (occasionally referred to as an aromatic hydrocarbon group) herein is exemplified by an aryl group $Sub_1$. The aryl group $Sub_1$ is at least one group selected from the group consisting of a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Herein, the aryl group $Sub_1$ preferably has 6 to 30 ring carbon atoms, more preferably 6 to 20 ring carbon atoms, further preferably 6 to 14 ring carbon atoms, further more preferably 6 to 12 ring carbon atoms. Among the aryl group $Sub_1$, a phenyl group, biphenyl group, naphthyl group, phenanthryl group, terphenyl group and fluorenyl group are preferable. A carbon atom in a position 9 of each of 1-fluorenyl group, 2-fluorenyl group, 3-fluorenyl group and 4-fluorenyl group is preferably substituted by a substituted or unsubstituted alkyl group $Sub_3$ or a substituted or unsubstituted aryl group $Sub_1$ described later herein.

The heteroaryl group (occasionally referred to as a heterocyclic group, heteroaromatic ring group or aromatic heterocyclic group) herein is exemplified by a heterocyclic group $Sub_2$. The heterocyclic group $Sub_2$ is a group containing, as a hetero atom(s), at least one atom selected from the group consisting of nitrogen, sulfur, oxygen, silicon, selenium atom and germanium atom. The heterocyclic group $Sub_2$ preferably contains, as a hetero atom(s), at least one atom selected from the group consisting of nitrogen, sulfur and oxygen.

The heterocyclic group $Sub_2$ herein are, for instance, at least one group selected from the group consisting of a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Herein, the heterocyclic group $Sub_2$ preferably has 5 to 30 ring atoms, more preferably 5 to 20 ring atoms, further preferably 5 to 14 ring atoms. Among the above heterocyclic group $Sub_2$, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further more preferable. A nitrogen atom in position 9 of 1-carbazolyl group, 2-carbazolyl group, 3-carbazolyl group and 4-carbazolyl group is preferably substituted by the substituted or unsubstituted aryl group $Sub_1$ or the substituted or unsubstituted heterocyclic group $Sub_2$ described herein.

Herein, the heterocyclic group $Sub_2$ may be a group derived from any one of moieties represented by formulae (XY-1) to (XY-18) below.

(XY-1)

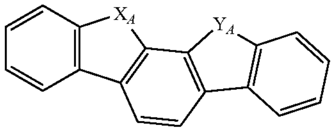

-continued (XY-2)

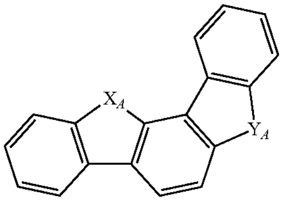

(XY-3)

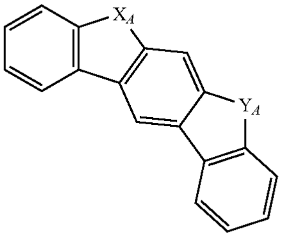

(XY-4)

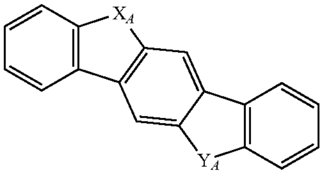

(XY-5)

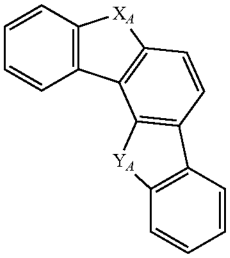

(XY-6)

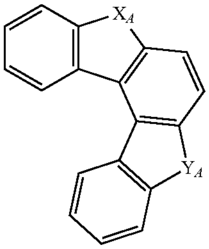

(XY-7)

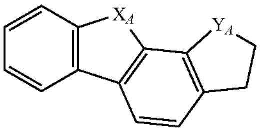

(XY-8)

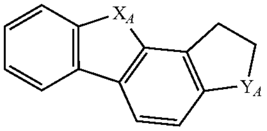

(XY-9)

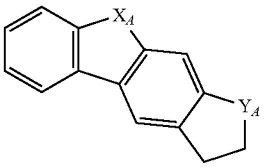

-continued (XY-10)

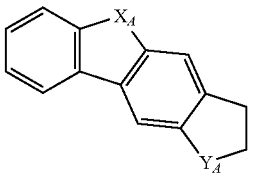

(XY-11)

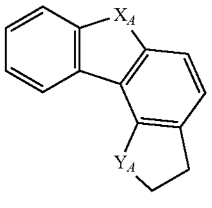

(XY-12)

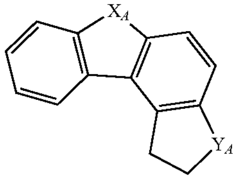

(XY-13)

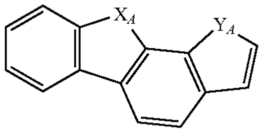

(XY-14)

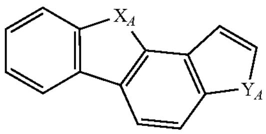

(XY-15)

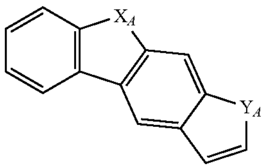

(XY-16)

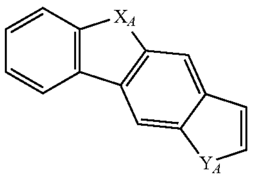

(XY-17)

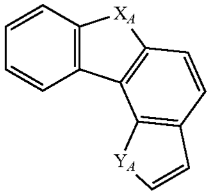

-continued (XY-18)

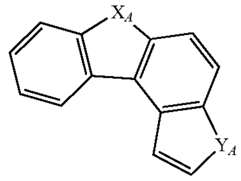

In the formulae (XY-1) to (XY-18), $X_A$ and $Y_A$ each independently represent a hetero atom, and preferably represent an oxygen atom, sulfur atom, selenium atom, silicon atom or germanium atom. Each of the moieties represented by the respective formulae (XY-1) to (XY-18) has a bond at any position to provide a heterocyclic group. The heterocyclic group may be substituted.

Herein, the heterocyclic group $Sub_2$ may be a group represented by one of formulae (XY-19) to (XY-22) below. Moreover, the position of the bond may be changed as needed (XY-19)

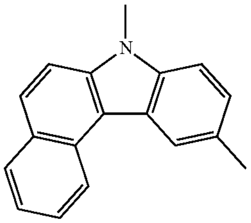

(XY-20)

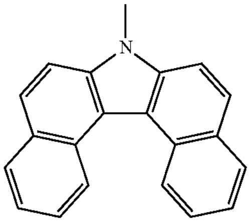

(XY-21)

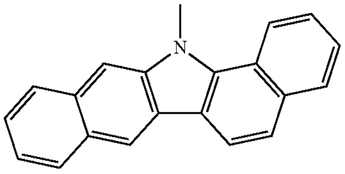

(XY-22)

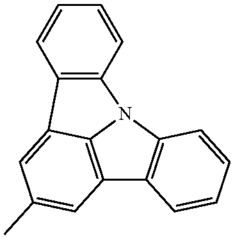

The alkyl group herein may be any one of a linear alkyl group, branched alkyl group and cyclic alkyl group.

The alkyl group herein is exemplified by an alkyl group $Sub_3$.

The linear alkyl group herein is exemplified by a linear alkyl group $Sub_{31}$.

The branched alkyl group herein is exemplified by a branched alkyl group $Sub_{32}$.

The cyclic alkyl group herein is exemplified by a cyclic alkyl group $Sub_{33}$.

For instance, the alkyl group $Sub_3$ is at least one group selected from the group consisting of the linear alkyl group $Sub_{31}$, branched alkyl group $Sub_{32}$, and cyclic alkyl group $Sub_{33}$.

The linear alkyl group $Sub_{31}$ or branched alkyl group $Sub_{32}$ is exemplified by at least one group selected from the group consisting of a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

Herein, the linear alkyl group $Sub_{31}$ or branched alkyl group $Sub_{32}$ preferably has 1 to 30 carbon atoms, more preferably 1 to 20 carbon atoms, further preferably 1 to 10 carbon atoms, further more preferably 1 to 6 carbon atoms. The linear alkyl group $Sub_{31}$ or branched alkyl group $Sub_{32}$ is further more preferably a methyl group, ethyl group, propyl group, isopropyl group, n-butyl group, s-butyl group, isobutyl group, t-butyl group, n-pentyl group, n-hexyl group, amyl group, isoamyl group and neopentyl group.

Herein, the cyclic alkyl group $Sub_{33}$ is exemplified by a cycloalkyl group $Sub_{331}$.

The cycloalkyl group $Sub_{331}$ herein is exemplified by at least one group selected from the group consisting of a cyclopropyl group, cyclobutyl group, cyclopentyl group, cyclohexyl group, 4-metylcyclohexyl group, adamantyl group and norbornyl group. The cycloalkyl group $Sub_{331}$ preferably has 3 to 30 ring carbon atoms, more preferably 3 to 20 ring carbon atoms, further preferably 3 to 10 ring carbon atoms, further more preferably 5 to 8 ring carbon atoms. Among the cycloalkyl group $Sub_{331}$, a cyclopentyl group and a cyclohexyl group are further more preferable.

Herein, an alkyl halide group is exemplified by an alkyl halide group $Sub_4$. The alkyl halide group $Sub_4$ is provided by substituting the alkyl group $Sub_3$ with at least one halogen atom, preferably at least one fluorine atom.

Herein, the alkyl halide group $Sub_4$ is exemplified by at least one group selected from the group consisting of a fluoromethyl group, difluoromethyl group, trifluoromethyl group, fluoroethyl group, trifluoromethylmethyl group, trifluoroethyl group, and pentafluoroethyl group.

Herein, a substituted silyl group is exemplified by a substituted silyl group $Sub_5$. The substituted silyl group $Sub_5$ is exemplified by at least one group selected from the group consisting of an alkylsilyl group $Sub_{51}$ and an arylsilyl group $Sub_{52}$.

Herein, the alkylsilyl group $Sub_{51}$ is exemplified by a trialkylsilyl group $Sub_{511}$ having the above-described alkyl group $Sub_3$.

The trialkylsilyl group $Sub_{511}$ is exemplified by at least one group selected from the group consisting of a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups $Sub_3$ in the trialkylsilyl group $Sub_{511}$ may be mutually the same or different.

Herein, the arylsilyl group $Sub_{52}$ is exemplified by at least one group selected from the group consisting of a dialkylarylsilyl group $Sub_{521}$, alkyldiarylsilyl group $Sub_{522}$ and triarylsilyl group $Sub_{523}$.

The dialkylarylsilyl group $Sub_{521}$ is exemplified by a dialkylarylsilyl group including two alkyl groups $Sub_3$ and one aryl group $Sub_1$. The dialkylarylsilyl group $Sub_{521}$ preferably has 8 to 30 carbon atoms.

The alkyldiarylsilyl group $Sub_{522}$ is exemplified by an alkyldiarylsilyl group including one alkyl group $Sub_3$ and two aryl groups $Sub_1$. The alkyldiarylsilyl group $Sub_{522}$ preferably has 13 to 30 carbon atoms.

The triarylsilyl group $Sub_{523}$ is exemplified by a triarylsilyl group including three aryl groups $Sub_1$. The triarylsilyl group $Sub_{523}$ preferably has 18 to 30 carbon atoms.

Herein, a substituted or unsubstituted alkyl sulfonyl group is exemplified by an alkyl sulfonyl group $Sub_6$. The alkyl sulfonyl group $Sub_6$ is represented by $-SO_2Rw$. $R_w$ in $-SO_2R_w$ represents a substituted or unsubstituted alkyl group $Sub_3$ described above.

Herein, an aralkyl group (occasionally referred to as an arylalkyl group) is exemplified by an aralkyl group $Sub_7$. An aryl group in the aralkyl group $Sub_7$ includes, for instance, at least one of the above-described aryl group $Sub_1$ and the above-described heteroaryl group $Sub_2$.

The aralkyl group $Sub_7$ herein is preferably a group having the aryl group $Sub_1$ and is represented by $-Z_3-Z_4$. $Z_3$ is exemplified by an alkylene group corresponding to the above alkyl group $Sub_3$. $Z_4$ is exemplified by the above aryl group $Sub_1$. In this aralkyl group $Sub_7$, an aryl moiety has 6 to 30 carbon atoms (preferably 6 to 20 carbon atoms, more preferably 6 to 12 carbon atoms) and an alkyl moiety has 1 to 30 carbon atoms (preferably 1 to 20 carbon atoms, more preferably 1 to 10 carbon atoms, further preferably 1 to 6 carbon atoms). The aralkyl group $Sub_7$ is exemplified by at least one group selected from the group consisting of a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

The alkoxy group herein is exemplified by an alkoxy group $Sub_8$. The alkoxy group $Sub_8$ is represented by $-OZ_1$. $Z_1$ is exemplified by the above alkyl group $Sub_3$. The alkoxy group $Sub_8$ is exemplified by at least one group selected from the group consisting of a methoxy group, ethoxy group, propoxy group, butoxy group, pentyloxy group and hexyloxy group. The alkoxy group $Sub_8$ preferably has 1 to 30 carbon atoms, more preferably 1 to 20 carbon atoms.

Herein, an alkoxy halide group is exemplified by an alkoxy halide group $Sub_9$. The alkoxy halide group $Sub_9$ is provided by substituting the alkoxy group $Sub_8$ with at least one halogen atom, preferably at least one fluorine atom.

Herein, an aryloxy group (sometimes referred to as an arylalkoxy group) is exemplified by an arylalkoxy group $Sub_{10}$. An aryl group in the arylalkoxy group $Sub_{10}$ includes at least one of the aryl group $Sub_1$ and the heteroaryl group $Sub_2$.

The arylalkoxy group $Sub_{10}$ herein is represented by $-OZ_2$. $Z_2$ is exemplified by the aryl group $Sub_1$ or the heteroaryl group $Sub_2$. The arylalkoxy group $Sub_{10}$ preferably has 6 to 30 ring carbon atoms, more preferably 6 to 20 ring carbon atoms. The arylalkoxy group $Sub_{10}$ is exemplified by a phenoxy group.

Herein, a substituted amino group is exemplified by a substituted amino group $Sub_{11}$. The substituted amino group $Sub_{11}$ is exemplified by at least one group selected from the group consisting of an arylamino group $Sub_{111}$ and an alkylamino group $Sub_{112}$.

The arylamino group $Sub_{111}$ is represented by —$NHR_{V1}$ or —$N(R_{V1})2$. $R_{V1}$ is exemplified by the aryl group $Sub_1$. Two $R_{V1}$ in —$N(R_{V1})2$ are mutually the same or different.

The alkylamino group $Sub_{112}$ is represented by —$NHR_{V2}$ or —$N(R_{V2})2$. $R_{V2}$ is exemplified by the alkyl group $Sub_3$. Two $R_{V2}$ in —$N(R_{V2})2$ are mutually the same or different.

Herein, the alkenyl group is exemplified by an alkenyl group $Sub_{12}$. The alkenyl group $Sub_{12}$, which is linear or branched, is exemplified by at least one group selected from the group consisting of a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

The alkynyl group herein is exemplified by an alkynyl group $Sub_{13}$. The alkynyl group $Sub_{13}$ may be linear or branched and is at least one group selected from the group consisting of an ethynyl group, a propynyl group and a 2-phenylethynyl group.

The alkylthio group herein is exemplified by an alkylthio group $Sub_{14}$.

The alkylthio group $Sub_{14}$ is represented by —$SR_{V3}$. $R_{V3}$ is exemplified by the alkyl group $Sub_3$. The alkylthio group $Sub_{14}$ preferably has 1 to 30 carbon atoms, more preferably 1 to 20 carbon atoms.

The arylthio group herein is exemplified by an arylthio group $Sub_{15}$.

The arylthio group $Sub_{15}$ is represented by —$SR_{V4}$. $R_{V4}$ is exemplified by the aryl group $Sub_1$. The arylthio group $Sub_{15}$ preferably has 6 to 30 ring carbon atoms, more preferably 6 to 20 ring carbon atoms.

Herein, examples of the halogen atom include a fluorine atom, a chlorine atom, a bromine atom and an iodine atom, among which a fluorine atom is preferable.

A substituted phosphino group herein is exemplified by a substituted phosphino group $Sub_{16}$. The substituted phosphino group $Sub_{16}$ is exemplified by a phenyl phosphanyl group.

An arylcarbonyl group herein is exemplified by an arylcarbonyl group $Sub_{17}$. The arylcarbonyl group $Sub_{17}$ is represented by —COY'. Y' is exemplified by the aryl group $Sub_1$. Herein, the arylcarbonyl group $Sub_{17}$ is exemplified by at least one group selected from the group consisting of a phenyl carbonyl group, diphenyl carbonyl group, naphthyl carbonyl group, and triphenyl carbonyl group.

An acyl group herein is exemplified by an acyl group $Sub_{18}$. The acyl group $Sub_{18}$ is represented by —COR'. R' is exemplified by the alkyl group $Sub_3$. The acyl group $Sub_{18}$ herein is exemplified by at least one group selected from the group consisting of an acetyl group and a propionyl group.

A substituted phosphoryl group herein is exemplified by a substituted phosphoryl group $Sub_{19}$. The substituted phosphoryl group $Sub_{19}$ is represented by a formula (P) below.

(P)

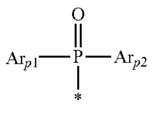

In the formula (P), $Ar_{P1}$ and $Ar_{P2}$ are any one substituent selected from the group consisting of the above alkyl group $Sub_3$ and the above aryl group $Sub_1$.

An ester group herein is exemplified by an ester group $Sub_{20}$. The ester group $Sub_{20}$ is exemplified by at least one group selected from the group consisting of an alkyl ester group and an aryl ester group.

An alkyl ester group herein is exemplified by an alkyl ester group $Sub_{201}$. The alkyl ester group $Sub_{201}$ is represented by —C(═O)$OR^E$. $R^E$ is exemplified by a substituted or unsubstituted alkyl group $Sub_3$ described above.

An aryl ester group herein is exemplified by an aryl ester group $Sub_{202}$. The aryl ester group $Sub_{202}$ is represented by —C(═O)$OR^{Ar}$. $R^{Ar}$ is exemplified by a substituted or unsubstituted aryl group $Sub_1$ described above.

A siloxanyl group herein is exemplified by a siloxanyl group $Sub_{21}$. The siloxanyl group $Sub_{21}$ is a silicon compound group through an ether bond. The siloxanyl group $Sub_{21}$ is exemplified by a trimethylsiloxanyl group.

A carbamoyl group herein is represented by —$CONH_2$.

A substituted carbamoyl group herein is exemplified by a carbamoyl group $Sub_{22}$. The carbamoyl group $Sub_{22}$ is represented by —CONH—$Ar^C$ or —CONH—$R^C$. $Ar^C$ is exemplified by at least one group selected from the group consisting of a substituted or unsubstituted aryl group $Sub_1$ (preferably 6 to 10 ring carbon atoms) and a substituted or unsubstituted heteroaryl group $Sub_2$ (preferably 5 to 14 ring atoms). $Ar^C$ may be a group formed by bonding the aryl group $Sub_1$ and the heteroaryl group $Sub_2$.

$R^C$ is exemplified by a substituted or unsubstituted alkyl group $Sub_3$ described above (preferably having 1 to 6 carbon atoms).

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

In chemical formulae herein, it is assumed that a hydrogen atom (i.e. protium, deuterium or tritium) is bonded to each of bondable positions that are not annexed with signs "R" or the like or "D" representing a protium.

Hereinafter, an alkyl group $Sub_3$ means at least one group of a linear alkyl group $Sub_{31}$, a branched alkyl group $Sub_{32}$, and a cyclic alkyl group $Sub_{33}$ described in "Description of Each Substituent."

Similarly, a substituted silyl group $Sub_5$ means at least one group of an alkylsilyl group $Sub_{51}$ and an arylsilyl group $Sub_{52}$.

Similarly, a substituted amino group $Sub_{11}$ means at least one group of an arylamino group $Sub_{111}$ and an alkylamino group $Sub_{112}$.

Herein, a substituent for a "substituted or unsubstituted" group is exemplified by a substituent $R_{F1}$. The substituent $R_{F1}$ is at least one group selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, nitro group, and carboxy group.

Herein, the substituent $R_{F1}$ for a "substituted or unsubstituted" group may be a diaryl boron group ($Ar_{B1}Ar_{B2}B$—). $Ar_{B1}$ and $Ar_{B2}$ are exemplified by the above-described aryl group $Sub_1$. $Ar_{B1}$ and $Ar_{B2}$ in $Ar_{B1}Ar_{B2}B$— are the same or different.

Specific examples and preferable examples of the substituent $R_{F1}$ are the same as those of the substituents described in "Description of Each Substituent" (e.g., an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, and carbamoyl group $Sub_{22}$).

The substituent $R_{F1}$ for a "substituted or unsubstituted" group may be further substituted by at least one group (hereinafter, also referred to as a substituent $R_{F2}$) selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, nitro group, and carboxy group. Moreover, a plurality of substituents $R_{F2}$ may be bonded to each other to form a ring.

"Unsubstituted" for a "substituted or unsubstituted" group means that a group is not substituted by the above-described substituent $R_{F1}$ but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of the substituent $R_{F1}$ of the substituted ZZ group.

Herein, "XX to YY atoms" in the description of "substituted or unsubstituted ZZ group having XX to YY atoms" represent atoms of an unsubstituted ZZ group and do not include atoms of the substituent $R_{F1}$ of the substituted ZZ group.

The same description as the above applies to "substituted or unsubstituted" in compounds or moieties thereof described herein.

Herein, when the substituents are bonded to each other to form a ring, the ring is structured to be a saturated ring, an unsaturated ring, an aromatic hydrocarbon ring or a hetero ring.

Herein, examples of the aromatic hydrocarbon group in the linking group include a divalent or multivalent group obtained by eliminating one or more atoms from the above monovalent aryl group $Sub_1$.

Herein, examples of the heterocyclic group in the linking group include a divalent or multivalent group obtained by eliminating one or more atoms from the above monovalent heteroaryl group $Sub_2$.

EXAMPLES

Compounds

The first compound represented by the formula (1), which was used for manufacturing organic EL devices, are shown below.

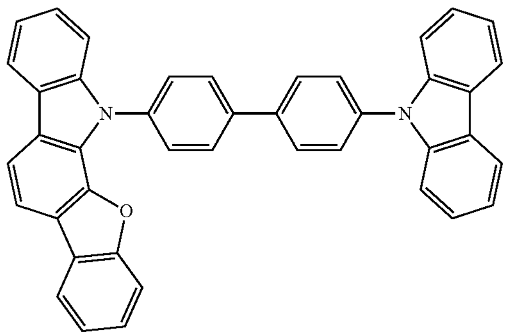

p1

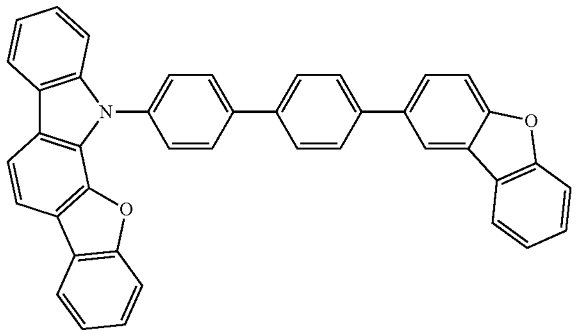

p2

The second compound represented by the formula (2), which was used for manufacturing organic EL devices, are shown below.

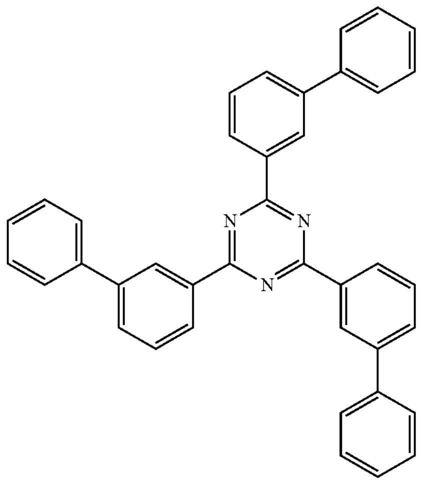

n1

-continued
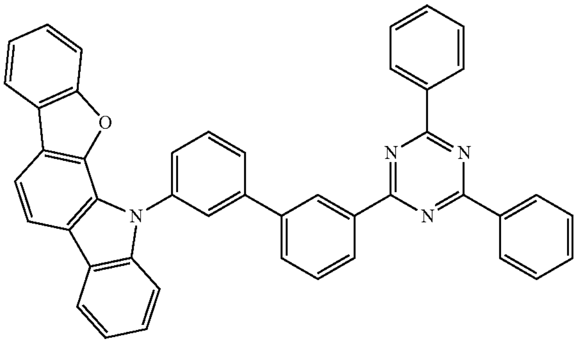
n2
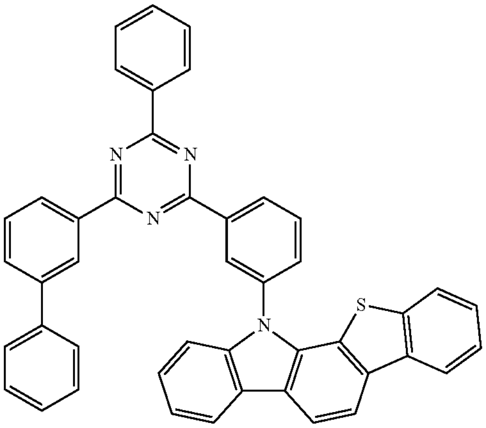
n3
Structures of compounds used for manufacturing organic EL devices in Comparatives are shown below.
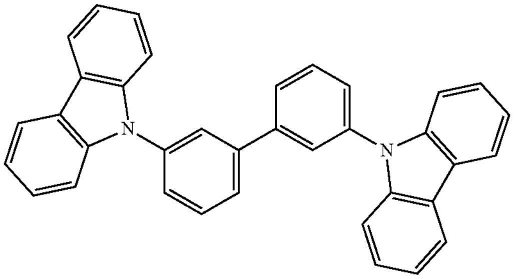
Ref-p1
-continued
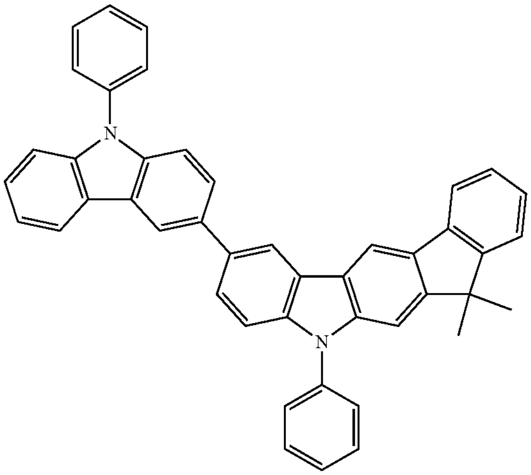
Ref-p2
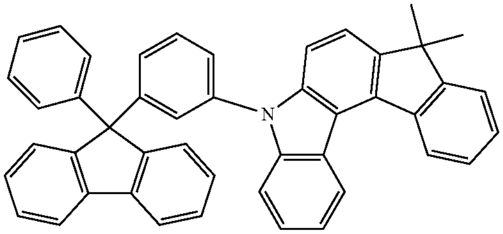
Ref-p3
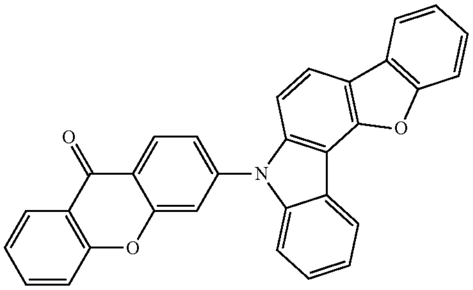
Ref-p4
Structures of other compounds used for manufacturing organic EL devices in Examples and Comparatives are shown below.

-continued
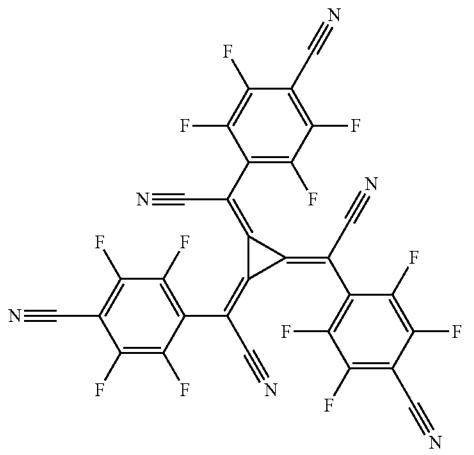
HA
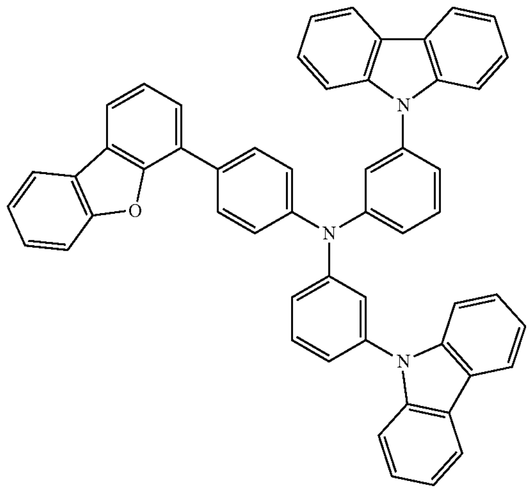
EBL
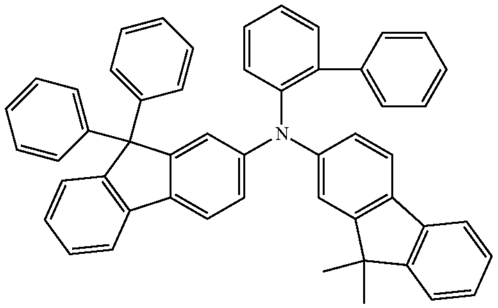
HT
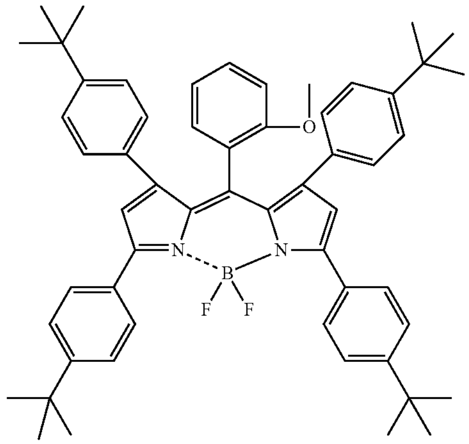
RD
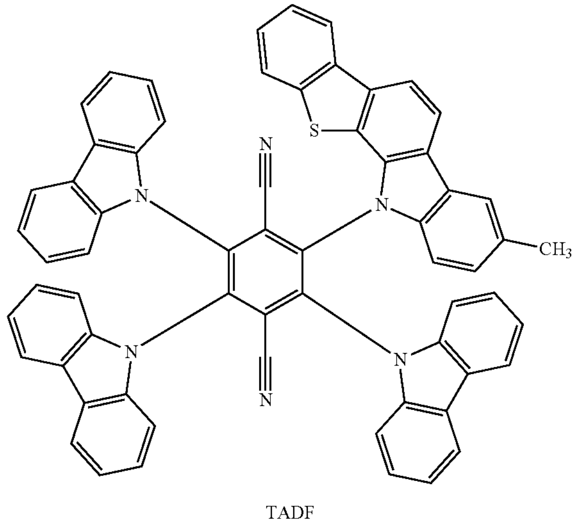
TADF
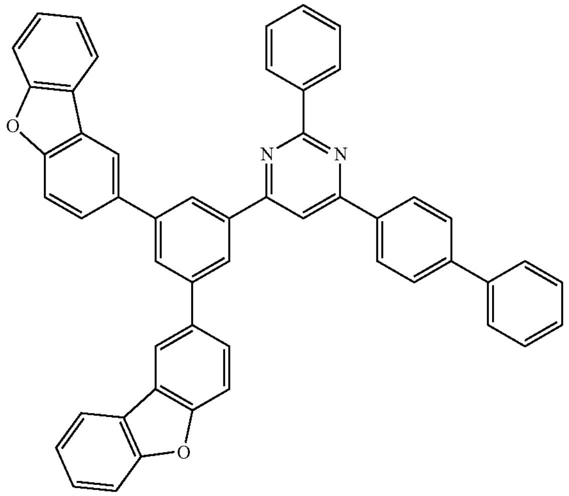
HBL -continued

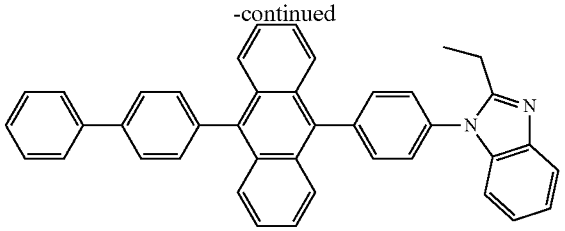

ET

Preparation of Organic EL Device

The organic EL devices were prepared and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum evaporation apparatus. Firstly, a compound HT and a compound HA were co-deposited on a surface of the glass substrate where the transparent electrode line was provided in a manner to cover the transparent electrode, thereby forming a 10-nm-thick hole injecting layer. The concentrations of the compound HT and the compound HA in the hole injecting layer were 97 mass % and 3 mass %, respectively.

Next, the compound HT was vapor-deposited on the hole injecting layer to form a 200-nm-thick hole transporting layer.

Next, a compound EBL was vapor-deposited on the hole transporting layer to form a 10-nm-thick electron blocking layer.

Next, a compound p1 as the first compound, a compound n1 as the second compound, a compound TADF as the third compound, and RD as the fourth compound were co-deposited on the electron blocking layer to form a 25-nm-thick emitting layer. The concentrations of the compound p1, the compound n1, the compound TADF, and the compound RD in the emitting layer were 37 mass %, 37 mass %, 25 mass %, and 1 mass % respectively.

Next, the compound HBL was vapor-deposited on the emitting layer to form a 10-nm-thick hole blocking layer.

Next, the compound ET was vapor-deposited on the hole blocking layer to form a 30-nm-thick electron transporting layer.

Next, lithium fluoride (LiF) was vapor-deposited on the electron transporting layer to form a 1-nm-thick electron injecting electrode (cathode).

Subsequently, metal aluminum (Al) was vapor-deposited on the electron injectable electrode to form an 80-nm-thick metal Al cathode.

A device arrangement of the organic EL device of Example 1 is roughly shown as follows.

ITO(130)/HT:HA(10.97/0:3%)/HT(200)/EBL(10)/p1:n1:TADF:RD(25.37%:37%:25%: 1%)/HBL(10)/ET(30)/LiF(1)/Al(80)

Numerals in parentheses represent a film thickness (unit: nm).

The numerals (97%:3%) represented by percentage in the same parentheses indicate a ratio (mass %) between the compound HT and the compound HA in the hole injecting layer, and the numerals (37%:37%:25%:1%) represented by percentage in the same parentheses indicate a ratio (mass %) between the compound p1 and the compound n1 and the compound TADF and the compound RD in the emitting layer.

Examples 2 to 4 and Comparatives 1 to 4

The organic EL devices in Examples 2 to 4 and Comparatives 1 to 4 were prepared in the same manner as in Example 1 except that compounds shown in Table 1 were used in place of the compound p1 and the compound n1 in the emitting layer of Example 1.

Evaluation of Organic EL Device

The organic EL devices manufactured in Examples 1 to 4 and Comparatives 1 to 4 were evaluated as follows. The results are shown in Table 1. Although compounds Ref-p1 to Ref-p4 used in Comparatives 1 to 4 do not correspond to the first compound represented by the above formula, Ref-p1 to Ref-p4 are shown in the same column as the compound p1 in Example 1 for convenience.

Main Peak Wavelength (λp)

Voltage was applied on each of the organic EL devices such that a current density of the organic EL device was 10 $mA/cm^2$, where spectral radiance spectrum was measured by a spectroradiometer CS-2000 (manufactured by Konica Minolta, Inc.). The main peak wavelength λp (unit: nm) was calculated based on the obtained spectral-radiance spectra.

External Quantum Efficiency EQE

Voltage was applied on each of the organic EL devices such that a current density was 10 $mA/cm^2$, where spectral radiance spectra were measured by a spectroradiometer CS-2000 (manufactured by Konica Minolta, Inc.). The external quantum efficiency EQE (unit: %) was calculated based on the obtained spectral-radiance spectra, assuming that the spectra was provided under a Lambertian radiation.

EQE (%) of Comparative 1 was set to be 100 and EQE (%) of each of Examples was obtained as a "EQE (relative value: %)" using a numerical formula (numerical formula 100) below.

EQE (relative value: %) of each of Examples=(EQE (%) of each of Examples and Comparatives/EQE (%) of Comparative 1)×100 (Numerical Formula 100)

TABLE 1

| | Emitting Layer | | | | | | | | | | | | | | Device Evaluation Result(@10 mA/cm$^2$) |
|---|---|---|---|---|---|---|---|---|---|---|---|---|---|---|---|
| | First Compound | | | Second Compound | | | Third Compound | | | | Fourth Compound | | | | EQE |
| | Type | $S_1$ [eV] | $T_{77K}$ [eV] | Type | $S_1$ [eV] | $T_{77K}$ [eV] | Type | ΔST [eV] | $S_1$ [eV] | λ [nm] | Type | $S_1$ [eV] | λ [nm] | λ p [nm] | [Relative Value: %] |
| Example 1 | p1 | 3.42 | 2.89 | n1 | 3.65 | 2.92 | TADF | <0.01 | 2.32 | 545 | RD | 2.02 | 609 | 621 | 120 |
| Example 2 | p2 | 3.41 | 2.72 | n1 | 3.65 | 2.92 | TADF | <0.01 | 2.32 | 545 | RD | 2.02 | 609 | 621 | 111 |
| Example 3 | p1 | 3.42 | 2.89 | n2 | 3.46 | 2.89 | TADF | <0.01 | 2.32 | 545 | RD | 2.02 | 609 | 621 | 124 |
| Example 4 | p1 | 3.42 | 2.89 | n3 | 3.08 | 2.84 | TADF | <0.01 | 2.32 | 545 | RD | 2.02 | 609 | 621 | 122 |
| Comparative 1 | Ref-p1 | 3.56 | 2.96 | n1 | 3.65 | 2.92 | TADF | <0.01 | 2.32 | 545 | RD | 2.02 | 609 | 621 | 100 |
| Comparative 2 | Ref-p2 | 3.27 | 2.82 | n1 | 3.65 | 2.92 | TADF | <0.01 | 2.32 | 545 | RD | 2.02 | 609 | 621 | 9 |
| Comparative 3 | Ref-p3 | 3.43 | 2.66 | n1 | 3.65 | 2.92 | TADF | <0.01 | 2.32 | 545 | RD | 2.02 | 609 | 621 | 84 |
| Comparative 4 | Ref-p4 | 2.89 | 2.75 | n1 | 3.65 | 2.92 | TADF | <0.01 | 2.32 | 545 | RD | 2.02 | 609 | 621 | 89 |

Explanation of Table 1

"<0.01" represents ΔST of less than 0.01 eV.

The organic EL devices in Examples 1 to 4 exhibited an improved external quantum efficiency EQE as compared with the organic EL devices in Comparatives 1 to 4 in which the compounds Ref-p1 to Ref-p4 were used in place of the first compound in the emitting layer.

Here, the organic EL devices of Comparatives 1 and 2 correspond to Examples of Literature 1. From the comparison between Comparative 1 and Examples 1 to 2, it is understood that the luminous efficiency is improved as compared with that in Literature 1 by using the first compound represented by the formula (1) together with the second compound represented by the formula (2). The compounds Ref-p2 and Ref-p3 used in Comparatives 2 and 3 are compounds used in Examples of Literature 2. From the comparison between Comparatives 2 to 3 and Examples 1 to 2, it is understood that the luminous efficiency is significantly improved as compared with that in Literature 2 by using the first compound represented by the formula (1) together with the second compound represented by the formula (2).

Evaluation of Compounds

Values of physical properties of the compounds shown in Table 1 were measured by the following method.

Thermally Activated Delayed Fluorescence

Delayed Fluorescence of Compound TADF

Delayed fluorescence properties were checked by measuring transient photoluminescence (PL) using a device shown in FIG. 2. The compound TADF was dissolved in toluene to prepare a dilute solution with an absorbance of 0.05 or less at the excitation wavelength to eliminate the contribution of self-absorption. In order to prevent quenching due to oxygen, the sample solution was frozen and degassed and then sealed in a cell with a lid under an argon atmosphere to obtain an oxygen-free sample solution saturated with argon.

The fluorescence spectrum of the above sample solution was measured with a spectrofluorometer FP-8600 (manufactured by JASCO Corporation), and the fluorescence spectrum of a 9,10-diphenylanthracene ethanol solution was measured under the same conditions. Using the fluorescence area intensities of both spectra, the total fluorescence quantum yield is calculated by an equation (1) in Morris et al. J. Phys. Chem. 80 (1976) 969.

Prompt emission was observed immediately when the excited state was achieved by exciting the compound TADF with a pulse beam (i.e., a beam emitted from a pulse laser) having a wavelength to be absorbed by the compound TADF, and Delay emission was observed not immediately when the excited state was achieved but after the excited state was achieved. The delayed fluorescence in Examples means that an amount of Delay Emission is 5% or more with respect to an amount of Prompt Emission. Specifically, provided that the amount of Prompt emission is denoted by $X_P$ and the amount of Delay emission is denoted by $X_0$, the delayed fluorescence means that a value of $X_D/X_P$ is 0.05 or more.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

It was confirmed that the amount of Delay Emission was 5% or more with respect to the amount of Prompt Emission in the compound TADF.

Specifically, it was found that a value of $X_D/X_P$ was 0.05 or more in the compound TADF.

Singlet Energy $S_1$

Singlet energy $S_1$ of each of the compound p1 to the compound p2, the compound n1 to the compound n3, the compound TADF, the compound RD, and the comparative compound Ref-p1 to the comparative compound Ref-p4 was measured according to the above-described solution method.

Energy Gap $T_{77K}$ at 77K

An energy gap $T_{77K}$ of each of the compound p1 to the compound p2, the compound n1 to the compound n3, the compound TADF, and the comparative compound Ref-p1 to the comparative compound Ref-p4 was measured according to the measurement method of energy gap$T_{77K}$ described in the above "Relationship between Triplet Energy and Energy Gap at 77K." ST were configured from the measurement results of $T_{77K}$ and the values of the singlet energy $S_1$.

Main Peak Wavelength A of Compound

A main peak wavelength A of each of the compounds RD and TADF was measured by the following method.

A toluene solution containing a measurement target compound at 5 μmol/L was prepared and put in a quartz cell. An emission spectrum (ordinate axis: luminous intensity, abscissa axis: wavelength) of each of the samples was measured at a normal temperature (300K). In Examples, the emission spectrum was measured using a spectrophotometer manufactured by Hitachi, Ltd. (device name: F-7000). It should be noted that the machine for measuring the emission spectrum is not limited to the machine used herein. A peak wavelength of the emission spectrum exhibiting the maximum luminous intensity was defined as a main peak wavelength A.

Synthesis of Compounds

The compound p1 represented by the formula (1) and the compound n2 represented by the formula (2) were synthesized.

Synthesis Example 1: Synthesis of Compound p1

A synthesis scheme of the compound p1 is shown below.

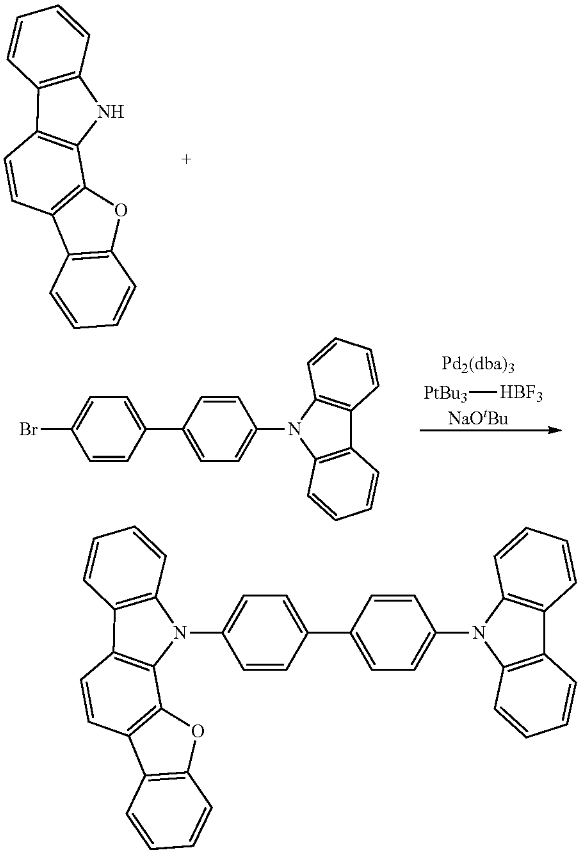

p1

Under nitrogen atmosphere, xylene (675 mL) was added into a mixture of 12H-benzofuro[2,3-a]carbazole (26.6 g, 103 mmol), 9-(4'-bromo-[1,1'-biphenyl]-4-yl)-9H-carbazole (41.2 g, 103 mmol), tris(dibenzylideneacetone)dipalladium (1.90 g, 2.07 mmol), tri-tert-butylphosphonium tetrafluoroborate (1.20 mg, 4.14 mmol), and sodium tert-butoxide (11.9 g, 124 mmol), and stirred at 130 degrees C. for eight hours. After the reaction, a solid was collected by filtration. The filtrated solid was recrystallized with toluene to obtain the compound p1 (51.5 g, a yield of 87%). The obtained compound was identified as the compound p1 by analysis according to LC-MS (Liquid chromatography mass spectrometry).

Synthesis Example 2: Synthesis of Compound n2

A synthesis scheme of the compound n2 is shown below.

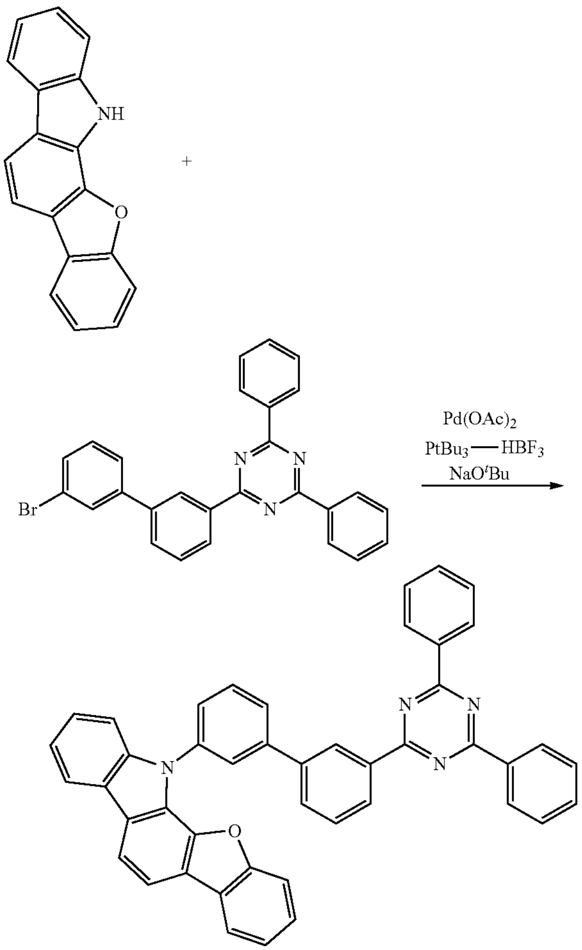

n2

Under nitrogen atmosphere, xylene (40 mL) was added into a mixture of 12H-benzofuro[2,3-a]carbazole (2.06 g, 8.00 mmol), 2-(3'-bromo-[1,1'-biphenyl]-3-yl)-4,6-diphenyl-1,3,5-triazine (3.71 g, 8.00 mmol), palladium acetate (35.9 mg, 0.160 mmol), tri-tert-butylphosphonium tetrafluoroborate (92.8 mg, 0.32 mmol), and sodium tert-butoxide (2.31 g, 24.0 mmol), and stirred at 130 degrees C. for six hours. After the reaction a solid was filtrated and recrystallized with toluene to obtain the compound n2 (3.52 g, a yield of 69%). The obtained compound was identified as the compound n2 by analysis according to LC-MS.

What is claimed is:

1. An organic electroluminescence device, comprising:

an anode;

a cathode; and an emitting layer which is a single layer between the anode and the cathode;

wherein the emitting layer comprises a first compound represented by formula (1), a second compound represented by formula (2), a third compound that exhibits delayed fluorescence, and a fourth compound that fluoresces, the third compound is a compound represented by formula (31), a singlet energy $S_1$(M1) of the first compound and a singlet energy $S_1$ (M3) of the third compound satisfy a relationship of Numerical Formula 1, a singlet energy $S_1$(M2) of the second compound and the singlet energy S; (M3) of the third compound satisfy a relationship of Numerical Formula 2, the singlet energy $S_1$(M3) of the third compound and a singlet energy $S_1$(M4) of the fourth compound satisfy a relationship of Numerical Formula 3, the singlet energy $S_1$(M1) of the first compound and the singlet energy $S_1$(M4) of the fourth compound satisfy a relationship of Numerical Formula 4, the singlet energy $S_1$(M2) of the second compound and the singlet energy $S_1$(M4) of the fourth compound satisfy a relationship of Numerical Formula 5, an energy gap $T_{77K}$(M1) at 77K of the first compound and an energy gap $T_{77K}$(M3) at 77K of the third compound satisfy a relationship of Numerical Formula 1a, and an energy gap $T_{77K}$(M2) at 77K of the second compound and the energy gap $T_{77K}$(M3) at 77K of the third compound satisfy a relationship of Numerical Formula 2b, $S_1(M1)>S_1(M3)$ (Numerical Formula 1)

$S_1(M2)>S_1(M3)$ (Numerical Formula 2)

$S_1(M3)>S_1(M4)$ (Numerical Formula 3)

$S_1(M1)>S_1(M4)$ (Numerical Formula 4)

$S_1(M2)>S_1(M4)$ (Numerical Formula 5)

$T_{77K}(M1)>T_{77K}(M3)$ (Numerical Formula 1a)

$T_{77K}(M2)>T_{77K}(M3)$ (Numerical Formula 2b)

(1)

A—L—B (a1)

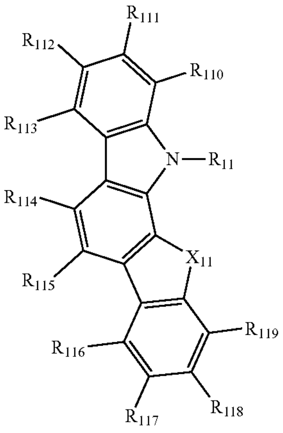

-continued (a2)

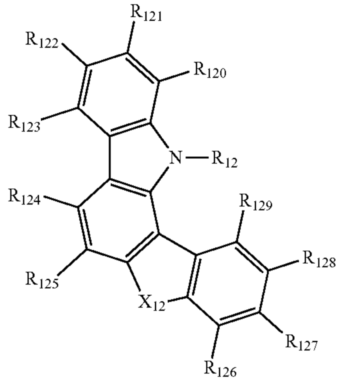

(a3)

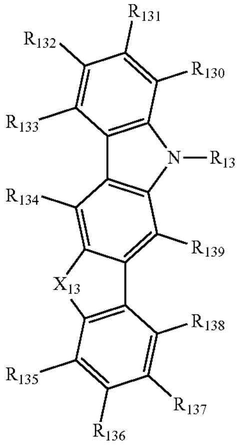

(a4)

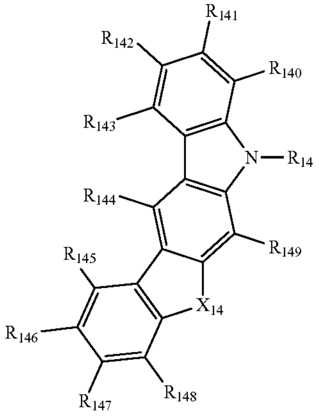

(a5)

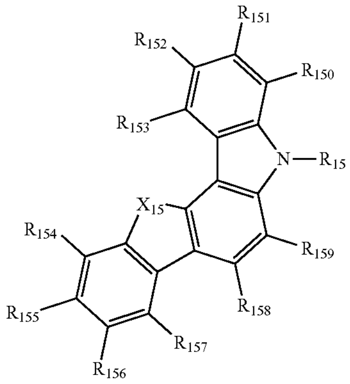

-continued (a6)

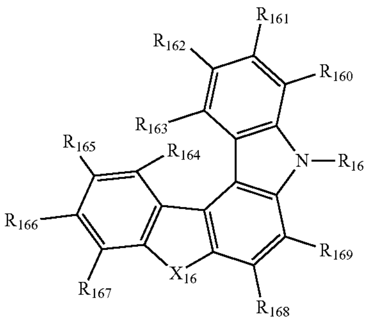

wherein in the formula (1):

λ is a group represented by formula (a1), (a2), (a3) (a4), (a5), or (a6);

L is a substituted or unsubstituted para-biphenylene group, or a substituted or unsubstituted para-terphenylene group; B is a group selected from the group consisting of groups of formulae (b1) to (b6); and the first compound represented by the formula (1) does not comprise a carbonyl group, in the formulae (a1) to (a6):

$R_{11}$, $R_{12}$, $R_{13}$, $R_{14}$, $R_{15}$, and Rig are each a single bond bonded to L;

$X_{11}$, $X_{12}$, $X_{13}$, $X_{14}$, $X_{15}$, and $X_{16}$ are each independently an oxygen atom or a sulfur atom;

$R_{110}$ to $R_{119}$ are each a hydrogen atom;

$R_{120}$ to $R_{129}$ are each a hydrogen atom;

$R_{130}$ to $R_{139}$ are each a hydrogen atom;

$R_{140}$ to $R_{149}$ are each a hydrogen atom;

$R_{150}$ to Rise are each a hydrogen atom; and $R_{160}$ to $R_{169}$ are each a hydrogen atom;

(b1)

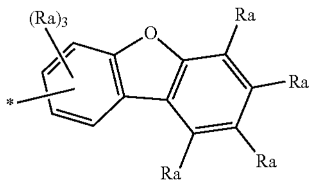

(b2)

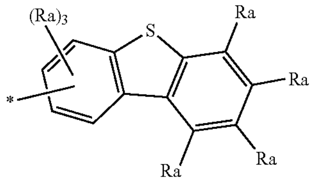

(b3)

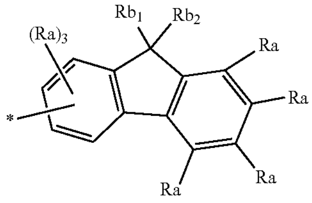

-continued (b4)

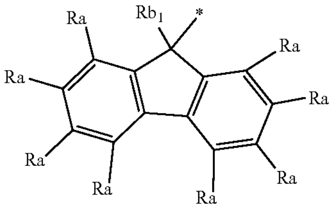

(b5)

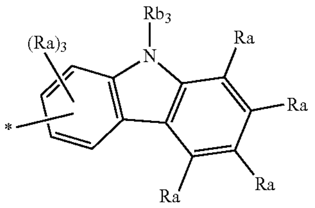

(b6)

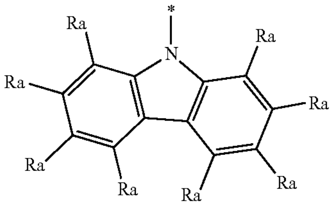

wherein in the formulae (b1) to (b6):

Ra is a hydrogen atom or a substituent, a plurality of Ra being mutually the same or different;

$Rb_1$ and $Rb_2$ are each independently a hydrogen atom or a substituent, or a pair of $Rb_1$ and $Rb_2$ are bonded to each other to form a ring;

$Rb_3$ is a hydrogen atom or a substituent; and when Ra, $Rb_1$, $Rb_2$, and $Rb_3$ are each a substituent, each substituent independently represents a halogen atom, a cyano group, an unsubstituted aryl group having 6 to 30 ring carbon atoms, an unsubstituted heterocyclic group having 5 to 30 ring atoms, an unsubstituted alkyl group having 1 to 30 carbon atoms, an unsubstituted alkyl halide group having 1 to 30 carbon atoms, an unsubstituted alkenyl group having 2 to 30 carbon atoms, an unsubstituted alkynyl group having 2 to 30 carbon atoms, an unsubstituted alkylsilyl group having 3 to 30 carbon atoms, an unsubstituted arylsilyl group having 6 to 60 ring carbon atoms, an unsubstituted arylphosphoryl group having 6 to 60 ring carbon atoms, a hydroxyl group, an unsubstituted alkoxy group having 1 to 30 carbon atoms, an unsubstituted aryloxy group having 6 to 30 ring carbon atoms, a group represented by $—N(Rz)_2$, a thiol group, an unsubstituted alkylthio group having 1 to 30 carbon atoms, an unsubstituted aralkyl group having 7 to 30 ring carbon atoms, a substituted germanium group, a substituted phosphine oxide group, a nitro group, a substituted boryl group, or an unsubstituted arylthio group having 6 to 30 ring carbon atoms;

none of pairs of adjacent ones of Ra are bonded to each other,

Rz is an unsubstituted aryl group having 6 to 30 ring carbon atoms, an unsubstituted heterocyclic group having 5 to 30 ring atoms, or an unsubstituted alkyl group having 1 to 30 carbon atoms; and two Rz in —$N(Rz)_2$ are mutually the same or different, (2)

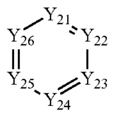

(2A)

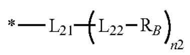

in the formula (2):

$Y_{21}$ to $Y_{26}$ are each independently a nitrogen atom or $CR_A$, and at least one of $Y_{21}$ to $Y_{26}$ is a nitrogen atom;

$R_A$ is a hydrogen atom, a substituent or a group represented by the formula (2A), or at least one pair of adjacent ones of $R_A$ are bonded to each other to form a ring;

$R_B$ is a substituent;

when a plurality of $R_B$ are present, the plurality of $R_B$ are the same or different;

* represents a bonding position to a carbon atom in a six-membered ring in the formula (2);

$L_{21}$ is a single bond, a substituted or unsubstituted arylene group having 6 to 22 ring carbon atoms, or a trivalent, tetravalent, pentavalent, or hexavalent group derived from the arylene group;

$L_{22}$ is a single bond or a substituted or unsubstituted arylene group having 6 to 22 ring carbon atoms;

n2 is 1, 2, 3, 4, or 5;

when $L_{21}$ is a single bond, n2 is 1, and $L_{22}$ is bonded to a carbon atom in the six-membered ring in the formula (2);

when a plurality of $L_{22}$ are present, the plurality of $L_{22}$ are the same or different;

$R_A$ as a substituent is a substituted or unsubstituted aryl group having 6 to 50 ring carbon atoms, or a substituted or unsubstituted heterocyclic group having 5 to 50 ring atoms;

$R_B$ is a group selected from the group consisting of formulae (c1) to (c9);

Rz is an unsubstituted aryl group having 6 to 30 ring carbon atoms or an unsubstituted alkyl group having 1 to 30 carbon atoms;

two Rz in —$N(Rz)_2$ are mutually the same or different;

(c1)

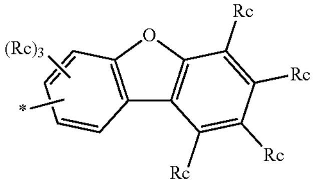

(c2)

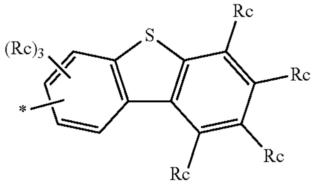

-continued (c3)

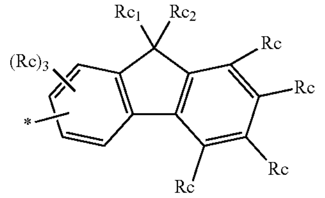

(c4)

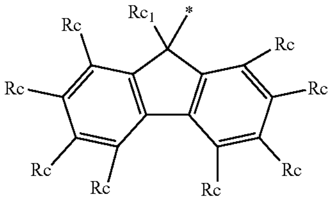

(c5)

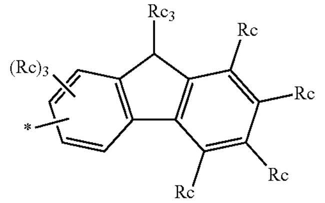

(c6)

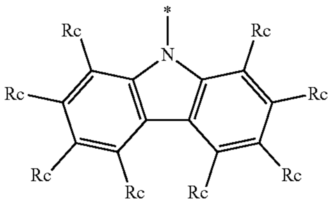

(c7)

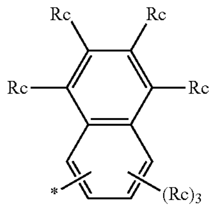

(c8)

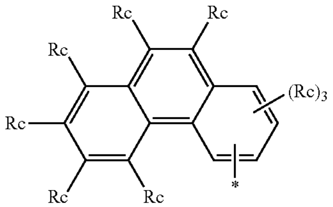

(c9)

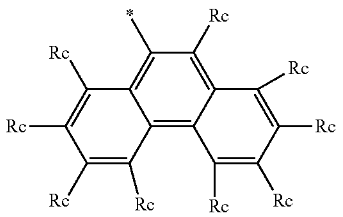

where in the formulae (c1) to (c9):

Rc is a hydrogen atom or a substituent, or at least one pair of adjacent ones of Rc are bonded to each other to form a ring, a plurality of Rc being mutually the same or different;

$Rc_1$ and $Rc_2$ are each independently a hydrogen atom or a substituent, or a pair of $Rc_1$ and $Rc_2$ are bonded to each other to form a ring;

$Rc_3$ is a hydrogen atom or a substituent;

with a proviso that at least one pair of adjacent ones of Rc in the formula (c6) are bonded to each other to form a ring; and a substituent for a "substituted or unsubstituted" group as L in the formula (1), a substituent for a "substituted or unsubstituted" group as $L_{21}$, $L_{22}$ and $R_A$ in the formula (2) and a substituent group Rc, $Rc_1$, $Rc_2$ and $Rc_3$ in formulae (c1) to (c9) are each independently a halogen atom, a cyano group, an unsubstituted aryl group having 6 to 30 ring carbon atoms, an unsubstituted alkyl group having 1 to 30 carbon atoms, an unsubstituted alkyl halide group having 1 to 30 carbon atoms, an unsubstituted alkenyl group having 2 to 30 carbon atoms, an unsubstituted alkynyl group having 2 to 30 carbon atoms, an unsubstituted alkylsilyl group having 3 to 30 carbon atoms, an unsubstituted arylsilyl group having 6 to 60 ring carbon atoms, an unsubstituted arylphosphoryl group having 6 to 60 ring carbon atoms, a hydroxy group, an unsubstituted alkoxy group having 1 to 30 carbon atoms, an unsubstituted aryloxy group having 6 to 30 ring carbon atoms, a group represented by —N(Rz) 2, a thiol group, an unsubstituted alkylthio group having 1 to 30 carbon atoms, an unsubstituted aralkyl group having 7 to 30 ring carbon atoms, a substituted germanium group, a substituted phosphine oxide group, a nitro group a substituted boryl group, or an unsubstituted arylthio group having 6 to 30 ring carbon atoms;

Rz is an unsubstituted aryl group having 6 to 30 ring carbon atoms or an unsubstituted alkyl group having 1 to 30 carbon atoms; and two Rz in $—N(Rz)_2$ are mutually the same or different, (31)

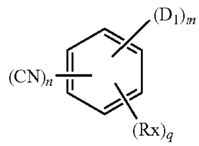

wherein in formula (31):

n is 1, 2, 3 or 4;

m is 1, 2, 3, or 4, q is 0, 1, 2, 3, or 4; m+n+q=6 is satisfied;

CN is a cyano group;

$D_1$ is a group represented by formula (3a), formula (3b) or formula (3c), when a plurality of $D_1$ are present, the plurality of $D_1$ are mutually the same or different;

Rx is a hydrogen atom or a substituent, or a pair of adjacent ones of Rx are bonded to each other to form a ring, and when a plurality of Rx are present, the plurality of Rx are mutually the same or different;

Rx as a substituent are each independently a halogen atom, a substituted or unsubstituted aryl group having 6 to 30 ring carbon atoms, a substituted or unsubstituted heterocyclic group having 5 to 30 ring atoms, a substituted or unsubstituted amino group, a substituted or unsubstituted carbonyl group, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkylsilyl group having 3 to 30 carbon atoms, or a substituted or unsubstituted arylsilyl group having 6 to 60 ring carbon atoms; and CN, $D_1$ and Rx are each bonded to a carbon atom of a six-membered ring, (3a)

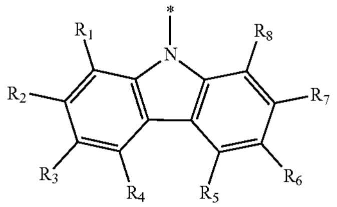

wherein in the formula (3a):

$R_1$ to $R_8$ are each independently a hydrogen atom or a substituent, or at least one pair of a pair of $R_1$ and $R_2$, a pair of $R_2$ and $R_3$, a pair of $R_3$ and $R_4$, a pair of $R_5$ and $R_6$, a pair of $R_6$ and $R_7$, or a pair of $R_7$ and $R_8$ are bonded to each other to form a ring;

with a proviso that at least one pair of a pair of $R_1$ and $R_2$, a pair of $R_2$ and $R_3$, a pair of $R_3$ and $R_4$, a pair of $R_5$ and $R_6$, a pair of $R_6$ and $R_7$, or a pair of $R_7$ and $R_8$ are bonded to each other to form a ring; and $R_1$ to $R_8$ as a substituent are each independently a halogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted alkylsilyl group having 3 to 30 carbon atoms, a substituted or unsubstituted arylsilyl group having 6 to 60 ring carbon atoms, a hydroxy group, a substituted or unsubstituted alkoxy group having 1 to 30 carbon atoms, a substituted or unsubstituted alkoxy halide group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms; and

* represents a bonding position to a carbon atom in a benzene ring in the formula (31), (3b)

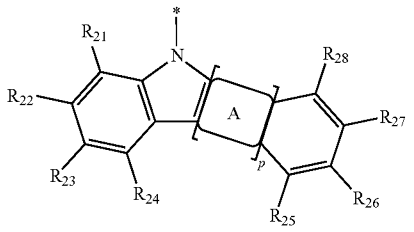

where in the formula (3b):

$R_{21}$ to $R_{28}$ are each independently a hydrogen atom or a substituent, or at least one pair of a pair of $R_{21}$ and $R_{22}$, a pair of $R_{22}$ and $R_{23}$, a pair of $R_{23}$ and $R_{24}$, a pair of $R_{25}$ and $R_{26}$, a pair of $R_{26}$ and $R_{27}$, or a pair of $R_{27}$ and $R_{28}$ are bonded to each other to form a ring;

$R_{21}$ to $R_{28}$ as a substituent each independently represent the same as $R_1$ to $R_8$ as a substituent in the formula (3a);

A represents a cyclic structure represented by formula (311) or (312), the cyclic structure A is fused at any positions with adjacent cyclic structures;

p is 1, 2, 3, or 4; when p is 2, 3, or 4, a plurality of cyclic structures A are mutually the same or different; and

* represents a bonding position to a carbon atom in a benzene ring in the formula (31), (3c)

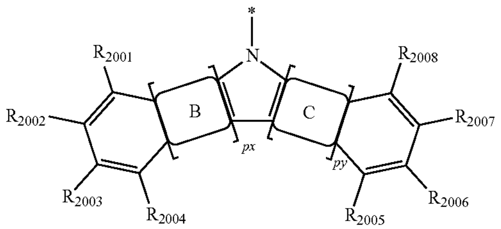

where in the formula (3c):

$R_{2001}$ to $R_{2008}$ are each independently a hydrogen atom or a substituent, or at least one pair of a pair of $R_{2001}$ and $R_{2002}$, a pair of $R_{2002}$ and $R_{2003}$, a pair of $R_{2003}$ and $R_{2004}$, a pair of $R_{2005}$ and $R_{2006}$, a pair of $R_{2006}$ and $R_{2007}$, or a pair of $R_{2007}$ and $R_{2008}$ are bonded to each other to form a ring;

$R_{2001}$ to $R_{2008}$ as a substituent each independently represent the same as $R_1$ to $R_8$ as a substituent in the formula (3a);

B represents a cyclic structure represented by the formula (311) or (312), the cyclic structure B is fused at any positions with adjacent cyclic structures;

px is 1, 2, 3, or 4; when px is 2, 3, or 4, a plurality of cyclic structures B are mutually the same or different;

C represents a cyclic structure represented by the formula (311) or (312), the cyclic structure C is fused at any positions with adjacent cyclic structures;

py is 1, 2, 3, or 4, when py is 2, 3, or 4, a plurality of cyclic structures C are mutually the same or different; and

* represents a bonding position to a carbon atom in a benzene ring in the formula (31), (311)

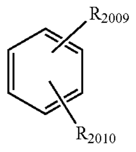

(312)

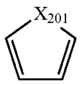

where in the formula (311), $R_{2009}$ and $R_{2010}$ are each independently a hydrogen atom or a substituent, or are bonded to a part of an adjacent cyclic structure to form a ring, or a pair of $R_{2009}$ and $R_{2010}$ are mutually bonded to form a ring, in the formula (312): $X_{201}$ is $CR_{2011}R_{2012}$, $NR_{2013}$, a sulfur atom, or an oxygen atom, $R_{2011}$, $R_{2012}$ and $R_{2013}$ are each independently a hydrogen atom or a substituent, or $R_{2011}$ and $R_{2012}$ are mutually bonded to form a ring, and $R_{2009}$, $R_{2010}$, $R_{2011}$, $R_{2012}$ and $R_{2013}$ as a substituent each independently represent the same as $R_1$ to $R_8$ as a substituent in the formula (3a), and the energy gap $T_{77K}$ at 77K is an energy amount calculated by dissolving a measurement target compound in EPA, which is a mixture of diethyl ether, isopentane, and ethanol in a volume ratio of 5:5:2, at a concentration of 10 μmol/L, encapsulating a solution thus obtained in a quartz cell to provide a measurement sample, measuring a phosphorescent spectrum of the measurement sample at 77K, an ordinate axis of the phosphorescent spectrum representing phosphorescent luminous intensity, an abscissa axis of the phosphorescent spectrum representing wavelength, drawing a tangent to a rise of the phosphorescent spectrum close to a short-wavelength region, and performing a calculation according to a conversion equation (F1) below based on a wavelength value $\lambda_{edge}$ [nm] at an intersection of the tangent and the abscissa axis, $$T_{77K}\,[\text{eV}]=1239.85/\lambda_{edge} \qquad \text{Conversion Equation (F1).}$$

2. The organic electroluminescence device according to claim 1, wherein

A is a group represented by the formula (a1), the formula (a2), the formula (a3), the formula (a4), or the formula (a6).

3. The organic electroluminescence device according to claim 1, wherein

A is a group represented by the formula (a1), the formula (a2), the formula (a3), or the formula (a4).

4. The organic electroluminescence device according to claim 1, wherein

A is a group represented by the formula (a1) or the formula (a4).

5. The organic electroluminescence device according to claim 1, wherein A is a group represented by the formula (a1).

6. The organic electroluminescence device according to claim 1, wherein $X_{11}$, $X_{12}$, $X_{13}$, $X_{14}$, $X_{15}$, and $X_{16}$ are oxygen atoms.

7. The organic electroluminescence device according to claim 1, wherein the formula (2) is represented by any one of formulae (21) to (23), (21)

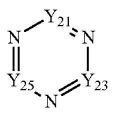

(22)

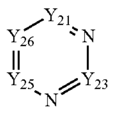

(23)

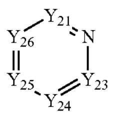

where in the formulae (21) to (23), $Y_{21}$ and $Y_{23}$ to $Y_{26}$ are $CR_A$, and $R_A$ each independently represents the same as $R_A$ defined when $Y_{21}$ to $Y_{26}$ are $CR_A$ in the formula (2).

8. The organic electroluminescence device according to claim 7, wherein the formula (2) is represented by the formula (21).

9. The organic electroluminescence device according to claim 1, wherein at least one of $Y_{21}$ to $Y_{26}$ is $CR_A$, and at least one of $R_A$ is the group represented by the formula (2A).

10. The organic electroluminescence device according to claim 1, wherein $R_B$ is any one of groups represented by the formulae (c1) to (c6).

11. The organic electroluminescence device according to claim 1, wherein $L_{21}$ is a single bond, or a divalent, trivalent, tetravalent, pentavalent, or hexavalent group derived from any one group selected from the group consisting of an unsubstituted phenyl group, an unsubstituted biphenyl group, an unsubstituted naphthyl group, an unsubstituted phenanthryl group, an unsubstituted terphenyl group, an unsubstituted fluorenyl group, and $L_{22}$ is a single bond, or a divalent group derived from any one group selected from the group consisting of an unsubstituted phenyl group, an unsubstituted biphenyl group, an unsubstituted naphthyl group, an unsubstituted phenanthryl group, an unsubstituted terphenyl group and an unsubstituted fluorenyl group.

12. The organic electroluminescence device according to claim 1, wherein $D_1$ is selected from the group consisting of groups represented by formulae (D-22) to (D-27), (D-22)

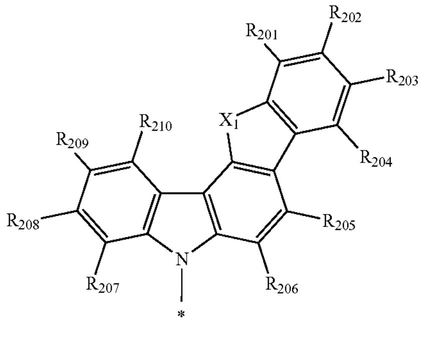

(D-23)

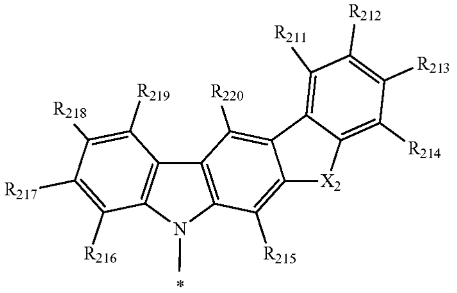

-continued (D-24)

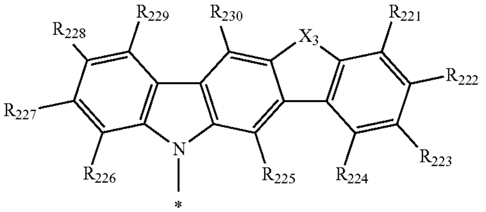

(D-25)

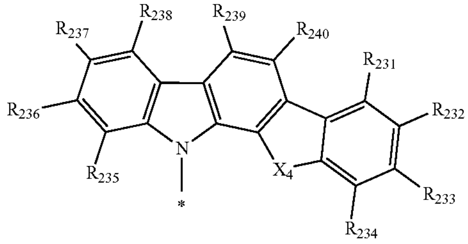

(D-26)

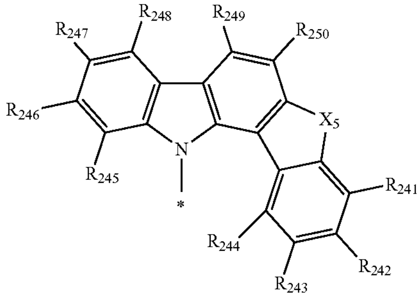

(D-27)

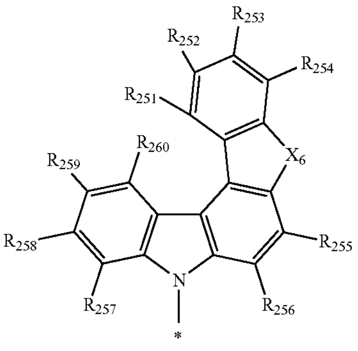

where in the formulae (D-22) to (D-27):

$X_1$ to $X_6$ are each independently an oxygen atom, a sulfur atom, or $CR_{151}R_{152}$;

$R_{151}$ and $R_{152}$ are each independently a hydrogen atom or a substituent, or $R_{151}$ and $R_{152}$ are bonded to each other to form a ring;

$R_{201}$ to $R_{260}$ are each independently a hydrogen atom or a substituent, or at least one pair of a pair of $R_{201}$ and $R_{202}$, a pair of $R_{202}$ and $R_{203}$, a pair of $R_{203}$ and $R_{204}$, a pair of $R_{205}$ and $R_{206}$, a pair of $R_{207}$ and $R_{208}$, a pair of $R_{208}$ and $R_{209}$, a pair of $R_{209}$ and $R_{210}$, a pair of $R_{211}$ and $R_{212}$, a pair of $R_{212}$ and $R_{213}$, a pair of $R_{213}$ and $R_{214}$, a pair of $R_{216}$ and $R_{217}$, a pair of $R_{217}$ and $R_{218}$, a pair of $R_{218}$ and $R_{219}$, a pair of $R_{221}$ and $R_{222}$, a pair of $R_{222}$ and $R_{223}$, a pair of $R_{223}$ and $R_{224}$, a pair of $R_{226}$ and $R_{227}$, a pair of $R_{227}$ and $R_{228}$, a pair of $R_{228}$ and $R_{229}$, a pair of $R_{231}$ and $R_{232}$, a pair of $R_{232}$ and $R_{233}$, a pair of $R_{233}$ and $R_{234}$, a pair of $R_{235}$ and $R_{236}$, a pair of $R_{236}$ and $R_{237}$, a pair of $R_{237}$ and $R_{238}$, a pair of $R_{239}$ and $R_{240}$, a pair of $R_{241}$ and $R_{242}$, a pair of $R_{242}$ and $R_{243}$, a pair of $R_{243}$ and $R_{244}$, a pair of $R_{245}$ and $R_{246}$, a pair of $R_{246}$ and $R_{247}$, a pair of $R_{247}$ and $R_{248}$, a pair of $R_{249}$ and $R_{250}$, a pair of $R_{251}$ and $R_{252}$, a pair of $R_{252}$ and $R_{253}$, a pair of $R_{253}$ and $R_{254}$, a pair of $R_{255}$ and $R_{256}$, a pair of $R_{257}$ and $R_{258}$, a pair of $R_{258}$ and $R_{259}$, or a pair of $R_{259}$ and $R_{260}$ are bonded to each other to form a ring;

$R_{151}$, $R_{152}$ and $R_{201}$ to $R_{260}$ as a substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted cycloalkyl group having 3 to 8 ring carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a thiol group, a substituted or unsubstituted alkylthio group having 1 to 6 carbon atoms, or a substituted or unsubstituted arylthio group having 6 to 14 ring carbon atoms; and

* represents a bonding position to a carbon atom in a benzene ring in the formula (31).

13. The organic electroluminescence device according to claim 1, wherein the emitting layer is formed by using, as a vapor deposition source, a composition comprising the first compound and the second compound.

14. The organic electroluminescence device according to claim 1, wherein the emitting layer does not comprise a metal complex.

15. An electronic device, comprising:

the organic electroluminescence device of claim 1.

* * * * *